US012760322B2

(12) United States Patent
Holm-von Laer et al.

(10) Patent No.: US 12,760,322 B2
(45) Date of Patent: Oct. 13, 2026

(54) MECHANISM TO CONTROL RNA VIRUS REPLICATION AND GENE EXPRESSION

(71) Applicants: Boehringer Ingelheim International GmbH, Ingelheim am Rhein (DE); ViraTherapeutics GmbH, Rum (AT)

(72) Inventors: Meike Dorothee Holm-von Laer, Innsbruck (AT); Emmanuel Heilmann, Innsbruck (AT); Janine Kimpel, Innsbruck (AT); Guido Wollmann, Innsbruck (AT); Lisa Egerer, Innsbruck (AT); Benedikt Hofer, Innsbruck (AT)

(73) Assignees: Boehringer Ingelheim International GmbH (DE); ViraTherapeutics GmbH (AT)

( * ) Notice: Subject to any disclaimer, the term of this patent is extended or adjusted under 35 U.S.C. 154(b) by 936 days.

(21) Appl. No.: 17/620,386

(22) PCT Filed: Jun. 19, 2020

(86) PCT No.: PCT/EP2020/067218
§ 371 (c)(1),
(2) Date: Dec. 17, 2021

(87) PCT Pub. No.: WO2020/254644
PCT Pub. Date: Dec. 24, 2020

(65) Prior Publication Data

US 2022/0228172 A1 Jul. 21, 2022

(30) Foreign Application Priority Data

Jun. 21, 2019 (EP) .................................... 19181717

(51) Int. Cl.
*C12N 15/86* (2006.01)
*A61P 35/00* (2006.01)
*C07K 14/81* (2006.01)

(52) U.S. Cl.
CPC .............. *C12N 15/86* (2013.01); *A61P 35/00* (2018.01); *C07K 14/81* (2013.01); *C12N 2760/00032* (2013.01); *C12N 2760/20211* (2013.01)

(58) Field of Classification Search
None
See application file for complete search history.

(56) References Cited

U.S. PATENT DOCUMENTS

2003/0148521 A1* 8/2003 Bell ........................ C12N 7/00 435/235.1

FOREIGN PATENT DOCUMENTS

WO 9958655 A2 11/1999
WO 2019094801 A1 5/2019

OTHER PUBLICATIONS

Chung, Hokyung K., et al. Nature chemical biology 11.9 (2015): 713-720. (Year: 2015).*
Afonso, Claudio L., et al. Archives of virology 161 (2016): 2351-2360. (Year: 2016).*
Lv, Zhengtong, Yuan Chu, and Yong Wang. HIV/AIDS-Research and palliative care (2015): 95-104. (Year: 2015).*
Das, Subash C., and Asit K. Pattnaik. Journal of virology 79.13 (2005): 8101-8112. (Year: 2005).*
Chung et al., "Tunable and reversible drug control of protein production via a self-excising degron", Nature Chemical Biology, vol. 11, No. 9, Sep. 1, 2015, pp. 713-720.
International Search Report from PCT/EP2020/067218, mailed Oct. 1, 2020, 3 pages.
Ketzer et al., "Artificial riboswitches for gene expression and replication control of DNA and RNA viruses", Proceedings of the National Academy of Sciences, vol. 111, No. 5, Jan. 21, 2014, pp. E554-E562.
Rodriguez et al., "Full-length genome analysis of natural isolates of vesicular stomatitis virus (Indiana 1 serotype) from North, Central and South America", Journal of General Virology (Jan. 31, 2002), 83, pp. 2475-2483.

* cited by examiner

*Primary Examiner* — Maria Marvich
*Assistant Examiner* — Brendan Thomas Tinsley
(74) *Attorney, Agent, or Firm* — McNeill PLLC

(57) ABSTRACT

The present invention relates to a novel mechanism to control RNA virus replication and gene expression using a conditional protease approach using a specific protease inhibitor for regulation. More specifically it relates to a single-stranded RNA virus, preferably of the order Mononegavirales, comprising a polynucleotide sequence encoding at least one protein essential for viral transcription and/or replication, a protease and a cleavage site for said protease. The protease can be inhibited using a protease inhibitor and hence the protease and the cleavage site for said protease form a regulatable switch. By changing the insertion site of the regulatable switch from an INTRA- to an INTER-molecular location in the at least one protein essential for viral transcription and/or replication, the effect of the protease inhibitor can be altered from an ON switch to an OFF switch. RNA virus may further encode a heterologous protein, the expression of which is then regulated by regulating viral activity. The ON switch may also be used in an RNA virus to directly regulate heterologous protein expression. Further provided are in vivo and in vitro uses of said virus with conditional viral activity or heterologous protein expression.

7 Claims, 34 Drawing Sheets

Specification includes a Sequence Listing.

Structure graph of HIV protease dimer

*FIG. 5*
P(N-term)
HxB2-PR
HxB2-PR
P(C-term)
GGSG linker 1 cut 1
dimer linker
cut 2 GGSG linker 2
G G S G G G S G G G S G V S F N F P Q V T L W Q R P L
GGSG-linker 1
cut 1
protease 1
V T I K I G G Q L K E A L L D T G A D D T V L E E M S
protease 1
L P G R W K P K M I G G I G G F I K V R Q Y D Q I L I
protease 1
E I C G H K A I G T V L V G P T P V N I I G R N L L T
protease 1
Q I G C T L N F A G A I G G A P Q V T L W Q R P L V T
protease 1
dimer linker
protease 2
I K I G G Q L K E A L L D T G A D D T V L E E M S L P
protease 2
G R W K P K M I G G I G G F I K V R Q Y D Q I L I E I
protease 2
C G H K A I G T V L V G P T P V N I I G R N L L T Q I
protease 2
G C T L N F P I S P I G G S G G G S G G G S G
prot...
cut 2
GGSG-linker 2

SEQUENCE LISTING

```
<160> NUMBER OF SEQ ID NOS: 35

<210> SEQ ID NO 1
<211> LENGTH: 795
<212> TYPE: DNA
<213> ORGANISM: Vesicular stomatitis Indiana virus
<220> FEATURE:
<223> OTHER INFORMATION: P-protein VSV Indiana

<400> SEQUENCE: 1

atggataatc tcacaaaagt tcgtgagtat ctcaagtcct attctcgtct ggatcaggcg     60

gtaggagaga tagatgagat cgaagcacaa cgagctgaaa agtccaatta tgagttgttc    120

caagaggatg gagtggaaga gcatactaag ccctcttatt ttcaggcagc agatgattct    180

gacacagaat ctgaaccaga aattgaagac aatcaaggct tgtatgcacc agatccagaa    240

gctgagcaag ttgaaggctt tatacagggg cctttagatg actatgcaga tgaggaagtg    300

gatgttgtat ttacttcgga ctggaaacag cctgagcttg aatctgacga gcatggaaag    360

accttacggt tgacatcgcc agagggttta agtggagagc agaaatccca gtggctttcg    420

acgattaaag cagtcgtgca aagtgccaaa tactggaatc tggcagagtg cacatttgaa    480

gcatcgggag aaggggtcat tatgaaggag cgccagataa ctccggatgt atataaggtc    540

actccagtga tgaacacaca tccgtcccaa tcagaagcag tatcagatgt ttggtctctc    600
```

tcaaagacat ccatgacttt ccaacccaag aaagcaagtc ttcagcctct caccatatcc 660
ttggatgaat tgttctcatc tagaggagag ttcatctctg tcggaggtga cggacgaatg 720
tctcataaag aggccatcct gctcggcctg agatacaaaa agttgtacaa tcaggcgaga 780
gtcaaatatt ctctg 795

<210> SEQ ID NO 2
<211> LENGTH: 6327
<212> TYPE: DNA
<213> ORGANISM: Vesicular stomatitis Indiana virus
<220> FEATURE:
<223> OTHER INFORMATION: L-protein VSV Indiana

<400> SEQUENCE: 2
atggaagtcc acgattttga gaccgacgag ttcaatgatt tcaatgaaga tgactatgcc 60
acaagagaat tcctgaatcc cgatgagcgc atgacgtact tgaatcatgc tgattacaac 120
ctgaattctc ctctaattag tgatgatatt gacaatttaa tcaggaaatt caattctctt 180
ccaattccct cgatgtggga tagtaagaac tgggatggag ttcttgagat gttaacgtca 240
tgtcaagcca atcccatccc aacatctcag atgcataaat ggatgggaag ttggttaatg 300
tctgataatc atgatgccag tcaagggtat agttttttac atgaagtgga caaagaggca 360
gaaataacat ttgacgtggt ggagaccttc atccgcggct ggggcaacaa accaattgaa 420
tacatcaaaa aggaaagatg gactgactca ttcaaaattc tcgcttattt gtgtcaaaag 480
tttttggact tacacaagtt gacattaatc ttaaatgctg tctctgaggt ggaattgctc 540
aacttggcga ggactttcaa aggcaaagtc agaagaagtt ctcatggaac gaacatatgc 600
aggattaggg ttcccagctt gggtcctact tttatttcag aaggatgggc ttacttcaag 660
aaacttgata ttctaatgga ccgaaacttt ctgttaatgg tcaaagatgt gattataggg 720
aggatgcaaa cggtgctatc catggtatgt agaatagaca acctgttctc agagcaagac 780
atcttctccc ttctaaatat ctacagaatt ggagataaaa ttgtggagag gcagggaaat 840
ttttcttatg acttgattaa aatggtggaa ccgatatgca acttgaagct gatgaaatta 900
gcaagagaat caaggccttt agtcccacaa ttccctcatt ttgaaaatca tatcaagact 960
tctgttgatg aaggggcaaa aattgaccga ggtataagat tcctccatga tcagataatg 1020
agtgtgaaaa cagtggatct cacactggtg atttatggat cgttcagaca ttggggtcat 1080
ccttttatag attattacac tggactagaa aaattacatt cccaagtaac catgaagaaa 1140
gatattgatg tgtcatatgc aaaagcactt gcaagtgatt tagctcggat tgttctattt 1200
caacagttca atgatcataa aaagtggttc gtgaatggag acttgctccc tcatgatcat 1260
ccctttaaaa gtcatgttaa agaaaataca tggcccacag ctgctcaagt tcaagatttt 1320
ggagataaat ggcatgaact tccgctgatt aaatgttttg aaatacccga cttactagac 1380
ccatcgataa tatactctga caaaagtcat tcaatgaata ggtcagaggt gttgaaacat 1440
gtccgaatga atccgaacac tcctatccct agtaaaaagg tgttgcagac tatgttggac 1500
acaaaggcta ccaattggaa agaatttctt aaagagattg atgagaaggg cttagatgat 1560
gatgatctaa ttattggtct taaaggaaag gagagggaac tgaagttggc aggtagattt 1620
ttctccctaa tgtcttggaa attgcgagaa tactttgtaa ttaccgaata tttgataaag 1680
actcatttcg tccctatgtt taaaggcctg acaatggcgg acgatctaac tgcagtcatt 1740
aaaaagatgt tagattcctc atccggccaa ggattgaagt catatgaggc aatttgcata 1800
gccaatcaca ttgattacga aaaatggaat aaccaccaaa ggaagttatc aaacggccca 1860
gtgttccgag ttatgggcca gttcttaggt tatccatcct taatcgagag aactcatgaa 1920
ttttttgaga aaagtcttat atactacaat ggaagaccag acttgatgcg tgttcacaac 1980
aacacactga tcaattcaac ctcccaacga gtttgttggc aaggacaaga gggtggactg 2040
gaaggtctac ggcaaaaagg atggagtatc ctcaatctac tggttattca aagagaggct 2100
aaaatcagaa acactgctgt caaagtcttg gcacaaggtg ataatcaagt tatttgcaca 2160
cagtataaaa cgaagaaatc gagaaacgtt gtagaattac agggtgctct caatcaaatg 2220
gtttctaata atgagaaaat tatgactgca atcaaaatag ggacagggaa gttaggactt 2280
ttgataaatg acgatgagac tatgcaatct gcagattact tgaattatgg aaaaataccg 2340
attttccgtg gagtgattag agggttagag accaagagat ggtcacgagt gacttgtgtc 2400
accaatgacc aaatacccac ttgtgctaat ataatgagct cagtttccac aaatgctctc 2460
accgtagctc attttgctga gaacccaatc aatgccatga tacagtacaa ttattttggg 2520
acatttgcta gactcttgtt gatgatgcat gatcctgctc ttcgtcaatc attgtatgaa 2580
gttcaagata agataccggg cttgcacagt tctactttca aatacgccat gttgtatttg 2640
gacccttcca ttggaggagt gtcgggcatg tctttgtcca ggtttttgat tagagccttc 2700
ccagatcccg taacagaaag tctctcattc tggagattca tccatgtaca tgctcgaagt 2760
gagcatctga aggagatgag tgcagtattt ggaaaccccg agatagccaa gtttcgaata 2820
actcacatag acaagctagt agaagatcca acctctctga acatcgctat gggaatgagt 2880
ccagcgaact tgttaaagac tgaggttaaa aaatgcttaa tcgaatcaag acaaaccatc 2940
aggaaccagg tgattaagga tgcaaccata tatttgtatc atgaagagga tcggctcaga 3000
agtttcttat ggtcaataaa tcctctgttc cctagatttt taagtgaatt caaatcaggc 3060
actttttgg gagtcgcaga cgggctcatc agtctatttc aaaattctcg tactattcgg 3120
aactccttta agaaaaagta tcatagggaa ttggatgatt tgattgtgag gagtgaggta 3180
tcctctttga cacatttagg gaaacttcat ttgagaaggg gatcatgtaa aatgtggaca 3240
tgttcagcta ctcatgctga cacattaaga tacaaatcct ggggccgtac agttattggg 3300
acaactgtac cccatccatt agaaatgttg ggtccacaac atcgaaaaga gactccttgt 3360
gcaccatgta acacatcagg gttcaattat gtttctgtgc attgtccaga cgggatccat 3420
gacgtcttta gttcacgggg accattgcct gcttatctag ggtctaaaac atctgaatct 3480
acatctattt tgcagccttg ggaaagggaa agcaaagtcc cactgattaa aagagctaca 3540
cgtcttagag atgctatctc ttggtttgtt gaacccgact ctaaactagc aatgactata 3600
ctttctaaca tccactcttt aacaggcgaa gaatggacca aaaggcagca tgggttcaaa 3660
agaacagggt ctgcccttca taggttttcg acatctcgga tgagccatgg tgggttcgca 3720
tctcagagca ctgcagcatt gaccaggttg atggcaacta cagacaccat gagggatctg 3780
ggagatcaga atttcgactt tttattccaa gcaacgttgc tctatgctca aattaccacc 3840
actgttgcaa gagacggatg gatcaccagt tgtacagatc attatcatat tgcctgtaag 3900
tcctgtttga gacccataga agagatcacc ctggactcaa gtatggacta cacgccccca 3960
gatgtatccc atgtgctgaa gacatggagg aatggggaag gttcgtgggg acaagagata 4020
aaacagatct atcctttaga agggaattgg aagaatttag cacctgctga gcaatcctat 4080
caagtcggca gatgtatagg ttttctatat ggagacttgg cgtatagaaa atctactcat 4140
gccgaggaca gttctctatt tcctctatct atacaaggtc gtattagagg tcgaggtttc 4200

-continued

```
ttaaaagggt tgctagacgg attaatgaga gcaagttgct gccaagtaat acaccggaga   4260
agtctggctc atttgaagag gccggccaac gcagtgtacg gaggtttgat ttacttgatt   4320
gataaattga gtgtatcacc tccattcctt tctcttacta gatcaggacc tattagagac   4380
gaattagaaa cgattcccca caagatccca acctcctatc cgacaagcaa ccgtgatatg   4440
ggggtgattg tcagaaatta cttcaaatac caatgccgtc taattgaaaa gggaaaatac   4500
agatcacatt attcacaatt atggttattc tcagatgtct tatccataga cttcattgga   4560
ccattctcta tttccaccac cctcttgcaa atcctataca agccattttt atctgggaaa   4620
gataagaatg agttgagaga gctggcaaat ctttcttcat tgctaagatc aggagagggg   4680
tgggaagaca tacatgtgaa attcttcacc aaggacatat tattgtgtcc agaggaaatc   4740
agacatgctt gcaagttcgg gattgctaag gataataata aagacatgag ctatccccct   4800
tggggaaggg aatccagagg gacaattaca acaatccctg tttattatac gaccacccct   4860
tacccaaaga tgctagagat gcctccaaga atccaaaatc ccctgctgtc cggaatcagg   4920
ttgggccaat taccaactgg cgctcattat aaaattcgga gtatattaca tggaatggga   4980
atccattaca gggacttctt gagttgtgga gacggctccg gagggatgac tgctgcatta   5040
ctacgagaaa atgtgcatag cagaggaata ttcaatagtc tgttagaatt atcagggtca   5100
gtcatgcgag gcgcctctcc tgagcccccc agtgccctag aaactttagg aggagataaa   5160
tcgagatgtg taaatggtga aacatgttgg gaatatccat ctgacttatg tgacccaagg   5220
acttgggact atttcctccg actcaaagca ggcttggggc ttcaaattga tttaattgta   5280
atggatatgg aagttcggga ttcttctact agcctgaaaa ttgagacgaa tgttagaaat   5340
tatgtgcacc ggattttgga tgagcaagga gttttaatct acaagactta tggaacatat   5400
atttgtgaga gcgaaaagaa tgcagtaaca atccttggtc ccatgttcaa gacggtcgac   5460
ttagttcaaa cagaatttag tagttctcaa acgtctgaag tatatatggt atgtaaaggt   5520
ttgaagaaat taatcgatga acccaatccc gattggtctt ccatcaatga atcctggaaa   5580
aacctgtacg cattccagtc atcagaacag gaatttgcca gagcaaagaa ggttagtaca   5640
tactttacct tgacaggtat tccctcccaa ttcattcctg atccttttgt aaacattgag   5700
actatgctac aaatattcgg agtacccacg ggtgtgtctc atgcggctgc cttaaaatca   5760
tctgatagac ctgcagattt attgaccatt agcctttttt atatggcgat tatatcgtat   5820
tataacatca atcatatcag agtaggaccg atacctccga accccccatc agatggaatt   5880
gcacaaaatg tggggatcgc tataactggt ataagctttt ggctgagttt gatggagaaa   5940
gacattccac tatatcaaca gtgtttagca gttatccagc aatcattccc gattaggtgg   6000
gaggctgttt cagtaaaagg aggatacaag cagaagtgga gtactagagg tgatgggctc   6060
ccaaaagata cccgaatttc agactccttg gccccaatcg ggaactggat cagatctctg   6120
gaattggtcc gaaaccaagt tcgtctaaat ccattcaatg agatcttgtt caatcagcta   6180
tgtcgtacag tggataatca tttgaaatgg tcaaatttgc gaagaaacac aggaatgatt   6240
gaatggatca atagacgaat ttcaaaagaa gaccggtcta tactgatgtt gaagagtgac   6300
ctacacgagg aaaactcttg gagagat                                       6327
```

<210> SEQ ID NO 3
<211> LENGTH: 1512
<212> TYPE: DNA
<213> ORGANISM: Artificial Sequence
<220> FEATURE:
<223> OTHER INFORMATION: P-protein with protease insert

<400> SEQUENCE: 3
atggataatc tcacaaaagt tcgtgagtat ctcaagtcct attctcgtct ggatcaggcg 60
gtaggagaga tagatgagat cgaagcacaa cgagctgaaa agtccaatta tgagttgttc 120
caagaggatg gagtggaaga gcatactaag ccctcttatt ttcaggcagc agatgattct 180
gacacagaat ctgaaccaga aattgaagac aatcaaggct tgtatgcacc agatccagaa 240
gctgagcaag ttgaaggctt tatacagggg cctttagatg actatgcaga tgaggaagtg 300
gatgttgtat ttacttcgga ctggaaacag cctgagcttg aatctgacga gcatggaaag 360
accttacggt tgacattgcc agagggttta agtggagagc agaaatccca gtggctttcg 420
acgattaaag cagtcgtgca aagtgccaaa tactggaatc tggcagagtg cacatttgaa 480
gcatcgggag aaggggtcat tatgaaggag cgccagataa ctccggatgt atataaggtc 540
actccagtga tgaacacaca tccgtcccaa tcagaagcag tatcagatgg cggaagcggc 600
ggagggagcg ggggcgggag cggagtgtcc tttaacttcc ctcaagtgac cctgtggcag 660
cggcctctgg ttacaatcaa gatcggcgga cagctgaaag aggccctgct ggatacaggc 720
gctgacgata cagtgctgga agagatgtct ctgcccggca gatggaagcc caaaatgatc 780
ggaggaatcg gcggcttcat caaagtgcgg cagtacgacc agatcctgat cgagatctgc 840
gggcacaagg ccatcggaac agtgctcgtg ggccctacac ctgtgaacat catcggcaga 900
aatctgctga cccagatcgg ctgcaccctg aactttgctg gtgctattgg aggggcccca 960
caagttacac tgtggcaaag acccctcgtg accatcaaga ttggaggcca actcaaagaa 1020
gctctgctgg acactggggc cgatgacacc gtgcttgaag aaatgagcct gcctggccgg 1080
tggaaaccta agatgattgg cggcattgga ggttttatca aagtccgcca gtatgatcaa 1140
attctcatcg aaatctgtgg ccataaggct attggcaccg tgctcgtcgg acccactcca 1200
gttaatatca tcggacggaa cctgctcaca cagatcgggt gtacactgaa tttccccatc 1260
tcccccatcg gagggtccgg aggcggctca ggcggtggat ccggcgtttg gtctctctca 1320
aagacatcca tgactttcca acccaagaaa gcaagtcttc agcctctcac catatccttg 1380
gatgaattgt tctcatctag aggagagttc atctctgtcg gaggtgacgg acgaatgtct 1440
cataaagagg ccatcctgct cggcctgaga tacaaaaagt tgtacaatca ggcgagagtc 1500
aaatattctc tg 1512

<210> SEQ ID NO 4
<211> LENGTH: 717
<212> TYPE: DNA
<213> ORGANISM: Artificial Sequence
<220> FEATURE:
<223> OTHER INFORMATION: protease dimer with cut and linker

<400> SEQUENCE: 4
ggcggaagcg gcggagggag cgggggcggg agcggagtgt cctttaactt ccctcaagtg 60
accctgtggc agcggcctct ggttacaatc aagatcggcg gacagctgaa agaggccctg 120
ctggatacag gcgctgacga tacagtgctg gaagagatgt ctctgcccgg cagatggaag 180
cccaaaatga tcggaggaat cggcggcttc atcaaagtgc ggcagtacga ccagatcctg 240
atcgagatct gcgggcacaa ggccatcgga acagtgctcg tgggccctac acctgtgaac 300
atcatcggca gaaatctgct gacccagatc ggctgcaccc tgaactttgc tggtgctatt 360
ggaggggccc cacaagttac actgtggcaa agacccctcg tgaccatcaa gattggaggc 420

```
caactcaaag aagctctgct ggacactggg gccgatgaca ccgtgcttga agaaatgagc    480

ctgcctggcc ggtggaaacc taagatgatt ggcggcattg gaggttttat caaagtccgc    540

cagtatgatc aaattctcat cgaaatctgt ggccataagg ctattggcac cgtgctcgtc    600

ggacccactc cagttaatat catcggacgg aacctgctca cacagatcgg gtgtacactg    660

aatttcccca tctcccccat cggagggtcc ggaggcggct caggcggtgg atccggc       717
```

<210> SEQ ID NO 5
<211> LENGTH: 615
<212> TYPE: DNA
<213> ORGANISM: Artificial Sequence
<220> FEATURE:
<223> OTHER INFORMATION: single chain HIV protease dimer

<400> SEQUENCE: 5

```
cctcaagtga ccctgtggca gcggcctctg gttacaatca agatcggcgg acagctgaaa     60

gaggccctgc tggatacagg cgctgacgat acagtgctgg aagagatgtc tctgcccggc    120

agatggaagc ccaaaatgat cggaggaatc ggcggcttca tcaaagtgcg gcagtacgac    180

cagatcctga tcgagatctg cgggcacaag gccatcggaa cagtgctcgt gggccctaca    240

cctgtgaaca tcatcggcag aaatctgctg acccagatcg gctgcaccct gaactttgct    300

ggtgctattg gaggggcccc acaagttaca ctgtggcaaa gacccctcgt gaccatcaag    360

attggaggcc aactcaaaga agctctgctg gacactgggg ccgatgacac cgtgcttgaa    420

gaaatgagcc tgcctggccg gtggaaacct aagatgattg gcggcattgg aggttttatc    480

aaagtccgcc agtatgatca aattctcatc gaaatctgtg gccataaggc tattggcacc    540

gtgctcgtcg gacccactcc agttaatatc atcggacgga acctgctcac acagatcggg    600

tgtacactga atttc                                                     615
```

<210> SEQ ID NO 6
<211> LENGTH: 15
<212> TYPE: DNA
<213> ORGANISM: Artificial Sequence
<220> FEATURE:
<223> OTHER INFORMATION: HIV protease cleavage site 1 (cut1)

<400> SEQUENCE: 6

```
gtgtccttta acttc                                                      15
```

<210> SEQ ID NO 7
<211> LENGTH: 15
<212> TYPE: DNA
<213> ORGANISM: Artificial Sequence
<220> FEATURE:
<223> OTHER INFORMATION: HIV protease cleavage site 2 (cut2)

<400> SEQUENCE: 7

```
cccatctccc ccatc                                                      15
```

<210> SEQ ID NO 8
<211> LENGTH: 36
<212> TYPE: DNA
<213> ORGANISM: Artificial Sequence
<220> FEATURE:
<223> OTHER INFORMATION: GGSG linker 1

<400> SEQUENCE: 8

```
ggcggaagcg gcggagggag cgggggcggg agcgga                               36
```

```
<210> SEQ ID NO 9
<211> LENGTH: 36
<212> TYPE: DNA
<213> ORGANISM: Artificial Sequence
<220> FEATURE:
<223> OTHER INFORMATION: GGSG linker 2

<400> SEQUENCE: 9

ggagggtccg gaggcggctc aggcggtgga tccggc                              36


<210> SEQ ID NO 10
<211> LENGTH: 7047
<212> TYPE: DNA
<213> ORGANISM: Artificial Sequence
<220> FEATURE:
<223> OTHER INFORMATION: L-protein with protease insert

<400> SEQUENCE: 10

atggaagtcc acgattttga gaccgacgag ttcaatgatt tcaatgaaga tgactatgcc     60

acaagagaat tcctgaatcc cgatgagcgc atgacgtact tgaatcatgc tgattacaac    120

ctgaattctc ctctaattag tgatgatatt gacaatttaa tcaggaaatt caattctctt    180

ccaattccct cgatgtggga tagtaagaac tgggatggag ttcttgagat gttaacgtca    240

tgtcaagcca atcccatccc aacatctcag atgcataaat ggatgggaag ttggttaatg    300

tctgataatc atgatgccag tcaagggtat agtttttttac atgaagtgga caaagaggca    360

gaaataacat ttgacgtggt ggagaccttc atccgcggct ggggcaacaa accaattgaa    420

tacatcaaaa aggaaagatg gactgactca ttcaaaattc tcgcttattt gtgtcaaaag    480

tttttggact tacacaagtt gacattaatc ttaaatgctg tctctgaggt ggaattgctc    540

aacttggcga ggactttcaa aggcaaagtc agaagaagtt ctcatggaac gaacatatgc    600

aggattaggg ttcccagctt gggtcctact tttatttcag aaggatgggc ttacttcaag    660

aaacttgata ttctaatgga ccgaaacttt ctgttaatgg tcaaagatgt gattataggg    720

aggatgcaaa cggtgctatc catggtatgt agaatagaca acctgttctc agagcaagac    780

atcttctccc ttctaaatat ctacagaatt ggagataaaa ttgtggagag gcagggaaat    840

ttttcttatg acttgattaa aatggtggaa ccgatatgca acttgaagct gatgaaatta    900

gcaagagaat caaggccttt agtcccacaa ttccctcatt ttgaaaatca tatcaagact    960

tctgttgatg aaggggcaaa aattgaccga ggtataagat tcctccatga tcagataatg   1020

agtgtgaaaa cagtggatct cacactggtg atttatggat cgttcagaca ttggggtcat   1080

ccttttatag attattacac tggactagaa aaattacatt cccaagtaac catgaagaaa   1140

gatattgatg tgtcatatgc aaaagcactt gcaagtgatt tagctcggat tgttctattt   1200

caacagttca atgatcataa aaagtggttc gtgaatggag acttgctccc tcatgatcat   1260

ccctttaaaa gtcatgttaa agaaaataca tggcccacag ctgctcaagt tcaagatttt   1320

ggagataaat ggcatgaact tccgctgatt aaatgttttg aaatacccga cttactagac   1380

ccatcgataa tatactctga caaaagtcat tcaatgaata ggtcagaggt gttgaaacat   1440

gtccgaatga atccgaacac tcctatccct agtaaaaagg tgttgcagac tatgttggac   1500

acaaaggcta ccaattggaa agaatttctt aaagagattg atgagaaggg cttagatgat   1560

gatgatctaa ttattggtct taaaggaaag gagagggaac tgaagttggc aggtagattt   1620

ttctccctaa tgtcttggaa attgcgagaa tactttgtaa ttaccgaata tttgataaag   1680

actcatttcg tccctatgtt taaaggcctg acaatggcgg acgatctaac tgcagtcatt   1740
```

aaaaagatgt tagattcctc atccggccaa ggattgaagt catatgaggc aatttgcata 1800
gccaatcaca ttgattacga aaaatggaat aaccaccaaa ggaagttatc aaacggccca 1860
gtgttccgag ttatgggcca gttcttaggt tatccatcct taatcgagag aactcatgaa 1920
ttttttgaga aaagtcttat atactacaat ggaagaccag acttgatgcg tgttcacaac 1980
aacacactga tcaattcaac ctcccaacga gtttgttggc aaggacaaga gggtggactg 2040
gaaggtctac ggcaaaaagg atggagtatc ctcaatctac tggttattca aagagaggct 2100
aaaatcagaa acactgctgt caaagtcttg gcacaaggtg ataatcaagt tatttgcaca 2160
cagtataaaa cgaagaaatc gagaaacgtt gtagaattac agggtgctct caatcaaatg 2220
gtttctaata atgagaaaat tatgactgca atcaaaatag ggacagggaa gttaggactt 2280
ttgataaatg acgatgagac tatgcaatct gcagattact tgaattatgg aaaaataccg 2340
attttccgtg gagtgattag agggttagag accaagagat ggtcacgagt gacttgtgtc 2400
accaatgacc aaatacccac ttgtgctaat ataatgagct cagtttccac aaatgctctc 2460
accgtagctc attttgctga gaacccaatc aatgccatga tacagtacaa ttattttggg 2520
acatttgcta gactcttgtt gatgatgcat gatcctgctc ttcgtcaatc attgtatgaa 2580
gttcaagata agataccggg cttgcacagt tctactttca aatacgccat gttgtatttg 2640
gacccttcca ttggaggagt gtcgggcatg tctttgtcca ggtttttgat tagagccttc 2700
ccagatcccg taacagaaag tctctcattc tggagattca tccatgtaca tgctcgaagt 2760
gagcatctga aggagatgag tgcagtattt ggaaaccccg agatagccaa gtttcgaata 2820
actcacatag acaagctagt agaagatcca acctctctga acatcgctat gggaatgagt 2880
ccagcgaact tgttaaagac tgaggttaaa aaatgcttaa tcgaatcaag acaaaccatc 2940
aggaaccagg tgattaagga tgcaaccata tatttgtatc atgaagagga tcggctcaga 3000
agtttcttat ggtcaataaa tcctctgttc cctagatttt taagtgaatt caaatcaggc 3060
acttttttgg gagtcgcaga cgggctcatc agtctatttc aaaattctcg tactattcgg 3120
aactccttta agaaaaagta tcatagggaa ttggatgatt tgattgtgag gagtgaggta 3180
tcctctttga cacatttagg gaaacttcat ttgagaaggg gatcatgtaa aatgtggaca 3240
tgttcagcta ctcatgctga cacattaaga tacaaatcct ggggccgtac agttattggg 3300
acaactgtac cccatccatt agaaatgttg ggtccacaac atcgaaaaga gactccttgt 3360
gcaccatgta acacatcagg gttcaattat gtttctgtgc attgtccaga cgggatccat 3420
gacgtcttta gttcacgggg accattgcct gcttatctag ggtctaaaac atctgaatct 3480
acatctattt tgcagccttg ggaaagggaa agcaaagtcc cactgattaa aagagctaca 3540
cgtcttagag atgctatctc ttggtttgtt gaacccgact ctaaactagc aatgactata 3600
ctttctaaca tccactcttt aacaggcgaa gaatggacca aaaggcagca tgggttcaaa 3660
agaacagggt ctgcccttca taggttttcg acatctcgga tgagccatgg tgggttcgca 3720
tctcagagca ctgcagcatt gaccaggttg atggcaacta cagacaccat gagggatctg 3780
ggagatcaga atttcgactt tttattccaa gcaacgttgc tctatgctca aattaccacc 3840
actgttgcaa gagacggatg gatcaccagt tgtacagatc attatcatat tgcctgtaag 3900
tcctgtttga gacccataga agagatcacc ctggactcaa gtatggacta cacgcccccca 3960
gatgtatccc atgtgctgaa gacatggagg aatggggaag gttcgtgggg acaagagata 4020
aaacagatct atcctttaga agggaattgg aagaatttag cacctgctga gcaatcctat 4080
caagtcggca gatgtatagg ttttctatat ggagacttgg cgtatagaaa atctactcat 4140
gccgaggaca gttctctatt tcctctatct atacaaggtc gtattagagg tcgaggtttc 4200
ttaaaagggt tgctagacgg attaatgaga gcaagttgct gccaagtaat acaccggaga 4260
agtctggctc atttgaagag gccggccaac gcagtgtacg gaggtttgat ttacttgatt 4320
gataaattga gtgtatcacc tccattcctt tctcttacta gatcaggacc tattagagac 4380
gaattagaaa cgattcccca caagatccca acctcctatc cgacaagcaa ccgtgatatg 4440
ggggtgattg tcagaaatta cttcaaatac caatgccgtc taattgaaaa gggaaaatac 4500
agatcacatt attcacaatt atggttattc tcagatgtct tatccataga cttcattgga 4560
ccattctcta tttccaccac cctcttgcaa atcctataca agccattttt atctgggaaa 4620
gataagaatg agttgagaga gctggcaaat ctttcttcat tgctaagatc aggagagggg 4680
tgggaagaca tacatgtgaa attcttcacc aaggacatat tattgtgtcc agaggaaatc 4740
agacatgctt gcaagttcgg gattgctaag gataataata aagacatgag ctatccccct 4800
tggggaaggg aatccagagg gacaattaca acaatccctg tttattatac gaccacccct 4860
ggcggaagcg gcggagggag cgggggcggg agcggagtgt cctttaactt ccctcaagtg 4920
accctgtggc agcggcctct ggttacaatc aagatcggcg gacagctgaa agaggccctg 4980
ctggatacag gcgctgacga tacagtgctg gaagagatgt ctctgcccgg cagatggaag 5040
cccaaaatga tcggaggaat cggcggcttc atcaaagtgc ggcagtacga ccagatcctg 5100
atcgagatct gcgggcacaa ggccatcgga acagtgctcg tgggccctac acctgtgaac 5160
atcatcggca gaaatctgct gacccagatc ggctgcaccc tgaactttgc tggtgctatt 5220
ggaggggccc cacaagttac actgtggcaa agacccctcg tgaccatcaa gattggaggc 5280
caactcaaag aagctctgct ggacactggg gccgatgaca ccgtgcttga agaaatgagc 5340
ctgcctggcc ggtggaaacc taagatgatt ggcggcattg gaggttttat caaagtccgc 5400
cagtatgatc aaattctcat cgaaatctgt ggccataagg ctattggcac cgtgctcgtc 5460
ggacccactc cagttaatat catcggacgg aacctgctca cacagatcgg gtgtacactg 5520
aatttcccca tctcccccat cggagggtcc ggaggcggct caggcggtgg atccggctac 5580
ccaaagatgc tagagatgcc tccaagaatc caaaatcccc tgctgtccgg actcaggttg 5640
ggccaattac caactggcgc tcattataaa attcggagta tattacatgg aatgggaatc 5700
cattacaggg acttcttgag ttgtggagac ggctccggag ggatgactgc tgcattacta 5760
cgagaaaatg tgcatagcag aggaatattc aatagtctgt tagaattatc agggtcagtc 5820
atgcgaggcg cctctcctga gccccccagt gccctagaaa ctttaggagg agataaatcg 5880
agatgtgtaa atggtgaaac atgttgggaa tatccatctg acttatgtga cccaaggact 5940
tgggactatt tcctccgact caaagcaggc ttggggcttc aaattgattt aattgtaatg 6000
gatatggaag ttcgggattc ttctactagc ctgaaaattg agacgaatgt tagaaattat 6060
gtgcaccgga ttttggatga gcaaggagtt ttaatctaca agacttatgg aacatatatt 6120
tgtgagagcg aaaagaatgc agtaacaatc cttggtccca tgttcaagac ggtcgactta 6180
gttcaaacag aatttagtag ttctcaaacg tctgaagtat atatggtatg taaaggtttg 6240
aagaaattaa tcgatgaacc caatcccgat tggtcttcca tcaatgaatc ctggaaaaac 6300
ctgtacgcat tccagtcatc agaacaggaa tttgccagag caaagaaggt tagtacatac 6360
tttaccttga caggtattcc ctcccaattc gttcctgatc cttttgtaaa cattgagact 6420
atgctacaaa tattcggagt acccacgggt gtgtctcatg cggctgcctt aaaatcatct 6480
gatagacctg cagatttatt gaccattagc ctttttttata tggcgattat atcgtattat 6540
aacatcaatc atatcagagt aggaccgata cctccgaacc ccccatcaga tggaattgca 6600
caaaatgtgg ggatcgctat aactggtata agcttttggc tgagtttgat ggaggaagac 6660
attccactat atcaacagtg tttagcagtt atccagcaat cattcccgat taggtgggag 6720
gctgtttcag taaaaggagg atacaagcag aagtggagta ctagaggtga tgggctccca 6780
aaagataccc gaatttcaga ctccttggcc ccaatcggga actggatcag atctctggaa 6840
ttggtccgaa accaagttcg tctaaatcca ttcaatgaga tcttgttcaa tcagctatgt 6900
cgtacagtgg ataatcattt gaaatggtca aatttgcgaa gaaacacagg aatgattgaa 6960
tggatcaata gacgaatttc aaaagaagac cggtctatac tgatgttgaa gagtgaccta 7020
cacgaggaaa actcttggag agattaa 7047

<210> SEQ ID NO 11
<211> LENGTH: 780
<212> TYPE: DNA
<213> ORGANISM: Artificial Sequence
<220> FEATURE:
<223> OTHER INFORMATION: mCherry with linker

<400> SEQUENCE: 11
ggcggaagcg gcggagggag cgggggcggg agcggaatgg tgagcaaggg cgaggaggat 60
aacatggcca tcatcaagga gttcatgcgc ttcaaggtgc acatggaggg ctccgtgaac 120
ggccacgagt tcgagatcga gggcgagggc gagggccgcc cctacgaggg cacccagacc 180
gccaagctga aggtgaccaa gggtggcccc ctgcccttcg cctgggacat cctgtcccct 240
cagttcatgt acggctccaa ggcctacgtg aagcaccccg ccgacatccc cgactacttg 300
aagctgtcct tccccgaggg cttcaagtgg gagcgcgtga tgaacttcga ggacggcggc 360
gtggtgaccg tgacccagga ctcctccctg caggacggcg agttcatcta caaggtgaag 420
ctgcgcggca ccaacttccc ctccgacggc cccgtaatgc agaagaagac catgggctgg 480
gaggcctcct ccgagcggat gtaccccgag gacggcgccc tgaagggcga gatcaagcag 540
aggctgaagc tgaaggacgg cggccactac gacgctgagg tcaagaccac ctacaaggcc 600
aagaagcccg tgcagctgcc cggcgcctac aacgtcaaca tcaagttgga catcacctcc 660
cacaacgagg actacaccat cgtggaacag tacgaacgcg ccgagggccg ccactccacc 720
ggcggcatgg acgagctgta caagggaggg tccggaggcg gctcaggcgg tggatccggc 780

<210> SEQ ID NO 12
<211> LENGTH: 780
<212> TYPE: DNA
<213> ORGANISM: Artificial Sequence
<220> FEATURE:
<223> OTHER INFORMATION: mWasabi with linker

<400> SEQUENCE: 12
ggcggaagcg gcggagggag cgggggcggg agcggaatgg tgagcaaggg cgaggagacc 60
acaatgggcg taatcaagcc cgacatgaag atcaagctga agatggaggg caacgtgaat 120
ggccacgcct tcgtgatcga gggcgagggc gagggcaagc cctacgacgg caccaacacc 180
atcaacctgg aggtgaagga gggagccccc ctgcccttct cctacgacat tctgaccacc 240
gcgttcagtt acggcaacag ggccttcacc aagtaccccg acgacatccc caactacttc 300
aagcagtcct tccccgaggg ctactcttgg gagcgcacca tgaccttcga ggacaagggc 360
atcgtgaagg tgaagtccga catctccatg gaggaggact ccttcatcta cgagatacac 420

```
ctcaagggcg agaacttccc ccccaacggc cccgtgatgc agaaggagac caccggctgg    480

gacgcctcca ccgagaggat gtacgtgcgc gacggcgtgc tgaagggcga cgtcaagatg    540

aagctgctgc tggagggcgg cggccaccac cgcgttgact tcaagaccat ctacagggcc    600

aagaaggcgg tgaagctgcc cgactatcac tttgtggacc accgcatcga gatcctgaac    660

cacgacaagg actacaacaa ggtgaccgtt tacgagatcg ccgtggcccg caactccacc    720

gacggcatgg acgagctgta caagggaggg tccggaggcg gctcaggcgg tggatccggc    780
```

```
<210> SEQ ID NO 13
<211> LENGTH: 7107
<212> TYPE: DNA
<213> ORGANISM: Artificial Sequence
<220> FEATURE:
<223> OTHER INFORMATION: L-protein with mCherry insert

<400> SEQUENCE: 13
```

```
atggaagtcc acgattttga gaccgacgag ttcaatgatt tcaatgaaga tgactatgcc     60

acaagagaat tcctgaatcc cgatgagcgc atgacgtact tgaatcatgc tgattacaac    120

ctgaattctc ctctaattag tgatgatatt gacaatttaa tcaggaaatt caattctctt    180

ccaattccct cgatgtggga tagtaagaac tgggatggag ttcttgagat gttaacgtca    240

tgtcaagcca atcccatccc aacatctcag atgcataaat ggatgggaag ttggttaatg    300

tctgataatc atgatgccag tcaagggtat agtttttttac atgaagtgga caaagaggca    360

gaaataacat ttgacgtggt ggagaccttc atccgcggct ggggcaacaa accaattgaa    420

tacatcaaaa aggaaagatg gactgactca ttcaaaattc tcgcttattt gtgtcaaaag    480

tttttggact tacacaagtt gacattaatc ttaaatgctg tctctgaggt ggaattgctc    540

aacttggcga ggactttcaa aggcaaagtc agaagaagtt ctcatggaac gaacatatgc    600

aggattaggg ttcccagctt gggtcctact tttatttcag aaggatgggc ttacttcaag    660

aaacttgata ttctaatgga ccgaaacttt ctgttaatgg tcaaagatgt gattataggg    720

aggatgcaaa cggtgctatc catggtatgt agaatagaca acctgttctc agagcaagac    780

atcttctccc ttctaaatat ctacagaatt ggagataaaa ttgtggagag gcagggaaat    840

ttttcttatg acttgattaa aatggtggaa ccgatatgca acttgaagct gatgaaatta    900

gcaagagaat caaggccttt agtcccacaa ttccctcatt ttgaaaatca tatcaagact    960

tctgttgatg aaggggcaaa aattgaccga ggtataagat tcctccatga tcagataatg   1020

agtgtgaaaa cagtggatct cacactggtg atttatggat cgttcagaca ttggggtcat   1080

ccttttatag attattacac tggactagaa aaattacatt cccaagtaac catgaagaaa   1140

gatattgatg tgtcatatgc aaaagcactt gcaagtgatt tagctcggat tgttctattt   1200

caacagttca atgatcataa aaagtggttc gtgaatggag acttgctccc tcatgatcat   1260

ccctttaaaa gtcatgttaa agaaaataca tggcccacag ctgctcaagt tcaagatttt   1320

ggagataaat ggcatgaact tccgctgatt aaatgttttg aaatacccga cttactagac   1380

ccatcgataa tatactctga caaaagtcat tcaatgaata ggtcagaggt gttgaaacat   1440

gtccgaatga atccgaacac tcctatccct agtaaaaagg tgttgcagac tatgttggac   1500

acaaaggcta ccaattggaa agaatttctt aaagagattg atgagaaggg cttagatgat   1560

gatgatctaa ttattggtct taaaggaaag gagagggaac tgaagttggc aggtagattt   1620

ttctccctaa tgtcttggaa attgcgagaa tactttgtaa ttaccgaata tttgataaag   1680
```

-continued

```
actcatttcg tccctatgtt taaaggcctg acaatggcgg acgatctaac tgcagtcatt   1740
aaaaagatgt tagattcctc atccggccaa ggattgaagt catatgaggc aatttgcata   1800
gccaatcaca ttgattacga aaaatggaat aaccaccaaa ggaagttatc aaacggccca   1860
gtgttccgag ttatgggcca gttcttaggt tatccatcct taatcgagag aactcatgaa   1920
ttttttgaga aaagtcttat atactacaat ggaagaccag acttgatgcg tgttcacaac   1980
aacacactga tcaattcaac ctcccaacga gtttgttggc aaggacaaga gggtggactg   2040
gaaggtctac ggcaaaaagg atggagtatc ctcaatctac tggttattca aagagaggct   2100
aaaatcagaa acactgctgt caaagtcttg gcacaaggtg ataatcaagt tatttgcaca   2160
cagtataaaa cgaagaaatc gagaaacgtt gtagaattac agggtgctct caatcaaatg   2220
gtttctaata atgagaaaat tatgactgca atcaaaatag ggacagggaa gttaggactt   2280
ttgataaatg acgatgagac tatgcaatct gcagattact tgaattatgg aaaaataccg   2340
attttccgtg gagtgattag agggttagag accaagagat ggtcacgagt gacttgtgtc   2400
accaatgacc aaatacccac ttgtgctaat ataatgagct cagtttccac aaatgctctc   2460
accgtagctc attttgctga gaacccaatc aatgccatga tacagtacaa ttattttggg   2520
acatttgcta gactcttgtt gatgatgcat gatcctgctc ttcgtcaatc attgtatgaa   2580
gttcaagata agataccggg cttgcacagt tctactttca aatacgccat gttgtatttg   2640
gacccttcca ttggaggagt gtcgggcatg tctttgtcca ggtttttgat tagagccttc   2700
ccagatcccg taacagaaag tctctcattc tggagattca tccatgtaca tgctcgaagt   2760
gagcatctga aggagatgag tgcagtattt ggaaaccccg agatagccaa gtttcgaata   2820
actcacatag acaagctagt agaagatcca acctctctga acatcgctat gggaatgagt   2880
ccagcgaact tgttaaagac tgaggttaaa aaatgcttaa tcgaatcaag acaaaccatc   2940
aggaaccagg tgattaagga tgcaaccata tatttgtatc atgaagagga tcggctcaga   3000
agtttcttat ggtcaataaa tcctctgttc cctagatttt taagtgaatt caaatcaggc   3060
actttttggg gagtcgcaga cgggctcatc agtctatttc aaaattctcg tactattcgg   3120
aactccttta agaaaaagta tcatagggaa ttggatgatt tgattgtgag gagtgaggta   3180
tcctctttga cacatttagg gaaacttcat ttgagaaggg gatcatgtaa aatgtggaca   3240
tgttcagcta ctcatgctga cacattaaga tacaaatcct ggggccgtac agttattggg   3300
acaactgtac cccatccatt agaaatgttg ggtccacaac atcgaaaaga gactccttgt   3360
gcaccatgta acacatcagg gttcaattat gtttctgtgc attgtccaga cgggatccat   3420
gacgtcttta gttcacgggg accattgcct gcttatctag ggtctaaaac atctgaatct   3480
acatctattt tgcagccttg ggaaagggaa agcaaagtcc cactgattaa aagagctaca   3540
cgtcttagag atgctatctc ttggtttgtt gaacccgact ctaaactagc aatgactata   3600
ctttctaaca tccactcttt aacaggcgaa gaatggacca aaaggcagca tgggttcaaa   3660
agaacagggt ctgcccttca taggttttcg acatctcgga tgagccatgg tgggttcgca   3720
tctcagagca ctgcagcatt gaccaggttg atggcaacta cagacaccat gagggatctg   3780
ggagatcaga atttcgactt tttattccaa gcaacgttgc tctatgctca aattaccacc   3840
actgttgcaa gagacggatg gatcaccagt tgtacagatc attatcatat tgcctgtaag   3900
tcctgtttga gacccataga agagatcacc ctggactcaa gtatggacta cacgccccca   3960
gatgtatccc atgtgctgaa gacatggagg aatggggaag gttcgtgggg acaagagata   4020
aaacagatct atcctttaga agggaattgg aagaatttag cacctgctga gcaatcctat   4080
```

caagtcggca gatgtatagg ttttctatat ggagacttgg cgtatagaaa atctactcat 4140
gccgaggaca gttctctatt tcctctatct atacaaggtc gtattagagg tcgaggtttc 4200
ttaaaagggt tgctagacgg attaatgaga gcaagttgct gccaagtaat acaccggaga 4260
agtctggctc atttgaagag gccggccaac gcagtgtacg gaggtttgat ttacttgatt 4320
gataaattga gtgtatcacc tccattcctt tctcttacta gatcaggacc tattagagac 4380
gaattagaaa cgattcccca caagatccca acctcctatc cgacaagcaa ccgtgatatg 4440
ggggtgattg tcagaaatta cttcaaatac caatgccgtc taattgaaaa gggaaaatac 4500
agatcacatt attcacaatt atggttattc tcagatgtct tatccataga cttcattgga 4560
ccattctcta tttccaccac cctcttgcaa atcctataca agccattttt atctgggaaa 4620
gataagaatg agttgagaga gctggcaaat ctttcttcat tgctaagatc aggagagggg 4680
tgggaagaca tacatgtgaa attcttcacc aaggacatat tattgtgtcc agaggaaatc 4740
agacatgctt gcaagttcgg gattgctaag gataataata aagacatgag ctatcccccct 4800
tggggaaggg aatccagagg gacaattaca acaatccctg tttattatac gaccacccct 4860
ggcggaagcg gcggagggag cgggggcggg agcggaatgg tgagcaaggg cgaggaggat 4920
aacatggcca tcatcaagga gttcatgcgc ttcaaggtgc acatggaggg ctccgtgaac 4980
ggccacgagt tcgagatcga gggcgagggc gagggccgcc cctacgaggg cacccagacc 5040
gccaagctga aggtgaccaa gggtggcccc ctgcccttcg cctgggacat cctgtcccct 5100
cagttcatgt acggctccaa ggcctacgtg aagcaccccg ccgacatccc cgactacttg 5160
aagctgtcct tccccgaggg cttcaagtgg gagcgcgtga tgaacttcga ggacggcggc 5220
gtggtgaccg tgacccagga ctcctccctg caggacggcg agttcatcta caaggtgaag 5280
ctgcgcggca ccaacttccc ctccgacggc cccgtaatgc agaagaagac catgggctgg 5340
gaggcctcct ccgagcggat gtaccccgag gacggcgccc tgaagggcga gatcaagcag 5400
aggctgaagc tgaaggacgg cggccactac gacgctgagg tcaagaccac ctacaaggcc 5460
aagaagcccg tgcagctgcc cggcgcctac aacgtcaaca tcaagttgga catcacctcc 5520
cacaacgagg actacaccat cgtggaacag tacgaacgcg ccgagggccg ccactccacc 5580
ggcggcatgg acgagctgta caagggaggg tccggaggcg gctcaggcgg tggatccggc 5640
tacccaaaga tgctagagat gcctccaaga atccaaaatc ccctgctgtc cggaatcagg 5700
ttgggccaat taccaactgg cgctcattat aaaattcgga gtatattaca tggaatggga 5760
atccattaca gggacttctt gagttgtgga gacggctccg gagggatgac tgctgcatta 5820
ctacgagaaa atgtgcatag cagaggaata ttcaatagtc tgttagaatt atcagggtca 5880
gtcatgcgag gcgcctctcc tgagcccccc agtgccctag aaactttagg aggagataaa 5940
tcgagatgtg taaatggtga aacatgttgg gaatatccat ctgacttatg tgacccaagg 6000
acttgggact atttcctccg actcaaagca ggcttggggc ttcaaattga tttaattgta 6060
atggatatgg aagttcggga ttcttctact agcctgaaaa ttgagacgaa tgttagaaat 6120
tatgtgcacc ggattttgga tgagcaagga gttttaatct acaagactta tggaacatat 6180
atttgtgaga gcgaaaagaa tgcagtaaca atccttggtc ccatgttcaa gacggtcgac 6240
ttagttcaaa cagaatttag tagttctcaa acgtctgaag tatatatggt aggtaaaggt 6300
ttgaagaaat taatcgatgc acccaatccc gattggtctt ccatcaatga atcctggaaa 6360
aacctgtacg cattccagtc atcagaacag gaatttgcca gagcaaagaa ggttagtaca 6420
tactttacct tgacaggtat tccctcccaa ttcattcctg atccttttgt aaacattgag 6480
actatgctac aaatattcgg agtacccacg ggtgtgtctc atgcggctgc cttaaaatca 6540
tctgatagac ctgcagattt attgaccatt agccttttt atatggcgat tatatcgtat 6600
tataacatca atcatatcag agtaggaccg atacctccga accccccatc agatggaatt 6660
gcacaaaatg tggggatcgc tataactggt ataagctttt ggctgagttt gatggagaaa 6720
gacattccac tatatcaaca gtgtttagca gttatccagc aatcattccc gattaggtgg 6780
gaggctgttt cagtaaaagg aggatacaag cagaagtgga gtactagagg tgatgggctc 6840
ccaaaagata cccgaatttc agactccttg gccccaatcg ggaactggat cagatctctg 6900
gaattggtcc gaaaccaagt tcgtctaaat ccattcaatg agatcttgtt caatcagcta 6960
tgtcgtacag tggataatca tttgaaatgg tcaaatttgc gaagaaacac aggaatgatt 7020
gaatggatca atagacgaat ttcaaaagaa gaccggtcta tactgatgtt gaagagtgac 7080
ctacacgagg aaaactcttg gagagat 7107

<210> SEQ ID NO 14
<211> LENGTH: 7107
<212> TYPE: DNA
<213> ORGANISM: Artificial Sequence
<220> FEATURE:
<223> OTHER INFORMATION: L-protein with mCherry insert (P-mWasabi-L-mCherry)

<400> SEQUENCE: 14
atggaagtcc acgattttga gaccgacgag ttcaatgatt tcaatgaaga tgactatgcc 60
acaagagaat tcctgaatcc cgatgagcgc atgacgtact tgaatcatgc tgattacaac 120
ctgaattctc ctctaattag tgatgatatt gacaatttaa tcaggaaatt caattctctt 180
ccaattccct cgatgtggga tagtaagaac tgggatggag ttcttgagat gttaacgtca 240
tgtcaagcca atcccatccc aacatctcag atgcataaat ggatgggaag ttggttaatg 300
tctgataatc atgatgccag tcaagggtat agtttttttac atgaagtgga caaagaggca 360
gaaataacat ttgacgtggt ggagaccttc atccgcggct ggggcaacaa accaattgaa 420
tacatcaaaa aggaaagatg gactgactca ttcaaaattc tcgcttattt gtgtcaaaag 480
tttttggact tacacaagtt gacattaatc ttaaatgctg tctctgaggt ggaattgctc 540
aacttggcga ggactttcaa aggcaaagtc agaagaagtt ctcatggaac gaacatatgc 600
aggattaggg ttcccagctt gggtcctact tttatttcag aaggatgggc ttacttcaag 660
aaacttgata ttctaatgga ccgaaacttt ctgttaatgg tcaaagatgt gattataggg 720
aggatgcaaa cggtgctatc catggtatgt agaatagaca acctgttctc agagcaagac 780
atcttctccc ttctaaatat ctacagaatt ggagataaaa ttgtggagag gcagggaaat 840
ttttcttatg acttgattaa aatggtggaa ccgatatgca acttgaagct gatgaaatta 900
gcaagagaat caaggccttt agtcccacaa ttccctcatt ttgaaaatca tatcaagact 960
tctgttgatg aaggggcaaa aattgaccga ggtataagat tcctccatga tcagataatg 1020
agtgtgaaaa cagtggatct cacactggtg atttatggat cgttcagaca ttggggtcat 1080
ccttttatag attattacac tggactagaa aaattacatt cccaagtaac catgaagaaa 1140
gatattgatg tgtcatatgc aaaagcactt gcaagtgatt tagctcggat tgttctattt 1200
caacagttca atgatcataa aaagtggttc gtgaatggag acttgctccc tcatgatcat 1260
ccctttaaaa gtcatgttaa agaaaataca tggcccacag ctgctcaagt tcaagatttt 1320

```
ggagataaat ggcatgaact tccgctgatt aaatgttttg aaatacccga cttactagac   1380
ccatcgataa tatactctga caaaagtcat tcaatgaata ggtcagaggt gttgaaacat   1440
gtccgaatga atccgaacac tcctatccct agtaaaaagg tgttgcagac tatgttggac   1500
acaaaggcta ccaattggaa agaatttctt aaagagattg atgagaaggg cttagatgat   1560
gatgatctaa ttattggtct taaaggaaag gagagggaac tgaagttggc aggtagattt   1620
ttctccctaa tgtcttggaa attgcgagaa tactttgtaa ttaccgaata tttgataaag   1680
actcatttcg tccctatgtt taaaggcctg acaatggcgg acgatctaac tgcagtcatt   1740
aaaaagatgt tagattcctc atccggccaa ggattgaagt catatgaggc aatttgcata   1800
gccaatcaca ttgattacga aaaatggaat aaccaccaaa ggaagttatc aaacggccca   1860
gtgttccgag ttatgggcca gttcttaggt tatccatcct taatcgagag aactcatgaa   1920
tttttgaga aaagtcttat atactacaat ggaagaccag acttgatgcg tgttcacaac    1980
aacacactga tcaattcaac ctcccaacga gtttgttggc aaggacaaga gggtggactg   2040
gaaggtctac ggcaaaaagg atggagtatc ctcaatctac tggttattca aagagaggct   2100
aaaatcagaa acactgctgt caaagtcttg gcacaaggtg ataatcaagt tatttgcaca   2160
cagtataaaa cgaagaaatc gagaaacgtt gtagaattac agggtgctct caatcaaatg   2220
gtttctaata atgagaaaat tatgactgca atcaaaatag ggacagggaa gttaggactt   2280
ttgataaatg acgatgagac tatgcaatct gcagattact tgaattatgg aaaaataccg   2340
attttccgtg gagtgattag agggttagag accaagagat ggtcacgagt gacttgtgtc   2400
accaatgacc aaatacccac ttgtgctaat ataatgagct cagtttccac aaatgctctc   2460
accgtagctc attttgctga gaacccaatc aatgccatga tacagtacaa ttattttggg   2520
acatttgcta gactcttgtt gatgatgcat gatcctgctc ttcgtcaatc attgtatgaa   2580
gttcaagata agataccggg cttgcacagt tctactttca aatacgccat gttgtatttg   2640
gacccttcca ttggaggagt gtcgggcatg tctttgtcca ggtttttgat tagagccttc   2700
ccagatcccg taacagaaag tctctcattc tggagattca tccatgtaca tgctcgaagt   2760
gagcatctga aggagatgag tgcagtattt ggaaaccccg agatagccaa gtttcgaata   2820
actcacatag acaagctagt agaagatcca acctctctga acatcgctat gggaatgagt   2880
ccagcgaact tgttaaagac tgaggttaaa aaatgcttaa tcgaatcaag acaaaccatc   2940
aggaaccagg tgattaagga tgcaaccata tatttgtatc atgaagagga tcggctcaga   3000
agtttcttat ggtcaataaa tcctctgttc cctagatttt taagtgaatt caaatcaggc   3060
acttttttgg gagtcgcaga cgggctcatc agtctatttc aaaattctcg tactattcgg   3120
aactccttta agaaaaagta tcatagggaa ttggatgatt tgattgtgag gagtgaggta   3180
tcctctttga cacatttagg gaaacttcat ttgagaaggg gatcatgtaa aatgtggaca   3240
tgttcagcta ctcatgctga cacattaaga tacaaatcct ggggccgtac agttattggg   3300
acaactgtac cccatccatt agaaatgttg ggtccacaac atcgaaaaga gactccttgt   3360
gcaccatgta acacatcagg gttcaattat gtttctgtgc attgtccaga cgggatccat   3420
gacgtcttta gttcacgggg accattgcct gcttatctag ggtctaaaac atctgaatct   3480
acatctattt tgcagccttg ggaaagggaa agcaaagtcc cactgattaa aagagctaca   3540
cgtcttagag atgctatctc ttggtttgtt gaacccgact ctaaactagc aatgactata   3600
ctttctaaca tccactcttt aacaggcgaa gaatggacca aaaggcagca tgggttcaaa   3660
agaacagggt ctgcccttca taggttttcg acatctcgga tgagccatgg tgggttcgca   3720
```

tctcagagca ctgcagcatt gaccaggttg atggcaacta cagacaccat gagggatctg 3780
ggagatcaga atttcgactt tttattccaa gcaacgttgc tctatgctca aattaccacc 3840
actgttgcaa gagacggatg gatcaccagt tgtacagatc attatcatat tgcctgtaag 3900
tcctgtttga gacccataga agagatcacc ctggactcaa gtatggacta cacgccccca 3960
gatgtatccc atgtgctgaa gacatggagg aatggggaag gttcgtgggg acaagagata 4020
aaacagatct atcctttaga agggaattgg aagaatttag cacctgctga gcaatcctat 4080
caagtcggca gatgtatagg ttttctatat ggagacttgg cgtatagaaa atctactcat 4140
gccgaggaca gttctctatt tcctctatct atacaaggtc gtattagagg tcgaggtttc 4200
ttaaaagggt tgctagacgg attaatgaga gcaagttgct gccaagtaat acaccggaga 4260
agtctggctc atttgaagag gccggccaac gcagtgtacg gaggtttgat ttacttgatt 4320
gataaattga gtgtatcacc tccattcctt tctcttacta gatcaggacc tattagagac 4380
gaattagaaa cgattcccca caagatccca acctcctatc cgacaagcaa ccgtgatatg 4440
ggggtgattg tcagaaatta cttcaaatac caatgccgtc taattgaaaa gggaaaatac 4500
agatcacatt attcacaatt atggttattc tcagatgtct tatccataga cttcattgga 4560
ccattctcta tttccaccac cctcttgcaa atcctataca agccattttt atctgggaaa 4620
gataagaatg agttgagaga gctggcaaat ctttcttcat tgctaagatc aggagagggg 4680
tgggaagaca tacatgtgaa attcttcacc aaggacatat tattgtgtcc agaggaaatc 4740
agacatgctt gcaagttcgg gattgctaag gataataata aagacatgag ctatccccct 4800
tggggaaggg aatccagagg gacaattaca acaatccctg tttattatac gaccacccct 4860
ggcggaagcg gcggagggag cgggggcggg agcggaatgg tgagcaaggg cgaggaggat 4920
aacatggcca tcatcaagga gttcatgcgc ttcaaggtgc acatggaggg ctccgtgaac 4980
ggccacgagt tcgagatcga gggcgagggc gagggccgcc cctacgaggg cacccagacc 5040
gccaagctga aggtgaccaa gggtggcccc ctgcccttcg cctgggacat cctgtcccct 5100
cagttcatgt acggctccaa ggcctacgtg aagcaccccg ccgacatccc cgactacttg 5160
aagctgtcct tccccgaggg cttcaagtgg gagcgcgtga tgaacttcga ggacggcggc 5220
gtggtgaccg tgacccagga ctcctccctg caggacggcg agttcatcta caaggtgaag 5280
ctgcgcggca ccaacttccc ctccgacggc cccgtaatgc agaagaagac catgggctgg 5340
gaggcctcct ccgagcggat gtaccccgag gacggcgccc tgaagggcga gatcaagcag 5400
aggctgaagc tgaaggacgg cggccactac gacgctgagg tcaagaccac ctacaaggcc 5460
aagaagcccg tgcagctgcc cggcgcctac aacgtcaaca tcaagttgga catcacctcc 5520
cacaacgagg actacaccat cgtggaacag tacgaacgcg ccgagggccg ccactccacc 5580
ggcggcatgg acgagctgta caagggaggg tccggaggcg gctcaggcgg tggatccggc 5640
tacccaaaga tgctagagat gcctccaaga atccaaaatc ccctgctgtc cggaatcagg 5700
ttgggccaat taccaactgg cgctcattat aaaattcgga gtatattaca tggaatggga 5760
atccattaca gggacttctt gagttgtgga gacggctccg gagggatgac tgctgcatta 5820
ctacgagaaa atgtgcatag cagaggaata ttcaatagtc tgttagaatt atcagggtca 5880
gtcatgcgag gcgcctctcc tgagcccccc agtgccctag aaactttagg aggagataaa 5940
tcgagatgtg taaatggtga aacatgttgg gaatatccat ctgacttatg tgacccaagg 6000
acttgggact atttcctccg actcaaagca ggcttggggc ttcaaattga tttaattgta 6060
atggatatgg aagttcggga ttcttctact agcctgaaaa ttgagacgaa tgttagaaat 6120
tatgtgcacc ggattttgga tgagcaagga gttttaatct acaagactta tggaacatat 6180
atttgtgaga gcgaaaagaa tgcagtaaca atccttggtc ccatgttcaa gacggtcgac 6240
ttagttcaaa cagaatttag tagttctcaa acgtctgaag tatatatggt atgtaaaggt 6300
ttgaagaaat taatcgatga accctatccc gattggtctt ccatcaatga atcctggaaa 6360
aacctgtacg cattccagtc atcagaacag gaatttgcca gagcaaagaa ggttagtaca 6420
tactttacct tgacaggtat tccctcccaa ttcattcctg atccttttgt aaacattgag 6480
actatgctac aaatattcgg agtacccacg ggtgtgtctc atgcggctgc cttaaaatca 6540
tctgatagac ctgcagattt attgaccatt agcctttttt atatggcgat tatatcgtat 6600
tataacatca atcatatcag agtaggaccg atacctccga accccccatc agatggaatt 6660
gcacaaaatg tggggatcgc tataactggt ataagctttt ggctgagttt gatggagaaa 6720
gacattccac tatatcaaca gtgtttagca gttatccagc aatcattccc gattaggtgg 6780
gaggctgttt cagtaaaagg aggatacaag cagaagtgga gtactagagg tgatgggctc 6840
ccaaaagata cccgaatttc agactccttg gccccaatcg ggaactggat cagatctctg 6900
gaattggtcc gaaaccaagt tcgtctaaat ccattcaatg agatcttgtt caatcagcta 6960
tgtcgtacag tggataatca tttgaaatgg tcaaatttgc gaagaaacac aggaatgatt 7020
gaatggatca atagacgaat ttcaaaagaa gaccggtcta tactgatgtt gaagagtgac 7080
ctacacgagg aaaactcttg gagagat 7107

<210> SEQ ID NO 15
<211> LENGTH: 1575
<212> TYPE: DNA
<213> ORGANISM: Artificial Sequence
<220> FEATURE:
<223> OTHER INFORMATION: P-protein with mWasabi (P-mWasabi-L-mCherry)

<400> SEQUENCE: 15
atggataatc tcacaaaagt tcgtgagtat ctcaagtcct attctcgtct ggatcaggcg 60
gtaggagaga tagatgagat cgaagcacaa cgagctgaaa agtccaatta tgagttgttc 120
caagaggatg gagtggaaga gcatactaag ccctcttatt ttcaggcagc agatgattct 180
gacacagaat ctgaaccaga aattgaagac aatcaaggct tgtatgcacc agatccagaa 240
gctgagcaag ttgaaggctt tatacagggg cctttagatg actatgcaga tgaggaagtg 300
gatgttgtat ttacttcgga ctggaaacag cctgagcttg aatctgacga gcatggaaag 360
accttacggt tgacatcgcc agagggttta agtggagagc agaaatccca gtggctttcg 420
acgattaaag cagtcgtgca aagtgccaaa tactggaatc tggcagagtg cacatttgaa 480
gcatcgggag aaggggtcat tatgaaggag cgccagataa ctccggatgt atataaggtc 540
actccagtga tgaacacaca tccgtcccaa tcagaagcag tatcagatgg cggaagcggc 600
ggagggagcg gggcgggag cggaatggtg agcaagggcg aggagaccac aatgggcgta 660
atcaagcccg acatgaagat caagctgaag atggagggca acgtgaatgg ccacgccttc 720
gtgatcgagg gcgagggcga gggcaagccc tacgacggca ccaacaccat caacctggag 780
gtgaaggagg gagcccccct gcccttctcc tacgacattc tgaccaccgc gttcagttac 840
ggcaacaggg ccttcaccaa gtaccccgac gacatcccca actacttcaa gcagtccttc 900
cccgagggct actcttggga gcgcaccatg accttcgagg acaagggcat cgtgaaggtg 960
aagtccgaca tctccatgga ggaggactcc ttcatctacg agatacacct caagggcgag 1020
aacttccccc ccaacggccc cgtgatgcag aaggagacca ccggctggga cgcctccacc 1080
gagaggatgt acgtgcgcga cggcgtgctg aagggcgacg tcaagatgaa gctgctgctg 1140
gagggcggcg gccaccaccg cgttgacttc aagaccatct acagggccaa gaaggcggtg 1200
aagctgcccg actatcactt tgtggaccac cgcatcgaga tcctgaacca cgacaaggac 1260
tacaacaagg tgaccgttta cgagatcgcc gtggcccgca actccaccga cggcatggac 1320
gagctgtaca agggagggtc cggaggcggc tcaggcggtg gatccggcgt ttggtctctc 1380
tcaaagacat ccatgacttt ccaacccaag aaagcaagtc ttcagcctct caccatatcc 1440
ttggatgaat tgttctcatc tagaggagag ttcatctctg tcggaggtga cggacgaatg 1500
tctcataaag aggccatcct gctcggcctg agatacaaaa agttgtacaa tcaggcgaga 1560
gtcaaatatt ctctg 1575

<210> SEQ ID NO 16
<211> LENGTH: 7761
<212> TYPE: DNA
<213> ORGANISM: Artificial Sequence
<220> FEATURE:
<223> OTHER INFORMATION: GFP-protease (with linker)-L-protein

<400> SEQUENCE: 16
atgagcaagg gcgaggaact gttcactggc gtggtcccaa ttctcgtgga actggatggc 60
gatgtgaatg ggcacaaatt ttctgtcagc ggagagggtg aaggagatgc cacatacgga 120
aagctcaccc tgaaattcat ctgcaccact ggaaagctcc ctgtgccatg gccaacactg 180
gtcactacct tcacctatgg cgtgcagtgc ttttccagat acccagacca tatgaagcag 240
catgactttt tcaagagcgc catgcccgag ggctatgtgc aggagagaac catctttttc 300
aaagatgacg ggaactacaa gacccgcrct gaagtcaagt tcgaaggtga caccctggtg 360
aatagaatcg agctgaaggg cattgacttt aaggaggatg gaaacattct cggccacaag 420
ctggaataca actataactc ccacaatgtg tacatcatgg ccgacaagca aaagaatggc 480
atcaaggtca acttcaagat cagacacaac attgaggatg gatccgtgca gctggccgac 540
cattatcaac agaacactcc aatcggcgac ggccctgtgc tcctcccaga caaccattac 600
ctgtccaccc agtctgccct gtctaaagat cccaacgaaa agagagacca catggtcctg 660
ctggagtttg tgaccgctgc tgggatcaca catggcatgg acgagctgta caagggcgga 720
agcggcggag ggagcggggg cgggagcgga gtgtccttta acttccccca agtgaccctg 780
tggcagcggc ccctcgtgac catcaagatc ggcggccagc tgaaagaggc cctgctggat 840
acaggcgccg acgacacagt gctggaagag atgagcctgc ccggcagatg gaagcccaag 900
atgatcggcg gaatcggcgg cttcatcaaa gtgcggcagt atgatcagat cctgatcgag 960
atctgcggac acaaggccat cggcaccgtg ctcgtgggac ccacccccgt gaatatcatc 1020
ggccggaacc tgctgaccca gatcggctgc accctgaact tcgctggcgc cattggaggc 1080
gcccctcaag tgacactgtg gcagaggcca ctcgtgacta ttaagattgg agggcagctg 1140
aaagaagctc tgctggacac cggggctgat gataccgtgc tggaagaaat gtccctgcct 1200
ggccggtgga aacctaagat gattggaggc attgggggct ttatcaaagt gcgccagtat 1260
gatcagatcc tgattgaaat ttgtggccat aaggccattg ggacagtgct cgtgggccct 1320
acacctgtga acattaccgg cagaaatctg ctgacacaga ttgggtgtac actgaatttc 1380
cccatctccc ccatcggagg gtccggaggc ggctcaggcg gtggatccgg catggaagtc 1440

-continued

```
cacgattttg agaccgacga gttcaatgat ttcaatgaag atgactatgc cacaagagaa   1500
ttcctgaatc ccgatgagcg catgacgtac ttgaatcatg ctgattacaa cctgaattct   1560
cctctaatta gtgatgatat tgacaattta atcaggaaat tcaattctct tccaattccc   1620
tcgatgtggg atagtaagaa ctgggatgga gttcttgaga tgttaacgtc atgtcaagcc   1680
aatcccatcc caacatctca gatgcataaa tggatgggaa gttggttaat gtctgataat   1740
catgatgcca gtcaagggta tagtttttta catgaagtgg acaaagaggc agaaataaca   1800
tttgacgtgg tggagacctt catccgcggc tggggcaaca aaccaattga atacatcaaa   1860
aaggaaagat ggactgactc attcaaaatt ctcgcttatt tgtgtcaaaa gtttttggac   1920
ttacacaagt tgacattaat cttaaatgct gtctctgagg tggaattgct caacttggcg   1980
aggactttca aaggcaaagt cagaagaagt tctcatggaa cgaacatatg caggattagg   2040
gttcccagct tgggtcctac ttttatttca gaaggatggg cttacttcaa gaaacttgat   2100
attctaatgg accgaaactt tctgttaatg gtcaaagatg tgattatagg gaggatgcaa   2160
acggtgctat ccatggtatg tagaatagac aacctgttct cagagcaaga catcttctcc   2220
cttctaaata tctacagaat tggagataaa attgtggaga ggcagggaaa tttttcttat   2280
gacttgatta aaatggtgga accgatatgc aacttgaagc tgatgaaatt agcaagagaa   2340
tcaaggcctt tagtcccaca attccctcat tttgaaaatc atatcaagac ttctgttgat   2400
gaaggggcaa aaattgaccg aggtataaga ttcctccatg atcagataat gagtgtgaaa   2460
acagtggatc tcacactggt gatttatgga tcgttcagac attggggtca tccttttata   2520
gattattaca ctggactaga aaaattacat tcccaagtaa ccatgaagaa agatattgat   2580
gtgtcatatg caaaagcact tgcaagtgat ttagctcgga ttgttctatt tcaacagttc   2640
aatgatcata aaaagtggtt cgtgaatgga gacttgctcc ctcatgatca tccctttaaa   2700
agtcatgtta aagaaaatac atggcccaca gctgctcaag ttcaagattt tggagataaa   2760
tggcatgaac ttccgctgat taaatgtttt gaaatacccg acttactaga cccatcgata   2820
atatactctg acaaaagtca ttcaatgaat aggtcagagg tgttgaaaca tgtccgaatg   2880
aatccgaaca ctcctatccc tagtaaaaag gtgttgcaga ctatgttgga cacaaaggct   2940
accaattgga aagaatttct taaagagatt gatgagaagg gcttagatga tgatgatcta   3000
attattggtc ttaaaggaaa ggagagggaa ctgaagttgg caggtagatt tttctcccta   3060
atgtcttgga aattgcgaga atactttgta attaccgaat atttgataaa gactcatttc   3120
gtccctatgt ttaaaggcct gacaatggcg gacgatctaa ctgcagtcat taaaaagatg   3180
ttagattcct catccggcca aggattgaag tcatatgagg caatttgcat agccaatcac   3240
attgattacg aaaaatggaa taaccaccaa aggaagttat caaacggccc agtgttccga   3300
gttatgggcc agttcttagg ttatccatcc ttaatcgaga gaactcatga atttttttgag   3360
aaaagtctta tatactacaa tggaagacca gacttgatgc gtgttcacaa caacacactg   3420
atcaattcaa cctcccaacg agtttgttgg caaggacaag agggtggact ggaaggtcta   3480
cggcaaaaag gatggagtat cctcaatcta ctggttattc aaagagaggc taaaatcaga   3540
aacactgctg tcaaagtctt ggcacaaggt gataatcaag ttatttgcac acagtataaa   3600
acgaagaaat cgagaaacgt tgtagaatta cagggtgctc tcaatcaaat ggtttctaat   3660
aatgagaaaa ttatgactgc aatcaaaata gggacaggga agttaggact tttgataaat   3720
gacgatgaga ctatgcaatc tgcagattac ttgaattatg gaaaaatacc gattttccgt   3780
ggagtgatta gagggttaga gaccaagaga tggtcacgag tgacttgtgt caccaatgac   3840
```

```
caaataccca cttgtgctaa tataatgagc tcagtttcca caaatgctct caccgtagct   3900
cattttgctg agaacccaat caatgccatg atacagtaca attattttgg gacatttgct   3960
agactcttgt tgatgatgca tgatcctgct cttcgtcaat cattgtatga agttcaagat   4020
aagataccgg gcttgcacag ttctactttc aaatacgcca tgttgtattt ggacccttcc   4080
attggaggag tgtcgggcat gtctttgtcc aggtttttga ttagagcctt cccagatccc   4140
gtaacagaaa gtctctcatt ctggagattc atccatgtac atgctcgaag tgagcatctg   4200
aaggagatga gtgcagtatt tggaaacccc gagatagcca agtttcgaat aactcacata   4260
gacaagctag tagaagatcc aacctctctg aacatcgcta tgggaatgag tccagcgaac   4320
ttgttaaaga ctgaggttaa aaaatgctta atcgaatcaa gacaaaccat caggaaccag   4380
gtgattaagg atgcaaccat atatttgtat catgaagagg atcggctcag aagtttctta   4440
tggtcaataa atcctctgtt ccctagattt ttaagtgaat tcaaatcagg cacttttttg   4500
ggagtcgcag acgggctcat cagtctattt caaaattctc gtactattcg gaactccttt   4560
aagaaaaagt atcataggga attggatgat ttgattgtga ggagtgaggt atcctctttg   4620
acacatttag ggaaacttca tttgagaagg ggatcatgta aaatgtggac atgttcagct   4680
actcatgctg acacattaag atacaaatcc tggggccgta cagttattgg gacaactgta   4740
ccccatccat tagaaatgtt gggtccacaa catcgaaaag agactccttg tgcaccatgt   4800
aacacatcag ggttcaatta tgtttctgtg cattgtccag acgggatcca tgacgtcttt   4860
agttcacggg gaccattgcc tgcttatcta gggtctaaaa catctgaatc tacatctatt   4920
ttgcagcctt gggaaaggga aagcaaagtc ccactgatta aaagagctac acgtcttaga   4980
gatgctatct cttggtttgt tgaacccgac tctaaactag caatgactat actttctaac   5040
atccactctt taacaggcga agaatggacc aaaaggcagc atgggttcaa aagaacaggg   5100
tctgcccttc ataggttttc gacatctcgg atgagccatg gtgggttcgc atctcagagc   5160
actgcagcat tgaccaggtt gatggcaact acagacacca tgagggatct gggagatcag   5220
aatttcgact ttttattcca agcaacgttg ctctatgctc aaattaccac cactgttgca   5280
agagacggat ggatcaccag ttgtacagat cattatcata ttgcctgtaa gtcctgtttg   5340
agacccatag aagagatcac cctggactca agtatggact acacgccccc agatgtatcc   5400
catgtgctga agacatggag gaatggggaa ggttcgtggg gacaagagat aaaacagatc   5460
tatcctttag aagggaattg gaagaattta gcacctgctg agcaatccta tcaagtcggc   5520
agatgtatag gttttctata tggagacttg gcgtatagaa aatctactca tgccgaggac   5580
agttctctat ttcctctatc tatacaaggt cgtattagag gtcgaggttt cttaaaaggg   5640
ttgctagacg gattaatgag agcaagttgc tgccaagtaa tacaccggag aagtctggct   5700
catttgaaga ggccggccaa cgcagtgtac ggaggtttga tttacttgat tgataaattg   5760
agtgtatcac ctccattcct ttctcttact agatcaggac ctattagaga cgaattagaa   5820
acgattcccc acaagatccc aacctcctat ccgacaagca accgtgatat gggggtgatt   5880
gtcagaaatt acttcaaata ccaatgccgt ctaattgaaa agggaaaata cagatcacat   5940
tattcacaat tatggttatt ctcagatgtc ttatccatag acttcattgg accattctct   6000
atttccacca ccctcttgca aatcctatac aagccatttt tatctgggaa agataagaat   6060
gagttgagag agctggcaaa tctttcttca ttgctaagat caggagaggg gtgggaagac   6120
atacatgtga aattcttcac caaggacata ttattgtgtc cagaggaaat cagacatgct   6180
```

tgcaagttcg ggattgctaa ggataataat aaagacatga gctatccccc ttggggaagg 6240
gaatccagag ggacaattac aacaatccct gtttattata cgaccacccc ttacccaaag 6300
atgctagaga tgcctccaag aatccaaaat cccctgctgt ccggaatcag gttgggccaa 6360
ttaccaactg gcgctcatta taaaattcgg agtatattac atggaatggg aatccattac 6420
agggacttct tgagttgtgg agacggctcc ggagggatga ctgctgcatt actacgagaa 6480
aatgtgcata gcagaggaat attcaatagt ctgttagaat tatcagggtc agtcatgcga 6540
ggcgcctctc ctgagccccc cagtgcccta gaaactttag gaggagataa atcgagatgt 6600
gtaaatggtg aaacatgttg ggaatatcca tctgacttat gtgacccaag gacttgggac 6660
tatttcctcc gactcaaagc aggcttgggg cttcaaattg atttaattgt aatggatatg 6720
gaagttcggg attcttctac tagcctgaaa attgagacga atgttagaaa ttatgtgcac 6780
cggattttgg atgagcaagg agttttaatc tacaagactt atggaacata tatttgtgag 6840
agcgaaaaga atgcagtaac aatccttggt cccatgttca agacggtcga cttagttcaa 6900
acagaattta gtagttctca aacgtctgaa gtatatatgg tatgtaaagg tttgaagaaa 6960
ttaatcgatg aacccaatcc cgattggtct tccatcaatg aatcctggaa aaacctgtac 7020
gcattccagt catcagaaca ggaatttgcc agagcaaaga aggttagtac atactttacc 7080
ttgacaggta ttccctccca attcattcct gatccttttg taaacattga gactatgcta 7140
caaatattcg gagtacccac gggtgtgtct catgcggctg ccttaaaatc atctgataga 7200
cctgcagatt tattgaccat tagccttttt tatatggcga ttatatcgta ttataacatc 7260
aatcatatca gagtaggacc gatacctccg aacccccat cagatggaat tgcacaaaat 7320
gtggggatcg ctataactgg tataagcttt tggctgagtt tgatggagaa agacattcca 7380
ctatatcaac agtgtttagc agttatccag caatcattcc cgattaggtg ggaggctgtt 7440
tcagtaaaag gaggatacaa gcagaagtgg agtactagag gtgatgggct cccaaaagat 7500
acccgaattt cagactcctt ggccccaatc gggaactgga tcagatctct ggaattggtc 7560
cgaaaccaag ttcgtctaaa tccattcaat gagatcttgt tcaatcagct atgtcgtaca 7620
gtggataatc atttgaaatg gtcaaatttg cgaagaaaca caggaatgat tgaatggatc 7680
aatagacgaa tttcaaaaga agaccggtct atactgatgt tgaagagtga cctacacgag 7740
gaaaactctt ggagagatta a 7761

<210> SEQ ID NO 17
<211> LENGTH: 7689
<212> TYPE: DNA
<213> ORGANISM: Artificial Sequence
<220> FEATURE:
<223> OTHER INFORMATION: GFP-protease (without linker)-L-protein

<400> SEQUENCE: 17
atgagcaagg gcgaggaact gttcactggc gtggtcccaa ttctcgtgga actggatggc 60
gatgtgaatg ggcacaaatt ttctgtcagc ggagagggtg aaggagatgc cacatacgga 120
aagctcaccc tgaaattcat ctgcaccact ggaaagctcc ctgtgccatg gccaacactg 180
gtcactacct tcacctatgg cgtgcagtgc ttttccagat acccagacca tatgaagcag 240
catgactttt tcaagagcgc catgcccgag ggctatgtgc aggagagaac catctttttc 300
aaagatgacg ggaactacaa gacccgcrct gaagtcaagt tcgaaggtga caccctggtg 360
aatagaatcg agctgaaggg cattgacttt aaggaggatg gaaacattct cggccacaag 420
ctggaataca actataactc ccacaatgtg tacatcatgg ccgacaagca aaagaatggc 480

```
atcaaggtca acttcaagat cagacacaac attgaggatg gatccgtgca gctggccgac    540
cattatcaac agaacactcc aatcggcgac ggccctgtgc tcctcccaga caaccattac    600
ctgtccaccc agtctgccct gtctaaagat cccaacgaaa agagagacca catggtcctg    660
ctggagtttg tgaccgctgc tgggatcaca catggcatgg acgagctgta caaggtgtcc    720
tttaacttcc cccaagtgac cctgtggcag cggcccctcg tgaccatcaa gatcggcggc    780
cagctgaaag aggccctgct ggatacaggc gccgacgaca cagtgctgga agagatgagc    840
ctgcccggca gatggaagcc caagatgatc ggcggaatcg gcggcttcat caaagtgcgg    900
cagtatgatc agatcctgat cgagatctgc ggacacaagg ccatcggcac cgtgctcgtg    960
ggacccaccc ccgtgaatat catcggccgg aacctgctga cccagatcgg ctgcaccctg   1020
aacttcgctg gcgccattgg aggcgcccct caagtgacac tgtggcagag gccactcgtg   1080
actattaaga ttggagggca gctgaaagaa gctctgctgg acaccggggc tgatgatacc   1140
gtgctggaag aaatgtccct gcctggccgg tggaaaccta agatgattgg aggcattggg   1200
ggctttatca aagtgcgcca gtatgatcag atcctgattg aaatttgtgg ccataaggcc   1260
attgggacag tgctcgtggg ccctacacct gtgaacatta tcagcagaaa tctgctgaca   1320
cagattgggt gtacactgaa tttccccatc tcccccatca tggaagtcca cgattttgag   1380
accgacgagt tcaatgattt caatgaagat gactatgcca caagagaatt cctgaatccc   1440
gatgagcgca tgacgtactt gaatcatgct gattacaacc tgaattctcc tctaattagt   1500
gatgatattg acaatttaat caggaaattc aattctcttc caattccctc gatgtgggat   1560
agtaagaact gggatggagt tcttgagatg ttaacgtcat gtcaagccaa tcccatccca   1620
acatctcaga tgcataaatg gatgggaagt tggttaatgt ctgataatca tgatgccagt   1680
caagggtata gtttttttaca tgaagtggac aaagaggcag aaataacatt tgacgtggtg   1740
gagaccttca tccgcggctg ggcaacaaa ccaattgaat acatcaaaaa ggaaagatgg   1800
actgactcat tcaaaattct cgcttatttg tgtcaaaagt ttttggactt acacaagttg   1860
acattaatct taaatgctgt ctctgaggtg gaattgctca acttggcgag gactttcaaa   1920
ggcaaagtca gaagaagttc tcatggaacg aacatatgca ggattagggt tcccagcttg   1980
ggtcctactt ttatttcaga aggatgggct tacttcaaga aacttgatat tctaatggac   2040
cgaaactttc tgttaatggt caaagatgtg attataggga ggatgcaaac ggtgctatcc   2100
atggtatgta gaatagacaa cctgttctca gagcaagaca tcttctccct tctaaatatc   2160
tacagaattg gagataaaat tgtggagagg cagggaaatt tttcttatga cttgattaaa   2220
atggtggaac cgatatgcaa cttgaagctg atgaaattag caagagaatc aaggccttta   2280
gtcccacaat tccctcattt tgaaaatcat atcaagactt ctgttgatga aggggcaaaa   2340
attgaccgag gtataagatt cctccatgat cagataatga gtgtgaaaac agtggatctc   2400
acactggtga tttatggatc gttcagacat tggggtcatc cttttataga ttattacact   2460
ggactagaaa aattacattc ccaagtaacc atgaagaaag atattgatgt gtcatatgca   2520
aaagcacttg caagtgattt agctcggatt gttctatttc aacagttcaa tgatcataaa   2580
aagtggttcg tgaatggaga cttgctccct catgatcatc cctttaaaag tcatgttaaa   2640
gaaaatacat ggcccacagc tgctcaagtt caagattttg gagataaatg gcatgaactt   2700
ccgctgatta aatgttttga aatacccgac ttactagacc catcgataat atactctgac   2760
aaaagtcatt caatgaatag gtcagaggtg ttgaaacatg tccgaatgaa tccgaacact   2820
```

```
cctatcccta gtaaaaaggt gttgcagact atgttggaca caaaggctac caattggaaa   2880
gaatttctta aagagattga tgagaagggc ttagatgatg atgatctaat tattggtctt   2940
aaaggaaagg agagggaact gaagttggca ggtagatttt tctccctaat gtcttggaaa   3000
ttgcgagaat actttgtaat taccgaatat ttgataaaga ctcatttcgt ccctatgttt   3060
aaaggcctga caatggcgga cgatctaact gcagtcatta aaaagatgtt agattcctca   3120
tccggccaag gattgaagtc atatgaggca atttgcatag ccaatcacat tgattacgaa   3180
aaatggaata accaccaaag gaagttatca aacggcccag tgttccgagt tatgggccag   3240
ttcttaggtt atccatcctt aatcgagaga actcatgaat tttttgagaa aagtcttata   3300
tactacaatg gaagaccaga cttgatgcgt gttcacaaca acacactgat caattcaacc   3360
tcccaacgag tttgttggca aggacaagag ggtggactgg aaggtctacg gcaaaaagga   3420
tggagtatcc tcaatctact ggttattcaa agagaggcta aaatcagaaa cactgctgtc   3480
aaagtcttgg cacaaggtga taatcaagtt atttgcacac agtataaaac gaagaaatcg   3540
agaaacgttg tagaattaca gggtgctctc aatcaaatgg tttctaataa tgagaaaatt   3600
atgactgcaa tcaaaatagg gacagggaag ttaggacttt tgataaatga cgatgagact   3660
atgcaatctg cagattactt gaattatgga aaaataccga ttttccgtgg agtgattaga   3720
gggttagaga ccaagagatg gtcacgagtg acttgtgtca ccaatgacca aatacccact   3780
tgtgctaata taatgagctc agtttccaca aatgctctca ccgtagctca ttttgctgag   3840
aacccaatca atgccatgat acagtacaat tattttggga catttgctag actcttgttg   3900
atgatgcatg atcctgctct tcgtcaatca ttgtatgaag ttcaagataa gataccgggc   3960
ttgcacagtt ctactttcaa atacgccatg ttgtatttgg acccttccat tggaggagtg   4020
tcgggcatgt ctttgtccag gtttttgatt agagccttcc cagatcccgt aacagaaagt   4080
ctctcattct ggagattcat ccatgtacat gctcgaagtg agcatctgaa ggagatgagt   4140
gcagtatttg gaaaccccga gatagccaag tttcgaataa ctcacataga caagctagta   4200
gaagatccaa cctctctgaa catcgctatg ggaatgagtc cagcgaactt gttaaagact   4260
gaggttaaaa aatgcttaat cgaatcaaga caaaccatca ggaaccaggt gattaaggat   4320
gcaaccatat atttgtatca tgaagaggat cggctcagaa gtttcttatg gtcaataaat   4380
cctctgttcc ctagattttt aagtgaattc aaatcaggca ctttttttggg agtcgcagac   4440
gggctcatca gtctatttca aaattctcgt actattcgga actcctttaa gaaaaagtat   4500
catagggaat tggatgattt gattgtgagg agtgaggtat cctctttgac acatttaggg   4560
aaacttcatt tgagaagggg atcatgtaaa atgtggacat gttcagctac tcatgctgac   4620
acattaagat acaaatcctg gggccgtaca gttattggga caactgtacc ccatccatta   4680
gaaatgttgg gtccacaaca tcgaaaagag actccttgtg caccatgtaa cacatcaggg   4740
ttcaattatg tttctgtgca ttgtccagac gggatccatg acgtctttag ttcacgggga   4800
ccattgcctg cttatctagg gtctaaaaca tctgaatcta catctatttt gcagccttgg   4860
gaaagggaaa gcaaagtccc actgattaaa agagctacac gtcttagaga tgctatctct   4920
tggtttgttg aacccgactc taaactagca atgactatac tttctaacat ccactcttta   4980
acaggcgaag aatggaccaa aaggcagcat gggttcaaaa gaacagggtc tgcccttcat   5040
aggttttcga catctcggat gagccatggt gggttcgcat ctcagagcac tgcagcattg   5100
accaggttga tggcaactac agacaccatg agggatctgg gagatcagaa tttcgacttt   5160
ttattccaag caacgttgct ctatgctcaa attaccacca ctgttgcaag agacggatgg   5220
```

```
atcaccagtt gtacagatca ttatcatatt gcctgtaagt cctgtttgag acccatagaa   5280
gagatcaccc tggactcaag tatggactac acgcccccag atgtatccca tgtgctgaag   5340
acatggagga atggggaagg ttcgtgggga caagagataa aacagatcta tcctttagaa   5400
gggaattgga agaatttagc acctgctgag caatcctatc aagtcggcag atgtataggt   5460
tttctatatg gagacttggc gtatagaaaa tctactcatg ccgaggacag ttctctattt   5520
cctctatcta tacaaggtcg tattagaggt cgaggtttct taaaagggtt gctagacgga   5580
ttaatgagag caagttgctg ccaagtaata caccggagaa gtctggctca tttgaagagg   5640
ccggccaacg cagtgtacgg aggtttgatt tacttgattg ataaattgag tgtatcacct   5700
ccattccttt ctcttactag atcaggacct attagagacg aattagaaac gattccccac   5760
aagatcccaa cctcctatcc gacaagcaac cgtgatatgg gggtgattgt cagaaattac   5820
ttcaaatacc aatgccgtct aattgaaaag ggaaaataca gatcacatta ttcacaatta   5880
tggttattct cagatgtctt atccatagac ttcattggac cattctctat ttccaccacc   5940
ctcttgcaaa tcctatacaa gccatttta tctgggaaag ataagaatga gttgagagag   6000
ctggcaaatc tttcttcatt gctaagatca ggagaggggt gggaagacat acatgtgaaa   6060
ttcttcacca aggacatatt attgtgtcca gaggaaatca gacatgcttg caagttcggg   6120
attgctaagg ataataataa agacatgagc tatcccctt ggggaaggga atccagaggg   6180
acaattacaa caatccctgt ttattatacg accacccctt acccaaagat gctagagatg   6240
cctccaagaa tccaaaatcc cctgctgtcc ggaatcaggt tgggccaatt accaactggc   6300
gctcattata aaattcggag tatattacat ggaatgggaa tccattacag ggacttcttg   6360
agttgtggag acggctccgg agggatgact gctgcattac tacgagaaaa tgtgcatagc   6420
agaggaatat tcaatagtct gttagaatta tcagggtcag tcatgcgagg cgcctctcct   6480
gagcccccca gtgccctaga aactttagga ggagataaat cgagatgtgt aaatggtgaa   6540
acatgttggg aatatccatc tgacttatgt gacccaagga cttgggacta tttcctccga   6600
ctcaaagcag gcttggggct tcaaattgat ttaattgtaa tggatatgga agttcgggat   6660
tcttctacta gcctgaaaat tgagacgaat gttagaaatt atgtgcaccg gattttggat   6720
gagcaaggag ttttaatcta caagacttat ggaacatata tttgtgagag cgaaaagaat   6780
gcagtaacaa tccttggtcc catgttcaag acggtcgact tagttcaaac agaatttagt   6840
agttctcaaa cgtctgaagt atatatggta tgtaaaggtt tgaagaaatt aatcgatgaa   6900
cccaatcccg attggtcttc catcaatgaa tcctggaaaa acctgtacgc attccagtca   6960
tcagaacagg aatttgccag agcaaagaag gttagtacat actttacctt gacaggtatt   7020
ccctcccaat tcattcctga tccttttgta aacattgaga ctatgctaca aatattcgga   7080
gtacccacgg gtgtgtctca tgcggctgcc ttaaaatcat ctgatagacc tgcagattta   7140
ttgaccatta gcctttttta tatggcgatt atatcgtatt ataacatcaa tcatatcaga   7200
gtaggaccga tacctccgaa ccccccatca gatggaattg cacaaaatgt ggggatcgct   7260
ataactggta taagcttttg gctgagtttg atggagaaag acattccact atatcaacag   7320
tgtttagcag ttatccagca atcattcccg attaggtggg aggctgtttc agtaaaagga   7380
ggatacaagc agaagtggag tactagaggt gatgggctcc caaaagatac ccgaatttca   7440
gactccttgg ccccaatcgg gaactggatc agatctctgg aattggtccg aaaccaagtt   7500
cgtctaaatc cattcaatga gatcttgttc aatcagctat gtcgtacagt ggataatcat   7560
```

ttgaaatggt caaatttgcg aagaaacaca ggaatgattg aatggatcaa tagacgaatt 7620
tcaaaagaag accggtctat actgatgttg aagagtgacc tacacgagga aaactcttgg 7680
agagattaa 7689

<210> SEQ ID NO 18
<211> LENGTH: 717
<212> TYPE: DNA
<213> ORGANISM: Artificial Sequence
<220> FEATURE:
<223> OTHER INFORMATION: Prot-off protease dimer with mutation with linker

<400> SEQUENCE: 18
ggcggaagcg gcggagggag cgggggcggg agcggagtgt cctttaactt cccccaagtg 60
accctgtggc agcggcccct cgtgaccatc aagatcggcg gccagctgaa agaggccctg 120
ctggatacag gcgccgacga cacagtgctg gaagagatga gcctgcccgg cagatggaag 180
cccaagatga tcggcggaat cggcggcttc atcaaagtgc ggcagtatga tcagatcctg 240
atcgagatct gcggacacaa ggccatcggc accgtgctcg tgggacccac ccccgtgaat 300
atcatcggcc ggaacctgct gacccagatc ggctgcaccc tgaacttcgc tggcgccatt 360
ggaggcgccc ctcaagtgac actgtggcag aggccactcg tgactattaa gattggaggg 420
cagctgaaag aagctctgct ggacaccggg gctgatgata ccgtgctgga agaaatgtcc 480
ctgcctggcc ggtggaaacc taagatgatt ggaggcattg ggggctttat caaagtgcgc 540
cagtatgatc agatcctgat tgaaatttgt ggccataagg ccattgggac agtgctcgtg 600
ggccctacac ctgtgaacat taccggcaga aatctgctga cacagattgg gtgtacactg 660
aatttcccca tctcccccat cggagggtcc ggaggcggct caggcggtgg atccggc 717

<210> SEQ ID NO 19
<211> LENGTH: 645
<212> TYPE: DNA
<213> ORGANISM: Artificial Sequence
<220> FEATURE:
<223> OTHER INFORMATION: Prot-off protease dimer with mutation without linker

<400> SEQUENCE: 19
gtgtccttta acttccccca agtgaccctg tggcagcggc ccctcgtgac catcaagatc 60
ggcggccagc tgaaagaggc cctgctggat acaggcgccg acgacacagt gctggaagag 120
atgagcctgc ccggcagatg gaagcccaag atgatcggcg gaatcggcgg cttcatcaaa 180
gtgcggcagt atgatcagat cctgatcgag atctgcggac acaaggccat cggcaccgtg 240
ctcgtgggac ccacccccgt gaatatcatc ggccggaacc tgctgaccca gatcggctgc 300
accctgaact tcgctggcgc cattggaggc gcccctcaag tgacactgtg gcagaggcca 360
ctcgtgacta ttaagattgg agggcagctg aaagaagctc tgctggacac cggggctgat 420
gataccgtgc tggaagaaat gtccctgcct ggccggtgga aacctaagat gattggaggc 480
attgggggct ttatcaaagt gcgccagtat gatcagatcc tgattgaaat ttgtggccat 540
aaggccattg ggacagtgct cgtgggccct acacctgtga acattatcag cagaaatctg 600
ctgacacaga ttgggtgtac actgaatttc cccatctccc ccatc 645

<210> SEQ ID NO 20
<211> LENGTH: 14351
<212> TYPE: DNA
<213> ORGANISM: Artificial Sequence
<220> FEATURE:
<223> OTHER INFORMATION: VSV Indiana vector

<400> SEQUENCE: 20
cacctaaatt gtaagcgtta atattttgtt aaaattcgcg ttaaattttt gttaaatcag 60
ctcatttttt aaccaatagg ccgaaatcgg caaaatccct tataaatcaa aagaatagac 120
cgagataggg ttgagtgttg ttccagtttg gaacaagagt ccactattaa agaacgtgga 180
ctccaacgtc aaagggcgaa aaaccgtcta tcagggcgat ggcccactac gtgaaccatc 240
accctaatca agttttttgg ggtcgaggtg ccgtaaagca ctaaatcgga accctaaagg 300
gagcccccga tttagagctt gacggggaaa gccggcgaac gtggcgagaa aggaagggaa 360
gaaagcgaaa ggagcgggcg ctagggcgct ggcaagtgta gcggtcacgc tgcgcgtaac 420
caccacaccc gccgcgctta atgcgccgct acagggcgcg tcccattcgc cattcaggct 480
gcgcaactgt tgggaagggc gatcggtgcg ggcctcttcg ctattacgcc agctggcgaa 540
agggggatgt gctgcaaggc gattaagttg ggtaacgcca gggttttccc agtcacgacg 600
ttgtaaaacg acggccagtg aattgtaata cgactcacta taggacgaag acaaacaaac 660
cattattatc attaaaaggc tcaggagaaa ctttaacagt aatcaaaatg tctgttacag 720
tcaagagaat cattgacaac acagtcgtag ttccaaaact tcctgcaaat gaggatccag 780
tggaataccc ggcagattac ttcagaaaat caaaggagat tcctctttac atcaatacta 840
caaaaagttt gtcagatcta agaggatatg tctaccaagg cctcaaatcc ggaaatgtat 900
caatcataca tgtcaacagc tacttgtatg gagcattaaa ggacatccgg ggtaagttgg 960
ataaagattg gtcaagtttc ggaataaaca tcgggaaagc aggggataca atcggaatat 1020
ttgaccttgt atccttgaaa gccctggacg gcgtacttcc agatggagta tcggatgctt 1080
ccagaaccag cgcagatgac aaatggttgc ctttgtatct acttggctta tacagagtgg 1140
gcagaacaca aatgcctgaa tacagaaaaa agctcatgga tgggctgaca aatcaatgca 1200
aaatgatcaa tgaacagttt gaacctcttg tgccagaagg tcgtgacatt tttgatgtgt 1260
ggggaaatga cagtaattac acaaaaattg tcgctgcagt ggacatgttc ttccacatgt 1320
tcaaaaaaca tgaatgtgcc tcgttcagat acggaactat tgtttccaga ttcaaagatt 1380
gtgctgcatt ggcaacattt ggacacctct gcaaaataac cggaatgtct acagaagatg 1440
taacgacctg gatcttgaac cgagaagttg cagatgaaat ggtccaaatg atgcttccag 1500
gccaagaaat tgacaaggcc gattcataca tgccttattt gatcgacttt ggattgtctt 1560
ctaagtctcc atattcttcc gtcaaaaacc ctgccttcca cttctggggg caattgacag 1620
ctcttctgct cagatccacc agagcaagga atgcccgaca gcctgatgac attgagtata 1680
catctcttac tacagcaggt ttgttgtacg cttatgcagt aggatcctct gccgacttgg 1740
cacaacagtt ttgtgttgga gataacaaat acactccaga tgatagtacc ggaggattga 1800
cgactaatgc accgccacaa ggcagagatg tggtcgaatg gctcggatgg tttgaagatc 1860
aaaacagaaa accgactcct gatatgatgc agtatgcgaa aagagcagtc atgtcactgc 1920
aaggcctaag agagaagaca attggcaagt atgctaagtc agaatttgac aaatgaccct 1980
ataattctca gatcacctat tatatattat gctacatatg aaaaaaacta acagatatca 2040
tggataatct cacaaaagtt cgtgagtatc tcaagtccta ttctcgtctg gatcaggcgg 2100
taggagagat agatgagatc gaagcacaac gagctgaaaa gtccaattat gagttgttcc 2160
aagaggatgg agtggaagag catactaagc cctcttattt tcaggcagca gatgattctg 2220
acacagaatc tgaaccagaa attgaagaca atcaaggctt gtatgcacca gatccagaag 2280
ctgagcaagt tgaaggcttt atacaggggc ctttagatga ctatgcagat gaggaagtgg 2340
atgttgtatt tacttcggac tggaaacagc ctgagcttga atctgacgag catggaaaga 2400
ccttacggtt gacatcgcca gagggtttaa gtggagagca gaaatcccag tggctttcga 2460
cgattaaagc agtcgtgcaa agtgccaaat actggaatct ggcagagtgc acatttgaag 2520
catcgggaga aggggtcatt atgaaggagc gccagataac tccggatgta tataaggtca 2580
ctccagtgat gaacacacat ccgtcccaat cagaagcagt atcagatgtt tggtctctct 2640
caaagacatc catgactttc caacccaaga aagcaagtct tcagcctctc accatatcct 2700
tggatgaatt gttctcatct agaggagagt tcatctctgt cggaggtgac ggacgaatgt 2760
ctcataaaga ggccatcctg ctcggcctga gatacaaaaa gttgtacaat caggcgagag 2820
tcaaatattc tctgtagact atgaaaaaaa gtaacagata tcacgatcta agtgttatcc 2880
caatccattc atcatgagtt ccttaaagaa gattctcggt ctgaagggga aaggtaagaa 2940
atctaagaaa ttagggatcg caccaccccc ttatgaagag gacactagca tggagtatgc 3000
tccgagcgct ccaattgaca aatcctattt tggagttgac gagatggaca cctatgatcc 3060
gaatcaatta agatatgaga aattcttctt tacagtgaaa atgacggtta gatctaatcg 3120
tccgttcaga acatactcag atgtggcagc cgctgtatcc cattgggatc acatgtacat 3180
cggaatggca gggaaacgtc ccttctacaa aatcttggct tttttgggtt cttctaatct 3240
aaaggccact ccagcggtat tggcagatca aggtcaacca gagtatcacg ctcactgcga 3300
aggcagggct tatttgccac ataggatggg gaagacccct cccatgctca atgtaccaga 3360
gcacttcaga agaccattca atataggtct ttacaaggga acgattgagc tcacaatgac 3420
catctacgat gatgagtcac tggaagcagc tcctatgatc tgggatcatt tcaattcttc 3480
caaattttct gatttcagag agaaggcctt aatgtttggc ctgattgtcg agaaaaaggc 3540
atctggagcg tgggtcctgg actctatcgg ccacttcaaa tgagctagtc taacttctag 3600
cttctgaaca atccccggtt tactcagtct cccctaattc cagcctctcg aacaactaat 3660
atcctgtctt ttctatccct atgaaaaaaa ctaacagaga tcgatctgtt tacgcgtcac 3720
tatgaagtgc cttttgtact tagccttttt attcattggg gtgaattgca agttcaccat 3780
agtttttcca cacaaccaaa aaggaaactg gaaaaatgtt ccttctaatt accattattg 3840
cccgtcaagc tcagatttaa attggcataa tgacttaata ggcacagcct tacaagtcaa 3900
aatgcccaag agtcacaagg ctattcaagc agacggttgg atgtgtcatg cttccaaatg 3960
ggtcactact tgtgatttcc gctggtatgg accgaagtat ataacacatt ccatccgatc 4020
cttcactcca tctgtagaac aatgcaagga aagcattgaa caaacgaaac aaggaacttg 4080
gctgaatcca ggcttccctc ctcaaagttg tggatatgca actgtgacgg atgccgaagc 4140
agtgattgtc caggtgactc ctcaccatgt gctggttgat gaatacacag gagaatgggt 4200
tgattcacag ttcatcaacg gaaaatgcag caattacata tgccccactg tccataactc 4260
tacaacctgg cattctgact ataaggtcaa agggctatgt gattctaacc tcatttccat 4320
ggacatcacc ttcttctcag aggacggaga gctatcatcc ctgggaaagg agggcacagg 4380
gttcagaagt aactactttg cttatgaaac tggaggcaag gcctgcaaaa tgcaatactg 4440
caagcattgg ggagtcagac tcccatcagg tgtctggttc gagatggctg ataaggatct 4500
ctttgctgca gccagattcc ctgaatgccc agaagggtca agtatctctg ctccatctca 4560
gacctcagtg gatgtaagtc taattcagga cgttgagagg atcttggatt attccctctg 4620
ccaagaaacc tggagcaaaa tcagagcggg tcttccaatc tctccagtgg atctcagcta 4680
tcttgctcct aaaaacccag gaaccggtcc tgctttcacc ataatcaatg gtaccctaaa 4740
atactttgag accagataca tcagagtcga tattgctgct ccaatcctct caagaatggt 4800
cggaatgatc agtggaacta ccacagaaag ggaactgtgg gatgactggg caccatatga 4860
agacgtggaa attggaccca atggagttct gaggaccagt tcaggatata agtttccttt 4920
atacatgatt ggacatggta tgttggactc cgatcttcat cttagctcaa aggctcaggt 4980
gttcgaacat cctcacattc aagacgctgc ttcgcaactt cctgatgatg agagtttatt 5040
ttttggtgat actgggctat ccaaaaatcc aatcgagctt gtagaaggtt ggttcagtag 5100
ttggaaaagc tctattgcct ctttttctt tatcataggg ttaatcattg gactattctt 5160
ggttctccga gttggtatcc atctttgcat taaattaaag cacaccaaga aaagacagat 5220
ttatacagac atagagatga accgacttgg aaagtaactc aaatcctgct aggtatgaaa 5280
aaaactaaca gatatcacgc tcgagaatta attgctaggt atgaaaaaaa ctaacagata 5340
tcacgctcga gaattaattg ctagccagat tcttcatgtt tggaccaaat caacttgtga 5400
taccatgctc aaagaggcct caattatatt tgagttttta atttttatga aaaaaactaa 5460
cagcaatcat ggaagtccac gattttgaga ccgacgagtt caatgatttc aatgaagatg 5520
actatgccac aagagaattc ctgaatcccg atgagcgcat gacgtacttg aatcatgctg 5580
attacaacct gaattctcct ctaattagtg atgatattga caatttaatc aggaaattca 5640
attctcttcc aattccctcg atgtgggata gtaagaactg ggatggagtt cttgagatgt 5700
taacgtcatg tcaagccaat cccatcccaa catctcagat gcataaatgg atgggaagtt 5760
ggttaatgtc tgataatcat gatgccagtc aagggtatag tttttttacat gaagtggaca 5820
aagaggcaga aataacattt gacgtggtgg agaccttcat ccgcggctgg ggcaacaaac 5880
caattgaata catcaaaaag gaaagatgga ctgactcatt caaaattctc gcttatttgt 5940
gtcaaaagtt tttggactta cacaagttga cattaatctt aaatgctgtc tctgaggtgg 6000
aattgctcaa cttggcgagg actttcaaag gcaaagtcag aagaagttct catggaacga 6060
acatatgcag gattagggtt cccagcttgg gtcctacttt tatttcagaa ggatgggctt 6120
acttcaagaa acttgatatt ctaatggacc gaaactttct gttaatggtc aaagatgtga 6180
ttatagggag gatgcaaacg gtgctatcca tggtatgtag aatagacaac ctgttctcag 6240
agcaagacat cttctccctt ctaaatatct acagaattgg agataaaatt gtggagaggc 6300
agggaaattt ttcttatgac ttgattaaaa tggtggaacc gatatgcaac ttgaagctga 6360
tgaaattagc aagagaatca aggcctttag tcccacaatt ccctcatttt gaaaatcata 6420
tcaagacttc tgttgatgaa ggggcaaaaa ttgaccgagg tataagattc ctccatgatc 6480
agataatgag tgtgaaaaca gtggatctca cactggtgat ttatggatcg ttcagacatt 6540
ggggtcatcc ttttatagat tattacactg gactagaaaa attacattcc caagtaacca 6600
tgaagaaaga tattgatgtg tcatatgcaa aagcacttgc aagtgattta gctcggattg 6660
ttctatttca acagttcaat gatcataaaa agtggttcgt gaatggagac ttgctccctc 6720
atgatcatcc ctttaaaagt catgttaaag aaaatacatg gcccacagct gctcaagttc 6780
aagattttgg agataaatgg catgaacttc cgctgattaa atgttttgaa atacccgact 6840
tactagaccc atcgataata tactctgaca aaagtcattc aatgaatagg tcagaggtgt 6900
tgaaacatgt ccgaatgaat ccgaacactc ctatccctag taaaaaggtg ttgcagacta 6960

```
tgttggacac aaaggctacc aattggaaag aatttcttaa agagattgat gagaagggct   7020
tagatgatga tgatctaatt attggtctta aaggaaagga gagggaactg aagttggcag   7080
gtagattttt ctccctaatg tcttggaaat tgcgagaata ctttgtaatt accgaatatt   7140
tgataaagac tcatttcgtc cctatgttta aaggcctgac aatggcggac gatctaactg   7200
cagtcattaa aaagatgtta gattcctcat ccggccaagg attgaagtca tatgaggcaa   7260
tttgcatagc caatcacatt gattacgaaa aatggaataa ccaccaaagg aagttatcaa   7320
acggcccagt gttccgagtt atgggccagt tcttaggtta tccatcctta atcgagagaa   7380
ctcatgaatt ttttgagaaa agtcttatat actacaatgg aagaccagac ttgatgcgtg   7440
ttcacaacaa cacactgatc aattcaacct cccaacgagt ttgttggcaa ggacaagagg   7500
gtggactgga aggtctacgg caaaaaggat ggagtatcct caatctactg gttattcaaa   7560
gagaggctaa aatcagaaac actgctgtca aagtcttggc acaaggtgat aatcaagtta   7620
tttgcacaca gtataaaacg aagaaatcga gaaacgttgt agaattacag ggtgctctca   7680
atcaaatggt ttctaataat gagaaaatta tgactgcaat caaaataggg acagggaagt   7740
taggactttt gataaatgac gatgagacta tgcaatctgc agattacttg aattatggaa   7800
aaataccgat tttccgtgga gtgattagag ggttagagac caagagatgg tcacgagtga   7860
cttgtgtcac caatgaccaa atacccactt gtgctaatat aatgagctca gtttccacaa   7920
atgctctcac cgtagctcat tttgctgaga acccaatcaa tgccatgata cagtacaatt   7980
attttgggac atttgctaga ctcttgttga tgatgcatga tcctgctctt cgtcaatcat   8040
tgtatgaagt tcaagataag ataccgggct tgcacagttc tactttcaaa tacgccatgt   8100
tgtatttgga cccttccatt ggaggagtgt cgggcatgtc tttgtccagg tttttgatta   8160
gagccttccc agatcccgta acagaaagtc tctcattctg gagattcatc catgtacatg   8220
ctcgaagtga gcatctgaag gagatgagtg cagtatttgg aaaccccgag atagccaagt   8280
ttcgaataac tcacatagac aagctagtag aagatccaac ctctctgaac atcgctatgg   8340
gaatgagtcc agcgaacttg ttaaagactg aggttaaaaa atgcttaatc gaatcaagac   8400
aaaccatcag gaaccaggtg attaaggatg caaccatata tttgtatcat gaagaggatc   8460
ggctcagaag tttcttatgg tcaataaatc ctctgttccc tagattttta agtgaattca   8520
aatcaggcac tttttttggga gtcgcagacg ggctcatcag tctatttcaa aattctcgta   8580
ctattcggaa ctcctttaag aaaaagtatc atagggaatt ggatgatttg attgtgagga   8640
gtgaggtatc ctctttgaca catttaggga aacttcattt gagaagggga tcatgtaaaa   8700
tgtggacatg ttcagctact catgctgaca cattaagata caaatcctgg ggccgtacag   8760
ttattgggac aactgtaccc catccattag aaatgttggg tccacaacat cgaaaagaga   8820
ctccttgtgc accatgtaac acatcagggt tcaattatgt ttctgtgcat tgtccagacg   8880
ggatccatga cgtctttagt tcacggggac cattgcctgc ttatctaggg tctaaaacat   8940
ctgaatctac atctattttg cagccttggg aaagggaaag caaagtccca ctgattaaaa   9000
gagctacacg tcttagagat gctatctctt ggtttgttga acccgactct aaactagcaa   9060
tgactatact ttctaacatc cactctttaa caggcgaaga atggaccaaa aggcagcatg   9120
ggttcaaaag aacagggtct gcccttcata ggttttcgac atctcggatg agccatggtg   9180
ggttcgcatc tcagagcact gcagcattga ccaggttgat ggcaactaca gacaccatga   9240
gggatctggg agatcagaat ttcgactttt tattccaagc aacgttgctc tatgctcaaa   9300
ttaccaccac tgttgcaaga gacggatgga tcaccagttg tacagatcat tatcatattg   9360
```

cctgtaagtc ctgtttgaga cccatagaag agatcaccct ggactcaagt atggactaca 9420
cgcccccaga tgtatcccat gtgctgaaga catggaggaa tggggaaggt tcgtggggac 9480
aagagataaa acagatctat cctttagaag ggaattggaa gaatttagca cctgctgagc 9540
aatcctatca agtcggcaga tgtataggtt ttctatatgg agacttggcg tatagaaaat 9600
ctactcatgc cgaggacagt tctctatttc ctctatctat acaaggtcgt attagaggtc 9660
gaggtttctt aaaagggttg ctagacggat taatgagagc aagttgctgc caagtaatac 9720
accggagaag tctggctcat ttgaagaggc cggccaacgc agtgtacgga ggtttgattt 9780
acttgattga taaattgagt gtatcacctc cattcctttc tcttactaga tcaggaccta 9840
ttagagacga attagaaacg attccccaca agatcccaac ctcctatccg acaagcaacc 9900
gtgatatggg ggtgattgtc agaaattact tcaaatacca atgccgtcta attgaaaagg 9960
gaaaatacag atcacattat tcacaattat ggttattctc agatgtctta tccatagact 10020
tcattggacc attctctatt tccaccaccc tcttgcaaat cctatacaag ccatttttat 10080
ctgggaaaga taagaatgag ttgagagagc tggcaaatct ttcttcattg ctaagatcag 10140
gagaggggtg ggaagacata catgtgaaat tcttcaccaa ggacatatta ttgtgtccag 10200
aggaaatcag acatgcttgc aagttcggga ttgctaagga taataataaa gacatgagct 10260
atcccccttg gggaagggaa tccagaggga caattacaac aatccctgtt tattatacga 10320
ccacccctta cccaaagatg ctagagatgc ctccaagaat ccaaaatccc ctgctgtccg 10380
gaatcaggtt gggccaatta ccaactggcg ctcattataa aattcggagt atattacatg 10440
gaatgggaat ccattacagg gacttcttga gttgtggaga cggctccgga gggatgactg 10500
ctgcattact acgagaaaat gtgcatagca gaggaatatt caatagtctg ttagaattat 10560
cagggtcagt catgcgaggc gcctctcctg agcccccag tgccctagaa actttaggag 10620
gagataaatc gagatgtgta aatggtgaaa catgttggga atatccatct gacttatgtg 10680
acccaaggac ttgggactat ttcctccgac tcaaagcagg cttggggctt caaattgatt 10740
taattgtaat ggatatggaa gttcgggatt cttctactag cctgaaaatt gagacgaatg 10800
ttagaaatta tgtgcaccgg attttggatg agcaaggagt tttaatctac aagacttatg 10860
gaacatatat ttgtgagagc gaaaagaatg cagtaacaat ccttggtccc atgttcaaga 10920
cggtcgactt agttcaaaca gaatttagta gttctcaaac gtctgaagta tatatggtat 10980
gtaaaggttt gaagaaatta atcgatgaac ccaatcccga ttggtcttcc atcaatgaat 11040
cctggaaaaa cctgtacgca ttccagtcat cagaacagga atttgccaga gcaaagaagg 11100
ttagtacata ctttaccttg acaggtattc cctcccaatt cattcctgat ccttttgtaa 11160
acattgagac tatgctacaa atattcggag tacccacggg tgtgtctcat gcggctgcct 11220
taaaatcatc tgatagacct gcagatttat tgaccattag cctttttat atggcgatta 11280
tatcgtatta taacatcaat catatcagag taggaccgat acctccgaac cccccatcag 11340
atggaattgc acaaaatgtg gggatcgcta taactggtat aagcttttgg ctgagtttga 11400
tggagaaaga cattccacta tatcaacagt gtttagcagt tatccagcaa tcattcccga 11460
ttaggtggga ggctgtttca gtaaaaggag gatacaagca gaagtggagt actagaggtg 11520
atgggctccc aaaagatacc cgaatttcag actccttggc cccaatcggg aactggatca 11580
gatctctgga attggtccga aaccaagttc gtctaaatcc attcaatgag atcttgttca 11640
atcagctatg tcgtacagtg gataatcatt tgaaatggtc aaatttgcga agaaacacag 11700

-continued

```
gaatgattga atggatcaat agacgaattt caaaagaaga ccggtctata ctgatgttga  11760
agagtgacct acacgaggaa aactcttgga gagattaaaa aatcatgagg agactccaaa  11820
ctttaagtat gaaaaaaact ttgatcctta agaccctctt gtggttttta tttttatct  11880
ggttttgtgg tcttcgtggg tcggcatggc atctccacct cctcgcggtc cgacctgggc  11940
atccgaagga ggacgtcgtc cactcggatg gctaagggag gggcccccgc ggggctgcta  12000
acaaagcccg aaaggaagct gagttggctg ctgccaccgc tgagcaataa ctagcataac  12060
cccttggggc ctctaaacgg gtcttgaggg gtttttttgct gaaaggagga actatatccg  12120
gatcgagacc tcgatactag tgcggtggag ctccagcttt tgttcccttt agtgagggtt  12180
aatttcgagc ttggcgtaat catggtcata gctgtttcct gtgtgaaatt gttatccgct  12240
cacaattcca cacaacatac gagccggaag cataaagtgt aaagcctggg gtgcctaatg  12300
agtgagctaa ctcacattaa ttgcgttgcg ctcactgccc gctttccagt cgggaaacct  12360
gtcgtgccag ctgcattaat gaatcggcca acgcgcgggg agaggcggtt tgcgtattgg  12420
gcgctcttcc gcttcctcgc tcactgactc gctgcgctcg gtcgttcggc tgcggcgagc  12480
ggtatcagct cactcaaagg cggtaatacg gttatccaca gaatcagggg ataacgcagg  12540
aaagaacatg tgagcaaaag gccagcaaaa ggccaggaac cgtaaaaagg ccgcgttgct  12600
ggcgtttttc cataggctcc gcccccctga cgagcatcac aaaaatcgac gctcaagtca  12660
gaggtggcga aacccgacag gactataaag ataccaggcg tttccccctg gaagctccct  12720
cgtgcgctct cctgttccga ccctgccgct taccggatac ctgtccgcct ttctcccttc  12780
gggaagcgtg gcgctttctc atagctcacg ctgtaggtat ctcagttcgg tgtaggtcgt  12840
tcgctccaag ctgggctgtg tgcacgaacc ccccgttcag cccgaccgct gcgccttatc  12900
cggtaactat cgtcttgagt ccaacccggt aagacacgac ttatcgccac tggcagcagc  12960
cactggtaac aggattagca gagcgaggta tgtaggcggt gctacagagt tcttgaagtg  13020
gtggcctaac tacggctaca ctagaaggac agtatttggt atctgcgctc tgctgaagcc  13080
agttaccttc ggaaaaagag ttggtagctc ttgatccggc aaacaaacca ccgctggtag  13140
cggtggtttt tttgtttgca agcagcagat tacgcgcaga aaaaaaggat ctcaagaaga  13200
tcctttgatc ttttctacgg ggtctgacgc tcagtggaac gaaaactcac gttaagggat  13260
tttggtcatg agattatcaa aaaggatctt cacctagatc cttttaaatt aaaaatgaag  13320
ttttaaatca atctaaagta tatatgagta aacttggtct gacagttacc aatgcttaat  13380
cagtgaggca cctatctcag cgatctgtct atttcgttca tccatagttg cctgactccc  13440
cgtcgtgtag ataactacga tacgggaggg cttaccatct ggccccagtg ctgcaatgat  13500
accgcgagac ccacgctcac cggctccaga tttatcagca ataaaccagc cagccggaag  13560
ggccgagcgc agaagtggtc ctgcaacttt atccgcctcc atccagtcta ttaattgttg  13620
ccgggaagct agagtaagta gttcgccagt taatagtttg cgcaacgttg ttgccattgc  13680
tacaggcatc gtggtgtcac gctcgtcgtt tggtatggct tcattcagct ccggttccca  13740
acgatcaagg cgagttacat gatcccccat gttgtgcaaa aaagcggtta gctccttcgg  13800
tcctccgatc gttgtcagaa gtaagttggc cgcagtgtta tcactcatgg ttatggcagc  13860
actgcataat tctcttactg tcatgccatc cgtaagatgc ttttctgtga ctggtgagta  13920
ctcaaccaag tcattctgag aatagtgtat gcggcgaccg agttgctctt gcccggcgtc  13980
aatacgggat aataccgcgc cacatagcag aactttaaaa gtgctcatca ttggaaaacg  14040
ttcttcgggg cgaaaactct caaggatctt accgctgttg agatccagtt cgatgtaacc  14100
```

cactcgtgca cccaactgat cttcagcatc ttttactttc accagcgttt ctgggtgagc 14160
aaaaacagga aggcaaaatg ccgcaaaaaa gggaataagg gcgacacgga aatgttgaat 14220
actcatactc ttcctttttc aatattattg aagcatttat cagggttatt gtctcatgag 14280
cggatacata tttgaatgta tttagaaaaa taaacaaata ggggttccgc gcacatttcc 14340
ccgaaaagtg c 14351

<210> SEQ ID NO 21
<211> LENGTH: 15061
<212> TYPE: DNA
<213> ORGANISM: Artificial Sequence
<220> FEATURE:
<223> OTHER INFORMATION: VSV Indiana GFP vector

<400> SEQUENCE: 21
cacctaaatt gtaagcgtta atattttgtt aaaattcgcg ttaaattttt gttaaatcag 60
ctcatttttt aaccaatagg ccgaaatcgg caaaatccct tataaatcaa aagaatagac 120
cgagataggg ttgagtgttg ttccagtttg gaacaagagt ccactattaa agaacgtgga 180
ctccaacgtc aaagggcgaa aaaccgtcta tcagggcgat ggcccactac gtgaaccatc 240
accctaatca agttttttgg ggtcgaggtg ccgtaaagca ctaaatcgga accctaaagg 300
gagcccccga tttagagctt gacggggaaa gccggcgaac gtggcgagaa aggaagggaa 360
gaaagcgaaa ggagcgggcg ctagggcgct ggcaagtgta gcggtcacgc tgcgcgtaac 420
caccacaccc gccgcgctta atgcgccgct acagggcgcg tcccattcgc cattcaggct 480
gcgcaactgt tgggaagggc gatcggtgcg ggcctcttcg ctattacgcc agctggcgaa 540
agggggatgt gctgcaaggc gattaagttg ggtaacgcca gggttttccc agtcacgacg 600
ttgtaaaacg acggccagtg aattgtaata cgactcacta taggacgaag acaaacaaac 660
cattattatc attaaaaggc tcaggagaaa ctttaacagt aatcaaaatg tctgttacag 720
tcaagagaat cattgacaac acagtcgtag ttccaaaact tcctgcaaat gaggatccag 780
tggaataccc ggcagattac ttcagaaaat caaaggagat tcctctttac atcaatacta 840
caaaaagttt gtcagatcta agaggatatg tctaccaagg cctcaaatcc ggaaatgtat 900
caatcataca tgtcaacagc tacttgtatg gagcattaaa ggacatccgg ggtaagttgg 960
ataaagattg gtcaagtttc ggaataaaca tcgggaaagc aggggataca atcggaatat 1020
ttgaccttgt atccttgaaa gccctggacg gcgtacttcc agatggagta tcggatgctt 1080
ccagaaccag cgcagatgac aaatggttgc ctttgtatct acttggctta tacagagtgg 1140
gcagaacaca aatgcctgaa tacagaaaaa agctcatgga tgggctgaca aatcaatgca 1200
aaatgatcaa tgaacagttt gaacctcttg tgccagaagg tcgtgacatt tttgatgtgt 1260
ggggaaatga cagtaattac acaaaaattg tcgctgcagt ggacatgttc ttccacatgt 1320
tcaaaaaaca tgaatgtgcc tcgttcagat acggaactat tgtttccaga ttcaaagatt 1380
gtgctgcatt ggcaacattt ggacacctct gcaaaataac cggaatgtct acagaagatg 1440
taacgacctg gatcttgaac cgagaagttg cagatgaaat ggtccaaatg atgcttccag 1500
gccaagaaat tgacaaggcc gattcataca tgccttattt gatcgacttt ggattgtctt 1560
ctaagtctcc atattcttcc gtcaaaaacc ctgccttcca cttctggggg caattgacag 1620
ctcttctgct cagatccacc agagcaagga atgcccgaca gcctgatgac attgagtata 1680
catctcttac tacagcaggt ttgttgtacg cttatgcagt aggatcctct gccgacttgg 1740

```
cacaacagtt ttgtgttgga gataacaaat acactccaga tgatagtacc ggaggattga   1800
cgactaatgc accgccacaa ggcagagatg tggtcgaatg gctcggatgg tttgaagatc   1860
aaaacagaaa accgactcct gatatgatgc agtatgcgaa aagagcagtc atgtcactgc   1920
aaggcctaag agagaagaca attggcaagt atgctaagtc agaatttgac aaatgaccct   1980
ataattctca gatcacctat tatatattat gctacatatg aaaaaaacta acagatatca   2040
tggataatct cacaaaagtt cgtgagtatc tcaagtccta ttctcgtctg gatcaggcgg   2100
taggagagat agatgagatc gaagcacaac gagctgaaaa gtccaattat gagttgttcc   2160
aagaggatgg agtggaagag catactaagc cctcttattt tcaggcagca gatgattctg   2220
acacagaatc tgaaccagaa attgaagaca atcaaggctt gtatgcacca gatccagaag   2280
ctgagcaagt tgaaggcttt atacaggggc ctttagatga ctatgcagat gaggaagtgg   2340
atgttgtatt tacttcggac tggaaacagc ctgagcttga atctgacgag catggaaaga   2400
ccttacggtt gacatcgcca gagggtttaa gtggagagca gaaatcccag tggctttcga   2460
cgattaaagc agtcgtgcaa agtgccaaat actggaatct ggcagagtgc acatttgaag   2520
catcgggaga aggggtcatt atgaaggagc gccagataac tccggatgta tataaggtca   2580
ctccagtgat gaacacacat ccgtcccaat cagaagcagt atcagatgtt tggtctctct   2640
caaagacatc catgactttc caacccaaga aagcaagtct tcagcctctc accatatcct   2700
tggatgaatt gttctcatct agaggagagt tcatctctgt cggaggtgac ggacgaatgt   2760
ctcataaaga ggccatcctg ctcggcctga gatacaaaaa gttgtacaat caggcgagag   2820
tcaaatattc tctgtagact atgaaaaaaa gtaacagata tcacgatcta agtgttatcc   2880
caatccattc atcatgagtt ccttaaagaa gattctcggt ctgaagggga aaggtaagaa   2940
atctaagaaa ttagggatcg caccaccccc ttatgaagag gacactagca tggagtatgc   3000
tccgagcgct ccaattgaca aatcctattt tggagttgac gagatggaca cctatgatcc   3060
gaatcaatta agatatgaga aattcttctt tacagtgaaa atgacggtta gatctaatcg   3120
tccgttcaga acatactcag atgtggcagc cgctgtatcc cattgggatc acatgtacat   3180
cggaatggca gggaaacgtc ccttctacaa aatcttggct tttttgggtt cttctaatct   3240
aaaggccact ccagcggtat tggcagatca aggtcaacca gagtatcacg ctcactgcga   3300
aggcagggct tatttgccac ataggatggg gaagacccct cccatgctca atgtaccaga   3360
gcacttcaga agaccattca atataggtct ttacaaggga acgattgagc tcacaatgac   3420
catctacgat gatgagtcac tggaagcagc tcctatgatc tgggatcatt tcaattcttc   3480
caaattttct gatttcagag agaaggcctt aatgtttggc ctgattgtcg agaaaaaggc   3540
atctggagcg tgggtcctgg actctatcgg ccacttcaaa tgagctagtc taacttctag   3600
cttctgaaca atccccggtt tactcagtct cccctaattc cagcctctcg aacaactaat   3660
atcctgtctt ttctatccct atgaaaaaaa ctaacagaga tcgatctgtt tacgcgtcac   3720
tatgaagtgc cttttgtact tagccttttt attcattggg gtgaattgca agttcaccat   3780
agtttttcca cacaaccaaa aaggaaactg gaaaaatgtt ccttctaatt accattattg   3840
cccgtcaagc tcagatttaa attggcataa tgacttaata ggcacagcct tacaagtcaa   3900
aatgcccaag agtcacaagg ctattcaagc agacggttgg atgtgtcatg cttccaaatg   3960
ggtcactact tgtgatttcc gctggtatgg accgaagtat ataacacatt ccatccgatc   4020
cttcactcca tctgtagaac aatgcaagga aagcattgaa caaacgaaac aaggaacttg   4080
gctgaatcca ggcttccctc ctcaaagttg tggatatgca actgtgacgg atgccgaagc   4140
```

agtgattgtc caggtgactc ctcaccatgt gctggttgat gaatacacag gagaatgggt 4200
tgattcacag ttcatcaacg gaaaatgcag caattacata tgccccactg tccataactc 4260
tacaacctgg cattctgact ataaggtcaa agggctatgt gattctaacc tcatttccat 4320
ggacatcacc ttcttctcag aggacggaga gctatcatcc ctgggaaagg agggcacagg 4380
gttcagaagt aactactttg cttatgaaac tggaggcaag gcctgcaaaa tgcaatactg 4440
caagcattgg ggagtcagac tcccatcagg tgtctggttc gagatggctg ataaggatct 4500
ctttgctgca gccagattcc ctgaatgccc agaagggtca agtatctctg ctccatctca 4560
gacctcagtg gatgtaagtc taattcagga cgttgagagg atcttggatt attccctctg 4620
ccaagaaacc tggagcaaaa tcagagcggg tcttccaatc tctccagtgg atctcagcta 4680
tcttgctcct aaaaacccag gaaccggtcc tgctttcacc ataatcaatg gtaccctaaa 4740
atactttgag accagataca tcagagtcga tattgctgct ccaatcctct caagaatggt 4800
cggaatgatc agtggaacta ccacagaaag ggaactgtgg gatgactggg caccatatga 4860
agacgtggaa attggaccca atggagttct gaggaccagt tcaggatata agtttccttt 4920
atacatgatt ggacatggta tgttggactc cgatcttcat cttagctcaa aggctcaggt 4980
gttcgaacat cctcacattc aagacgctgc ttcgcaactt cctgatgatg agagtttatt 5040
ttttggtgat actgggctat ccaaaaatcc aatcgagctt gtagaaggtt ggttcagtag 5100
ttggaaaagc tctattgcct ctttttcttt tatcataggg ttaatcattg gactattctt 5160
ggttctccga gttggtatcc atctttgcat taaattaaag cacaccaaga aaagacagat 5220
ttatacagac atagagatga accgacttgg aaagtaactc aaatcctgct aggtatgaaa 5280
aaaactaaca gatatcacgc tcgaggcaat tgcgcgctag ctatgaaaaa aactaacaga 5340
tatcaccatg agcaagggcg aggaactgtt cactggcgtg gtcccaattc tcgtggaact 5400
ggatggcgat gtgaatgggc acaaattttc tgtcagcgga gagggtgaag gagatgccac 5460
atacggaaag ctcaccctga aattcatctg caccactgga aagctccctg tgccatggcc 5520
aacactggtc actaccttca cctatggcgt gcagtgcttt tccagatacc cagaccatat 5580
gaagcagcat gactttttca agagcgccat gcccgagggc tatgtgcagg agagaaccat 5640
ctttttcaaa gatgacggga actacaagac ccgcrctgaa gtcaagttcg aaggtgacac 5700
cctggtgaat agaatcgagc tgaagggcat tgactttaag gaggatggaa acattctcgg 5760
ccacaagctg gaatacaact ataactccca caatgtgtac atcatggccg acaagcaaaa 5820
gaatggcatc aaggtcaact tcaagatcag acacaacatt gaggatggat ccgtgcagct 5880
ggccgaccat tatcaacaga acactccaat cggcgacggc cctgtgctcc tcccagacaa 5940
ccattacctg tccacccagt ctgccctgtc taaagatccc aacgaaaaga gagaccacat 6000
ggtcctgctg gagtttgtga ccgctgctgg gatcacacat ggcatggacg agctgtacaa 6060
gtgatctagc cagattcttc atgtttggac caaaatcaac ttgtgatacc atgctcaaag 6120
aggcctcaaa ttatatttga gtttttttaat ttttatgaaa aaaaactacc agcaatcaat 6180
ggaagtccac gattttgaga ccgacgagtt caatgatttc aatgaagatg actatgccac 6240
aagagaattc ctgaatcccg atgagcgcat gacgtacttg aatcatgctg attacaacct 6300
gaattctcct ctaattagtg atgatattga caatttaatc aggaaattca attctcttcc 6360
aattccctcg atgtgggata gtaagaactg ggatggagtt cttgagatgt taacgtcatg 6420
tcaagccaat cccatcccaa catctcagat gcataaatgg atgggaagtt ggttaatgtc 6480
tgataatcat gatgccagtc aagggtatag ttttttacat gaagtggaca aagaggcaga 6540
aataacattt gacgtggtgg agaccttcat ccgcggctgg ggcaacaaac caattgaata 6600
catcaaaaag gaaagatgga ctgactcatt caaaattctc gcttatttgt gtcaaaagtt 6660
tttggactta cacaagttga cattaatctt aaatgctgtc tctgaggtgg aattgctcaa 6720
cttggcgagg actttcaaag gcaaagtcag aagaagttct catggaacga acatatgcag 6780
gattagggtt cccagcttgg gtcctacttt tatttcagaa ggatgggctt acttcaagaa 6840
acttgatatt ctaatggacc gaaactttct gttaatggtc aaagatgtga ttatagggag 6900
gatgcaaacg gtgctatcca tggtatgtag aatagacaac ctgttctcag agcaagacat 6960
cttctccctt ctaaatatct acagaattgg agataaaatt gtggagaggc agggaaattt 7020
ttcttatgac ttgattaaaa tggtggaacc gatatgcaac ttgaagctga tgaaattagc 7080
aagagaatca aggcctttag tcccacaatt ccctcatttt gaaaatcata tcaagacttc 7140
tgttgatgaa ggggcaaaaa ttgaccgagg tataagattc ctccatgatc agataatgag 7200
tgtgaaaaca gtggatctca cactggtgat ttatggatcg ttcagacatt ggggtcatcc 7260
ttttatagat tattacactg gactagaaaa attacattcc caagtaacca tgaagaaaga 7320
tattgatgtg tcatatgcaa aagcacttgc aagtgattta gctcggattg ttctatttca 7380
acagttcaat gatcataaaa agtggttcgt gaatggagac ttgctccctc atgatcatcc 7440
ctttaaaagt catgttaaag aaaatacatg gcccacagct gctcaagttc aagattttgg 7500
agataaatgg catgaacttc cgctgattaa atgttttgaa atacccgact tactagaccc 7560
atcgataata tactctgaca aaagtcattc aatgaatagg tcagaggtgt tgaaacatgt 7620
ccgaatgaat ccgaacactc ctatccctag taaaaaggtg ttgcagacta tgttggacac 7680
aaaggctacc aattggaaag aatttcttaa agagattgat gagaagggct tagatgatga 7740
tgatctaatt attggtctta aggaaaagga gagggaactg aagttggcag gtagattttt 7800
ctccctaatg tcttggaaat tgcgagaata ctttgtaatt accgaatatt tgataaagac 7860
tcatttcgtc cctatgttta aaggcctgac aatggcggac gatctaactg cagtcattaa 7920
aaagatgtta gattcctcat ccggccaagg attgaagtca tatgaggcaa tttgcatagc 7980
caatcacatt gattacgaaa aatggaataa ccaccaaagg aagttatcaa acggcccagt 8040
gttccgagtt atgggccagt tcttaggtta tccatcctta atcgagagaa ctcatgaatt 8100
ttttgagaaa agtcttatat actacaatgg aagaccagac ttgatgcgtg ttcacaacaa 8160
cacactgatc aattcaacct cccaacgagt ttgttggcaa ggacaagagg gtggactgga 8220
aggtctacgg caaaaaggat ggagtatcct caatctactg gttattcaaa gagaggctaa 8280
aatcagaaac actgctgtca aagtcttggc acaaggtgat aatcaagtta tttgcacaca 8340
gtataaaacg aagaaatcga gaaacgttgt agaattacag ggtgctctca atcaaatggt 8400
ttctaataat gagaaaatta tgactgcaat caaaataggg acagggaagt taggactttt 8460
gataaatgac gatgagacta tgcaatctgc agattacttg aattatggaa aaataccgat 8520
tttccgtgga gtgattagag ggttagagac caagagatgg tcacgagtga cttgtgtcac 8580
caatgaccaa atacccactt gtgctaatat aatgagctca gtttccacaa atgctctcac 8640
cgtagctcat tttgctgaga acccaatcaa tgccatgata cagtacaatt attttgggac 8700
atttgctaga ctcttgttga tgatgcatga tcctgctctt cgtcaatcat tgtatgaagt 8760
tcaagataag ataccgggct tgcacagttc tactttcaaa tacgccatgt tgtatttgga 8820
cccttccatt ggaggagtgt cgggcatgtc tttgtccagg tttttgatta gagccttccc 8880

```
agatcccgta acagaaagtc tctcattctg gagattcatc catgtacatg ctcgaagtga   8940
gcatctgaag gagatgagtg cagtatttgg aaaccccgag atagccaagt ttcgaataac   9000
tcacatagac aagctagtag aagatccaac ctctctgaac atcgctatgg gaatgagtcc   9060
agcgaacttg ttaaagactg aggttaaaaa atgcttaatc gaatcaagac aaaccatcag   9120
gaaccaggtg attaaggatg caaccatata tttgtatcat gaagaggatc ggctcagaag   9180
tttcttatgg tcaataaatc ctctgttccc tagattttta agtgaattca aatcaggcac   9240
tttttggga gtcgcagacg ggctcatcag tctatttcaa aattctcgta ctattcggaa   9300
ctcctttaag aaaaagtatc atagggaatt ggatgatttg attgtgagga gtgaggtatc   9360
ctctttgaca catttaggga aacttcattt gagaagggga tcatgtaaaa tgtggacatg   9420
ttcagctact catgctgaca cattaagata caaatcctgg ggccgtacag ttattgggac   9480
aactgtaccc catccattag aaatgttggg tccacaacat cgaaaagaga ctccttgtgc   9540
accatgtaac acatcagggt tcaattatgt ttctgtgcat tgtccagacg ggatccatga   9600
cgtctttagt tcacggggac cattgcctgc ttatctaggg tctaaaacat ctgaatctac   9660
atctattttg cagccttggg aaagggaaag caaagtccca ctgattaaaa gagctacacg   9720
tcttagagat gctatctctt ggtttgttga acccgactct aaactagcaa tgactatact   9780
ttctaacatc cactctttaa caggcgaaga atggaccaaa aggcagcatg ggttcaaaag   9840
aacagggtct gcccttcata ggttttcgac atctcggatg agccatggtg ggttcgcatc   9900
tcagagcact gcagcattga ccaggttgat ggcaactaca gacaccatga gggatctggg   9960
agatcagaat ttcgactttt tattccaagc aacgttgctc tatgctcaaa ttaccaccac  10020
tgttgcaaga gacggatgga tcaccagttg tacagatcat tatcatattg cctgtaagtc  10080
ctgtttgaga cccatagaag agatcaccct ggactcaagt atggactaca cgcccccaga  10140
tgtatcccat gtgctgaaga catggaggaa tggggaaggt tcgtggggac aagagataaa  10200
acagatctat cctttagaag ggaattggaa gaatttagca cctgctgagc aatcctatca  10260
agtcggcaga tgtataggtt ttctatatgg agacttggcg tatagaaaat ctactcatgc  10320
cgaggacagt tctctatttc ctctatctat acaaggtcgt attagaggtc gaggtttctt  10380
aaaagggttg ctagacggat taatgagagc aagttgctgc caagtaatac accggagaag  10440
tctggctcat ttgaagaggc cggccaacgc agtgtacgga ggtttgattt acttgattga  10500
taaattgagt gtatcacctc cattcctttc tcttactaga tcaggaccta ttagagacga  10560
attagaaacg attccccaca agatcccaac ctcctatccg acaagcaacc gtgatatggg  10620
ggtgattgtc agaaattact tcaaatacca atgccgtcta attgaaaagg gaaaatacag  10680
atcacattat tcacaattat ggttattctc agatgtctta tccatagact tcattggacc  10740
attctctatt tccaccaccc tcttgcaaat cctatacaag ccatttttat ctgggaaaga  10800
taagaatgag ttgagagagc tggcaaatct ttcttcattg ctaagatcag gagaggggtg  10860
ggaagacata catgtgaaat tcttcaccaa ggacatatta ttgtgtccag aggaaatcag  10920
acatgcttgc aagttcggga ttgctaagga taataataaa gacatgagct atcccccttg  10980
gggaagggaa tccagaggga caattacaac aatccctgtt tattatacga ccacccctta  11040
cccaaagatg ctagagatgc ctccaagaat ccaaaatccc ctgctgtccg gaatcaggtt  11100
gggccaatta ccaactggcg ctcattataa aattcggagt atattacatg gaatgggaat  11160
ccattacagg gacttcttga gttgtggaga cggctccgga gggatgactg ctgcattact  11220
```

acgagaaaat gtgcatagca gaggaatatt caatagtctg ttagaattat cagggtcagt 11280
catgcgaggc gcctctcctg agccccccag tgccctagaa actttaggag gagataaatc 11340
gagatgtgta aatggtgaaa catgttggga atatccatct gacttatgtg acccaaggac 11400
ttgggactat ttcctccgac tcaaagcagg cttggggctt caaattgatt taattgtaat 11460
ggatatggaa gttcgggatt cttctactag cctgaaaatt gagacgaatg ttagaaatta 11520
tgtgcaccgg attttggatg agcaaggagt tttaatctac aagacttatg gaacatatat 11580
ttgtgagagc gaaaagaatg cagtaacaat ccttggtccc atgttcaaga cggtcgactt 11640
agttcaaaca gaatttagta gttctcaaac gtctgaagta tatatggtat gtaaaggttt 11700
gaagaaatta atcgatgaac ccaatcccga ttggtcttcc atcaatgaat cctggaaaaa 11760
cctgtacgca ttccagtcat cagaacagga atttgccaga gcaaagaagg ttagtacata 11820
ctttaccttg acaggtattc cctcccaatt cattcctgat ccttttgtaa acattgagac 11880
tatgctacaa atattcggag tacccacggg tgtgtctcat gcggctgcct taaaatcatc 11940
tgatagacct gcagatttat tgaccattag cctttttat atggcgatta tatcgtatta 12000
taacatcaat catatcagag taggaccgat acctccgaac cccccatcag atggaattgc 12060
acaaaatgtg ggatcgcta taactggtat aagcttttgg ctgagtttga tggagaaaga 12120
cattccacta tatcaacagt gtttagcagt tatccagcaa tcattcccga ttaggtggga 12180
ggctgtttca gtaaaaggag gatacaagca gaagtggagt actagaggtg atgggctccc 12240
aaaagatacc cgaatttcag actccttggc cccaatcggg aactggatca gatctctgga 12300
attggtccga aaccaagttc gtctaaatcc attcaatgag atcttgttca atcagctatg 12360
tcgtacagtg gataatcatt tgaaatggtc aaatttgcga agaaacacag gaatgattga 12420
atggatcaat agacgaattt caaaagaaga ccggtctata ctgatgttga agagtgacct 12480
acacgaggaa aactcttgga gagattaaaa aatcatgagg agactccaaa ctttaagtat 12540
gaaaaaaact ttgatcctta agaccctctt gtggttttta ttttttatct ggttttgtgg 12600
tcttcgtggg tcggcatggc atctccacct cctcgcggtc cgacctgggc atccgaagga 12660
ggacgtcgtc cactcggatg gctaagggag gggcccccgc ggggctgcta acaaagcccg 12720
aaaggaagct gagttggctg ctgccaccgc tgagcaataa ctagcataac cccttggggc 12780
ctctaaacgg gtcttgaggg gtttttgct gaaaggagga actatatccg gatcgagacc 12840
tcgatactag tgcggtggag ctccagcttt tgttcccttt agtgagggtt aatttcgagc 12900
ttggcgtaat catggtcata gctgtttcct gtgtgaaatt gttatccgct cacaattcca 12960
cacaacatac gagccggaag cataaagtgt aaagcctggg gtgcctaatg agtgagctaa 13020
ctcacattaa ttgcgttgcg ctcactgccc gctttccagt cgggaaacct gtcgtgccag 13080
ctgcattaat gaatcggcca acgcgcgggg agaggcggtt tgcgtattgg gcgctcttcc 13140
gcttcctcgc tcactgactc gctgcgctcg gtcgttcggc tgcggcgagc ggtatcagct 13200
cactcaaagg cggtaatacg gttatccaca gaatcagggg ataacgcagg aaagaacatg 13260
tgagcaaaag gccagcaaaa ggccaggaac cgtaaaaagg ccgcgttgct ggcgtttttc 13320
cataggctcc gcccccctga cgagcatcac aaaaatcgac gctcaagtca gaggtggcga 13380
aacccgacag gactataaag ataccaggcg tttccccctg gaagctccct cgtgcgctct 13440
cctgttccga ccctgccgct taccggatac ctgtccgcct ttctcccttc gggaagcgtg 13500
gcgctttctc atagctcacg ctgtaggtat ctcagttcgg tgtaggtcgt tcgctccaag 13560
ctgggctgtg tgcacgaacc ccccgttcag cccgaccgct gcgccttatc cggtaactat 13620
cgtcttgagt ccaacccggt aagacacgac ttatcgccac tggcagcagc cactggtaac 13680
aggattagca gagcgaggta tgtaggcggt gctacagagt tcttgaagtg gtggcctaac 13740
tacggctaca ctagaaggac agtatttggt atctgcgctc tgctgaagcc agttaccttc 13800
ggaaaaagag ttggtagctc ttgatccggc aaacaaacca ccgctggtag cggtggtttt 13860
tttgtttgca agcagcagat tacgcgcaga aaaaaaggat ctcaagaaga tcctttgatc 13920
ttttctacgg ggtctgacgc tcagtggaac gaaaactcac gttaagggat tttggtcatg 13980
agattatcaa aaaggatctt cacctagatc cttttaaatt aaaaatgaag ttttaaatca 14040
atctaaagta tatatgagta aacttggtct gacagttacc aatgcttaat cagtgaggca 14100
cctatctcag cgatctgtct atttcgttca tccatagttg cctgactccc cgtcgtgtag 14160
ataactacga tacgggaggg cttaccatct ggccccagtg ctgcaatgat accgcgagac 14220
ccacgctcac cggctccaga tttatcagca ataaaccagc cagccggaag ggccgagcgc 14280
agaagtggtc ctgcaacttt atccgcctcc atccagtcta ttaattgttg ccgggaagct 14340
agagtaagta gttcgccagt taatagtttg cgcaacgttg ttgccattgc tacaggcatc 14400
gtggtgtcac gctcgtcgtt tggtatggct tcattcagct ccggttccca acgatcaagg 14460
cgagttacat gatcccccat gttgtgcaaa aaagcggtta gctccttcgg tcctccgatc 14520
gttgtcagaa gtaagttggc cgcagtgtta tcactcatgg ttatggcagc actgcataat 14580
tctcttactg tcatgccatc cgtaagatgc ttttctgtga ctggtgagta ctcaaccaag 14640
tcattctgag aatagtgtat gcggcgaccg agttgctctt gcccggcgtc aatacgggat 14700
aataccgcgc cacatagcag aactttaaaa gtgctcatca ttggaaaacg ttcttcgggg 14760
cgaaaactct caaggatctt accgctgttg agatccagtt cgatgtaacc cactcgtgca 14820
cccaactgat cttcagcatc ttttactttc accagcgttt ctgggtgagc aaaaacagga 14880
aggcaaaatg ccgcaaaaaa gggaataagg gcgacacgga aatgttgaat actcatactc 14940
ttcctttttc aatattattg aagcatttat cagggttatt gtctcatgag cggatacata 15000
tttgaatgta tttagaaaaa taaacaaata ggggttccgc gcacatttcc ccgaaaagtg 15060
c 15061

<210> SEQ ID NO 22
<211> LENGTH: 11115
<212> TYPE: DNA
<213> ORGANISM: Vesicular stomatitis Indiana virus
<220> FEATURE:
<223> OTHER INFORMATION: Vesicular stomatitis Indiana virus strain T1026R1, complete genome (GeneBank: MH919398.1)

<400> SEQUENCE: 22
tcaggagaaa ctttaacagt aatcaaaatg tctgttacag tcaagagaat cattgacaac 60
acagtcatag ttccaaaact tcctgcaaat gaggatccag tggaataccc ggcagattac 120
ttcagaaaat caaaggagat tcctctttac atcaatacta caaaaagttt gtcagatcta 180
agaggatatg tctaccaagg cctcaaatcc ggaaatgtat caatcataca tgtcaacagc 240
tacttgtatg gagcattgaa ggacatccgg ggtaagttgg ataaagattg gtcaagtttc 300
ggaataaaca tcgggaaggc aggggataca atcggaatat ttgaccttgt atccttgaaa 360
gccctggacg gtgtacttcc agatggagta tcggatgctt ccagaaccag cgcagatgac 420
aaatggttgc ctttgtatct acttggctta tacagagtgg gcagaacaca aatgcctgaa 480
tacagaaaaa ggctcatgga tgggctgaca aatcaatgca aaatgatcaa tgaacagttt 540

```
gaacctcttg tgccagaagg tcgtgacatt tttgatgtgt ggggaaatga cagtaattac    600
acaaaaattg tcgctgcagt ggacatgttc ttccacatgt tcaaaaaaca tgaatgtgcc    660
tcgttcagat acggaactat tgtttccaga ttcaaagatt gtgctgcatt ggcaacattt    720
ggacacctct gcaaaataac cggaatgtct acagaagatg taacgacctg gatcttgaac    780
cgagaagttg cagatgagat ggtccaaatg atgcttccag gccaagaaat tgacaaggcc    840
gattcataca tgccttattt gatcgacttt ggattgtctt ctaagtctcc atattcttcc    900
gtcaaaaacc ctgccttcca cttctggggg caattgacag ctcttctgct cagatccacc    960
agagcaagga atgcccgaca gcctgatgac attgagtata catctcttac tacagcaggt   1020
ttgttgtacg cttatgcagt aggatcctct gctgacttgg cacaacagtt ttgtgttgga   1080
gatagcaaat acactccaga tgatagtacc ggaggattga cgactaatgc accgccacaa   1140
ggcagagatg tggtcgaatg gctcggatgg tttgaagatc aaaacagaaa accgactcct   1200
gatatgatgc agtatgcgaa acgagcagtc atgtcactgc aaggcctaag agagaagaca   1260
attggcaagt atgctaagtc agaatttgac aaatgaccct ataattctca gatcacctat   1320
tatatattat gctacatatg aaaaaaacta acagatatca tggataatct cacaaaagtt   1380
cgtgagtatc tcaagtccta ttctcgtcta gatcaggcgg taggagagat agatgagatc   1440
gaagcacaac gagctgaaaa gtccaattat gagttgttcc aagaggacgg agtggaagag   1500
catactaggc cctcttattt tcaggcagca gatgattctg acacagaatc tgaaccagaa   1560
attgaagaca atcaaggctt gtatgtacca gatccggaag ctgagcaagt tgaaggcttt   1620
atacaggggc ctttagatga ctatgcggat gaggacgtgg atgttgtatt cacttcggac   1680
tggaaacagc ctgagcttga atccgacgag catggaaaga ccttacggtt gacattgcca   1740
gagggtttaa gtggagagca gaaatcccag tggcttttga cgattaaagc agtcgttcaa   1800
agtgccaaac actggaatct ggcagagtgc acatttgaag catcgggaga aggggtcatc   1860
ataaaaaagc gccagataac tccggatgta tataaggtca ctccagtgat gaacacacat   1920
ccgtcccaat cggaagccgt atcagatgtt tggtctctct caaagacatc catgactttc   1980
caacccaaga aagcaagtct tcagcctctc accatatcct tggatgaatt gttctcatct   2040
agaggagaat tcatctctgt cggaggtaac ggacgaatgt ctcataaaga ggccatcctg   2100
ctcggtctga ggtacaaaaa gttgtacaat caggcgagag tcaaatattc tctgtagact   2160
atgaaaaaaa gtaacagata tcacaatcta agtgttatcc caatccattc atcatgagtt   2220
ccttaaagaa gattctcggt ctgaagggga aaggtaagaa atctaagaaa ttagggatcg   2280
caccaccccc ttatgaagag gacactaaca tggagtatgc tccgagcgct ccaattgaca   2340
aatcctattt tggagttgac gagagggaca ctcatgatcc gcatcaatta agatatgaga   2400
aattcttctt tacagtgaaa atgacggtta gatctaatcg tccgttcaga acatactcag   2460
atgtggcagc cgctgtatcc cattgggatc acatgtacat cggaatggca gggaaacgtc   2520
ccttctacaa gatcttggct tttttgggtt cttctaatct aaaggccact ccagcggtat   2580
tggcagatca aggtcaacca gagtatcacg ctcactgtga aggcagggct tatttgccac   2640
acagaatggg gaagacccct cccatgctca atgtaccaga gcacttcaga agaccattca   2700
atataggtct ttacaaggga acggttgagc tcacaatgac catctacgat gatgagtcac   2760
tggaagcagc tcctatgatc tgggatcatt tcaattcttc caaattttct gatttcagag   2820
agaaggcctt aatgtttggc ctgattgtcg agaaaaaggc atctggagct tgggtcctgg   2880
```

-continued

```
attctgtcag ccacttcaaa tgagctagtc tagcttccag cttctgaaca atccccggtt   2940
tactcagtct ctcctaattc cagcctttcg aacaactaat atcctgtctt ttctatccct   3000
atgaaaaaaa ctaacagaga tcgatctgtt tccttgacac catgaagtgc cttttgtact   3060
tagctttttt attcatcggg gtgaattgca agttcaccat agtttttcca tacaaccaaa   3120
aaggaaactg gaaaaatgtt ccttccaatt accattattg cccgtcaagc tcagatttaa   3180
attggcataa tgacttaata ggcacagcct tacaagtcaa aatgcccaag agtcacaagg   3240
ctattcaagc agacggttgg atgtgtcatg cttccaaatg ggtcactact tgtgatttcc   3300
gctggtacgg accgaagtat ataacacatt ccatccgatc cttcactcca tctgtagaac   3360
aatgcaagga aagcattgaa caaacgaaac aaggaacttg gctgaatcca ggcttccctc   3420
ctcaaagttg tggatatgca actgtgacgg atgctgaagc agcgattgtc caggtgactc   3480
ctcaccatgt gcttgttgat gaatacacag gagaatgggt tgattcacag ttcatcaacg   3540
gaaaatgcag caatgacata tgccccactg tccataactc cacaacctgg cattccgact   3600
ataaggtcaa agggctatgt gattctaacc tcatttccat ggacatcacc ttcttctcag   3660
aggacggaga gctatcatcc ctaggaaagg agggcacagg gttcagaagt aactactttg   3720
cttatgaaac tggagacaag gcctgcaaaa tgcagtactg caagcattgg ggagtcagac   3780
tcccatcagg tgtctggttc gagatggctg ataaggatct ctttgctgca gccagattcc   3840
ctgaatgccc agaagggtca agtatctctg ctccatctca gacctcagtg gatgtaagtc   3900
tcattcagga cgttgagagg atcttggatt attccctctg ccaagaaacc tggagcaaaa   3960
tcagagcggg tcttcccatc tctccagtgg atctcagcta tcttgctcct aaaaacccag   4020
gaaccggtcc tgtctttacc ataatcaatg gtaccctaaa atactttgag accagataca   4080
tcagagtcga tattgctgct ccaatcctct caagaatggt cggaatgatc agtggaacta   4140
ccacagaaag ggaactgtgg gatgactggg ctccatatga agacgtggaa attggaccca   4200
atggagttct gaggaccagt tcaggatata agtttccttt atatatgatt ggacatggta   4260
tgttggactc cgatcttcat cttagctcaa aggctcaggt gtttgaacat cctcacattc   4320
aagacgctgc tgcgcagctt cctgatgatg agactttatt ttttggtgat actgggctat   4380
ccaaaaatcc aatcgagttt gtagaaggtt ggttcagtag ttggaagagc tctattgcct   4440
ctttttctt tatcataggg ttaatcattg gactattctt ggttctccga gttggtattt   4500
atctttgcat taaattaaag cacaccaaga aaagacagat ttatacagac atagagatga   4560
accgacttgg gaagtaactc aaatcctgca caacagattc ttcatgtttg aaccaaatca   4620
acttgtgata tcatgctcaa agaggcctta attatatttt aatttttaat ttttatgaaa   4680
aaaactaaca gcaatcatgg aagtccacga ttttgagacc gacgagttca atgatttcaa   4740
tgaagatgac tatgccacaa gagaattcct gaatcccgat gagcgcatga cgtacttgaa   4800
tcatgctgat tacaatttga attctcctct aattagtgat gatattgaca atttgatcag   4860
gaaattcaat tctcttccga ttccctcgat gtgggatagt aagaactggg atggagttct   4920
tgagatgtta acatcatgtc aagccaatcc catctcaaca tctcagatgc ataaatggat   4980
gggaagttgg ttaatgtctg ataatcatga tgccagtcaa gggtatagtt ttttacatga   5040
agtggacaaa gaggcagaaa taacatttga cgtggtggag accttcatcc gcggctgggg   5100
caacaaacca attgaataca tcaaaaagga aagatggact gactcattca aaattctcgc   5160
ttatttgtgt caaaagtttt tggacttaca caagttgaca ttaatcttaa atgctgtctc   5220
tgaggtggaa ttgctcaact tggcgaggac tttcaaaggc aaagtcagaa gaagttctca   5280
```

tggaacgaac atatgcaggc ttagggttcc cagcttgggt cctactttta tttcagaagg 5340
atgggcttac ttcaagaaac ttgatattct aatggaccga aactttctgt taatggtcaa 5400
agatgtgatt atagggagga tgcaaacggt gctatccatg gtatgtagaa tagacaacct 5460
gttctcagag caagacatct tctccctcct aaatatctac agaattggag ataaaattgt 5520
ggagaggcag ggaaattttt cttatgactt gattaaaatg gtggaaccga tatgcaactt 5580
gaagctgatg aaattagcaa gagaatcaag gcctttagtc ccacaattcc ctcattttga 5640
aaatcatatc aagacttctg ttgatgaagg ggcaaaaatt gaccgaggta taagattcct 5700
ccatgatcag ataatgagtg tgaaaacagt ggatctcaca ctggtgattt atggatcgtt 5760
cagacattgg ggtcatcctt ttatagatta ttacgctgga ctagaaaaat tacattccca 5820
agtaaccatg aagaaagata ttgatgtgtc atatgcaaaa gcacttgcaa gtgatttagc 5880
tcggattgtt ctatttcaac agttcaatga tcataaaaag tggttcgtga atggagactt 5940
gctccctcat gatcatccct ttaaaagtca tgttaaagaa aatacatggc ccacagctgc 6000
tcaagttcaa gattttggag ataaatggca tgaacttccg ctgattaaat gttttgaaat 6060
acccgactta ctagacccat cgataatata ctctgacaaa agtcattcaa tgaataggtc 6120
agaggtgttg aaacatgtcc gaatgaatcc gaacactcct atccctagta aaaaggtgtt 6180
gcagactatg ttggacacaa aggctaccaa ttggaaagaa tttcttaaag agattgatga 6240
gaagggctta gatgatgatg atctaattat tggtcttaaa ggaaaggaga gggaactgaa 6300
gttggcaggt agatttttct ccctaatgtc ttggaaattg cgagaatact ttgtaattac 6360
cgaatatttg ataaagactc atttcgtccc tatgtttaaa ggcctgacaa tggcggacga 6420
tctaaccgca gtcattaaaa agatgttaga ttcctcatcc ggccaaggat tgaagtcata 6480
tgaggcaatt tgcatagcca atcacattga ttacgaaaaa tggaataacc accaaaggaa 6540
gttatcaaac ggcccagtgt tccgagttat gggccagttc ttaggttatc catccttaat 6600
cgagagaact catgaatttt ttgagaaaag tcttatatac tacaatggaa gaccagactt 6660
gatgcgtgtt cacaacaaca cactgatcaa ttcaacctcc caacgagttt gttggcaagg 6720
acaagagggt ggactggaag gtctacggca aaaaggatgg agtatcctca atctactggt 6780
tattcaaaga gaggctaaaa tcagaaacac tgctgtcaaa gtcttggcac aaggtgataa 6840
tcaagttatt tgcacacagt ataaaacgaa gaaatcgaga aacgttgtag aattacaggg 6900
tgctctcaat caaatggttt ctaataatga gaaaattatg actgcaatca aaatagggac 6960
agggaagtta ggacttttga taaatgacga tgagactatg caatctgcag attacttgaa 7020
ttatggaaaa ataccgattt tccgtggagt gattagaggg ttagagacca agagatggtc 7080
acgagtgact tgtgtcacca atgaccaaat acccacttgt gctaatataa tgagctcagt 7140
ttccacaaat gctctcaccg tagctcattt tgctgagaac ccaatcaatg ccatgataca 7200
gtacaattat tttgggacat ttgctagact cttgttgatg atgcatgatc ctgctcttcg 7260
tcaatcattg tatgaagttc aagataagat accgggattg cacagttcta ctttcaaata 7320
cgccatgttg tatttggacc cttccattgg aggagtgtcg ggcatgtctt tgtccaggtt 7380
tttgattaga gccttcccag atcccgtaac agaaagtctc tcattctgga gattcatcca 7440
tgtacatgct cgaagtgagc atctgaagga gatgagtgca gtatttggaa accccgagat 7500
agccaagttt cgaataactc acatagacaa gctagtagaa gatccaacct ctctgaacat 7560
cgctatggga atgagtccag cgaacttgtt aaagactgag gttaaaaaat gcttaatcga 7620
atcaagacaa accatcagga accaggtgat taaggatgca accatatatt tgtatcatga 7680
agaggatcgg ctcagaagtt tcttatggtc aataaatcct ctgttcccta gatttttaag 7740
tgaattcaaa tcaggcactt ttttgggagt cgcagacggg ctcatcagtc tatttcaaaa 7800
ttctcgtact attcggaact cctttaagaa aaagtatcat agggaattgg atgatttgat 7860
tgtgaggagt gaggtatcct ctttgacaca tttagggaaa cttcatttga gaaggggatc 7920
atgtaaaatg tggacatgtt cagctactca tgctgacaca ttaagataca aatcctgggg 7980
ccgtacagtt attgggacaa ctgtacccca tccattagaa atgttgggtc cacaacatcg 8040
gaaagagact ccttgtgcac catgtaacac atcagggttc aattatgttt ctgtgcattg 8100
tccagacggg atccatgacg tctttagttc acggggacca ttgcctgctt atctagggtc 8160
taaaacatct gaatctacat ctattttgca gccttgggaa agggaaagca aagtcccact 8220
gattaaaaga gctacacgtc ttagagatgc tatctcttgg tttgttgaac ccgactctaa 8280
actagcaatg actatacttt ctaacatcca ctctttaaca ggcgaagaat ggaccaaaag 8340
gcagcatggg ttcaaaagaa cagggtctgc ccttcatagg ttttcgacat ctcggatgag 8400
ccatggtggg ttcgcatctc agagcactgc agcattgacc aggttgatgg caactacaga 8460
caccatgagg gatctgggag atcagaattt cgacttttta ttccaggcaa cgttgctcta 8520
tgctcagatt accaccactg ttgcaagaga cggatggatc accagttgta cagatcatta 8580
tcatattgcc tgtaagtcct gtttgagacc catagaagag atcaccctgg actcaagtat 8640
ggactacacg cccccagatg tatcccatgt gctgaagaca tggaggaatg gggaaggttc 8700
gtggggacaa gagataaaac agatctatcc tttagaaggg aattggaaga atttagcacc 8760
tgctgagcaa tcctatcaag tcggcagatg tataggtttt ctatatggag acttggcgta 8820
tagaaaatct actcatgccg aggacagttc tctatttcct ctatctatac aaggtcgtat 8880
tagaggtcga ggtttcttaa aagggttgct agacggatta atgagagcaa gttgctgcca 8940
agtaatacac cggagaagtc tggctcattt gaagaggccg gccaacgcag tgtacggagg 9000
tttgatttac ttgattgata aattgagtgt atcacctcca ttcctttctc ttactagatc 9060
aggacctatt agagacgaat tagaaacgat tccccacaag atcccaacct cctatccgac 9120
aagcaaccgt gatatggggg tgattgtcag aaattacttc aaataccaat gccgtctaat 9180
tgaaaaggga aaatacagat cacattattc acaattatgg ttattctcag atgtcttatc 9240
catagacttc attggaccat tctctatttc caccaccctc ttgcaaatcc tatacaagcc 9300
atttttatct gggaaagata agaatgagtt gagagagctg gcaaatcttt cttcattgct 9360
aagatcagga gaggggtggg aagacataca tgtgaaattc ttcaccaagg acatattatt 9420
gtgtccagag gaaatcagac atgcttgcaa gttcgggatt gctaaggata ataataaaga 9480
catgagctat ccccccttggg gaagggaatc cagagggaca attacaacaa tccctgttta 9540
ttatacgacc accccttacc caaagatgct agagatgcct ccaagaatcc aaaatcccct 9600
gctgtccgga atcaggttgg gccagttacc aactggcgct cattataaaa ttcggagtat 9660
attacatgga atgggaatcc attacaggga cttcttgagt tgtggagacg gctccggagg 9720
gatgactgct gcattactac gagaaaatgt gcatagcaga ggaatattca atagtctgtt 9780
agaattatca gggtcagtca tgcgaggcgc ctctcctgag ccccccagtg ccctagaaac 9840
tttaggagga gataaatcga gatgtgtaaa tggtgaaaca tgttgggaat atccatctga 9900
cttatgtgac ccaaggactt gggactattt cctccgactc aaagcaggct tggggcttca 9960
aattgattta attgtaatgg atatggaagt tcgggattct tctactagcc tgaaaattga 10020
gacgaatgtt agaaattatg tgcaccggat tttggatgag caaggagttt taatctacaa 10080
gacttatgga acatatattt gtgagagcga aaagaatgca gtaacaatcc ttggtcccat 10140
gttcaagacg gtcgacttag ttcaaacaga atttagtagt tctcaaacgt ctgaagtata 10200
tatggtatgt aaaggtttga agaaattaat cgatgaaccc aatcccgatt ggtcttccat 10260
caatgaatcc tggaaaaacc tgtacgcatt ccagtcatca gaacaggaat ttgccagagc 10320
aaagaaggtt agtacatact ttaccttgac aggtattccc tcccaattca ttcctgatcc 10380
ttttgtaaac attgagacta tgctacaaat attcggagta cccacgggtg tgtctcatgc 10440
ggctgcctta aaatcatctg atagacctgc agatttattg accattagcc tttttatat 10500 ggcgattata tcgtattata acatcaatca tatcagagta ggaccgatac ctccgaaccc 10560
cccatcagat ggaattgcac aaaatgtggg gatcgctata actggtataa gcttttggct 10620
gagtttgatg gagaaagaca ttccactata tcaacagtgt ttagcagtta tccagcaatc 10680
attcccgatt aggtgggagg ctgtttcagt aaaaggagga tacaagcaga agtggagtac 10740
tagaggtgat gggctcccaa aggatacccg aatttcagac tccttggccc caatcgggaa 10800
ctggatcaga tctctggaat tggtccgaaa ccaagttcgt ctaaatccat tcaatgagat 10860
cttgttcaat cagctatgtc gtacagtgga taatcatttg aaatggtcaa atttgcgaaa 10920
aaacacagga atgattgaat ggatcaatag acgaatttca aaagaagacc ggtctatact 10980
gatgttgaag agtgacctac atgaggaaaa ctcttggaga gattaaaaaa tcatgaggag 11040
actccaaact ttaagtatga aaaaaacttt gatccttaag accctcttgt ggtttttatt 11100
ttttatctgg ttttg 11115

<210> SEQ ID NO 23
<211> LENGTH: 20
<212> TYPE: DNA
<213> ORGANISM: Artificial Sequence
<220> FEATURE:
<223> OTHER INFORMATION: primer 49bp-before-FseI based on VSV Indiana GFP

<400> SEQUENCE: 23
gctgccaagt aatacaccgg 20

<210> SEQ ID NO 24
<211> LENGTH: 21
<212> TYPE: DNA
<213> ORGANISM: Artificial Sequence
<220> FEATURE:
<223> OTHER INFORMATION: primer 50bp-after-SfoI based on VSV Indiana GFP

<400> SEQUENCE: 24
tttatctcct cctaaagttt c 21

<210> SEQ ID NO 25
<211> LENGTH: 42
<212> TYPE: DNA
<213> ORGANISM: Artificial Sequence
<220> FEATURE:
<223> OTHER INFORMATION: MT1620insertGGSG for

<400> SEQUENCE: 25
ggctcaggcg gtggatccgg ctacccaaag atgctagaga tg 42

<210> SEQ ID NO 26
<211> LENGTH: 42

<212> TYPE: DNA
<213> ORGANISM: Artificial Sequence
<220> FEATURE:
<223> OTHER INFORMATION: MT1620insertGGSG rev

<400> SEQUENCE: 26
gctccctccg ccgcttccgc caggggtggt cgtataataa ac 42

<210> SEQ ID NO 27
<211> LENGTH: 265
<212> TYPE: PRT
<213> ORGANISM: Vesicular stomatitis Indiana virus
<220> FEATURE:
<223> OTHER INFORMATION: P-protein aa

<400> SEQUENCE: 27

Met Asp Asn Leu Thr Lys Val Arg Glu Tyr Leu Lys Ser Tyr Ser Arg
1 5 10 15

Leu Asp Gln Ala Val Gly Glu Ile Asp Glu Ile Glu Ala Gln Arg Ala
20 25 30

Glu Lys Ser Asn Tyr Glu Leu Phe Gln Glu Asp Gly Val Glu Glu His
35 40 45

Thr Lys Pro Ser Tyr Phe Gln Ala Ala Asp Asp Ser Asp Thr Glu Ser
50 55 60

Glu Pro Glu Ile Glu Asp Asn Gln Gly Leu Tyr Ala Pro Asp Pro Glu
65 70 75 80

Ala Glu Gln Val Glu Gly Phe Ile Gln Gly Pro Leu Asp Asp Tyr Ala
85 90 95

Asp Glu Glu Val Asp Val Val Phe Thr Ser Asp Trp Lys Gln Pro Glu
100 105 110

Leu Glu Ser Asp Glu His Gly Lys Thr Leu Arg Leu Thr Ser Pro Glu
115 120 125

Gly Leu Ser Gly Glu Gln Lys Ser Gln Trp Leu Ser Thr Ile Lys Ala
130 135 140

Val Val Gln Ser Ala Lys Tyr Trp Asn Leu Ala Glu Cys Thr Phe Glu
145 150 155 160

Ala Ser Gly Glu Gly Val Ile Met Lys Glu Arg Gln Ile Thr Pro Asp
165 170 175

Val Tyr Lys Val Thr Pro Val Met Asn Thr His Pro Ser Gln Ser Glu
180 185 190

Ala Val Ser Asp Val Trp Ser Leu Ser Lys Thr Ser Met Thr Phe Gln
195 200 205

Pro Lys Lys Ala Ser Leu Gln Pro Leu Thr Ile Ser Leu Asp Glu Leu
210 215 220

Phe Ser Ser Arg Gly Glu Phe Ile Ser Val Gly Gly Asp Gly Arg Met
225 230 235 240

Ser His Lys Glu Ala Ile Leu Leu Gly Leu Arg Tyr Lys Lys Leu Tyr
245 250 255

Asn Gln Ala Arg Val Lys Tyr Ser Leu
260 265

<210> SEQ ID NO 28
<211> LENGTH: 2109
<212> TYPE: PRT
<213> ORGANISM: Vesicular stomatitis Indiana virus
<220> FEATURE:
<223> OTHER INFORMATION: L-protein amino acid sequence

<400> SEQUENCE: 28

```
Met Glu Val His Asp Phe Glu Thr Asp Glu Phe Asn Asp Phe Asn Glu
1               5                   10                  15

Asp Asp Tyr Ala Thr Arg Glu Phe Leu Asn Pro Asp Glu Arg Met Thr
            20                  25                  30

Tyr Leu Asn His Ala Asp Tyr Asn Leu Asn Ser Pro Leu Ile Ser Asp
        35                  40                  45

Asp Ile Asp Asn Leu Ile Arg Lys Phe Asn Ser Leu Pro Ile Pro Ser
    50                  55                  60

Met Trp Asp Ser Lys Asn Trp Asp Gly Val Leu Glu Met Leu Thr Ser
65                  70                  75                  80

Cys Gln Ala Asn Pro Ile Pro Thr Ser Gln Met His Lys Trp Met Gly
                85                  90                  95

Ser Trp Leu Met Ser Asp Asn His Asp Ala Ser Gln Gly Tyr Ser Phe
            100                 105                 110

Leu His Glu Val Asp Lys Glu Ala Glu Ile Thr Phe Asp Val Val Glu
        115                 120                 125

Thr Phe Ile Arg Gly Trp Gly Asn Lys Pro Ile Glu Tyr Ile Lys Lys
    130                 135                 140

Glu Arg Trp Thr Asp Ser Phe Lys Ile Leu Ala Tyr Leu Cys Gln Lys
145                 150                 155                 160

Phe Leu Asp Leu His Lys Leu Thr Leu Ile Leu Asn Ala Val Ser Glu
                165                 170                 175

Val Glu Leu Leu Asn Leu Ala Arg Thr Phe Lys Gly Lys Val Arg Arg
            180                 185                 190

Ser Ser His Gly Thr Asn Ile Cys Arg Ile Arg Val Pro Ser Leu Gly
        195                 200                 205

Pro Thr Phe Ile Ser Glu Gly Trp Ala Tyr Phe Lys Lys Leu Asp Ile
    210                 215                 220

Leu Met Asp Arg Asn Phe Leu Leu Met Val Lys Asp Val Ile Ile Gly
225                 230                 235                 240

Arg Met Gln Thr Val Leu Ser Met Val Cys Arg Ile Asp Asn Leu Phe
                245                 250                 255

Ser Glu Gln Asp Ile Phe Ser Leu Leu Asn Ile Tyr Arg Ile Gly Asp
            260                 265                 270

Lys Ile Val Glu Arg Gln Gly Asn Phe Ser Tyr Asp Leu Ile Lys Met
        275                 280                 285

Val Glu Pro Ile Cys Asn Leu Lys Leu Met Lys Leu Ala Arg Glu Ser
    290                 295                 300

Arg Pro Leu Val Pro Gln Phe Pro His Phe Glu Asn His Ile Lys Thr
305                 310                 315                 320

Ser Val Asp Glu Gly Ala Lys Ile Asp Arg Gly Ile Arg Phe Leu His
                325                 330                 335

Asp Gln Ile Met Ser Val Lys Thr Val Asp Leu Thr Leu Val Ile Tyr
            340                 345                 350

Gly Ser Phe Arg His Trp Gly His Pro Phe Ile Asp Tyr Tyr Thr Gly
        355                 360                 365

Leu Glu Lys Leu His Ser Gln Val Thr Met Lys Lys Asp Ile Asp Val
    370                 375                 380

Ser Tyr Ala Lys Ala Leu Ala Ser Asp Leu Ala Arg Ile Val Leu Phe
385                 390                 395                 400

Gln Gln Phe Asn Asp His Lys Lys Trp Phe Val Asn Gly Asp Leu Leu
                405                 410                 415
```

```
Pro His Asp His Pro Phe Lys Ser His Val Lys Glu Asn Thr Trp Pro
            420                 425                 430

Thr Ala Ala Gln Val Gln Asp Phe Gly Asp Lys Trp His Glu Leu Pro
        435                 440                 445

Leu Ile Lys Cys Phe Glu Ile Pro Asp Leu Leu Asp Pro Ser Ile Ile
    450                 455                 460

Tyr Ser Asp Lys Ser His Ser Met Asn Arg Ser Glu Val Leu Lys His
465                 470                 475                 480

Val Arg Met Asn Pro Asn Thr Pro Ile Pro Ser Lys Lys Val Leu Gln
                485                 490                 495

Thr Met Leu Asp Thr Lys Ala Thr Asn Trp Lys Glu Phe Leu Lys Glu
            500                 505                 510

Ile Asp Glu Lys Gly Leu Asp Asp Asp Asp Leu Ile Ile Gly Leu Lys
        515                 520                 525

Gly Lys Glu Arg Glu Leu Lys Leu Ala Gly Arg Phe Phe Ser Leu Met
    530                 535                 540

Ser Trp Lys Leu Arg Glu Tyr Phe Val Ile Thr Glu Tyr Leu Ile Lys
545                 550                 555                 560

Thr His Phe Val Pro Met Phe Lys Gly Leu Thr Met Ala Asp Asp Leu
                565                 570                 575

Thr Ala Val Ile Lys Lys Met Leu Asp Ser Ser Ser Gly Gln Gly Leu
            580                 585                 590

Lys Ser Tyr Glu Ala Ile Cys Ile Ala Asn His Ile Asp Tyr Glu Lys
        595                 600                 605

Trp Asn Asn His Gln Arg Lys Leu Ser Asn Gly Pro Val Phe Arg Val
    610                 615                 620

Met Gly Gln Phe Leu Gly Tyr Pro Ser Leu Ile Glu Arg Thr His Glu
625                 630                 635                 640

Phe Phe Glu Lys Ser Leu Ile Tyr Tyr Asn Gly Arg Pro Asp Leu Met
                645                 650                 655

Arg Val His Asn Asn Thr Leu Ile Asn Ser Thr Ser Gln Arg Val Cys
            660                 665                 670

Trp Gln Gly Gln Glu Gly Gly Leu Glu Gly Leu Arg Gln Lys Gly Trp
        675                 680                 685

Ser Ile Leu Asn Leu Leu Val Ile Gln Arg Glu Ala Lys Ile Arg Asn
    690                 695                 700

Thr Ala Val Lys Val Leu Ala Gln Gly Asp Asn Gln Val Ile Cys Thr
705                 710                 715                 720

Gln Tyr Lys Thr Lys Lys Ser Arg Asn Val Val Glu Leu Gln Gly Ala
                725                 730                 735

Leu Asn Gln Met Val Ser Asn Asn Glu Lys Ile Met Thr Ala Ile Lys
            740                 745                 750

Ile Gly Thr Gly Lys Leu Gly Leu Leu Ile Asn Asp Asp Glu Thr Met
        755                 760                 765

Gln Ser Ala Asp Tyr Leu Asn Tyr Gly Lys Ile Pro Ile Phe Arg Gly
    770                 775                 780

Val Ile Arg Gly Leu Glu Thr Lys Arg Trp Ser Arg Val Thr Cys Val
785                 790                 795                 800

Thr Asn Asp Gln Ile Pro Thr Cys Ala Asn Ile Met Ser Ser Val Ser
                805                 810                 815

Thr Asn Ala Leu Thr Val Ala His Phe Ala Glu Asn Pro Ile Asn Ala
            820                 825                 830

Met Ile Gln Tyr Asn Tyr Phe Gly Thr Phe Ala Arg Leu Leu Leu Met
```

```
        835                 840                 845

Met His Asp Pro Ala Leu Arg Gln Ser Leu Tyr Glu Val Gln Asp Lys
    850                 855                 860

Ile Pro Gly Leu His Ser Ser Thr Phe Lys Tyr Ala Met Leu Tyr Leu
865                 870                 875                 880

Asp Pro Ser Ile Gly Gly Val Ser Gly Met Ser Leu Ser Arg Phe Leu
                885                 890                 895

Ile Arg Ala Phe Pro Asp Pro Val Thr Glu Ser Leu Ser Phe Trp Arg
            900                 905                 910

Phe Ile His Val His Ala Arg Ser Glu His Leu Lys Glu Met Ser Ala
        915                 920                 925

Val Phe Gly Asn Pro Glu Ile Ala Lys Phe Arg Ile Thr His Ile Asp
    930                 935                 940

Lys Leu Val Glu Asp Pro Thr Ser Leu Asn Ile Ala Met Gly Met Ser
945                 950                 955                 960

Pro Ala Asn Leu Leu Lys Thr Glu Val Lys Lys Cys Leu Ile Glu Ser
                965                 970                 975

Arg Gln Thr Ile Arg Asn Gln Val Ile Lys Asp Ala Thr Ile Tyr Leu
            980                 985                 990

Tyr His Glu Glu Asp Arg Leu Arg Ser Phe Leu Trp Ser Ile Asn Pro
        995                 1000                1005

Leu Phe Pro Arg Phe Leu Ser Glu Phe Lys Ser Gly Thr Phe Leu Gly
    1010                1015                1020

Val Ala Asp Gly Leu Ile Ser Leu Phe Gln Asn Ser Arg Thr Ile Arg
1025                1030                1035                1040

Asn Ser Phe Lys Lys Lys Tyr His Arg Glu Leu Asp Asp Leu Ile Val
                1045                1050                1055

Arg Ser Glu Val Ser Ser Leu Thr His Leu Gly Lys Leu His Leu Arg
            1060                1065                1070

Arg Gly Ser Cys Lys Met Trp Thr Cys Ser Ala Thr His Ala Asp Thr
        1075                1080                1085

Leu Arg Tyr Lys Ser Trp Gly Arg Thr Val Ile Gly Thr Thr Val Pro
    1090                1095                1100

His Pro Leu Glu Met Leu Gly Pro Gln His Arg Lys Glu Thr Pro Cys
1105                1110                1115                1120

Ala Pro Cys Asn Thr Ser Gly Phe Asn Tyr Val Ser Val His Cys Pro
                1125                1130                1135

Asp Gly Ile His Asp Val Phe Ser Ser Arg Gly Pro Leu Pro Ala Tyr
            1140                1145                1150

Leu Gly Ser Lys Thr Ser Glu Ser Thr Ser Ile Leu Gln Pro Trp Glu
        1155                1160                1165

Arg Glu Ser Lys Val Pro Leu Ile Lys Arg Ala Thr Arg Leu Arg Asp
    1170                1175                1180

Ala Ile Ser Trp Phe Val Glu Pro Asp Ser Lys Leu Ala Met Thr Ile
1185                1190                1195                1200

Leu Ser Asn Ile His Ser Leu Thr Gly Glu Glu Trp Thr Lys Arg Gln
                1205                1210                1215

His Gly Phe Lys Arg Thr Gly Ser Ala Leu His Arg Phe Ser Thr Ser
            1220                1225                1230

Arg Met Ser His Gly Gly Phe Ala Ser Gln Ser Thr Ala Ala Leu Thr
        1235                1240                1245

Arg Leu Met Ala Thr Thr Asp Thr Met Arg Asp Leu Gly Asp Gln Asn
    1250                1255                1260
```

```
Phe Asp Phe Leu Phe Gln Ala Thr Leu Leu Tyr Ala Gln Ile Thr Thr
1265                1270                1275                1280

Thr Val Ala Arg Asp Gly Trp Ile Thr Ser Cys Thr Asp His Tyr His
                1285                1290                1295

Ile Ala Cys Lys Ser Cys Leu Arg Pro Ile Glu Glu Ile Thr Leu Asp
            1300                1305                1310

Ser Ser Met Asp Tyr Thr Pro Pro Asp Val Ser His Val Leu Lys Thr
        1315                1320                1325

Trp Arg Asn Gly Glu Gly Ser Trp Gly Gln Glu Ile Lys Gln Ile Tyr
    1330                1335                1340

Pro Leu Glu Gly Asn Trp Lys Asn Leu Ala Pro Ala Glu Gln Ser Tyr
1345                1350                1355                1360

Gln Val Gly Arg Cys Ile Gly Phe Leu Tyr Gly Asp Leu Ala Tyr Arg
                1365                1370                1375

Lys Ser Thr His Ala Glu Asp Ser Ser Leu Phe Pro Leu Ser Ile Gln
            1380                1385                1390

Gly Arg Ile Arg Gly Arg Gly Phe Leu Lys Gly Leu Leu Asp Gly Leu
        1395                1400                1405

Met Arg Ala Ser Cys Cys Gln Val Ile His Arg Arg Ser Leu Ala His
    1410                1415                1420

Leu Lys Arg Pro Ala Asn Ala Val Tyr Gly Gly Leu Ile Tyr Leu Ile
1425                1430                1435                1440

Asp Lys Leu Ser Val Ser Pro Pro Phe Leu Ser Leu Thr Arg Ser Gly
                1445                1450                1455

Pro Ile Arg Asp Glu Leu Glu Thr Ile Pro His Lys Ile Pro Thr Ser
            1460                1465                1470

Tyr Pro Thr Ser Asn Arg Asp Met Gly Val Ile Val Arg Asn Tyr Phe
        1475                1480                1485

Lys Tyr Gln Cys Arg Leu Ile Glu Lys Gly Lys Tyr Arg Ser His Tyr
    1490                1495                1500

Ser Gln Leu Trp Leu Phe Ser Asp Val Leu Ser Ile Asp Phe Ile Gly
1505                1510                1515                1520

Pro Phe Ser Ile Ser Thr Thr Leu Leu Gln Ile Leu Tyr Lys Pro Phe
                1525                1530                1535

Leu Ser Gly Lys Asp Lys Asn Glu Leu Arg Glu Leu Ala Asn Leu Ser
            1540                1545                1550

Ser Leu Leu Arg Ser Gly Glu Gly Trp Glu Asp Ile His Val Lys Phe
        1555                1560                1565

Phe Thr Lys Asp Ile Leu Leu Cys Pro Glu Glu Ile Arg His Ala Cys
    1570                1575                1580

Lys Phe Gly Ile Ala Lys Asp Asn Asn Lys Asp Met Ser Tyr Pro Pro
1585                1590                1595                1600

Trp Gly Arg Glu Ser Arg Gly Thr Ile Thr Thr Ile Pro Val Tyr Tyr
                1605                1610                1615

Thr Thr Thr Pro Tyr Pro Lys Met Leu Glu Met Pro Pro Arg Ile Gln
            1620                1625                1630

Asn Pro Leu Leu Ser Gly Ile Arg Leu Gly Gln Leu Pro Thr Gly Ala
        1635                1640                1645

His Tyr Lys Ile Arg Ser Ile Leu His Gly Met Gly Ile His Tyr Arg
    1650                1655                1660

Asp Phe Leu Ser Cys Gly Asp Gly Ser Gly Gly Met Thr Ala Ala Leu
1665                1670                1675                1680
```

```
Leu Arg Glu Asn Val His Ser Arg Gly Ile Phe Asn Ser Leu Leu Glu
                1685                1690                1695

Leu Ser Gly Ser Val Met Arg Gly Ala Ser Pro Glu Pro Pro Ser Ala
            1700                1705                1710

Leu Glu Thr Leu Gly Gly Asp Lys Ser Arg Cys Val Asn Gly Glu Thr
        1715                1720                1725

Cys Trp Glu Tyr Pro Ser Asp Leu Cys Asp Pro Arg Thr Trp Asp Tyr
    1730                1735                1740

Phe Leu Arg Leu Lys Ala Gly Leu Gly Leu Gln Ile Asp Leu Ile Val
1745                1750                1755                1760

Met Asp Met Glu Val Arg Asp Ser Ser Thr Ser Leu Lys Ile Glu Thr
                1765                1770                1775

Asn Val Arg Asn Tyr Val His Arg Ile Leu Asp Glu Gln Gly Val Leu
            1780                1785                1790

Ile Tyr Lys Thr Tyr Gly Thr Tyr Ile Cys Glu Ser Glu Lys Asn Ala
        1795                1800                1805

Val Thr Ile Leu Gly Pro Met Phe Lys Thr Val Asp Leu Val Gln Thr
    1810                1815                1820

Glu Phe Ser Ser Ser Gln Thr Ser Glu Val Tyr Met Val Cys Lys Gly
1825                1830                1835                1840

Leu Lys Lys Leu Ile Asp Glu Pro Asn Pro Asp Trp Ser Ser Ile Asn
                1845                1850                1855

Glu Ser Trp Lys Asn Leu Tyr Ala Phe Gln Ser Ser Glu Gln Glu Phe
            1860                1865                1870

Ala Arg Ala Lys Lys Val Ser Thr Tyr Phe Thr Leu Thr Gly Ile Pro
        1875                1880                1885

Ser Gln Phe Ile Pro Asp Pro Phe Val Asn Ile Glu Thr Met Leu Gln
    1890                1895                1900

Ile Phe Gly Val Pro Thr Gly Val Ser His Ala Ala Ala Leu Lys Ser
1905                1910                1915                1920

Ser Asp Arg Pro Ala Asp Leu Leu Thr Ile Ser Leu Phe Tyr Met Ala
                1925                1930                1935

Ile Ile Ser Tyr Tyr Asn Ile Asn His Ile Arg Val Gly Pro Ile Pro
            1940                1945                1950

Pro Asn Pro Pro Ser Asp Gly Ile Ala Gln Asn Val Gly Ile Ala Ile
        1955                1960                1965

Thr Gly Ile Ser Phe Trp Leu Ser Leu Met Glu Lys Asp Ile Pro Leu
    1970                1975                1980

Tyr Gln Gln Cys Leu Ala Val Ile Gln Gln Ser Phe Pro Ile Arg Trp
1985                1990                1995                2000

Glu Ala Val Ser Val Lys Gly Gly Tyr Lys Gln Lys Trp Ser Thr Arg
                2005                2010                2015

Gly Asp Gly Leu Pro Lys Asp Thr Arg Ile Ser Asp Ser Leu Ala Pro
            2020                2025                2030

Ile Gly Asn Trp Ile Arg Ser Leu Glu Leu Val Arg Asn Gln Val Arg
        2035                2040                2045

Leu Asn Pro Phe Asn Glu Ile Leu Phe Asn Gln Leu Cys Arg Thr Val
    2050                2055                2060

Asp Asn His Leu Lys Trp Ser Asn Leu Arg Arg Asn Thr Gly Met Ile
2065                2070                2075                2080

Glu Trp Ile Asn Arg Arg Ile Ser Lys Glu Asp Arg Ser Ile Leu Met
                2085                2090                2095

Leu Lys Ser Asp Leu His Glu Glu Asn Ser Trp Arg Asp
```

2100 2105

<210> SEQ ID NO 29
<211> LENGTH: 239
<212> TYPE: PRT
<213> ORGANISM: Artificial Sequence
<220> FEATURE:
<223> OTHER INFORMATION: protease dimer with cut and linker

<400> SEQUENCE: 29

Gly Gly Ser Gly Gly Gly Ser Gly Gly Gly Ser Gly Val Ser Phe Asn
1 5 10 15

Phe Pro Gln Val Thr Leu Trp Gln Arg Pro Leu Val Thr Ile Lys Ile
20 25 30

Gly Gly Gln Leu Lys Glu Ala Leu Leu Asp Thr Gly Ala Asp Asp Thr
35 40 45

Val Leu Glu Glu Met Ser Leu Pro Gly Arg Trp Lys Pro Lys Met Ile
50 55 60

Gly Gly Ile Gly Gly Phe Ile Lys Val Arg Gln Tyr Asp Gln Ile Leu
65 70 75 80

Ile Glu Ile Cys Gly His Lys Ala Ile Gly Thr Val Leu Val Gly Pro
85 90 95

Thr Pro Val Asn Ile Ile Gly Arg Asn Leu Leu Thr Gln Ile Gly Cys
100 105 110

Thr Leu Asn Phe Ala Gly Ala Ile Gly Gly Ala Pro Gln Val Thr Leu
115 120 125

Trp Gln Arg Pro Leu Val Thr Ile Lys Ile Gly Gly Gln Leu Lys Glu
130 135 140

Ala Leu Leu Asp Thr Gly Ala Asp Asp Thr Val Leu Glu Glu Met Ser
145 150 155 160

Leu Pro Gly Arg Trp Lys Pro Lys Met Ile Gly Gly Ile Gly Gly Phe
165 170 175

Ile Lys Val Arg Gln Tyr Asp Gln Ile Leu Ile Glu Ile Cys Gly His
180 185 190

Lys Ala Ile Gly Thr Val Leu Val Gly Pro Thr Pro Val Asn Ile Ile
195 200 205

Gly Arg Asn Leu Leu Thr Gln Ile Gly Cys Thr Leu Asn Phe Pro Ile
210 215 220

Ser Pro Ile Gly Gly Ser Gly Gly Gly Ser Gly Gly Gly Ser Gly
225 230 235

<210> SEQ ID NO 30
<211> LENGTH: 41
<212> TYPE: PRT
<213> ORGANISM: Artificial Sequence
<220> FEATURE:
<223> OTHER INFORMATION: degron sequence

<400> SEQUENCE: 30

Pro Ile Thr Lys Ile Asp Thr Lys Tyr Ile Met Thr Cys Met Ser Ala
1 5 10 15

Asp Leu Glu Val Val Thr Ser Thr Trp Val Leu Val Gly Gly Val Leu
20 25 30

Ala Ala Leu Ala Ala Tyr Cys Leu Ser
35 40

<210> SEQ ID NO 31
<211> LENGTH: 24

<212> TYPE: PRT
<213> ORGANISM: Homo sapiens
<220> FEATURE:
<223> OTHER INFORMATION: CD4 TM domain

<400> SEQUENCE: 31

Met Ala Leu Ile Val Leu Gly Gly Val Ala Gly Leu Leu Leu Phe Ile
1               5                   10                  15

Gly Leu Gly Ile Phe Phe Cys Val
            20

<210> SEQ ID NO 32
<211> LENGTH: 72
<212> TYPE: DNA
<213> ORGANISM: Homo sapiens
<220> FEATURE:
<223> OTHER INFORMATION: CD4 TM domain

<400> SEQUENCE: 32
atggccctga ttgtgctggg tggcgtcgcc ggcctcctgc ttttcattgg gctaggcatc 60
ttcttctgtg tc 72

<210> SEQ ID NO 33
<211> LENGTH: 1620
<212> TYPE: DNA
<213> ORGANISM: Homo sapiens
<220> FEATURE:
<223> OTHER INFORMATION: IL12

<400> SEQUENCE: 33
atgggctggt cctgcatcat tctgtttctg gtggccacag ccaccggtgt ccactctatg 60
tgggaactcg agaaggacgt gtacgtggtg gaagtggact ggacacctga tgctccaggc 120
gagacagtga acctgacctg tgacacaccc gaagaggacg acatcacctg gacaagcgat 180
cagagacacg gcgtgatcgg cagcggcaag accctgacaa tcaccgtgaa agagtttctg 240
gacgccggcc agtacacctg tcacaaaggc ggagagacac tgtcccacag ccatctgctg 300
ctgcacaaga aagagaacgg catctggtcc accgagatcc tgaagaactt caagaacaag 360
accttcctga agtgcgaggc ccctaactac agcggcagat tcacatgtag ctggctggtg 420
cagagaaaca tggacctgaa gttcaacatc aagtcctcca gcagcagccc cgacagcaga 480
gctgttacat gtggcatggc tagcctgagc gccgagaaag tgacactgga ccagagagac 540
tacgagaagt acagcgtgtc ctgccaagag gacgtgacct gtcctacagc cgaggaaaca 600
ctgcctatcg agctggccct ggaagccaga cagcagaaca aatacgagaa ctactctacc 660
agcttcttca tccgggacat catcaagccc gatcctccaa agaacctgca gatgaagcct 720
ctgaagaaca gccaggtcga ggtgtcctgg gagtaccctg actcttggag cacccctcac 780
agctacttca gcctgaaatt cttcgtgcgc atccagcgca agaaagaaaa gatgaaggaa 840
accgaggaag gctgcaacca gaagggcgcc ttcctggtcg aaaagacctc taccgaggtg 900
cagtgcaaag gcggcaatgt ctgtgtgcag gcccaggata ggtactacaa cagcagctgc 960
agcaagtggg cctgcgtgcc atgtagagtt agaagcggag gcggaggaag tggtggcgga 1020
ggttctggcg gcggtggaag tagagttatc cctgtgtctg gccctgccag atgcctgtct 1080
cagagcagaa acctgctgaa aaccaccgac gacatggtca agaccgccag agagaagctg 1140
aagcactaca gctgcaccgc cgaggacatc gaccacgagg atatcacaag ggaccagacc 1200
agcacactga aaacctgcct gcctctggaa ctgcataaga acgagagctg cctggccaca 1260

-continued

```
agagagacaa gcagcaccac aagaggcagc tgtctgcctc ctcagaaaac cagcctgatg   1320

atgacactgt gcctgggcag catctacgag gatctgaaga tgtaccagac cgagttccag   1380

gccatcaacg ccgctctgca gaaccacaac caccagcaga tcatcctgga taagggcatg   1440

ctggtggcta tcgacgagct gatgcagagc ctgaaccaca atggcgagac actgagacag   1500

aagcctccag tcggagaggc cgatccttac agagtgaaga tgaagctgtg catcctgctg   1560

cacgccttca gcaccagagt ggtcaccatc aacagagtga tgggctacct gagtagtgca   1620


<210> SEQ ID NO 34
<211> LENGTH: 11
<212> TYPE: PRT
<213> ORGANISM: Artificial Sequence
<220> FEATURE:
<223> OTHER INFORMATION: Linker IL12_TM

<400> SEQUENCE: 34

Ala Pro Ala Glu Thr Lys Ala Glu Pro Met Thr
1               5                   10


<210> SEQ ID NO 35
<211> LENGTH: 33
<212> TYPE: DNA
<213> ORGANISM: Artificial Sequence
<220> FEATURE:
<223> OTHER INFORMATION: Linker IL12_TM

<400> SEQUENCE: 35

gcaccagcag aaacaaaagc agaaccaatg aca                                  33
```

MECHANISM TO CONTROL RNA VIRUS REPLICATION AND GENE EXPRESSION

CROSS REFERENCE TO RELATED APPLICATIONS

This application is a national phase entry pursuant to 35 U.S.C. § 371 of International Application No. PCT/EP2020/067218, filed Jun. 19, 2020, which claims priority to European Patent Application No. 19181717.0, filed Jun. 21, 2019, the entire contents of which are hereby incorporated by reference herein for all purposes.

SEQUENCE LISTING

This application contains a Sequence Listing in computer readable form entitled "2021-12-17_01251-0009-00US_Sequence-Listing," created Dec. 15, 2021, having a size of 146 KB, which is incorporated by reference herein.

TECHNICAL FIELD

The present invention relates to a novel mechanism to control RNA virus replication and gene expression using a conditional protease approach using a protease specific inhibitor for regulation. More specifically it relates to a single-stranded RNA virus, preferably of the order Mononegavirales, comprising a polynucleotide sequence encoding at least one protein essential for viral transcription and/or replication, a protease and a cleavage site for said protease. The protease can be inhibited using a protease inhibitor and hence the protease and the cleavage site for said protease form a regulatable switch. By changing the insertion site of the regulatable switch from an INTRA- to an INTER-molecular location in the at least one protein essential for viral transcription and/or replication, the effect of the protease inhibitor can be altered from an ON switch to an OFF switch. RNA virus may further encode a heterologous protein, the expression of which is then regulated by regulating viral activity. The ON switch may also be used in an RNA virus to directly regulate heterologous protein expression. Further provided are in vivo and in vitro uses of said virus with conditional viral activity or heterologous protein expression.

TECHNOLOGICAL BACKGROUND

Genetically modified viruses have shown great potential as efficient gene therapy vectors, for viral immunotherapy or as oncolytic viruses in cancer virotherapy. Generally these three different types of treatments utilize gene overexpression, gene knockdown using RNA interference and suicide gene delivery. In a therapeutic setting temporal control of transgene or viral gene expression constitutes both a safety switch and a potency dial. While modifiers of activity of DNA viruses are well established, such as regulatable promoters (e.g. Tet system), these mechanisms cannot be used to regulate most RNA viruses (retroviruses being the exception).

Aptazymes are a mechanism to tightly control RNA viruses (Ketzer et al., PNAS, 2014, 111(5): E554-62). An aptazyme consists of an RNA structure responding to a small compound (aptamer) and an enzymatically active RNA (ribozyme). This mechanism was shown to be able to regulate spread of the RNA measles virus by serving as an OFF-switch to its fusion protein. However, viral transcription or replication activity was not controlled. In measles virus, aptazymes had to be placed into both 3'- and 5' UTRs of the viral fusion protein to achieve effective inhibition of viral spread, resulting in reduction of viral progeny by 3 logarithmic orders. Inhibition was applied at a late stage of the virus replication cycle, i.e. fusion. Apparently, even small amounts of fusion protein are sufficient to facilitate virus spread. Therefore, the reduction of 3 logarithmic orders was only accomplished with a multistep infection assay (low MOI of 0.0001) and a long observation period of 8 days. Single insertions of aptazymes in either 3'- or 5' UTRs did not drastically reduce titers.

Following a different approach, OFF switch control of measles virus RNA replication was shown via small molecule-assisted shutoff (SMASh)-tags fused C-terminally to the viral P-protein (Chung et al. Nature Chemical Biology, 2015, 11:713-722) controlling degradation of the protein.

We sought to develop a regulatable systems based on conditional proteolysis, which involved cloning of the small human immunodeficiency virus (HIV) protease (99 amino acids) flanked by HIV protease cleavage sites into different loci of the genome of the RNA vesicular stomatis virus (VSV) as a model protease. The HIV protease is active as a homodimer and functions as aspartyl protease. In HIV, it cleaves the polyprotein that is translated from the positive strand genome, into functional proteins. Since the HIV protease is essential for its virus replication cycle, several protease inhibitors have been approved by drug administration agencies and new inhibitors are being developed. One such protease inhibitor is amprenavir, which binds in the catalytic center between the HIV protease homodimers, thereby mitigating its function.

Vesicular stomatitis virus (VSV), a negative-sense single-strand RNA virus and prototypical member of the family Rhabdoviridae, is widely studied as vaccine vector, oncolytic virus, and tracing tool. Despite its broad use in virology basic science and the development of therapeutic viruses, VSV, being an RNA virus, has so far not been shown to be externally regulatable. The VSV RNA genome includes five viral genes in the following order from 3' to 5': nucleoprotein (N-protein), followed by the phosphoprotein (P-protein), the matrix protein (M-protein), the glycoprotein (G-protein) and finally the polymerase or large protein (L-protein). All VSV genes are transcribed in a sequential manner by the VSV polymerase using the same entry site at the 3' end (upstream the N-protein) from which transcription is initiated. The genes are interspersed with intergenic regions that enable the transcription of several viral mRNAs from one RNA genome. The first viral protein, the N protein covers the viral RNA genome and interacts with the viral polymerase complex, which is formed by the P- and L-protein. The M-protein forms the viral capsid and obstructs cellular translation via blockage of nuclear pores. The G-protein facilitates cell attachment and entry and its fusogenic characteristic constitutes another pathogenicity factor. VSVs clinical development has been limited by potential neurotoxic adverse effects shown in laboratory animals.

SUMMARY OF THE INVENTION

We present here for the first time a regulatory switch putting the activity of an RNA virus under conditional control in the presence of an exogenously applied clinically approved compound. By changing the insertion site of the switch from an INTRA- to an INTER-molecular location, we can flip the effect of the compound from an ON switch to an OFF switch. These regulatory elements provide novel safety measures for RNA viruses currently considered for development as therapeutic viruses in the field of oncology and vaccinations. Furthermore, dependence on the presence of an applied drug provides an environmental safety shield in case of shedding of viruses during therapy. For the ON-switch, an autocatalytically active protease, such as the HIV protease, is inserted into an intramolecular insertion site, i.e., into the open reading frame, of an essential protein, such as the P-protein and/or the L-protein of the prototypical negative-stranded RNA virus, such as VSV. Addition of protease specific inhibitors, such as HIV protease inhibitors, prevent the cleavage of these essential viral proteins and viral polymerase activity can proceed. We further identified a new insertion site in the L-protein that only mildly affects viral replication. For the OFF-switch the autocatalytically active protease is inserted into an intermolecular insertion site and is fused to an essential protein, generating a non-functional fusion protein. Autoproteolysis releases the functional essential protein, such as the L-protein of the prototypical negative-stranded RNA virus VSV. Addition of specific protease inhibitors, such as HIV protease inhibitors, prevent the cleavage of the dysfunctional polyprotein and therefore blocks viral polymerase activity.

In one aspect a single-stranded RNA virus is provided comprising a modified genome of the virus comprising a polynucleotide sequence encoding at least one protein essential for viral transcription and/or replication, a protease and a cleavage site for said protease, wherein (a) the at least one protein essential for viral transcription and/or replication comprises an insert at an intramolecular insertion site comprising at least the cleavage site for said protease and optionally further the protease; or (b) the at least one protein essential for viral transcription and/or replication is encoded as a fusion protein comprising the protease fused to the N-terminal or C-terminal end, separated by the cleavage site for said protease. Optionally the virus may further encode for a heterologous protein. In alternative (a) also referred to as ON-switch herein, the protease cleaves the least one protein essential for viral transcription and/or replication at the cleavage site for said protease at the intramolecular insertion site. In alternative (b) also referred to as OFF-switch herein, the protease cleaves at the cleavage site for said protease located at the N-terminal or C-terminal end of the at least one protein essential for viral transcription and/or replication encoded as a fusion protein to release the at least one protein essential for viral transcription and/or replication. In one embodiment of alternative (b) the fusion protein does not comprise an amino acid sequence of SEQ ID NO: 30. The protease may be any protease, as long as it can be inhibited using a protease inhibitor.

In one embodiment the at least one protein essential for viral transcription and/or replication is an RNA-dependent RNA polymerase or a protein of the polymerase complex comprising the RNA-dependent RNA polymerase or a nucleocapsid, preferably selected from the group consisting of polymerase cofactor (such as the P-Protein or a functional equivalent thereof), polymerase (such as the L-Protein) and nucleocapsid (such as the N-Protein).

Preferably the single-stranded RNA virus is a negative-sense single-stranded RNA virus, more preferably a negative-sense single-stranded RNA virus of the order Mononegavirales. In certain embodiments the single-stranded RNA virus is a virus of a family selected from the group consisting of Rhabdoviridae, Paramyxoviridae, Filoviridae, Nyamiviridae, Pneumoviridae and Bornaviridae. Preferably the single-stranded RNA virus is a virus of the family Paramyxoviridae, preferably a Measles morbillivirus (MeV) or a virus of the family Rhabdoviridae, preferably a virus of the genus Vesiculovirus, most preferred a Vesicular Stomatitis Virus (VSV). In one embodiment the virus is an oncolytic virus, preferably the oncolytic virus is VSV. In an even more preferred embodiment, the Vesiculovirus is a vesicular stomatitis virus with the glycoprotein GP of the lymphocytic choriomeningitis virus (LCMV), preferably with the strain WE-HPI. Such VSV is for example described in the WO2010/040526 and named VSV-GP.

In one embodiment the single-stranded RNA virus is a negative-sense single-stranded RNA virus of the order Mononegavirales and the at least one protein essential for viral transcription and/or replication is selected from the group consisting of polymerase cofactor, polymerase and nucleocapsid, preferably wherein the at least one protein essential for viral transcription and/or replication is (a) a polymerase cofactor, preferably a P-Protein or a functional equivalent thereof; (b) a polymerase, preferably a L-protein; and/or (c) combinations thereof.

The protease as used according to the invention regulates the activity of the at least one protein essential for viral transcription and/or replication. Thus, it also regulates viral transcription and/or replication. In one embodiment the protease is an autocatalytic protease. In another embodiment or in addition the protease is a viral protease, preferably the protease is from HCV or HIV. In another embodiment the protease is the HIV-1 protease, preferably a single chain dimer of the HIV-1 protease. Suitable HIV-1 protease inhibitors, without being limited thereto, are indinavir, saquinavir, ritonavir, nelfinavir, lopinavir, amprenavir, fosamprenavir, atazanavir, tipranavir or darunavir.

In the embodiment having the insert at the intramolecular insertion site (ON-switch), the insert at the intramolecular insertion site of the at least one protein essential for viral transcription and/or replication does not or not substantially affect activity of the at least one protein essential for viral transcription and/or replication.

In certain embodiments, at least the cleavage site for said protease and optionally further the protease is located within the intramolecular insertion site of the at least one protein essential for viral transcription and/or replication, and proteolytic cleavage of the protein cleaves the at least one protein essential for viral transcription and/or replication at the cleavage site for said protease within the intramolecular insertion site. Cleavage within the intramolecular insertion site inactivates the at least one protein essential for viral transcription and/or replication. Further cleavage within the intramolecular insertion site of the at least one protein essential for viral transcription and/or replication inhibits viral transcription and/or replication. Thus, the virus is active in the presence of a specific inhibitor of the protease and inactive in the absence of a specific inhibitor of the protease. The virus may further encode at least one heterologous protein, wherein the heterologous protein is expressed if the virus is active in the presence of a specific inhibitor of the protease and is not expressed if the virus is inactive in the absence of a specific inhibitor of the protease.

In another embodiment the single-stranded RNA virus is Vesicular Stomatitis Virus (VSV) and the at least one protein essential for viral transcription and/or replication is the P-protein and/or the L-protein. An example, without being limited thereto, for a suitable intramolecular insertion site in the P-protein is the flexible hinge region of the VSV P-protein, preferably at a position corresponding to amino acid position 193-199, more preferably amino acid position 196 of VSVi P-protein (such as of the amino acid sequence of SEQ ID NO: 27). In one embodiment the VSV P-protein is from VSV Indiana (VSVi) and the intramolecular insertion site in the P-Protein is the flexible hinge region of the VSV P-protein, preferably at amino acid position 193-199, more preferably amino acid position 196 of VSVi P-protein (such as of the amino acid sequence of SEQ ID NO: 27). An example, without being limited thereto, for a suitable intramolecular insertion in the L-protein is in the loop of the methyltransferase (MT) domain of the L-protein corresponding to amino acids 1614 to 1634, preferably to amino acids 1614 to 1629, more preferably to amino acids 1616 to 1625, and more preferably to amino acid 1620 of VSVi L-protein (such as of the amino acid sequence of SEQ ID NO: 28). In one embodiment the VSV L-protein is from VSV Indiana (VSVi) and the intramolecular insertion site in the L-protein is in the loop of the methyltransferase (MT) domain of the L-protein from amino acids 1614 to 1634, preferably from amino acids 1614 to 1629, more preferably from amino acids 1616 to 1625, and even more preferably at amino acid 1620 of VSVi L-protein (such as of the amino acid sequence of SEQ ID NO: 28). In one embodiment the Vesicular Stomatitis Virus (VSV) and the at least one protein essential for viral transcription and/or replication is the P-protein and the L-protein having an insert at an intramolecular insertion site as described above.

In the alternative having the insert at the intermolecular insertion site (OFF-switch), the at least one protein essential for viral transcription and/or replication is encoded as a fusion protein comprising the protease fused to the N-terminal or C-terminal end of the at least one protein essential for viral transcription and/or replication separated by the cleavage site for said protease. In certain embodiments proteolytic cleavage of the fusion protein releases the at least one protein essential for viral transcription and/or replication in its active form. The at least one protein essential for viral transcription and/or replication in the fusion protein comprising the protease fused to the N-terminal or C-terminal end of the at least one protein essential for viral transcription and/or replication separated by the cleavage site for said protease is inactive without proteolytic cleavage. Proteolytic cleavage of the fusion protein may be inhibited using a specific inhibitor of the protease. Thus, the virus is inactive in the presence of a specific protease inhibitor of the protease and active in the absence of a specific inhibitor of the protease. The virus may further encode at least one heterologous protein, wherein the heterologous protein is not expressed if the virus is inactive in the presence of a specific inhibitor of the protease and is expressed if the virus is active in the absence of a specific inhibitor of the protease. The fusion protein may also comprise a further viral protein fused to the opposite end of the protease fused to the N-terminal or C-terminal end of the at least one protein essential for viral transcription and/or replication, wherein said further viral protein and said protease are also separated by the cleavage site for said protease. In one embodiment the protease is flanked by the cleavage site for said protease on either side and replaces an intergenic region that links the at least one protein essential for viral transcription and/or replication with a further viral protein. Thus, loss of the protease leads to a further inactive fusion protein comprising the protein essential for viral transcription and/or replication and the further viral protein. The fusion protein may also comprise a heterologous protein fused to the opposite end of the protease fused to the N-terminal or C-terminal end of the at least one protein essential for viral transcription and/or replication, wherein said heterologous protein and said protease are separated by a cleavage site for said protease. In one embodiment the protease is flanked by a cleavage site for said protease on either side and replaces an intergenic region that links the at least one protein essential for viral transcription and/or replication with a heterologous protein. Thus, loss of the protease leads to a further inactive fusion protein comprising the protein essential for viral transcription and/or replication and the heterologous protein. The fusion protein may further comprise a linker between the protease and the at least one protein essential for viral transcription and/or replication or if applicable between the protease and the further viral protein or the heterologous protein. The linker may separate the protease and the cleavage site or the cleavage site and the at least one protein essential for viral transcription and/or replication; and/or the protease and the further viral protein or the heterologous protein.

In a preferred embodiment of this alternative (OFF-switch) the single-stranded RNA virus is a negative-sense single-stranded RNA virus of the order Mononegavirales and the at least one protein essential for viral transcription and/or replication is an L-protein. In another preferred embodiment of this alternative (OFF-switch) the fusion protein comprises the protease fused to the N-terminal end of the at least one protein essential for viral transcription and/or replication separated by the cleavage site for said protease. In yet another embodiment of this alternative (OFF-switch) the single-stranded RNA virus is a negative-sense single-stranded RNA virus of the order Mononegavirales and the at least one protein essential for viral transcription and/or replication is an L-protein, wherein the fusion protein comprises the protease fused to the N-terminal end of the L-protein separated by the cleavage site for said protease.

In another aspect the invention relates to an RNA virus comprising a modified genome of the virus comprising a polynucleotide sequence encoding at least one heterologous protein, a protease and a cleavage site for said protease, wherein the at least one heterologous protein comprises an insert at an intramolecular insertion site comprising at least the cleavage site for said protease and optionally further the protease. The virus may be an oncolytic virus, wherein the oncolytic virus is preferably VSV.

The heterologous protein may be a therapeutic protein, a reporter or a tumor antigen.

In a further aspect, the invention relates to the RNA viruses according to the invention for use in therapy, particularly for use in treating cancer. The cancer may be a solid tumor, preferably selected from the group consisting of colon carcinoma, prostate cancer, breast cancer, lung cancer, NSCLC, skin cancer, liver cancer, bone cancer, ovary cancer, pancreas cancer, brain cancer, head and neck cancer, HNSCC; lymphoma (Hodgkin's and non-Hodgkin's lymphoma), brain cancer, neuroblastoma, mesothelioma, Wilm's tumor, retinoblastoma and sarcoma.

In yet another aspect, the invention relates to a recombinant VSV L-protein comprising an insert in the loop of the methyltransferase domain of the L-protein corresponding to amino acids 1614 to 1634, preferably to amino acids 1614 to 1629, more preferably to amino acids 1616 to 1625 and more preferably to amino acid 1620 of VSVi L-protein (SEQ ID NO: 28). The insert may comprise a reporter protein (such as luciferase or a fluorescent protein) or alternatively a cleavage site for a protease or a protease and a cleavage site for said protease. In case the insert comprises a cleavage site for a protease or a protease and a cleavage site for said protease the protease may be a viral protease and/or an autocatalytic protease. Preferably the protease is from HCV or HIV. In one embodiment the protease is the HIV-1 protease, preferably a single chain dimer of the HIV-1 protease. Suitable HIV-1 protease inhibitors are, without being limited thereto, indinavir, saquinavir, ritonavir, nelfinavir, lopinavir, amprenavir, fosamprenavir, atazanavir, tipranavir or darunavir. In certain embodiments, the L-protein may comprise a secondary mutation. Also provided is a Vesicular Stomatitis Virus (VSV) comprising the recombinant VSV L-protein according to the invention.

The invention further provides a method for controlling RNA virus replication comprising (a) transducing or transfecting a host cell with the RNA virus according to the invention in the alternative having the insert at the intramolecular insertion site (ON-switch), and (b) maintaining the host cell in the presence or absence of a protease inhibitor specific for said protease, wherein the addition of said protease inhibitor allows viral transcription and/or replication and the absence of said protease inhibitor inhibits viral transcription and replication.

The invention also provides a method for controlling RNA virus replication comprising (a) transducing or transfecting a host cell with the RNA virus according to the invention in the alternative having the insert at the intermolecular insertion site (OFF-switch), and (b) maintaining the host cell in the presence or absence of a protease inhibitor specific for said protease, wherein the addition of said protease inhibitor inhibits viral transcription and/or replication and the absence of said protease inhibitor allows viral transcription and replication.

The invention also provides a method for controlling heterologous protein expression by a RNA virus comprising (a) transducing or transfecting a host cell with the RNA virus according to the invention in the alternative wherein the at least one heterologous protein comprises an insert at an intramolecular insertion site comprising at least the cleavage site for said protease and optionally further the protease; and (b) maintaining the host cell in the presence or absence of a protease inhibitor specific for said, protease, wherein the addition of said protease inhibitor allows heterologous protein expression and the absence of said protease inhibitor inhibits heterologous protein expression. The protein in the methods according may be an autocatalytic protease, preferably the autocatalytic protease is the HIV-1 protease, more preferably a single chain dimer of the HIV-1 protease. Suitable HIV-1 protease inhibitors are, without being limited thereto, indinavir, saquinavir, ritonavir, nelfinavir, lopinavir, amprenavir, fosamprenavir, atazanavir, tipranavir or darunavir.

DETAILED DESCRIPTION

Figure 1A:
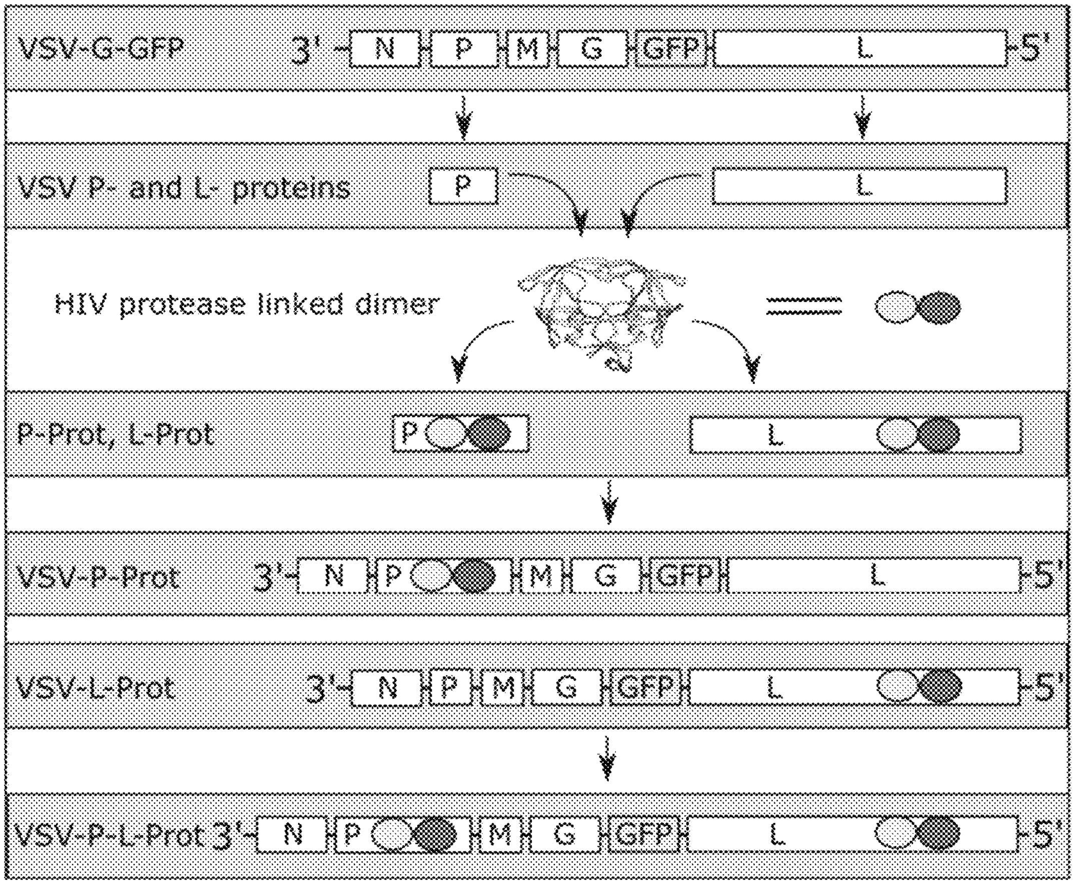
FIG. 1. Principle of the VSV-prot-ON system. A) An HIV protease dimer construct was inserted into the two VSV proteins, which form the polymerase complex, the P-protein and the L-protein. The HIV protease is functional as a dimer. To ensure the functionality of the HIV protease as part of the open reading frame of the VSV P-protein and polymerase (L-protein), we used a protease dimer that was a priori linked. This way, the P-protein already contains the functional protease dimer that becomes autocatalytically active upon translation and cleaves the P-protein, unless a protease inhibitor is present. B) Protein ribbon structure of HIV protease dimer. The HIV protease is functional as a dimer. To ensure the functionality of the HIV protease as part of the open reading frame of the VSV phosphoprotein and polymerase, we used a protease dimer that was a priori linked (dark grey loop at the bottom of the protein ribbon structure).

The general embodiments "comprising" or "comprised" encompass the more specific embodiment "consisting of". Furthermore, singular and plural forms are not used in a limiting way. As used herein, the singular forms "a", "an" and "the" designate both the singular and the plural, unless expressly stated to designate the singular only.

The term "homologue" or "homologous" as used in the present invention means a polypeptide molecule or a nucleic acid molecule, which is at least 80% identical in sequence with the original sequence or its complementary sequence. Preferably, the polypeptide molecule or nucleic acid molecule is at least 90% identical in sequence with the reference sequence or its complementary sequence. More preferably, the polypeptide molecule or nucleic acid molecule is at least 95% identical in sequence with the reference sequence or its complementary sequence. Most preferably, the polypeptide molecule or a nucleic acid molecule is at least 98% identical in sequence with the reference sequence or its complementary sequence. A homologous protein further displays the same or a similar protein activity as the original sequence.

The term "corresponding to amino acid position" or "corresponds to amino acid position", as used herein includes the defined sequence of VSVi, such as the amino acid sequence of the P-protein having the sequence of SEQ ID NO: 27 or the amino acid sequence of the L-protein having the sequence of SEQ ID NO: 28, but also to natural variations thereof or sequences from other VSV serotypes. Also, the skilled person will understand that genomic sequences of RNA viruses, such as of VSV, vary and may therefore not be identical with the sequences provided in SEQ ID NO: 27 or SEQ ID NO: 28, even if from the same serotype. However, using sequence alignment, the skilled person would know how to identify the position in a sequence in a specific VSV sequence, corresponding to the defined position in the sequence of SEQ ID NO:27 or SEQ ID NO: 28 of the P-protein or of the L-protein, respectively, i.e., the homologous position. Such sequence comprising the position corresponding to the defined position in the P-protein having the sequence of SEQ ID NO: 27 or the L-protein having the sequence of SEQ ID NO: 28 would have at least 80% sequence identity with the sequence of SEQ ID NO: 27 or with the sequence of SEQ ID NO: 28, preferably at least 90% identity with the sequence of SEQ ID NO: 27 or with the sequence of SEQ ID NO: 28. The corresponding sequence may also contain recombinant insertions, such as a protease and/or a cleavage site for said protease, which is not to be considered for determining the corresponding sequence.

The term "protein" is used interchangeably with "amino acid residue sequence" or "polypeptide" and refers to polymers of amino acids of any length. These terms also include proteins that are post-translationally modified through reactions that include, but are not limited to, glycosylation, acetylation, phosphorylation, glycation or protein processing. Modifications and changes, for example amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with the same properties. The term "polypeptide" typically refers to a sequence with more than 10 amino acids and the term "peptide" means sequences with up to 10 amino acids in length. However, the terms may sometimes be used interchangeably.

The term "fusion protein" refers to a chimeric protein made of parts from different sources, particularly created through joining of two or more genes or parts of genes that originally code for separate proteins or fragments thereof. Recombinant fusion proteins are created artificially by recombinant DNA technology. A fusion protein may contain full length proteins (i.e., comprising all functional domains) or a fragments thereof, such as one or more functional domain(s), a consensus motive, a cleavage site fused to another full length proteins (i.e., comprising all functional domains) or a fragments thereof. Fused means that the nucleotide sequence coding for the first polypeptide to the nucleotide sequence coding for the second polypeptide in frame, such that the nucleotide sequence will be expressed as a single protein. A polyprotein is a subtype of fusion proteins, typically occurring in RNA viruses. A polyprotein is a protein generated by translation of a single mRNA encoding several proteins in a single open reading frame, i.e., fused to each other (multicistronic mRNA). The polyprotein is processed post-translationally or co-translationally into single proteins, typically via proteases.

The term "genomic RNA" as used herein refers to the heritable genetic information of an RNA virus. However, in the context of the present invention the term "genome" typically also refers to the genome of an RNA virus and hence an RNA genome having a ribonucleic acid sequence. The person skilled in the art will understand that the genome of an RNA virus may also be provided as a DNA sequence in a vector, such as a plasmid. The RNA genome is then generated in a host cell following transfection of the host cell via transcription.

The term "gene" as used herein refers to a DNA or RNA locus of heritable genomic sequence which affects an organism's traits by being expressed as a functional product or by regulation of gene expression. Genes and polynucleotides may include introns and exons as in genomic sequence, or just the coding sequences as in cDNAs, such as an open reading frame (ORF), comprising a start codon (methionine codon) and a translation stop codon. Genes and polynucleotides can also include regions that regulate their expression, such as transcription initiation, translation and transcription termination. Thus, also included are regulatory elements such as a promoter.

The terms "nucleic acid", "nucleotide", and "polynucleotide" as used herein are used interchangeably and refer to a single or double-stranded polymer of deoxyribonucleotide bases or ribonucleotide bases read from the 5' to the 3' end and include double stranded DNA (dsDNA), single stranded DNA (ssDNA), single stranded RNA (ssRNA, negative-sense and positive-sense), double stranded RNA (dsRNA), genomic DNA, cDNA, CRNA, recombinant DNA or recombinant RNA and derivatives thereof, such as those containing modified backbones.

The term "ribonucleic acid", "RNA" or "RNA oligonucleotide" as used herein describes a molecule consisting of a sequence of nucleotides, which are built of a nucleobase a ribose sugar, and a phosphate group. RNAs are usually single stranded molecules and can exert various functions. The term ribonucleic acid specifically comprises messenger RNA (mRNA), transfer RNA (IRNA), ribosomal RNA (rRNA), short interfering RNA (siRNA), small hairpin RNA (shRNA) and micro RNA (miRNA), each of which plays a specific role in biological cells. It includes small non-coding RNAs, such as microRNAs (miRNA), short interfering RNAs (siRNA), small hairpin RNA (shRNA), and Piwi-interacting RNAs (piRNA). The term "non-coding" means that the RNA molecule is not translated into an amino acid sequence.

The terms "upstream" and "downstream" refer to a relative position in DNA or RNA. Each strand of DNA or RNA possesses a 5' end and a 3' end, relating to the terminal carbon position of the deoxyribose or ribose units. By convention, "upstream" means towards the 5' end of a polynucleotide, whereas "downstream" means towards the 3' end of a polynucleotide. In the case of double stranded DNA, e.g. genomic DNA, the term "upstream" means towards the 5' end of the coding strand, whereas "downstream" means towards the 3' end of the coding strand.

The term "coding strand" or "positive-sense strand" refers to a RNA strand encoding for proteins.

The term "non-coding strand" "anti-sense strand" or "negative-sense strand" or "negative-strand" refers to a RNA strand that needs to be transcribed by an RNA-dependent RNA polymerase into a positive strand RNA prior to translation.

A "vector" is a nucleic acid that can be used to introduce a heterologous polynucleotide into a cell. One type of vector is a "plasmid", which refers to a linear or circular double stranded DNA molecule into which additional nucleic acid segments can be ligated. Another type of vector is a viral vector (e.g., retroviruses, adenoviruses, adeno-associated viruses, VSV and MeV replication defective or active form), wherein additional DNA or RNA segments can be introduced into the viral genome.

The term "encodes" and "codes for" refers broadly to any process whereby the information in a polymeric macromolecule is used to direct the production of a second molecule that is different from the first. The second molecule may have a chemical structure that is different from the chemical nature of the first molecule. For example, the term "encode" describes the process of semi-conservative DNA replication, where one strand of a double-stranded DNA molecule is used as a template to encode a newly synthesized complementary sister strand by a DNA-dependent DNA polymerase. Further, a DNA molecule can encode an RNA molecule (e.g., by uses a DNA-dependent RNA polymerase) or a RNA molecule (negative stranded) can encode an RNA molecule (positive-stranded) (e.g., by use of a RNA-dependent RNA polymerase). Also, an RNA molecule (positive-stranded) can encode a polypeptide, as in the process of translation. When used to describe the process of translation, the term "encode" also extends to the triplet codon that encodes an amino acid. An RNA molecule can also encode a DNA molecule, e.g., by the process of reverse transcription using an RNA-dependent DNA polymerase. When referring to a DNA molecule encoding a polypeptide, a process of transcription and translation is referred to.

The term "heterologous polypeptide" or "heterologous protein" as used herein refers to a protein derived from a different organism or a different species from the recipient, i.e., the RNA virus. In the context of the present invention the skilled person would understand that it refers to a protein not naturally expressed by the virus. The term "heterologous" when used with reference to portions of a protein may also indicate that the protein comprises two or more amino acid sequences that are not found in the same relationship to each other in nature. In the context of the present invention it is typically a therapeutic protein, an antigen, such as a tumor-specific or tumor-associated antigen, or a reporter (such as luciferase or a fluorescent protein).

The term "therapeutic protein" refers to proteins that can be used in medical treatment of humans and/or animals. These include, but are not limited to antibodies, growth factors, blood coagulation factors, cytokines, such as interferons and interleukins, chemokines and hormones, preferably, growth factors, cytokines, chemokines and antibodies.

The term "cytokine" refers to small proteins, which are released by cells and act as intercellular mediators, for example influencing the behavior of the cells surrounding the secreting cell. Cytokines may be secreted by immune or other cells, such as T-cells, B-cells, NK cells and macrophages. Cytokines may be involved in intercellular signaling events, such as autocrine signaling, paracrine signaling and endocrine signaling. They may mediate a range of biological processes including, but not limited to immunity, inflammation, and hematopoiesis. Cytokines may be chemokines, interferons, interleukins, lymphokines or tumor necrosis factors.

As used herein, "growth factor" refers to proteins or polypeptides that are capable of stimulating cell growth.

The term "expression" as used herein refers to transcription and/or translation of a heterologous nucleic acid sequence within a host cell. The level of expression of a gene product of interest in a host cell may be determined on the basis of either the amount of the corresponding mRNA (or positive-stranded RNA) that is present in the cell, or the amount of the polypeptide encoded by the selected sequence. For example, RNA transcribed from a selected sequence can be quantified by Northern blot hybridization, ribonuclease RNA protection, in situ hybridization to cellular RNA or by PCR, such as qPCR. Proteins encoded by a selected sequence can be quantitated by various methods, e.g. by ELISA, by Western blotting, by radioimmunoassay, by immunoprecipitation, by assaying for the biological activity of the protein, by immunostaining of the protein followed by FACS analysis or by homogeneous time-resolved fluorescence (HTRF) assays. The level of expression of a non-coding RNA, such as a miRNA or shRNA may be quantified by PCR, such as qPCR.

The term "gene product" refers to both the mRNA polynucleotide and polypeptide that is encoded by a gene or DNA polynucleotide.

As used herein, a "reporter gene" is a polynucleotide encoding a reporter protein or "reporter" that can be easily detected and quantified. Thus, a measurement of the level of expression of the reporter is typically indicative of the level of transcription and/or translation. The gene encoding the reporter is a reporter gene. For example, a reporter gene can encode a reporter, for example, an enzyme whose activity can be quantified, for example, alkaline phosphatase (AP), chloramphenicol acetyltransferase (CAT), Renilla luciferase or firefly luciferase protein(s). Reporters also include fluorescent proteins, for example, green fluorescent protein (GFP) or any of the recombinant variants of GFP, including enhanced GFP (EGFP), blue fluorescent proteins (BFP and other derivatives), cyan fluorescent protein (CFP and other derivatives), yellow fluorescent protein (YFP and other derivatives) and red fluorescent protein (RFP and other derivatives) or other fluorescent proteins, such as mCherry and mWasabi.

The term "protease" or "proteinase" are used herein synonymously and refer to an enzyme that helps proteolysis, i.e., protein catabolism by hydrolysis of peptide bonds. Proteases can be classified into seven broad groups of serine proteases, cysteine proteases, threonine proteases, aspartic proteases, glutamic proteases, metalloproteases and asparagine peptide lyases. Proteases occur in all organisms, in prokaryotes, eukaryotes and viruses. In principle all proteases are suitable in the context of the present invention as long as they are highly specific, i.e., have a restricted set of substrate sequences, and a specific inhibitor is available. The protease inhibitor should be specific for the protease and be known to be suitable for in vivo use, i.e., being safe, bioavailable and active in vivo, such as following oral or parenteral administration to a subject, preferably a human subject. Viral proteases are advantageous as they are common targets for antiviral drugs and hence a number of protease inhibitors inhibiting viral proteases have been approved and tested to be safe in humans. For example, for the human immune deficiency (HIV) protease, various well-characterized protease inhibitors are available and allow regulation of the system with desired kinetics. Example of suitable HIV protease inhibitors are without being limited thereto, e.g., indinavir, saquinavir, ritonavir, nelfinavir, lopinavir, amprenavir, fosamprenavir, atazanavir, tipranavir and darunavir. In therapy the protease inhibitor, particularly the HIV protease inhibitor, may be administered in combination with ritonavir. Ritonavir augments the plasma concentration of the other protease inhibitors. Human proteases are advantages as they are endogenous proteins to human patients and hence do not elicit an immune response. The protease used in the RNA virus according to the invention is a heterologous protease, i.e., a protease not endogenous to the virus. The term "Prot" or "prot" as used herein is an abbreviation of protease, thus e.g., L-Prot refers to the L-protein comprising an intramolecular protease as disclosed herein and P-Prot refers to the P-protein comprising an intramolecular protease as disclosed herein or Prot-L refers to a protease fused to the L-protein and Prot-P refers to a protease fused to the P-protein.

The protease may be a monomer or a dimer. Preferably a dimer is used in form of a single-chain dimer, by linking the monomers via a flexible linker. Examples for a protease that is active only as a dimer is the HIV protease used in the Examples. As explained for the HIV-1 protease, single-chain dimers are preferably codon-optimized to avoid homology between the first and second protease. A codon optimized single-chain dimer of HIV 1 protease may, e.g., have the DNA sequence of SEQ ID NO: 5. This reduces the risk of "copy-choice" recombination events as previously described in VSV (Simon-Loriere and Holmes 2011), in which the viral polymerase, the L-protein, can switch between templates and skip sequence stretches. "Copy-choice" occurs when the polymerase is guided by sequence homology of the nascent RNA strand with the newly chosen template. Preferably the protease is autocatalytically active, i.e., it mediates cis-cleavage. This may be an inherent property of the protease or may be generated by cloning the respective cleavage site in close proximity to the protease, i.e., the protease has a N-terminal and/or a C-terminal cleavage site. Preferably the protease is framed by a cleavage site for said protease on either side. Thus, the protease has two cleavage sites for said protease, one on the N-terminal side and one on the C-terminal side of the protease. Preferably the two cleavage sites are not identical. The protease having a cleavage site may further have a linker on one or both side, either flanking the cleavage site on one or both sides or alternatively between the protease and the one or more cleavage sites.

Thus, the regulatory element or "switch" according to the present invention comprises a protease, at least one cleavage site for said protease and a protease inhibitor specific for said protease.

The term "RNA virus" as used herein refers to a virus that has a ribonucleic acid (RNA) as its genetic material. RNA viruses may be single-stranded (ssRNA) or double-stranded (dsRNA). Single-stranded RNA viruses include the category (Phylum) "negative-sense ssRNA virus" (Negarnaviricota), which includes among others the order Mononegavirales and Articulavirales (comprising the family orthomyxovirus, which includes the influenza virus) and the category "positive-sense ssRNA virus", such as Coronaviridae, Flaviviridae, and Enteroviridae. The negative-sense ssRNA viruses, particularly of the order Mononegavirales, include, Bornaviridae (e.g., Borna disease Virus (BDV), Nyamaviridae (Nyamanini virus (NYMV), Rhabdoviridae (rabies virus, vesicular stomatitis virus (VSV), Maraba virus), Filobiridae (Ebola virus including EBOV), Paramyxoviridae (comprising measles virus (MeV), Newcastle disease virus (NDV)), and Pneumoviridae (e.g., Human Respiratory Syncytial-Virus (HRSV)). In the context of the present invention Rhabdoviridae and Paramyxoviridae are preferred, more preferably RNA virus of the genus Vesiculovirus.

Negative-sense viral RNA is complementary to mRNA and must be converted into positive-sense RNA by an RNA-dependent RNA polymerase before translation. Thus, purified RNA of a negative-sense RNA is not infectious as it needs to be transcribed first, which requires an RNA-dependent RNA polymerase comprised in the virus particle (virion). The sequence of recombinant RNA viruses is commonly provided as cDNA sequence, as the RNA sequence is reverse transcribed for sequencing.

The term "linker" refers to a sequence coding for a separating peptide of variable length of about 6 to 30 amino acids; preferably 7 to 15 amino acids that separate different parts of a protein without affecting the function of the different parts of the protein or having a function on its own. A linker may be flexible or rigid, preferably the linker is a flexible linker. Preferably no linker is used between the protease cleavage site and the at least one protein essential for viral transcription and/or replication.

Conditional Regulation for an RNA Virus

In one aspect the invention relates to a single-stranded RNA virus comprising a modified genome of the virus comprising a polynucleotide sequence encoding at least one protein essential for viral transcription and/or replication, a protease and a cleavage site for said protease, wherein the at least one protein essential for viral transcription and/or replication comprises an insert at an intramolecular insertion site comprising at least the cleavage site for said protease and optionally further the protease. The protease cleaves the least one protein essential for viral transcription and/or replication at the cleavage site for said protease at the intramolecular insertion site. Cleavage at the intramolecular insertion site renders the protein essential for viral transcription and/or replication inactive. This aspect may also be referred to as the ON-switch in the context of the present invention, because the addition of a protease inhibitor "switches on" the at least one protein essential for viral transcription and/or replication. Preferably the insert comprises a flexible linker on either side, such as a glycine-serine linker.

In another aspect the invention relates to a single-stranded RNA virus comprising a modified genome of the virus comprising a polynucleotide sequence encoding at least one protein essential for viral transcription and/or replication, a protease and a cleavage site for said protease, wherein the at least one protein essential for viral transcription and/or replication is encoded as a fusion protein comprising the protease fused to the N-terminal or C-terminal end, separated by the cleavage site for said protease. The fusion protein may or may not comprise a linker between the cleavage site and the protein essential for viral transcription and/or replication, such as a glycine-serine linker. More generally the fusion protein may or may not comprise a linker between the protease and the protein essential for viral transcription and/or replication, i.e., between the protease and the cleavage site or between the cleavage site and the protein essential for viral transcription and/or replication. Preferably the fusion protein does not comprise a linker between the cleavage site and the protein essential for viral transcription and/or replication. Alternatively the fusion protein may or may not comprise a linker between the protease and the cleavage site. The protease cleaves at the cleavage site for said protease located at the N-terminal or C-terminal end of the at least one protein essential for viral transcription and/or replication encoded as a fusion protein to release the at least one protein essential for viral transcription and/or replication. Thus, the protease and the protease cleavage site for said protease are at an intermolecular location. Proteolytic release of the at least one protein essential for viral transcription and/or replication renders said protein essential for viral transcription and/or replication active. In other words the proteolytic cleavage releases the active at least one protein essential for viral transcription and/or replication. The term "release" or "proteolytic release" as used herein refers to the removal of sequences fused to the at least one protein essential for viral transcription and/or replication that inactivate said protein. This aspect may also be referred to as the OFF-switch in the context of the present invention, because the addition of a protease inhibitor "switches off" the at least one protein essential for viral transcription and/or replication.

Thus, the fusion protein may consist of the protease fused to the N-terminal or C-terminal end of the at least one protein essential for viral transcription and/or replication, separated by the cleavage site for said protease. The fusion protein may optionally further comprise a linker between the protease and the at least one protein essential for viral transcription and/or replication, such as a glycine-serine linker. Thus, the fusion protein may or may not comprise a linker between the cleavage site and the protein essential for viral transcription and/or replication; or alternatively the fusion protein may or may not comprise a linker between the protease and the cleavage site. Preferably the fusion protein does not comprise a linker between the cleavage site and the protein essential for viral transcription and/or replication. However, no further elements are required for inactivation of the at least one protein essential for viral transcription and/or replication in said fusion protein. Thus, the fusion protein may consist of the protease fused to the N-terminal or C-terminal end of the at least one protein essential for viral transcription and/or replication, separated by the cleavage site for said protease and optionally a linker. The fusion protein may also comprise or consist of (a) the protease fused to the N-terminal or C-terminal end of the protein essential for viral transcription and/or replication, separated by the cleavage site for said protease, and (b) a further viral protein or a heterologous protein fused to the opposite end of the protease fused to the N-terminal or C-terminal end of the protein essential for viral transcription and/or replication, and wherein said further viral protein or heterologous protein and said protease are also separated by a cleavage site for said protease. The fusion protein optionally further comprises a linker between the protease and the protein essential for viral transcription and/or replication, and/or a linker between the protease and the further viral protein or heterologous protein. In this context it is important that the protease comprises a cleavage site on either side of the protease (framed by a cleavage site for said protease on either side) in order to release both proteins, the protein essential for viral transcription and/or replication as well as the further viral protein or the heterologous protein. Preferably the protease is fused to the N-terminal end of the protein essential for viral transcription and/or replication, or the at least one protein essential for viral transcription and/or replication is an L-protein, or the protease is fused to the N-terminal end of an L-protein. The two cleavage sites for said protease (and the optional linkers) on either side are preferably different from each other. The protease having a cleavage site on either side may further have a linker on one or both side, either flanking the cleavage site on one or both sides or alternatively between the protease and the one or more cleavage site. Preferably the fusion protein does not comprise a linker between the cleavage site and the at least one protein essential for viral transcription and/or replication.

The RNA viruses suitable in the context of the present invention are particularly single-stranded RNA viruses. The term single-stranded RNA virus includes a positive-sense single-stranded RNA virus or a negative-sense single-stranded RNA virus. Preferably, the RNA virus is a negative-sense single stranded RNA virus. In one embodiment the RNA virus is of the order Mononegavirales. More specifically the single-stranded RNA virus of the order Mononegavirales may be a virus of a family selected from the group consisting of Rhabdoviridae, Paramyxoviridae, Filoviridae, Nyamiviridae, Pneumoviridae and Bornaviridae, preferably of the family Rhabdoviridae or Paramyxoviridae, preferably of the genus Vesiculovirus, more preferably a Vesicular Stomatitis Virus (VSV) or a Measles morbillivirus (MeV), even more preferably VSV.

In one embodiment the at least one protein essential for viral transcription and/or replication is an RNA-dependent RNA polymerase (RdRp) and/or a protein of the polymerase complex comprising the RNA-dependent RNA polymerase and/or a nucleocapsid protein. Preferably the at least one protein essential for viral transcription and/or replication is selected from the group consisting of polymerase cofactor, polymerase and nucleocapsid protein. The term polymerase cofactor refers to an essential component of the RNA polymerase transcription and replication complex. In VSV the RdRp complex comprises the large protein (L-protein) acting as the RdRp and the phosphoprotein (P-protein). The P-protein has two domains, the first being involved in transcription and the second in replication. It typically binds the viral ribonucleocapsid and positions the RNA-dependent RNA polymerase on the templates.

In certain embodiments the RNA virus is of the order Mononegavirales and the at least one protein essential for viral transcription and/or replication is a polymerase cofactor, e.g., the phosphoprotein (P-protein) or a functional equivalent thereof; a polymerase, e.g., the large protein (L-protein); and/or a nucleocapsid, e.g., the nucleoprotein (N-protein). The at least one protein essential for viral transcription and/or replication may be one, two or three proteins essential for viral transcription and/or replication, preferably one or two proteins essential for viral transcription and/or replication. The term "a functional equivalent" of the P-protein refers to an essential component of the RdRp complex other than the RNA-dependent RNA polymerase itself.

The order Mononegavirales includes without being limited thereto the families Bornoviridae, Nyamaviridae, Rhabdoviridae, Filoviridae and Paramyxoviridae, such as Paramyxovirinae and Pneumovirinae. The polymerase is referred to as L-protein in Bornoviridae (e.g., BDV), Nyamaviridae (e.g., NYMV), Rhabdoviridae (e.g., VSV, Maraba), Filoviridae (e.g., EBOV) and Paramyxoviridae, such as Paramyxovirinae (e.g., MeV) and Pneumovirinae (e.g., HRSV). The nucleocapsid is referred to as N-protein in Bornoviridae (e.g., BDV), Nyamaviridae (e.g., NYMV), Rhabdoviridae (e.g., VSV) and Paramyxoviridae, such as Paramyxovirinae (e.g., MeV) and Pneumovirinae (e.g., HRSV), whereas it is referred to as NP-protein in Filoviridae (e.g., EBOV). Thus, one example of a functional equivalent of the N-protein is the NP-protein in Filoviridae. The polymerase cofactor is referred to as P-protein in Nyamaviridae (e.g., NYMV), Rhabdoviridae (e.g., VSV) and Pneumovirinae (e.g., HRSV), whereas it is referred to as X/P-protein in Bornoviridae (e.g., BDV), VP35 in Filoviridae (e.g., EBOV) and P/V/C-protein in Paramyxovirinae (e.g., MeV). The Nyamaviridae comprise a further polymerase cofactor, the X-protein, in addition to the P-protein. Thus examples for a functional equivalent of the P-protein are the X/P-protein in Bornoviridae, the VP35-protein in Filoviridae, the P/V/C-protein in Paramyxovirinae and the X-protein in Nyamaviridae.

In one embodiment the RNA virus is of the order Mononegavirales and the at least one protein essential for viral transcription and/or replication is a polymerase cofactor, e.g., the P-protein or a functional equivalent thereof; and/or a polymerase, e.g., the L-protein; or a combination thereof. Preferably the at least one protein essential for viral transcription and/or replication is a polymerase, e.g. the L-protein. Without being bound by theory, as transcription of the viral genes occurs in sequential order from a single promoter at the 3' end of the genome resulting in decreasing amounts of each transcript, modifications at the L-protein being last in the genome results in less attenuation compared to modifications in other proteins.

The protease regulates the activity of the at least one protein essential for viral transcription and/or replication. The protease inactivates the protein essential for viral transcription and/or replication with at least a cleavage site for said protease at an intramolecular location, whereas at the intermolecular location the protease activates the protein essential for viral transcription and/or replication. This refers to the protease in its active state and in the absence of a protein inhibitor for said protease. Thus, the protease also regulates viral transcription and/or replication. The term "cleavage site for said protease" refers to a consensus amino acid sequence that serves as a substrate for proteolytic cleavage of the polypeptide. Cleavage sites for the respective proteases are known in the art.

In one embodiment the protease is an autocatalytic protease or the protease acts as an autocatalytic proteases. A protease acts as an autocatalytic protease means that the protease is autocatalytically active, i.e., it mediates cis-cleavage. Typically an autocatalytically active protease also mediates trans-cleavage, i.e., in a different polypeptide comprising the respective cleavage site, in addition to cis-cleavage. Mediating cis-cleavage may be an inherent property of the protease (autocatalytic protease). For example the protease is flanked by one or more cleavage site(s). The protease therefore mediates cleavage of the polypeptide comprising the protease. In specific cases the protease may be released from a polyprotein by autocatalytic cleavage. A protease may also become autocatalytically active by incorporation of one or two cleavage site(s) at the N-terminal or C-terminal end of the protease. Thus, a protease acting as an autocatalytic protease or a protease that is catalytically active may also be generated by cloning the respective cleavage site in close proximity to the protease (not naturally expressing the cleavage site on the same polypeptide), such that the recombinant protease has a N-terminal and/or a C-terminal cleavage site. Preferably the protease is framed by a cleavage site for said protease on either side. Thus, the protease has two cleavage sites for said protease, one on the N-terminal side and one on the C-terminal side of the protease. An autocatalytic protease or a protease that acts as an autocatalytic protease is preferred for the aspect relating to the ON-switch (the addition of a protease inhibitor "switches on" the at least one protein essential for viral transcription and/or replication) as well as the aspect relating to the OFF-switch (the addition of a protease inhibitor "switches off" the at least one protein essential for viral transcription and/or replication). However, in the aspect relating to the ON-switch, the insert at the intramolecular insertion site may comprise only the cleavage site for said protease, while the protease may be provided in trans, i.e., as a separate polypeptide preferably encoded by the RNA virus. Therefore, the at least one protein essential for viral transcription and/or replication comprises an insert at an intramolecular insertion site comprising at least the cleavage site for said protease, preferably the protease and the cleavage site for said protease. Thus, in case the insert at the intramolecular insertion site comprising only the cleavage site for said protease, the protease is provided in trans.

Further the protease or autocatalytic protease may be any protease, particularly a viral protease, a prokaryotic protease or a eukaryotic protease, particularly a viral or a eukaryotic protease. The protease used in the RNA virus according to the invention is a heterologous protease, i.e., a protease not endogenous to the virus. In one embodiment the protease is a viral protease, such as the protease is from HCV or HIV. The person skilled in the art will understand that proteases suitable in the context of the present invention are highly specific, i.e., have a restricted set of unique and rare substrate sequences, and further have a specific inhibitor available. The availability of a specific inhibitor allows for conditional regulation of the RNA virus. The protease inhibitor inhibits the proteolytic activity of the protease, wherein inhibits means that the protease shows at least 80% inhibition, at least 90% inhibition, at least 95% inhibition, at least 99% inhibition and preferably 100% inhibition compared to the protease in the absence of the inhibitor. Preferably, the inhibitor is used at a dose corresponding to a therapeutic serum concentration.

The protease inhibitor should be specific for the protease and suitable for in vivo use, i.e., being safe, bioavailable and active in vivo, such as following oral or parenteral administration to a subject, preferably a human subject. Viral proteases are advantageous as they are common targets for antiviral drugs and hence a number of protease inhibitors inhibiting viral proteases have been approved and tested to be safe in humans. For example, for the human immune deficiency (HIV) protease, various well-characterized protease inhibitors are available and allow regulation of the system with desired kinetics. Examples of suitable HIV protease inhibitors are, without being limited thereto, e.g., indinavir, saquinavir, ritonavir, nelfinavir, lopinavir, amprenavir, fosamprenavir, atazanavir, tipranavir and darunavir. Human proteases are advantageous as they are endogenous proteins to human patients and hence do not elicit an immune response. Examples for suitable human proteases, without being limited thereto, are caspases and metalloproteinases. Examples of suitable human protease inhibitors are, without being limited thereto, e.g. caspase inhibitors emricasan and nivocasan; matrix metalloproteinase inhibitor batimastat and tanomastat, and ecaliximab.

The protease may be a monomer or a dimer. Preferably a dimer is used in form of a single-chain dimer, by linking the monomers via a flexible linker. Examples for a protease that is active only as a dimer is the HIV protease used in the Examples. As explained for the HIV-1 protease, single-chain dimers are preferably codon-optimized to avoid homology between the first and second protease. This reduces the risk of "copy-choice" recombination events as previously described in VSV (Simon-Loriere and Holmes 2011), in which the viral polymerase, the L-protein, can switch between templates and skip sequence stretches. "Copy-choice" occurs when the polymerase is guided by sequence homology of the nascent RNA strand with the newly chosen template. Preferably the protease is autocatalytically active, i.e., it mediates cis-cleavage. In one embodiment the protease is the HIV-1 protease, preferably a single chain dimer of the HIV-1 protease (e.g., a single chain dimer of the HIV-1 protease having the DNA sequence of SEQ ID NO: 5). Suitable HIV-1 protease inhibitors are, without being limited thereto, indinavir, saquinavir, ritonavir, nelfinavir, lopinavir, amprenavir, fosamprenavir, atazanavir, tipranavir or darunavir, preferably amprenavir, saquinavir or indinavir. In another embodiment the protease is the HCV protease NS3 and suitable NS3 inhibitors are, without being limited thereto, boceprevir, telaprevir, asunaprevir, ciluprevir, feldaprevir, vaniprevir, narlaprevir, simeprevir or danoprevir, preferably vaniprevir, narlaprevir, simeprevir or danoprevir.

The single-stranded RNA virus according to the invention may further encode a heterologous protein, preferably a therapeutic protein, a reporter or a tumor antigen, more preferably a therapeutic protein or a tumor antigen. Production of such heterologous protein depends on intact activity of the viral transcription complex.

In certain embodiments the virus is an oncolytic virus. An oncolytic virus is a virus that preferentially infects and kills cancer cells. The killed cancer cells release new infectious virus particles that infect further cancer cells and release cell fragments that stimulate an anti-tumor immune response in the host. Clinically tested oncolytic RNA viruses include without being limited thereto, reovirus, measles virus, Newcastle disease virus, influenza virus, Semliki Forest virus, Sindbis virus, poliovirus, Coxsackie virus, Seneca Valley virus, Maraba and VSV. Preferably the oncolytic virus is VSV. This includes derivatives thereof, such as VSV-GP pseudotyped with the glycoprotein (GP) of the lymphocytic choriomeningitis virus (LCMV) as described in WO 2010/040526.

ON-Switch

Provided is a single stranded RNA virus comprising a modified genome of the virus comprising a polynucleotide sequence encoding at least one protein essential for viral transcription and/or replication, a protease and a cleavage site for said protease, wherein the at least one protein essential for viral transcription and/or replication comprises an insert at an intramolecular insertion site comprising at least the cleavage site for said protease and optionally further the protease, preferably comprising the protease and the cleavage site for said protease.

The insert at the intramolecular insertion site of the at least one protein essential for viral transcription and/or replication does not affect activity of the at least one protein essential for viral transcription and/or replication. Activity of the at least one protein essential for viral transcription and/or replication may be assessed by detecting viral reporter gene expression, TCID50 replication assays or MTT killing assays (see FIG. 13C), preferably using a TCID50 replication assay. Wherein the modified protein essential for viral transcription and/or replication carrying an insert at the intramolecular site may be expressed by the single-stranded RNA virus or may be expressed in trans on a plasmid together with a single-stranded RNA virus deficient in said protein essential for viral transcription and/or replication. The insert at the intramolecular insertion site of the at least one protein essential for viral transcription or replication is considered not to affect activity of the at least one protein essential for viral transcription and/or replication if the activity of the protein and hence viral replication as measured, e.g., by TCID50, provides titers of no more than 2 log lower titers, preferably no more than 1.5 log lower titers, more preferably no more than 1 log lower titers and more preferably equal titers compared to a recombinant single-stranded RNA virus without the insert at the intramolecular insertion site (control) and in case of a protease at the intramolecular insertion site in the presence of a protease inhibitor in the control and the test sample.

In the single-stranded RNA virus at least the cleavage site for said protease, and optionally further the protease, is located within the intramolecular insertion site of the least one protein essential for viral transcription and/or replication, and the proteolytic cleavage of the protein cleaves the at least one protein essential for viral transcription and/or replication at the cleavage site for said protease within the intramolecular insertion site. Cleavage within the intramolecular insertion site inactivates the at least one protein essential for viral transcription and/or replication. Thus, cleavage within the intramolecular insertion site of the at least one protein essential for viral transcription and/or replication further inhibits viral transcription and/or replication. Consequently, the virus is active in the presence of a specific inhibitor of the protease and inactive in the absence of a specific inhibitor of the protease. The single-stranded RNA virus may further encode at least one heterologous protein, wherein the heterologous protein is expressed if the virus is active in the presence of a specific inhibitor of the protease and is not expressed if the virus is inactive in the absence of a specific inhibitor of the protease. Production of such heterologous protein depends on intact activity of the viral transcription complex. A suitable heterologous protein is a protein such as a therapeutic protein, a reporter or a tumor antigen.

In a specific embodiment the protease is the autocatalytic HIV protease dimer inserted at the intramolecular insertion site of one or two proteins of the vesicular stomatitis virus (VSV) that make up the polymerase complex (P-protein and/or L-protein, separately and in combination). In the presence of protease inhibitor, the integrity of the viral proteins is preserved and the virus replicates. Without protease inhibitors, the HIV protease dimer is autocatalytically active, cleaving the essential viral proteins upon translation. Analogous to regulatory modules in DNA viruses (e.g. Tet-On), this mechanism is referred to as "prot-ON" in the Examples.

In one embodiment the insert at the intramolecular insertion site comprises a protease and at least one cleavage site for said protease. At the intramolecular location, the protease has a two cleavage sites. Thus, the protease has a cleavage site on either side and optionally a linker on one or both sides. The linker may either flank the cleavage site on one or both sides or alternatively may be located between the protease and the one or more cleavage site. The two cleavage sites for said protease (and the optional linkers) on either side of the protease are preferably different from each other.

In one embodiment the RNA virus is of the order Mononegavirales and the at least one protein essential for viral transcription and/or replication is a polymerase cofactor, e.g., the P-protein or a functional equivalent thereof; a polymerase, e.g., the L-protein; and/or a nucleocapsid, e.g., the N-protein. The at least one protein essential for viral transcription and/or replication may be one, two or three proteins essential for viral transcription and/or replication, preferably one or two proteins essential for viral transcription and/or replication. In certain embodiments the at least one protein essential for viral transcription and/or replication is the P-protein or a functional equivalent thereof or the L-protein or a combination thereof.

The codon usage of the flexible linkers and protease dimer has been optimized to avoid homology between the first and second protease. This precaution was taken, since so called "copy-choice" recombination events in VSV have been described previously (Simon-Loriere and Holmes 2011), in which the viral polymerase, the L-protein, can switch between templates and also skip sequence stretches. "Copy-choice" occurs preferentially when the polymerase is guided by sequence homology of the nascent RNA strand with the newly chosen template. Furthermore, point mutations arise frequently in RNA viruses, in the case of VSV at a mutation rate of about 1 nucleotide in 10,000. Theoretically, every genome carries one mutation, which leads virologists to refer to the VSV genome (and other RNA virus genomes) not as one sequence, but to a mixture of so called "quasi-species". Therefore, occurrence of mutations within the HIV protease sequence rendering the proteolytic switch inactive are a real possibility. To avoid such escape mutants or revertant viruses that may lose the conditional ON switch control, the protease module (ON-switch) may be doubled by introducing protease dimers in a first and a second essential VSV protein, such as the P-protein and the L-protein. The protease and the respective cleavage site may be the same in the two proteins essential for viral transcription and/or replication or may be different and hence may be regulated by the same or different protease inhibitors.

A suitable insertion site at amino acid 196 of the P-protein of VSV has already been described (Das et al., J Virol, 2006, 80 (13): 6368-6377 and Das and Pattnaik, J Virol, 2005, 79(13):8101-8112), wherein the numbering refers to the P-protein of serotype VSV Indiana (VSVI) (e.g., having the nucleotide sequence of SEQ ID NO: 1 and/or the amino acid sequence of SEQ ID NO: 27).

L-protein insertion sites have been described, but the resulting viruses were temperature sensitive and instable after passage (Ruedas and Perrault 2009, Ruedas and Perrault 2014). Based on the recently published full structure information on the VSV L-protein (Liang, Li et al. 2015) possible permissive sites were identified and tested, initially with fluorescence proteins and subsequently with the HIV protease dimer.

Thus, in one embodiment the single-stranded RNA virus is a Vesicular Stomatitis Virus (VSV). Although there are VSV serotypes, the VSV serotype best characterized and used in therapy is VSV Indiana (VSVi). All sequences disclosed and used herein are from VSVi. Also encompassed are derivatives of VSVi, such as VSV-GP as described in more detail in WO 2010/040526. Since VSV Indiana is a RNA virus, there are several complete genome nucleotide sequences available, one example is the cDNA sequence of SEQ ID NO: 22 (GenBank accession number MH919398.1). The viruses generated in the examples are derived from the DNA sequence of (SEQ ID NO: 20). The positions referred to in the following are therefore provided as corresponding to the provided amino acid position of the P-protein or the L-protein of VSVi or the P-protein or the L-protein of VSVi having the amino acid sequence of SEQ ID NOs: 27 or 28, respectively. The person skilled in the art would know how to identify the corresponding amino acid sequence in a further VSVi P-protein or L-protein sequence by sequence alignment.

In one embodiment the single-stranded RNA virus is VSV and the at least one protein essential for viral transcription and/or replication is the P-protein and/or the L-protein of VSV. A suitable intramolecular insertion site for the P-protein is in the flexible hinge region of the VSV P-protein, preferably at a position corresponding to amino acid position 193-199, more preferably amino acid position 196 of VSVi P-protein. In a specific embodiment the intramolecular insertion site of the P-protein is at amino acid position 193-199 of the P-protein of VSVi, preferably at amino acid 196 of the P-protein of VSVi. Wherein the numbering refers to the P-protein of VSVi, and one exemplary sequence of the P-protein of VSVi has the amino acid sequence of SEQ ID NO: 27. In one embodiment the intramolecular insertion site of the P-protein is at amino acid position 193-199 of the P-protein of VSVi having the sequence of SEQ ID NO: 27 or a homologue thereof, preferably at amino acid 196 of the P-protein of VSVi having the sequence of SEQ ID NO: 27 or a homologue thereof, wherein the homologue has at least 80% sequence identity with SEQ ID NO: 27, preferably at least 90% sequence identity with SEQ ID NO: 27. A suitable intramolecular insertion site for the L-protein is in the methyltransferase domain (MT) of the L-protein, particularly in the loop of the methyltransferase domain of the L-protein corresponding to amino acids 1614 to 1634, preferably to amino acids 1614 to 1629, more preferably to amino acids 1616 to 1625, and more preferably to amino acid 1620 of VSVi L-protein. In a specific embodiment the intramolecular insertion site of the L-protein is between amino acids 1614 and 1634, preferably between amino acids 1614 and 1629, more preferably between amino acids 1616 and 1625, and more preferably at amino acid 1620 of VSVi L-protein. Wherein the numbering refers to the L-protein of VSVi, and one exemplary sequence of the L-protein of VSVi has the amino acid sequence of SEQ ID NO: 28. In one embodiment the intramolecular insertion site of the L-protein is between amino acids 1614 and 1634, preferably between amino acids 1614 and 1629, more preferably between amino acids 1616 and 1625, and even more preferably at amino acid 1620 of the L-protein of VSVi having the sequence of SEQ ID NO: 28 or a homologue thereof, wherein the homologue has at least 80% sequence identity with SEQ ID NO: 28, preferably at least 90% sequence identity with SEQ ID NO: 28. In another embodiment the single-stranded RNA virus is VSV and the P-protein comprises an insert at the intramolecular insertion site comprising at least the cleavage site for said protease and optionally further the protease in the flexible hinge region of the VSV P-protein at a position corresponding to amino acid position 193-199 of VSVi P-protein, preferably at amino acid position 193-199 of VSVi P-protein or the L-protein comprises an insert at the intracellular insertion site comprising at least the cleavage site for said protease and optionally further the protease in the loop of the methyltransferase domain (MT) of the L-protein corresponding to amino acids 1614 to 1634 of VSVi L-protein, preferably between amino acids 1614 and 1634 of VSVi L-protein. In yet another embodiment the single-stranded RNA virus is VSV and the P-protein comprises an insert at the intramolecular insertion site comprising at least the cleavage site for said protease and optionally further the protease in the flexible hinge region of the VSV P-protein at a position corresponding to amino acid position 193-199 of VSVi P-protein, preferably at amino acid position 193-199 of VSVi P-protein and the L-protein comprises an insert at the intracellular insertion site comprising at least the cleavage site for said protease and optionally further the protease in the loop of the methyltransferase domain (MT) of the L-protein corresponding to amino acids 1614 to 1634 of VSVi L-protein, preferably between amino acids 1614 and 1634 of VSVi L-protein. Placing an ON-switch into more than one, preferable two proteins essential for viral transcription and/or replication reduces the risk of escape mutants. Although no ON-switch escape mutants have been observed despite repetitive passages an insert in two proteins essential for viral transcription and/or replication provides more stability. The term "at amino acid position" as used herein refers to after, i.e., at amino acid position 196 of VSVi P-protein having the sequence of SEQ ID NO: 27 and means between amino acid positions 196 and 197 of VSVi P-protein having the sequence of SEQ ID NO: 27 and at amino acid 1620 of the L-protein of VSVi having the sequence of SEQ ID NO: 28 means between amino acid positions 1620 and 1621 of the L-protein of VSVi having the sequence of SEQ ID NO: 28.

The ON-switch system inherently harbors an environmental safety element. As virus progeny depend on presence of protease inhibitor, potentially shed virus is not active for productive infection. This may be important in case a therapeutic RNA virus can cause animal disease.

VSV is typically associated with neurotoxicity and intracranial spread. In vivo data have shown that the ON-switch system resulted in complete abrogation of neurotoxicity and intracranial spread. As the protease inhibitor amprenavir does not cross the blood brain barrier, systemic application of the compound did not confer virus activity in the brain and neurotoxicity was absent despite a systemically present ON-switch system resulting in virus replication in the presence of systemic amprenavir.

In one embodiment the single stranded RNA virus according to the invention is for use in therapy, particularly for use in cancer therapy, particularly in humans.

OFF-Switch

Also provided is a single-stranded RNA virus comprising a modified genome of the virus comprising a polynucleotide sequence encoding at least one protein essential for viral transcription and/or replication, a protease and a cleavage site for said protease, wherein the at least one protein essential for viral transcription and/or replication is encoded as a fusion protein comprising the protease fused to the N-terminal or C-terminal end, separated by the cleavage site for said protease. In one embodiment the fusion protein does not comprise an amino acid sequence of SEQ ID NO: 30. Preferably the protease is fused to the N-terminal end of the at least one protein essential for viral transcription and/or replication. Thus, the at least one protein essential for viral transcription and/or replication is encoded as a fusion protein comprising the protease directly fused to the N-terminal end of the at least one protein essential for viral transcription and/or replication, separated by the cleavage site for said protease and optionally a linker. The fusion protein may or may not comprise a linker between the protease and the protein essential for viral transcription and/or replication, such as a glycine-serine linker. Thus, the fusion protein may or may not comprise a linker between the cleavage site and the protein essential for viral transcription and/or replication; or alternatively the fusion protein may or may not comprise a linker between the protease and the cleavage site. Preferably the fusion protein does not comprise a linker between the cleavage site and the protein essential for viral transcription and/or replication.

The at least one protein essential for viral transcription and/or replication is encoded as a fusion protein comprising the protease fused to the N-terminal or C-terminal end of the at least one protein essential for viral transcription and/or replication separated by the cleavage site for said protease and wherein proteolytic cleavage of the fusion protein releases the at least one protein essential for viral transcription and/or replication in its active form. Thus, the at least one protein essential for viral transcription and/or replication and the protease are expressed as a fusion protein separated by a cleavage site for said protease. Upon proteolytic cleavage, the protease and the at least one protein essential for viral transcription and/or replication are separated. The at least one protein essential for viral transcription and/or replication is inactive in the fusion protein and gets activated upon release by proteolytic cleavage (also referred to as proteolytic release). According to the invention, the fusion protein does not comprise an amino acid sequence of SEQ ID NO: 30. This sequence functions as a degron in a SMASh tag described by Chung et al. (Nature Chemical Biology (2015), 11:713-722) resulting in degradation of a protein. By contrast, according to the present invention the fusion of the protease to the at least one protein essential for viral transcription and/or replication separated by the cleavage site for said protease inactivates the at least one protein essential for viral transcription and/or replication. The fusion protein is therefore expressed and detectable, i.e., not degraded. Thus, within the fusion protein the at least one protein essential for viral transcription and/or replication is functionally inactive. Rendering the at least one protein essential for viral transcription and/or replication, such as the L-protein, functionally inactive in the fusion protein, is sufficient to efficiently switch-off virus production, without the need for protein degradation. The single-stranded RNA virus may further encode at least one heterologous protein, wherein the heterologous protein is expressed if the virus is active in the presence of a specific inhibitor of the protease and is not expressed if the virus is inactive in the absence of a specific inhibitor of the protease. Production of such heterologous protein depends on intact activity of the viral transcription complex. A suitable heterologous protein is a protein such as a therapeutic protein, a reporter or a tumor antigen.

Thus, the at least one protein essential for viral transcription and/or replication in the fusion protein comprising the protease fused to the N-terminal or C-terminal end of the at least one protein essential for viral transcription and/or replication separated by the cleavage site for said protease without proteolytic cleavage is inactive. The proteolytic cleavage of the fusion protein is inhibited using a specific inhibitor of the protease. The single-stranded RNA virus is therefore inactive in the presence of a specific protease inhibitor of the protease and active in the absence of a specific inhibitor of the protease.

In one embodiment the protease and the cleavage site for said protease replace an intergenic region that links a protein essential for viral transcription and/or replication with a further viral protein. Thus, in one embodiment the fusion protein comprises a protein essential for viral transcription and/or replication and a further viral protein separated by the protease and the cleavage site for said protease, wherein the protease is preferably flanked by a cleavage site for said protease on either side (i.e., at the N-terminal and the C-terminal end of the protease). Thus, loss of the protease leads to a further inactive fusion protein comprising the protein essential for viral transcription and/or replication and the further viral protein. In other words, deletion of the protease and the cleavage site(s) for said protease in a revertant or escape mutant would lead to a new non-functional fusion protein comprising the protein essential for viral transcription and/or replication in its inactive state fused to the further viral protein. Thus, replacing the entire intergenic region makes the virus safer as deletion of the insert comprising the protease and the cleavage site for said protease results in a further fusion protein, wherein the further fusion protein comprises the protein essential for viral transcription and/or replication and the further viral protein. The further viral protein may be a second protein essential for viral transcription and/or replication. Since deletion of the protease insert does not provide any advantage to this virus, this feature provides protection from escape mutants.

In case the viral genome does not contain two proteins essential for viral transcription and/or replication adjacent to each other, this may be achieved by gene shuffling. For VSV it is known that the genes can be shuffled. However, the order of the genes in the genome correlates with translation frequency. Thus, gene shuffling usually comes with some degree of attenuation. Alternatively the further viral protein is a viral protein that is not essential for viral transcription and/or replication.

Figure 17A:
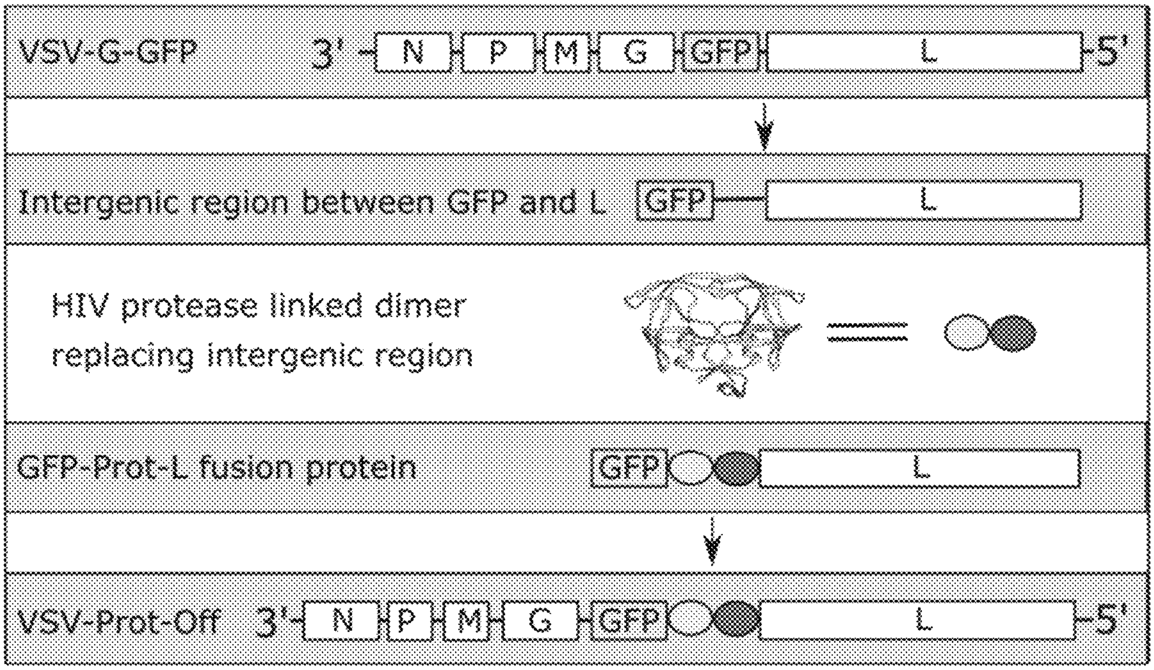
FIG. 17. Principle of the VSV-Prot-OFF system and protein ribbon structure of HIV protease dimer. A: The intergenic region between GFP and L-protein were replaced with an HIV protease construct. B: The HIV protease is functional as a dimer. To ensure the functionality of the HIV protease as part of the open reading frame of the GFP-Prot-L fusion protein, we used a protease dimer that was a priori linked.
Figure 17B:
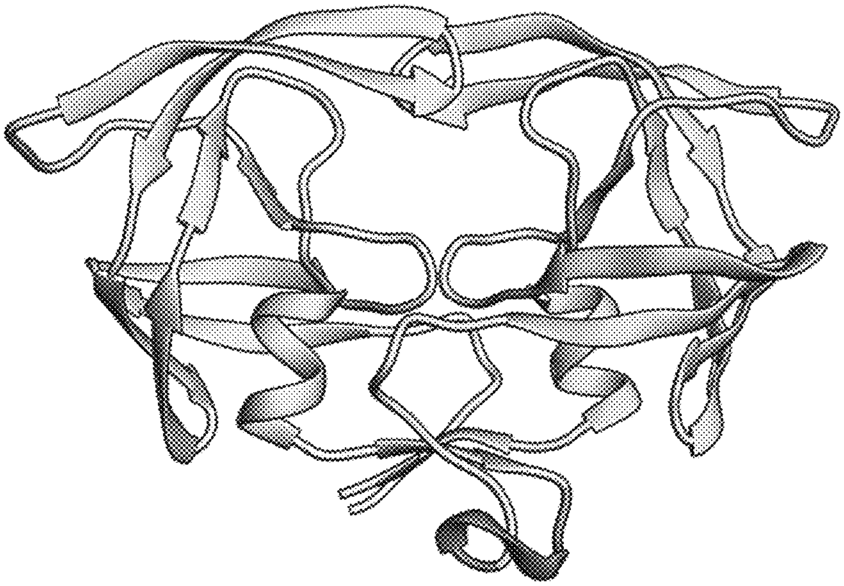

In another embodiment the protease and the cleavage site for said protease replace an intergenic region that links a protein essential for viral transcription and/or replication with a heterologous protein, such as shown in FIG. 17. In other words, the protease is fused to the protein essential for viral transcription and/or replication at one end and to at the heterologous protein at the other end, each separated by a cleavage site for said protease. Thus, in one embodiment the fusion protein may also comprise a heterologous protein fused to the opposite end of the protease fused to the N-terminal or C-terminal end of the at least one protein essential for viral transcription and/or replication, wherein said heterologous protein and said protease are also separated by the cleavage site for said protease. In one embodiment the protease is flanked by the cleavage site for said protease on either side and replaces an intergenic region that links the at least one protein essential for viral transcription and/or replication with a heterologous protein. Thus, loss of the protease leads to a further inactive fusion protein comprising the protein essential for viral transcription and/or replication and the heterologous protein.

In case the intergenic region is replaced by the protease, the protease should be an autocatalytic protease flanked on either side by a cleavage site for said protease, i.e., comprising two cleavage sites to said protease, one at the N-terminal and one at the C-terminal side of the protease (or the single chain dimer protease). Thus, in one embodiment the fusion protein further comprises a further viral protein or a heterologous protein fused to the opposite end of the protease fused to the N-terminal or C-terminal end of the at least one protein essential for viral transcription and/or replication, and wherein said further viral protein or heterologous protein and said protease are also separated by the cleavage site for said protease. In a specific embodiment the protease flanked by a cleavage site for said protease on either side replaces an intergenic region that links the at least one protein essential for viral transcription and/or replication with a further viral protein or heterologous protein, preferably wherein deletion of the protease in a revertant virus or an escape mutant leads to inactivation of the at least one protein essential for viral transcription and/or replication by forming a fusion protein with the at least one further viral protein or heterologous protein. Replacing the intergenic region with the protease has the advantage of reducing (in the case of a further viral protein) or of not increasing (in the case of a heterologous protein) the number of intergenic regions and hence reducing the risk of virus attenuation. The two cleavage sites for said protease (and the optional linkers) on either side of the protease are preferably different from each other.

In one embodiment the RNA virus is of the order Mononegavirales and the at least one protein essential for viral transcription and/or replication is a polymerase cofactor, e.g., the P-protein or a functional equivalent thereof; a polymerase, e.g., the L-protein; and/or a nucleocapsid, e.g., the N-protein. The at least one protein essential for viral transcription and/or replication may be one or two proteins essential for viral transcription and/or replication, preferably one protein essential for viral transcription and/or replication. Preferably the at least one protein essential for viral transcription and/or replication is the P-protein or a functional equivalent thereof or the L-protein, preferably the L-protein. Also, the protease is preferably fused to the N-terminal end of the P-protein (or a functional equivalent thereof) or the L-protein, more preferably to the N-terminal end of the L-protein.

In a preferred embodiment the at least one protein essential for viral transcription and/or replication is an L-protein; or the protease is fused to the N-terminal end of the at least one protein essential for viral transcription and/or replication separated by the cleavage site for said protease; or the at least one protein essential for viral transcription and/or replication is an L-protein and the protease is fused to the N-terminal end of the L-protein separated by the cleavage site for said protease. According to the invention, the at least one protein essential for viral transcription and/or replication, preferably the L-protein, is inactive in the fusion protein, preferably the fusion protein comprising the protease fused to the N-terminal end of the at least one protein essential for viral transcription and/or replication, and gets activated upon release by proteolytic cleavage.

In one embodiment the single-stranded RNA virus comprises a modified genome of the virus comprising a polynucleotide sequence encoding at least one protein essential for viral transcription and/or replication, a protease and a cleavage site for said protease, wherein the at least one protein essential for viral transcription and/or replication is encoded as a fusion protein consisting of the protease fused to the N-terminal or C-terminal end of the protein essential for viral transcription and/or replication, separated by the cleavage site for said protease, wherein the fusion protein optionally further comprises a linker between the protease and the protein essential for viral transcription and/or replication, such as a glycine-serine linker. Thus, the fusion protein may or may not comprise a linker between the cleavage site and the protein essential for viral transcription and/or replication; or alternatively the fusion protein may or may not comprise a linker between the protease and the cleavage site. Preferably the fusion protein does not comprise a linker between the cleavage site and the protein essential for viral transcription and/or replication. Preferably the protease is fused to the N-terminal end of the protein essential for viral transcription and/or replication, or the at least one protein essential for viral transcription and/or replication is an L-protein, or the protease is fused to the N-terminal end of the L-protein.

In another embodiment the single-stranded RNA virus comprises a modified genome of the virus comprising a polynucleotide sequence encoding at least one protein essential for viral transcription and/or replication, a protease and a cleavage site for said protease, wherein the at least one protein essential for viral transcription and/or replication is encoded as a fusion protein comprising or consisting of (a) the protease fused to the N-terminal or C-terminal end of the at least one protein essential for viral transcription and/or replication, separated by the cleavage site for said protease, and (b) a further viral protein or a heterologous protein fused to the opposite end of the protease fused to the N-terminal or C-terminal end of the at least one protein essential for viral transcription and/or replication, and wherein said further viral protein or heterologous protein and said protease are also separated by a cleavage site for said protease, wherein the fusion protein optionally further comprises a linker between the protease and the protein essential for viral transcription and/or replication, and/or a linker between the protease and the further viral protein or heterologous protein. Thus, the fusion protein may or may not comprise a linker between the cleavage site and the protein essential for viral transcription and/or replication; or alternatively the fusion protein may or may not comprise a linker between the protease and the cleavage site; and/or the fusion protein may or may not comprise a linker between the cleavage site and the further viral protein or heterologous protein; or alternatively the fusion protein may or may not comprise a linker between the other side of protease and the cleavage site. Preferably the fusion protein does not comprise a linker between the cleavage site and the protein essential for viral transcription and/or replication.

Preferably the protease is fused to the N-terminal end of the protein essential for viral transcription and/or replication, or the at least one protein essential for viral transcription and/or replication is an L-protein, or the protease is fused to the N-terminal end of an L-protein. The two cleavage sites for said protease (and the optional linkers) on either side of the protease are preferably different from each other. The protease having a cleavage site on either side may have a linker on one or both side, either flanking the cleavage site on one or both sides or alternatively between the protease and the one or more cleavage site. Preferably the fusion protein does not comprise a linker between the cleavage site and the at least one protein essential for viral transcription and/or replication.

In one embodiment the single stranded RNA virus according to the invention is for use in therapy, particularly for use in cancer therapy, particularly in humans.

Conditional Expression of a Heterologous Protein

The single-stranded RNA virus according to the invention comprising a modified genome of the virus comprising a polynucleotide sequence encoding at least one protein essential for viral transcription and/or replication, a protease and a cleavage site for said protease, wherein (a) the at least one protein essential for viral transcription and/or replication comprises an insert at an intramolecular insertion site comprising at least the cleavage site for said protease and optionally further the protease, or (b) the at least one protein essential for viral transcription and/or replication is encoded as a fusion protein comprising the protease fused to the N-terminal or C-terminal end, separated by the cleavage site for said protease, may further encode at least one heterologous protein. Production of such heterologous protein depends on intact viral transcription and/or replication and therefore requires that the at least one protein essential for viral transcription and/or replication is active. Thus, in alternative (a) (ON-switch) the heterologous protein is expressed if the virus is active in the presence of a specific inhibitor of the protease and is not expressed if the virus is inactive in the absence of a specific inhibitor of the protease and in alternative (b) (OFF-switch) the heterologous protein is not expressed if the virus is inactive in the presence of a specific inhibitor of the protease and is expressed if the virus is active in the absence of a specific inhibitor of the protease. A suitable heterologous protein is a protein such as a therapeutic protein, a reporter or a tumor antigen. Particularly for therapeutic purposes, the heterologous protein is preferably a therapeutic protein with immune-modulatory or cell death modulatory function or a tumor antigen. The therapeutic protein may also be a protein encoded by suicide gene.

Also provided herein is an RNA virus comprising a modified genome of the virus comprising a polynucleotide sequence encoding at least one heterologous protein, a protease and a cleavage site for said protease, wherein the at least one heterologous protein comprises an insert at an intramolecular insertion site comprising at least the cleavage site for said protease and optionally further the protease. In one embodiment the RNA virus is a single-stranded RNA virus.

The term single-stranded RNA virus includes a positive-sense single-stranded RNA virus or a negative-sense single-stranded RNA virus. Preferably, the RNA virus is a negative-sense single stranded RNA virus. In one embodiment the RNA virus is of the order Mononegavirales. More specifically the single-stranded RNA virus of the order Mononegavirales may be a virus of a family selected from the group consisting of Rhabdoviridae, Paramyxoviridae, Filoviridae, Nyamiviridae, Pneumoviridae and Bornaviridae, preferably of the family Rhabdoviridae or Paramyxoviridae, preferably of the genus Vesiculovirus, more preferably a Vesicular Stomatitis Virus (VSV) or a Measles morbillivirus (MeV), even more preferably VSV.

In certain embodiments the virus is an oncolytic virus. An oncolytic virus is a virus that preferentially infects and kills cancer cells. The killed cancer cells release new infectious virus particles that infect further cancer cells and release cell fragments that stimulate an anti-tumor immune response in the host. Clinically tested oncolytic RNA viruses include without being limited thereto, reovirus, measles virus, Newcastle disease virus, influenza virus, Semliki Forest virus, Sindbis virus, poliovirus, Coxsackie virus, Seneca Valley virus, Maraba virus and VSV. Preferably the oncolytic virus is VSV.

The term heterologous refers to the RNA virus rather than the host or patient infected with the virus and therefore explicitly encompasses eukaryotic, particularly human proteins. The heterologous protein is a protein derived from a different organism or a different species from the recipient, i.e., the RNA virus. The at least one heterologous protein encoded by the RNA virus according to the invention may be a therapeutic protein, a reporter or a tumor antigen. Preferably the at least one heterologous protein is a therapeutic protein with immune-modulatory or cell death modulatory function, preferably selected from the group consisting of cytokines, chemokines, growth factors and antibodies. The therapeutic protein may be also a membrane bound protein or may be rendered membrane bound by fusing a transmembrane domain, such as the transmembrane domain of CD4, to the heterologous protein, preferably linked via a linker. The therapeutic protein may also be an encoded suicide gene. Alternatively or in addition the at least one heterologous protein is a tumor antigen (including a tumor-specific and/or tumor-associated antigen), such as lineage antigens, neoantigens, testis antigens and oncoviral antigens. The term "tumor-specific antigen" refers to an antigen exclusively expressed in the tumor cell but not in any other tissue of the organism. The term "tumor-associated antigen" refers to an antigen overexpressed in the tumor cell compared to other tissue in the organism, i.e., expressed at a higher level. The tumor antigen may also be a neoantigen or neoantigens. Wherein neoantigens are newly formed antigens arising from tumor somatic mutations. The person skilled in the art would know how to detect and determine neoantigens from a patient. In another embodiment the heterologous protein is a reporter protein, such as green florescent protein, red florescent protein, mCherry or mWasabi. Particularly for therapeutic purposes, the heterologous protein is preferably a therapeutic protein with immune-modulatory or cell death modulatory function or a tumor antigen.

The person skilled in the art would understand that the insert comprising at least the cleavage site for said protease and optionally further the protease in the intramolecular insertion site corresponds to the insert comprising at least the cleavage site for said protease and optionally further the protease in the intramolecular insertion site of the at least one protein essential for viral transcription and/or replication, i.e., the ON-switch. Thus, the above disclosure and the embodiments relating to the ON-switch likewise apply to the RNA virus comprising a modified genome of the virus comprising at least one heterologous protein, a protease and a cleavage site for said protease, wherein the at least one heterologous protein comprises an insert at an intramolecular insertion site comprising at least the cleavage site for said protease and optionally further the protease. In one embodiment the RNA virus is a single-stranded RNA virus.

The person skilled in the art would further understand that the aspect relating to the ON-switch in the heterologous protein may be combined with the ON-switch in the at least one protein essential for viral transcription and/or replication. Thus also envisaged are armed viruses with two independent switches, one controlling virus activity and one controlling the activity of the virus-encoded therapeutic proteins. Both switches would preferably be controlled by two independent compounds.

In one embodiment the RNA virus according to the invention is for use in therapy, particularly for use in cancer therapy, particularly in humans.

Also provided is a polynucleotide sequence encoding at least one recombinant protein, a protease and a cleavage site for said protease, wherein the at least one recombinant protein comprises an insert at an intramolecular insertion site comprising the protease and the cleavage site for said protease or a recombinant protein comprising an insert at an intramolecular insertion site comprising the protease and the cleavage site for said protease. Thus, the ON-switch as described herein can also be used for therapeutic proteins, particularly for therapeutic proteins with a small therapeutic window. Examples for such therapeutic proteins are cytokines.

In one embodiment the polynucleotide or the recombinant protein according to the invention is for use in therapy, particularly for use in therapy in humans. The protease is therefore preferably of human origin to prevent immune reactions.

Thus, in one embodiment the protease is a human protease, such as a metalloprotease or a caspase. Examples of suitable human protease inhibitors are, without being limited thereto, e.g. emricasan, nivocasan, batimastat, tanomastat, and ecaliximab. In a further embodiment the protease is an autocatalytic protease or a protease that acts as an autocatalytic protease. Thus, the protease may be flanked by a cleavage site for said protease, preferably the protease is flanked by a cleavage site for said protease on either side. The two cleavage sites for said protease (and the optional linkers) on either side of the protease are preferably different from each other. Preferably the insert comprises a flexible linker on either side, such as a glycine-serine linker.

Therapeutic Use

Also provided herein is the single-stranded RNA virus according to the present invention comprising a modified genome of the virus comprising a polynucleotide sequence encoding at least one protein essential for viral transcription and/or replication, a protease and a cleavage site for said protease, wherein (a) the at least one protein essential for viral transcription and/or replication comprises an insert at an intramolecular insertion site comprising at least the cleavage site for said protease and optionally further the protease, or (b) the at least one protein essential for viral transcription and/or replication is encoded as a fusion protein comprising the protease fused to the N-terminal or C-terminal end, separated by the cleavage site for said protease for use in therapy, wherein the single-stranded RNA virus optionally further encodes at least one heterologous protein, e.g., a therapeutic protein or a tumor antigen. Suitable therapies are cancer therapy, gene therapy and/or preventive and therapeutic vaccination.

In a preferred embodiment the single-stranded RNA virus is for use in treating cancer.

Also provided herein is the RNA virus according to the present invention comprising a modified genome of the virus comprising a polynucleotide sequence encoding at least one heterologous protein, a protease and a cleavage site for said protease, wherein the at least one heterologous protein comprises an insert at an intramolecular insertion site comprising at least the cleavage site for said protease and optionally further the protease for use in therapy. Suitable therapies are cancer therapy, gene therapy and/or preventive and therapeutic vaccination.

In a preferred embodiment the RNA virus is for use in treating cancer.

The virus may be administered intravenously, intratumoral, subcutaneously, intramuscular, intradermally, intranasally, intraperitoneally, preferably intravenously or intratumoral. The virus may be administered using physiological buffers or related formulations. The protease inhibitor used is specific for said protease. Example of suitable HIV protease inhibitors are without being limited thereto, e.g., indinavir, saquinavir, ritonavir, nelfinavir, lopinavir, amprenavir, fosamprenavir, atazanavir, tipranavir and darunavir. Other suitable protease inhibitors are well known in the art. In therapy the protease inhibitor, particularly the HIV protease inhibitor, may be administered in combination with a blocker of a degradation enzyme such as the Cyp family, e.g., ritonavir. Ritonavir or other inhibitors of degradation enzymes augment the plasma concentration of the other protease inhibitors.

The protease inhibitor may be administered by any suitable route, preferably subcutaneously, orally or intravenously, more preferably orally.

The cancer may be a solid tumor, preferably selected from the group consisting of colon carcinoma, prostate cancer, breast cancer, lung cancer, skin cancer, liver cancer, bone cancer, ovary cancer, pancreas cancer, brain cancer, head and neck cancer, lymphoma (Hodgkin's and non-Hodgkin's lymphoma) brain cancer, neuroblastoma, mesothelioma, Wilm's tumor, retinoblastoma and sarcoma (such as rhabdomyo sarcoma).

L-Protein Insertion Site

Also provided is a recombinant VSV L-protein comprising an insert in the methyltransferase (MT) domain of the L-protein, particularly in the loop of the methyltransferase domain of the L-protein corresponding to amino acids 1614 to 1634, preferably to amino acids 1614 to 1629, more preferably to amino acids 1616 to 1625, and more preferably to amino acid 1620 of VSVi L-protein, particularly of VSVi L-protein having the amino acid sequence of SEQ ID NO: 28. In a specific embodiment the intramolecular insertion site of the L-protein is between amino acids 1614 and 1634, preferably between amino acids 1614 and 1629, more preferably between amino acids 1616 and 1625, and even more preferably at amino acid 1620 of VSVi L-protein. Wherein the numbering refers to the L-protein of VSVi, and one exemplary sequence of the L-protein of VSVi has the amino acid sequence of SEQ ID NO: 28. In one embodiment the intramolecular insertion site of the L-protein is between amino acids 1614 and 1634, preferably between amino acids 1614 and 1629, more preferably between amino acids 1616 and 1625, and even more preferably at amino acid 1620 of the L-protein of VSVi having the sequence of SEQ ID NO: 28 or a homologue thereof, wherein the homologue has at least 80% sequence identity with SEQ ID NO: 28, preferably at least 90% sequence identity with SEQ ID NO: 28.

The term "insert" as used herein refers to an amino acid sequence of variable length, including a few amino acids (such as at least 3, at least 5, at least 10, preferably at least 15 amino acids) to several hundreds of amino acids, such as up to 500, up to 300 and up to 250 amino acids. An insert is introduced into another sequence, in the present case the L-protein sequence and results in a net addition of amino acids. Thus, it may for example comprise at least a cleavage site of a protease (e.g., at least about 15 amino acids as in SEQ ID NOs: 6 and 7); a protease and at least a cleavage site for said protein; or a reporter protein. Preferably the insert comprises a flexible linker on either side, such as a glycine-serine linker. In certain embodiments the insert is from 15 to 500 amino acids, preferably from 15 to 300 amino acids, more preferably from 15 to 250 amino acids. An insert results in a net addition of amino acids and does not include an amino acid substitution, i.e., a simple replacement of one or more amino acids with the same number of different amino acids.

The insert at the intramolecular insertion site of the L-protein does not affect activity of the L-protein. Activity of the L-protein may be assessed by detecting viral reporter gene expression, TCID50 replication assays or MTT killing assays (see FIG. 13C), preferably using a TCID50 replication assay. Wherein the modified L-protein carrying an insert at the intramolecular site may be expressed by the single-stranded RNA virus or may be expressed in trans on a plasmid together with a single-stranded RNA virus lacking the L-protein. The insert at the intramolecular insertion site of the L-protein is considered not to affect activity of the L-protein if the activity of the protein and hence viral replication as measured, e.g., by TCID50, provides titers of no more than 2 log lower titers, preferably no more than 1.5 log lower titers, more preferably no more than 1 log lower titers and more preferably equal titers compared to a recombinant single-stranded RNA virus without the insert at the intramolecular insertion site (control) and in case of a protease at the intramolecular insertion site in the presence of a protease inhibitor in the control and the test sample.

In one embodiment the insert comprises a fluorescent protein. In another embodiment the insert comprises a cleavage site for a protease or a protease and a cleavage site for said protease. The protease may be a single-chain dimer flanked by two protease cleavage sites; or the protease may be a monomer flanked with an N-terminal and/or a C-terminal protease cleavage site. In one embodiment the protease is a viral protease, such as from HCV or HIV. Preferably the protease is an autocatalytic protease or acts as an autocatalytic protease.

The autocatalytic protease may be the HIV-1 protease, preferably a single chain dimer of the HIV-1 protease, and the protease can be inhibited by a protease inhibitor selected from the group consisting of indinavir, saquinavir, ritonavir, nelfinavir, lopinavir, amprenavir, fosamprenavir, atazanavir, tipranavir and darunavir.

The L-protein may further comprise a secondary mutation, preferably in the methyltransferase domain of the L-protein. In one embodiment the secondary mutation restores L-protein activity.

Also provided herein is a Vesicular Stomatitis Virus (VSV) comprising the recombinant VSV L-protein according to the invention.

In Vitro Method

Further provided is a method for controlling RNA virus replication comprising transducing or transfecting a host cell with the single-stranded RNA virus according to the invention comprising a modified genome of the virus comprising a polynucleotide sequence encoding at least one protein essential for viral transcription and/or replication, a protease and a cleavage site for said protease, wherein the at least one protein essential for viral transcription and/or replication comprises an insert at an intramolecular insertion site comprising at least the cleavage site for said protease and optionally further the protease; maintaining the host cell in the presence or absence of a protease inhibitor specific for said protease, wherein the addition of said protease inhibitor allows viral transcription and/or replication and the absence of said protease inhibitor inhibits viral transcription and replication.

Also provided is a method for controlling RNA virus replication comprising transducing or transfecting a host cell with the single-stranded RNA virus according to the invention comprising a modified genome of the virus comprising a polynucleotide sequence encoding at least one protein essential for viral transcription and/or replication, a protease and a cleavage site for said protease, wherein the at least one protein essential for viral transcription and/or replication is encoded as a fusion protein comprising the protease fused to the N-terminal or C-terminal end, separated by the cleavage site for said protease; maintaining the host cell in the presence or absence of a protease inhibitor specific for said protease, wherein the addition of said protease inhibitor inhibits viral transcription and/or replication and the absence of said protease inhibitor allows viral transcription and replication.

Further provided is a method for controlling heterologous protein expression by a RNA virus comprising transducing or transfecting a host cell with the RNA virus according to the invention, wherein the protease is located within an intramolecular insertion site of the at least one heterologous protein; maintaining the host cell in the presence or absence of a protease inhibitor specific for said protease, wherein the addition of said protease inhibitor allows heterologous protein expression and the absence of said protease inhibitor inhibits heterologous protein expression.

Preferably the methods according to the invention are in vitro methods. Thus the steps of transducing or transfecting and maintaining are performed in cell culture ex vivo.

The protease is preferably an autocatalytic protease, more preferably the HIV-1 protease, even more preferably a single chain dimer of the HIV-1 protease. This protease is particularly advantageous as a number of protease inhibitors are available. Suitable protease inhibitors are, e.g., indinavir, saquinavir, ritonavir, nelfinavir, lopinavir, amprenavir, fosamprenavir, atazanavir, tipranavir or darunavir.

In view of the above, it will be appreciated that the invention also encompasses the following items:

1. A single-stranded RNA virus comprising a modified genome of the virus comprising a polynucleotide sequence encoding at least one protein essential for viral transcription and/or replication, a protease and a cleavage site for said protease, wherein
   (a) the at least one protein essential for viral transcription and/or replication comprises an insert at an intramolecular insertion site comprising at least the cleavage site for said protease and optionally further the protease; or
   (b) the at least one protein essential for viral transcription and/or replication is encoded as a fusion protein comprising the protease fused to the N-terminal or C-terminal end, separated by the cleavage site for said protease.
2. The single-stranded RNA virus of item 1, wherein
   (a) the protease cleaves the least one protein essential for viral transcription and/or replication at the cleavage site for said protease at the intramolecular insertion site, or
   (b) the protease cleaves at the cleavage site for said protease located at the N-terminal or C-terminal end of the at least one protein essential for viral transcription and/or replication encoded as a fusion protein to release the at least one protein essential for viral transcription and/or replication.
3. The single-stranded RNA virus of item 1 or 2, wherein the protease can be inhibited using a protease inhibitor.
4. The single-stranded RNA virus of any one of the preceding items, wherein the at least one protein essential for viral transcription and/or replication is an RNA-dependent RNA polymerase or a protein of the polymerase complex comprising the RNA-dependent RNA polymerase or a nucleocapsid, preferably wherein the at least one protein essential for viral transcription and/or replication is selected from the group consisting of polymerase cofactor, polymerase and nucleocapsid.
5. The single-stranded RNA virus of any one of the preceding items, wherein the single-stranded RNA virus is a negative-sense single-stranded RNA virus, preferably a negative-sense single-stranded RNA virus of the order Mononegavirales.
6. The single-stranded RNA virus of any one of the preceding items, wherein the single-stranded RNA virus is
   (a) a virus of a family selected from the group consisting of Rhabdoviridae, Paramyxoviridae, Filoviridae, Nyamiviridae, Pneumoviridae and Bornaviridae; and/or
   (b) a virus of the family Paramyxoviridae, preferably a Measles morbillivirus (MeV) or a virus of the family Rhabdoviridae, preferably a Vesicular Stomatitis Virus (VSV).
7. The single-stranded RNA virus of item 5 or 6, wherein the at least one protein essential for viral transcription and/or replication is selected from the group consisting of polymerase cofactor, polymerase and nucleocapsid, preferably wherein the at least one protein essential for viral transcription and/or replication is
   (a) a polymerase cofactor, preferably a P-protein or a functional equivalent thereof;
   (b) a polymerase, preferably a L-protein; and/or
   (c) combinations thereof.
8. The single-stranded RNA virus of any one of the preceding items, wherein
   (a) the protease regulates the activity of the at least one protein essential for viral transcription and/or replication;

(b) the protease regulates viral transcription and/or replication;
(c) the protease is an autocatalytic protease;
(d) the protease is a viral protease; and/or
(e) the protease is from HCV or HIV.

9. The single-stranded RNA virus of any one of the preceding items, wherein the protease is the HIV-1 protease, preferably a single chain dimer of the HIV-1 protease, and the protease can be inhibited by a protease inhibitor selected from the group consisting of indinavir, saquinavir, ritonavir, nelfinavir, lopinavir, amprenavir, fosamprenavir, atazanavir, tipranavir and darunavir.

10. The single-stranded RNA virus of any one of the preceding items, wherein the insert at the intramolecular insertion site of the at least one protein essential for viral transcription and/or replication does not affect activity of the at least one protein essential for viral transcription and/or replication.

11. The single-stranded RNA virus of any one of the preceding items, wherein at least the cleavage site for said protease and optionally further the protease is located within the intramolecular insertion site of the least one protein essential for viral transcription and/or replication, and wherein
(a) proteolytic cleavage of the protein cleaves the at least one protein essential for viral transcription and/or replication at the cleavage site for said protease within the intramolecular insertion site;
(b) cleavage within the intramolecular insertion site inactivates the at least one protein essential for viral transcription and/or replication;
(c) cleavage within the intramolecular insertion site of the at least one protein essential for viral transcription and/or replication inhibits viral transcription and/or replication;
(d) the virus is active in the presence of a specific inhibitor of the protease and inactive in the absence of a specific inhibitor of the protease; and/or
(e) the virus further encodes at least one heterologous protein, wherein the heterologous protein is expressed if the virus is active in the presence of a specific inhibitor of the protease and is not expressed if the virus is inactive in the absence of a specific inhibitor of the protease.

12. The single-stranded RNA virus of any one of the preceding items, wherein the single-stranded RNA virus is Vesicular Stomatitis Virus (VSV), the at least one protein essential for viral transcription and/or replication is the P-protein and/or the L-protein and wherein the intramolecular insertion site is
(a) in the flexible hinge region of the VSV P-protein, preferably at a position corresponding to amino acid position 193-199, more preferably amino acid position 196 of VSVi P-protein (e.g., the sequence of SEQ ID NO: 27);
(b) in the loop of the methyltransferase domain of the L-protein corresponding to amino acids 1614 to 1634, preferably to amino acids 1614 to 1629, more preferably to amino acids 1616 to 1625, and more preferably to amino acid 1620 of VSVi L-protein having the sequence of SEQ ID NO: 28; or
(c) a combination of (a) and (b).

13. The single-stranded RNA virus of any one of items 1 to 9, wherein the at least one protein essential for viral transcription and/or replication is encoded as a fusion protein comprising the protease fused to the N-terminal or C-terminal end of the at least one protein essential for viral transcription and/or replication separated by the cleavage site for said protease and wherein
(a) proteolytic cleavage of the fusion protein releases the at least one protein essential for viral transcription and/or replication in its active form;
(b) the at least one protein essential for viral transcription and/or replication in the fusion protein comprising the protease fused to the N-terminal or C-terminal end of the at least one protein essential for viral transcription and/or replication separated by the cleavage site for said protease is inactive without proteolytic cleavage;
(c) the proteolytic cleavage of the fusion protein is inhibited using a specific inhibitor of the protease;
(d) the virus is inactive in the presence of a specific protease inhibitor of the protease and active in the absence of a specific inhibitor of the protease;
(e) the virus further encodes at least one heterologous protein, wherein the heterologous protein is not expressed if the virus is inactive in the presence of a specific inhibitor of the protease and is expressed if the virus is active in the absence of a specific inhibitor of the protease;
(d) the fusion protein further comprises a further viral protein or a heterologous protein fused to the opposite end of the protease fused to the N-terminal or C-terminal end of the at least one protein essential for viral transcription and/or replication, and wherein said further viral protein or heterologous protein and said protease are also separated by the cleavage site for said protease;
(e) the protease flanked by the cleavage site for said protease on either side replaces an intergenic region that links the at least one protein essential for viral transcription and/or replication with a further viral protein or a heterologous protein; and/or
(f) the protease flanked by the cleavage site for said protease on either side replaces an intergenic region that links the at least one protein essential for viral transcription and/or replication with a further viral protein or a heterologous protein, wherein loss of the protease leads to a further inactive fusion protein comprising the protein essential for viral transcription and/or replication and the further viral protein or heterologous protein.

14. The single-stranded RNA virus of item 1 or 13, wherein the single-stranded RNA virus is a negative-sense single-stranded RNA virus of the order Mononegavirales and the at least one protein essential for viral transcription and/or replication is encoded as a fusion protein comprising the protease fused to the N-terminal end or the C-terminal end of the at least one protein essential for viral transcription and/or replication separated by the cleavage site for said protease, wherein
(a) the at least one protein essential for viral transcription and/or replication is an L-protein; and/or
(b) the fusion protein comprises the protease fused to the N-terminal end of the at least one protein essential for viral transcription and/or replication separated by the cleavage site for said protease.

15. The single-stranded RNA virus of item 1 or 13, wherein the at least one protein essential for viral transcription and/or replication is encoded as a fusion protein
(a) consisting of the protease fused to the N-terminal or C-terminal end of the protein essential for viral transcription and/or replication, separated by the cleavage site for said protease, wherein the fusion protein optionally further comprises a linker between the protease and the protein essential for viral transcription and/or replication;

(b) comprising the protease fused to the N-terminal or C-terminal end of the at least one protein essential for viral transcription and/or replication, separated by the cleavage site for said protease and a further viral protein or a heterologous protein fused to the opposite end of the protease fused to the N-terminal or C-terminal end of the at least one protein essential for viral transcription and/or replication, and wherein said further viral protein or heterologous protein and said protease are also separated by a cleavage site for said protease, and wherein the fusion protein optionally further comprises a linker between the protease and the at least one protein essential for viral transcription and/or replication, and/or a linker between the protease and the further viral protein or heterologous protein; or (c) that does not comprise an amino acid sequence of SEQ ID NO: 30.

16. An RNA virus comprising a modified genome of the virus comprising a polynucleotide sequence encoding at least one heterologous protein, a protease and a cleavage site for said protease, wherein the at least one heterologous protein comprises an insert at an intramolecular insertion site comprising at least the cleavage site for said protease and optionally further the protease.

17. The RNA virus of item 16, wherein the heterologous protein is a therapeutic protein, a reporter or a tumor antigen.

18. The single-stranded RNA virus of any one of items 1 to 15 or the RNA virus of item 16 or 17 for use in therapy.

19. The single-stranded RNA virus of any one of items 1 to 15 or the RNA virus of item 16 or 17 for use in treating cancer.

20. The single-stranded RNA virus or the RNA virus for use of item 19, wherein the cancer is a solid tumor, preferably selected from the group consisting of colon carcinoma, prostate cancer, breast cancer, lung cancer, skin cancer, liver cancer, bone cancer, ovary cancer, pancreas cancer, brain cancer, head and neck cancer, lymphoma (Hodgkin's and non-Hodgkin's lymphoma), brain cancer, neuroblastoma, mesothelioma, Wilm's tumor, retinoblastoma and sarcoma.

21. A recombinant VSV L-protein comprising an insert in the loop of the methyltransferase domain of the L-protein corresponding to amino acids 1614 to 1634, preferably to amino acids 1614 to 1629, more preferably to amino acids 1616 to 1625 and more preferably to amino acid 1620 of VSVi L-protein having the sequence of SEQ ID NO: 28.

22. The recombinant VSV L-protein of item 21, wherein the L-protein further comprises a secondary mutation.

23. A Vesicular Stomatitis Virus (VSV) comprising the recombinant VSV L-protein according to item 21 or 22.

24. A method for controlling RNA virus replication comprising (a) transducing or transfecting a host cell with the RNA virus according to any one of items 10 to 12, and (b) maintaining the host cell in the presence or absence of a protease inhibitor specific for said protease, wherein the addition of said protease inhibitor allows viral transcription and/or replication and the absence of said protease inhibitor inhibits viral transcription and replication.

25. A method for controlling RNA virus replication comprising (a) transducing or transfecting a host cell with the RNA virus according to any one of items 13 to 15, and (b) maintaining the host cell in the presence or absence of a protease inhibitor specific for said protease, wherein the addition of said protease inhibitor inhibits viral transcription and/or replication and the absence of said protease inhibitor allows viral transcription and replication.

26. A method for controlling heterologous protein expression by a RNA virus comprising (a) transducing or transfecting a host cell with the RNA virus according to item 16 or 17, wherein the protease is located within an intramolecular insertion site of the at least one heterologous protein; and (b) maintaining the host cell in the presence or absence of a protease inhibitor specific for said protease, wherein the addition of said protease inhibitor allows heterologous protein expression and the absence of said protease inhibitor inhibits heterologous protein expression.

EXAMPLES

Materials and Methods

P-Protein

Figures 4A, 4B:
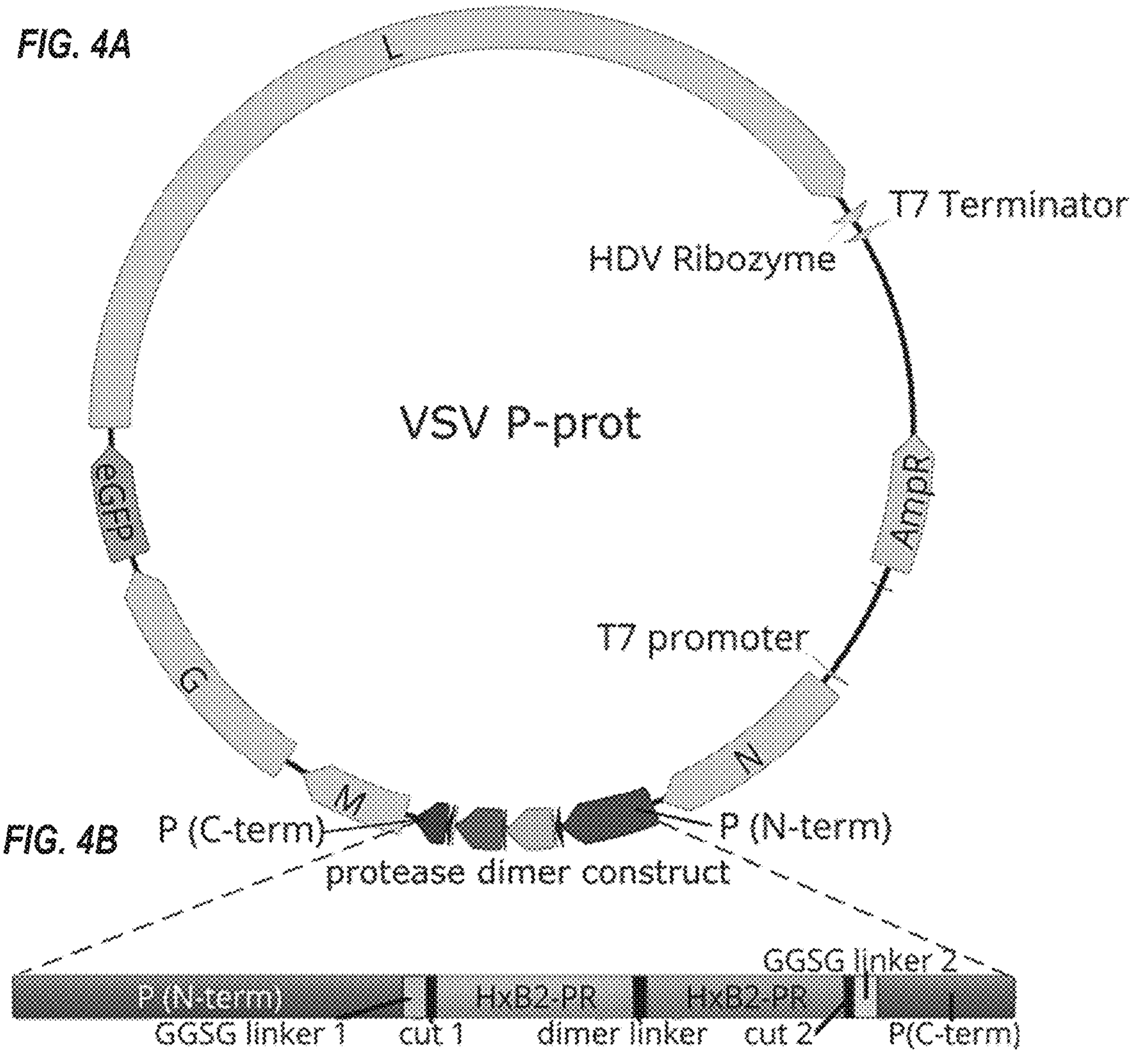
FIG. 4. Plasmid structure with full length VSV-P-prot sequence. B: Construct structure of the Phosphoprotein (P-protein) with the linked-dimer protease in position aa196 (P196PR2). The P-protein gene in VSV Indiana GFP was replaced by P-196PR2. Enhanced GFP (eGFP) at the 5th position of the VSV genome (between G and L-proteins) is used as marker gene.

The DNA sequence for the Phosphoprotein (P-protein having the cDNA sequence of SEQ ID NO: 1; corresponding to amino acid sequence of SEQ ID NO: 27) with a linked-dimer protease in position aa196 (P196PR2, DNA sequence of SEQ ID NO: 3) and the flanking sequences of the VSV Nucleoprotein and Matrix protein were synthetized by GeneArt. The P-protein gene in VSV Indiana was replaced by P196PR2. GFP at position 5 was used as marker gene. P196PR2 with flanking VSV-N and VSV-M sequences was amplified by PCR with sequences lapping over 2 restriction enzyme sites (XbaI and Bst1107I) by 30 bp to the full length VSV vector, which was cut with said enzymes. The construct was then generated by Gibson assembly cloning (FIG. 4).

The protease linked-dimer construct (DNA sequence of SEQ ID NO: 5) was flanked by $(GGSG)_3$ linker sequences (DNA sequence of SEQ ID NO: 4; amino acid sequence of SEQ ID NO: 29) to allow spatial separation between the P-protein and the protease dimer. The 5' GGSG linker has the DNA sequence of SEQ ID NO: 8 and the 3' GGSG linker has the DNA sequence of SEQ ID NO: 9. The linker codons were designed manually to avoid homologies of the upstream with the downstream linker. The cleavage sites are located between each protease domain and the linker and have the DNA sequences of SEQ ID NO: 6 and SEQ ID NO: 7). The protease dimer codons were chosen by the interplay of an optimization algorithm and manual adjustments. The optimization process was a compromise between human codon usage and avoidance of homologies between the first and second protease. Overhangs were introduced by Gibson assembly cloning.

Figures 2A, 2B:
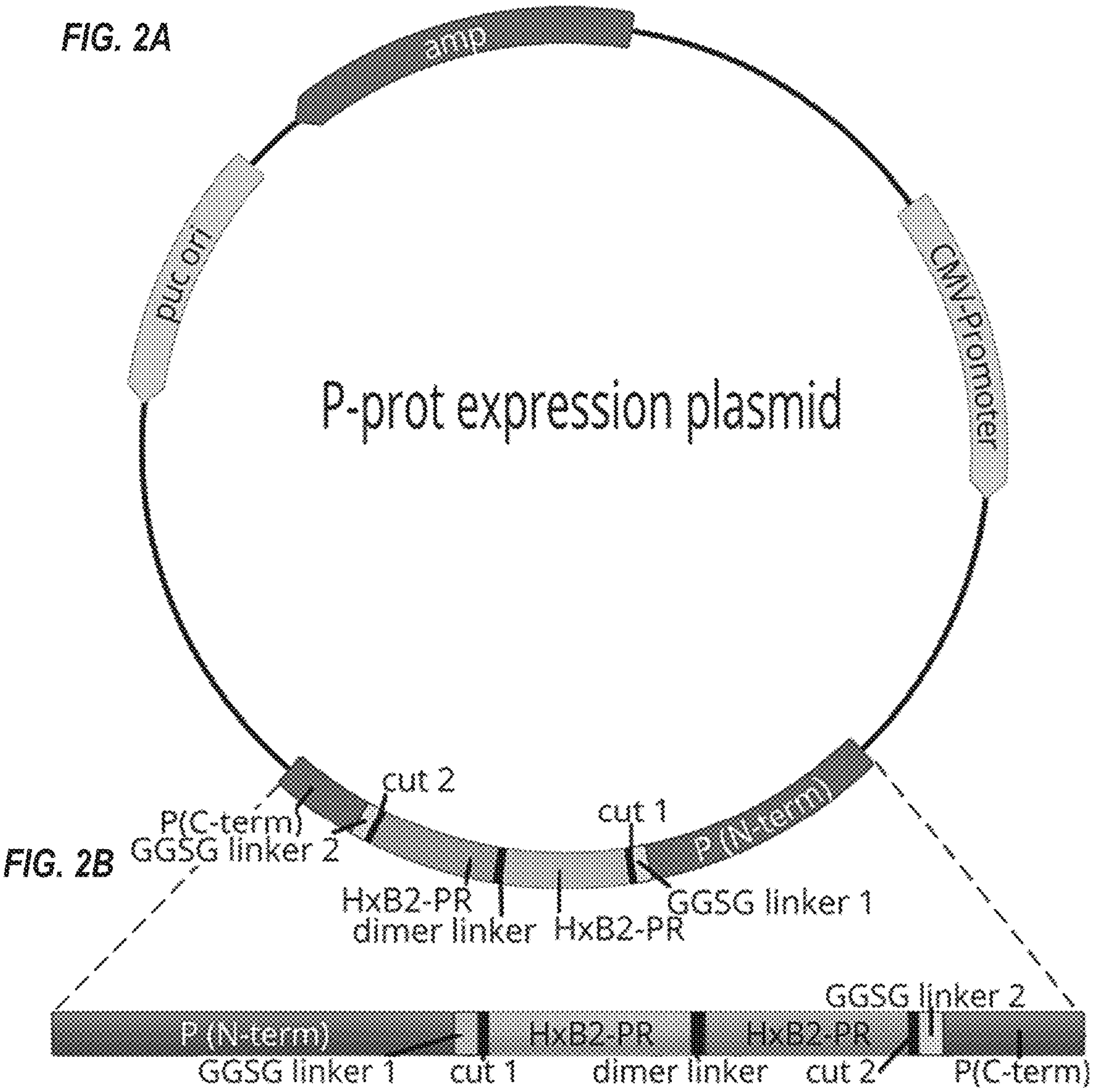
FIG. 2. A) Structure of linked-dimer protease in position aa196 (P-196PR2) expression plasmid. B) Construct structure of P-196PR2. The cDNA sequence for the P-protein with the linked-dimer protease in position aa196 (P-196PR2) and the flanking sequences of the VSV Nucleoprotein (N protein) and Matrix protein (M protein) were synthetized by GeneArt. The linked protease dimer is flanked by flexible linkers consisting of the amino acid sequences $(GGSG)_3$. This separation ensures minimal disturbance of the intramolecular insertion protein with the tertiary structure of the P and L-proteins. Before the first and after the second protease, the protease cleavage sequences are located. The two proteases are connected via a dimer linker sequence.

The functionality of the Phosphoprotein-protease construct was first tested with a P expression plasmid (FIG. 2) in which the DNA of P196PR2 as generated by GeneArt was cloned by digestion of vector and insert with XbaI and Bst1107I and then ligated with a T4 ligase. BHK cells were transfected with this P-Prot (P-Protein and protease) construct and infected with a VSV-ΔP variant. The VSV-ΔP was equipped with a red fluorescent protein (RFP) as reporter gene. For the function of VSV-ΔP a working P-protein is necessary, which was provided in trans by the cell expressing P-Prot. In this set-up we could show that the activity of VSV-ΔP-RFP was directly linked to the presence of protease inhibitor (amprenavir, concentrations 0.1, 1 and 10 μM). Without protease inhibitor the P-protein was cleaved and no RFP signal detectable.

L-Protein

VSV L virus insertions were introduced into the whole VSV genome by four-fragment Gibson assembly. The larger part of the vector (fragment 4) was provided by restriction enzyme digestion with enzymes SfoI and FseI of pVSV-GFP. The HIV protease dimer insert (fragment 1) was amplified with primer sequences specific for the flexible (GGSG)3-linkers, which are at both ends of the construct (DNA sequence of SEQ ID NO: 4; amino acid sequence of SEQ ID NO: 29). L-protein sequences surrounding fragment 1 (fragment 2 and 3), were amplified from pVSV introducing overhangs to the (GGSG)3 linker at the 5' end of fragment 3 with the primer MT1620-insertGGSG for (SEQ ID NO: 25) and at the 3' end of fragment 2 with primer MT1620-insertGGSG rev (SEQ ID NO: 26). The L-protein has the cDNA sequence of SEQ ID NO: 2 and the amino acid sequence of SEQ ID NO: 28, and the insert was introduced at amino acid position 1620 of SEQ ID NO: 28. The resulting L-protein with protease insert has the DNA sequence of SEQ ID NO: 10 as confirmed by sequencing. Additionally, overhangs to fragment 4 were introduced at the 5' end of fragment 2 using the forward primer 49 bp-before-FseI [5'-GCT GCC AAG TAA TAC ACC GG-3'] (SEQ ID NO: 23 binding 49 nucleotides upstream of the nearest restriction enzyme cutting site FseI and at the 3' end of Fragment 3 using the reverse primer 50 bp-after-SfoI [5'-TTT ATC TCC TCC TAA AGT TTC-3'] (SEQ ID NO: 24) binding 50 nucleotides downstream of the nearest restriction enzyme cutting site SfoI.

VSV Vectors

WT VSV vector (Indiana) and VSV-GFP vector (Indiana) have the DNA sequences of SEQ ID NO: 20 and SEQ ID NO: 21, respectively (for more details see Schnell et al., J Virol. 1996, 70(4): 2318-2323, Boritz et al., J Virol, 1999. 73(8): 6937-6945, and Muik et al., Cancer Res. 2014, 74(13): 3567-3578). VSV-GFP-AP (recombinant VSV Indiana strain lacking the viral envelope protein P) was generated analogous as described elsewhere (Muik et al., J Mol Med (Berl), 2012, 90(8):959-970). Infectious viruses were retrieved in the presence of 10 μM amprenavir for Prot-On viruses and without amprenavir for non-protease containing and Prot-Off viruses with a standard helper virus-free calcium phosphate rescue technique in 293T cells (Witko et al., J Virol, 2006, 135(1):91-101). BHK21 cells were used for amplification of replication competent VSV variants.

Cell Lines

BHK-21 cells (American Type Culture Collection, Manassas, VA) were cultured in Glasgow minimum essential medium (GMEM) supplemented with 10% fetal calf serum, 5% tryptose phosphate broth, 100 units/ml penicillin, and 0.1 mg/ml streptomycin.

293T cells (293tsA1609neo) and 293-VSV (293 cells expressing N, P-GFP and L of VSV (Panda et al., J Virol, 2010, 84(9): 4826-4831) were cultured in Dulbecco's Modified Eagle Medium (DMEM) supplemented with 10% FCS, 1% P/S, 2% glutamine, 1× sodium pyruvate and 1× non-essential amino acids.

In Silico Experiments

Structure visualization and molecular modeling: All structures were analyzed using Coot 0.8.7.1 (Emsley et al., Acta Crystallogr D Biol Crystallogr, 2010, 66(Pt4):486-501) and UCSF Chimera 1.12 (Pettersen et al., J Comp Chem, 2004, 25(13): 1605-1612). Images of molecular structures were generated with UCSF Chimera 1.12. A VSV-L-MT1620-mCherry model was generated as follows: VSV L-protein having the amino acid sequence of SEQ ID NO: 28 (Protein Data Bank (PDB) accession code 5a22) and mCherry (PDB accession code 2h5q) having the DNA sequence of SEQ ID NO: 11 (with linker) were docked with ZDock server (Pierce et al., Bioinformatics, 2014, 30(12):1771-1773). VSV L-protein was defined as the reference structure to which unrestrained mCherry was docked in rigid body mode. One of the top hits was chosen because N- and C-termini of mCherry were located nearby the MT1620 (amino acid 1620 of SEQ ID NO: 28 in the methyltransferase domain (MT) insertion site). Subsequently, FiberDock (Mashiach et al., Poteins, 2010, 78(6):1503-1519) was used for flexible refinement of the rigid-body protein docking solution. The $(GGSG)_3$-Linkers were manually introduced in Coot 0.8.7.1 and modelled using ModLoop (Pieper et al., Nucleic Acids Res, 2014, 42 (Database issue): D336-346).

RNA Extraction, cDNA Synthesis and PCR

First, viral RNA was purified by Viral DNA/RNA Kit, peqGOLD (Peqlab) according to manufacturer's instructions. Subsequently, cDNA synthesis was performed with RevertAid First Strand cDNA Synthesis Kit (Thermo Fisher Scientific) according to manufacturer's instructions. PCR was then performed with Q5® Hot Start High-Fidelity DNA Polymerase (NEB). Annealing temperature was chosen according to recommendations of NEB Annealing Temperature Calculator. Elongation time was 1 minute/1000 nucleotides.

Replication Kinetic

BHK-21 cells were seeded in 24-well plates with $1\times10^5$ cells/well and incubated overnight at 37° C. The next day, medium was removed and cells were infected with a multiplicity of infection (MOI) of 0.1 of according VSV variant. Cells were incubated for 1 h with the inoculum and subsequently washed twice with PBS. One ml of fresh medium was added to the cells and cells were incubated at 37° C. 0 h values were collected directly after washing. Further supernatants were collected after 4 h, 8 h, 12 h, 16 h, 24 h and 36 h. Samples were stored at −80° C. until viral titers were determined via $TCID_{50}$ assay on BHK21 cells.

Dose Response

BHK-21 cells were seeded in 24-well plates with $1\times10^5$ cells/well and incubated overnight at 37° C. The next day, medium was removed and cells were infected with a multiplicity of infection (MOI) of 1 of according VSV variant. Amprenavir concentrations of 0, 30 nM, 100 nM, 300 nM, 1 μM, 3 μM, 10 μM, 30 μM and 100 M were applied. Viral progeny were collected 24 hpi.

$TCID_{50}$ Assay

Virus titers were determined using a 50% tissue culture infective dose ($TCID_{50}$) assay using the method of Spearman-Kärber as described previously (Kaerber, Archiv für Experimentalle Pathologie und Pharmakologie, 1931, 162: 480-483). Briefly, 10-fold serial dilutions of virus were prepared. 100 μl of each dilution was added in quadruplicates to confluent BHK-21 cells in 96-well plates and incubated for 24-48 hours at 37° C. until a cytopathic effect was visible. Numbers of infected wells were counted and $TCID_{50}$-values were calculated.

In Vitro Cytotoxicity Assay:

Plaques were obtained by crystal violet staining and fixation of BHK-21 cells infected at a 60% confluency (15 g crystal violet from Fluka, 85 ml EtOH, 250 ml formaldehyde 37% ad 1000 ml H2O). The final confluency before fixation was approx. 80%, 5-fold serial dilutions of virus stocks were prepared: $1{:}10^{6.5}$, $1{:}10^{7}$, $1{:}10^{7.5}$, $1{:}10^{8}$, $1{:}10^{8.5}$ and $1{:}10^{9}$ were used to infect cells in 6-Well plates. One hour after infection, cells were washed with PBS and covered with a 2.5% plaque agarose/GMEM mixture. The agarose/medium mixture was carefully removed from the Wells prior to fixation, which was performed with crystal violet 24 h after infection.

IFN Killing Assay

Virus cell killing was assessed in an Interferon-response assay, in which IFN-competent BHK-21 cells were treated with increasing amounts (10, 100, 500 and 1000 U/ml) of recombinant universal type I IFN (PBL assay science, Piscataway Township, NJ) and infected with MOIs 0.1, 1 and 10. Cells were seeded at 104 one day before INF treatment. INF treatment was performed 16 h before infection. Infection proceeded for 72 h. After this period, Thiazolyl Blue was added for 4 h. Cells were then dissolved in 0.1 M NaCl with x g SDS for another 4 h. MTT-Formazan was measured at 540 nm.

Plaque Assay

Monolayers of BHK-21 cells were infected with serial dilutions of virus stock. One hour after infection, cells were washed twice with PBS and overlayed with a 1:1 dilution of 2.5% plaque agarose and complete GMEM medium. The following day the plaque agarose was removed and cells were stained using crystal violet.

Immunoblotting

BHK-21 cells were infected with VSV, VSV-GFP, VSV-L-mCherry or VSV-GPF-L-mCherry at a MOI of 5, and cell lysates were prepared 4, 8, 12 and 24 h later. Uninfected BHK-21 cells were used as a control. Cells were lysed in ice-cold cell lysis buffer (50 mmol/liter HEPES, pH 7.5; 150 mmol/liter NaCl; 1% Triton X-100; 2% aprotinin; 2 mmol/liter EDTA, pH 8.0; 50 mmol/liter sodium fluoride; 10 mmol/liter sodium pyrophosphate; 10% glycerol; 1 mmol/liter sodium vanadate; and 2 mmol/liter Pefabloc SC) for 30 min. To dispose of cellular debris, cell lysates were centrifuged at 13.000 rpm for 10 minutes. Supernatants containing proteins were stored at −80° C.

SDS-PAGE of protein lysates was performed under reducing conditions on a 12% polyacrylamide gel. For comparison of VSV, VSV-GFP, VSV-L-mCherry and VSV-GFP-L-mCherry the 8 h time point lysates were used. Proteins were transferred to 0.45-μm nitrocellulose membranes (Whatman, Dassel, Germany) by using a tank blotting system. The blotting time was 90 minutes. The membrane was blocked over night with 1×PBS containing 5% skim milk and 0.1% Tween 20 (PBS™) and incubated for 3 h at room temperature with a mCherry-specific rabbit monoclonal-antibody diluted 1:1,000 in PBS™. The antibody was raised against recombinant mCherry and purified in house (to be published later). After washing a peroxidase-conjugated rabbit IgG-specific antibody from goat (Invitrogen, Carlsbad, CA), diluted 1:5,000 in PBS™ was added and the blot was incubated for another hour. After extensive washing blots were developed with enhanced chemiluminescence (ECL). After the first detection the same blot was extensively washed and re-used to stain for loading control. Actin was stained with a β-actin specific monoclonal antibody from mouse (A2228; Sigma, Munich, Germany) diluted 1:5,000 in PBS™ and a secondary horseradish peroxidase-conjugated mouse IgG-specific antibody from goat was used. Washing, incubation times and Blot development were carried out as described above for the first detection.

Transfections

Transfection of L-mCherry expression plasmids was performed with a TransIT®-LT1 transfection kit from Mirus in 293T cells. Plasmid DNA and transfection reagent amounts were chosen according to manufactures' recommendations for 24-well plates, in which 2.7*105 293T cells per well were seeded one day before transfection. P-expression plasmids were co-transfected with L-mCherry expression plasmids. 24 h after transfection, 293T cells were infected with VSV-GFP-ΔL at an MOI of 10. Images were acquired 48 h after infection.

Animal Experiments

Animal experiments adhered to the national animal experimentation law. Animal trial permission was granted by national authorities.

Stereotaxis: Stereotactic mouse brain injections of virus were performed with a mouse stereotactic frame (Harvard Apparatus, Hollistion-MA). Anesthesia was induced by 100 mg/kg Ketamine and 10 mg/kg Xylazine mix. Analgesic therapy was performed with 5 mg/kg Ketoprofen, antibiotic therapy with 5 mg/kg Enrofloxacin after surgery. Analgesic therapy was sustained with oral Ibuprofen solution (0.1 mg/ml) in drinking water. During stereotactic surgery, mice were fixated in the stereotactic frame. Mouse heads were shaved, cleaned with 2× Betadine and 2× EtOH. Scalps were opened with a scalpel. The site for the injection hole was located by orienting towards the Bregma. The injection hole with a diameter of 1 mm was drilled with an electric drill (FST, Foster city CA). Virus injection volume was 10 μl applied at an injection rate of 1 μl/min. Mice were placed on a heating pad during surgery and their eyes protected with Vaseline.

Image analysis: A fluorescence microscope (Nikon, Japan) was used to analyze virus infected cells in culture and histological sections of mouse brain and tumor.

Statistical analysis: Statistical significance was determined by Student's t test and analysis of variance (ANOVA). P values of <0.05 were considered statistically significant. GraphPad prism software (GraphPad Software, Inc., La Jolla, CA) was used for statistical analysis and data presentation. Adobe Photoshop software was used for composition of multicolor photo panels and overlays.

Example 1: Generating a Protease-Regulated ON-Switch, VSV-P-Prot

Figure 1B:
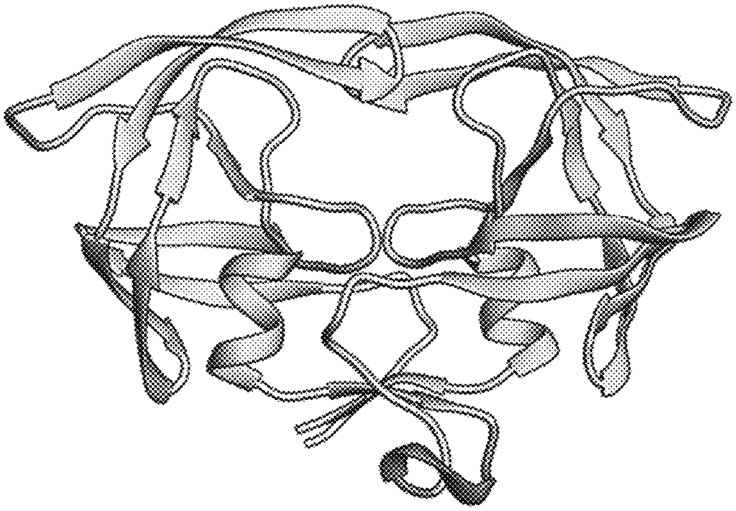
Figure 5:
FIG. 5. Schematic representation of VSV P-protein with HIV protease dimer insert construct and amino acid sequence (SEQ ID NO: 29) of HIV protease dimer insert, including protease cleavage sequences and flexible linker. The linked protease dimer is flanked by flexible linkers consisting of the amino acid sequences $(GGSG)_3$. Before the first and after the second protease, the protease cleavage sequences are located. The two proteases are connected via a linker sequence.

To generate a regulatable switch to control activity of RNA viruses, we developed a system that incorporates an autocatalytically active protease sequence into genes essential for VSV gene expression and replication (FIG. 1*a*). In our first ON-switch construct we introduced an HIV protease dimer into the cofactor of the polymerase of VSV, the P-protein (SEQ ID NO: 1), generating VSV-P-prot. The intramolecular insertion site was previously shown to not affect P-protein function (Das et al., J Virol., 2006, 80(13): 6368-6377). The HIV protease function requires dimerization. To facilitate instant post-translational proteolytic activity, the gene insertion construct was designed to harbor two copies of the HIV protease (PR) joined by a flexible linker (FIG. 1*b*, 2) (Krausslich, PNAS, 1991, 88(8): 3213-3217). Flexible linkers (SEQ ID Nos: 8 and 9) were also applied up- and downstream of the protease construct (SEQ ID NO: 5)

resulting in a protease dimer with cleavage sites and likers having the coding sequence of SEQ ID NO: 4 to ensure independent function of the proteases from the rest of the fusion protein (Chen et al., Adv Drug Deliv Rev, 2013, 65(10:1357-1369). The codon usage of both protease sequences was a compromise to take into consideration human codon usage and the coordination between the two sequences to avoid sequence homologies to minimize risk for copy-choice events during replication (Simon-Loriere and Holmes, Nat Rev Microbiol, 2011, 9(8):617-626). The resulting amino acid sequence (SEQ ID NO: 29) is shown in FIG. 5. The single chain linked dimer (PR2) was further flanked by corresponding cleavage sites (SEQ ID Nos: 6 and 7) (de Oliveira et al., J Virol, 2003, 77(17):9422-9430) as shown in FIGS. 4 and 5 and cloned into the flexible hinge region of the VSV P-protein at position aa196 (P196), which was previously described as a region tolerating functional intramolecular insertion (Das et al. 2006).

Figure 3:
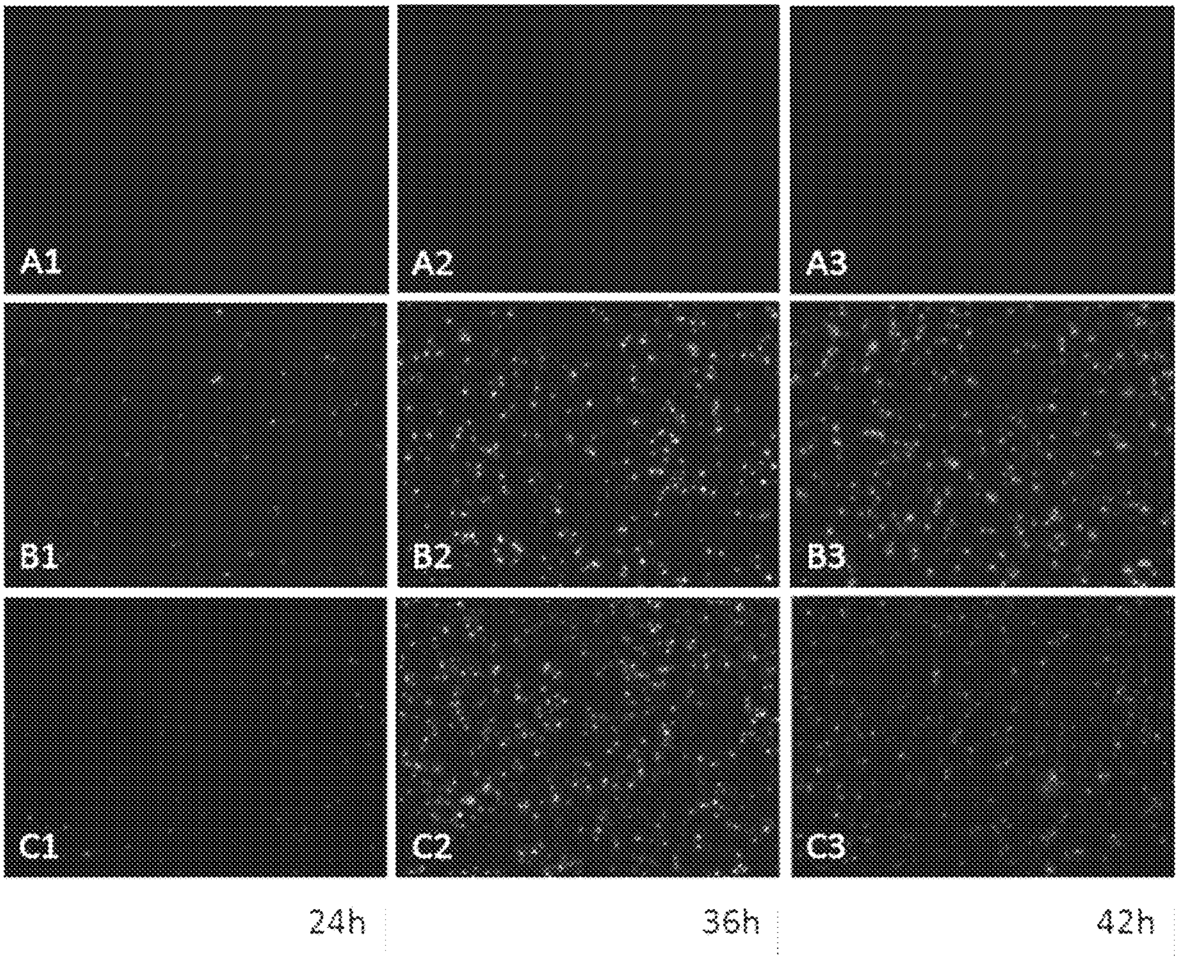
FIG. 3. Protease-linked regulation of trans-supplied VSV P-protein to complement VSV-ΔP virus. The functionality of the phosphoprotein-protease construct was first tested with a P expression plasmid in which the P-196PR2 was cloned (P-prot). BHK cells were transfected with this P-prot construct and infected with a VSV-ΔP variant. The VSV-ΔP was equipped with a red fluorescent protein as reporter gene. For the function of VSV-ΔP a working P-protein is necessary, which was provided in trans by the cell expressing P-Prot. Shown are representative photographs of transfected cells treated A(1-3): without amprenavir, B(1-3): 1 μM amprenavir, C(1-3): positive control using normal P expression plasmid, at the indicated time point post transfection.

To confirm intact VSV phospho-protein function with integrated autoproteolytic ON-switch we transfected BHK cells with a plasmid encoding the isolated P196PR2 construct followed by infection with a VSV lacking its P-protein and expressing an red fluorescent protein (RFP) reporter gene in its place (VSV-ΔP-RFP) (Muik et al., J Mol Med (Berl), 2012, 90(8):959-970). RFP signal in VSV-ΔP-RFP infected cells was only detectable in the presence of P196PR2 and a specific HIV protease inhibitor (here: amprenavir) (FIG. 3, photographs B1-B3). Absence of protease inhibitor resulted in lack of viral gene expression and virus replication (FIG. 3, photographs A1-A3) indicating P196PR2 maintains essential viral P-protein function and can be controlled via inhibition of the proteolytic on-switch.

Figure 6A:
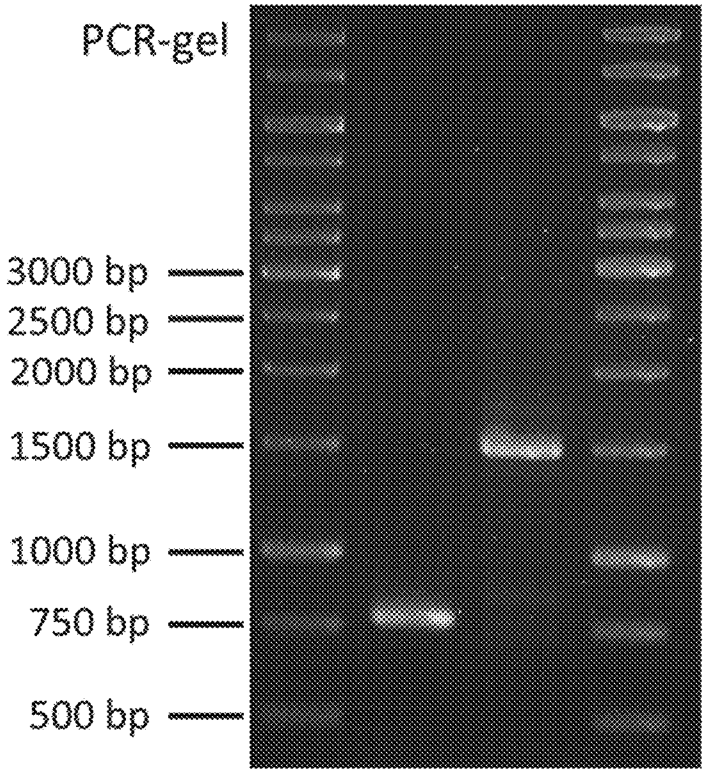
FIG. 6. Protease inhibitor amprenavir regulates activity of protease switch-expressing VSV-P-prot. A: To test genomic integrity of VSV-P-prot, viral genomic RNA was purified, reverse transcribed and a PCR performed on P196PR2. A VSV variant without protease insertion was used as negative control. In lines 1 and 4 of the gel a marker was used, line 2 show the PCR product of VSV control and line 3 shows the PCR product of VSV-P-Prot. We found the P196PR2 and the protease negative P-protein PCR fragments to be at their expected sizes (expected size P-protein with protease: 1490 bp; expected size P-protein without protease: 773 bp; VSV-P-Prot stock titer: $1.8\times10^7$). Subsequently the PCR product was sequenced. B: After the generation of the full length VSV-P-Prot, its functionality was tested by infection of BHK cells in the presence and absence of 10 μM amprenavir (APV). In the presence of APV, viral activity was visible through the expression of eGFP (left hand row) and the cytopathic effect in a standard cell culture dish (right hand row). C: Plaque assay of VSV-P-Prot with or without APV. In the presence of APV the cytopathic effect was visible in plaque assays. Without APV, neither eGFP signal nor a cytopathic effect could be observed. Sequencing of the site of insertion with two Sanger sequencing reactions to assess whether mutations have occurred within the protease dimer sequence having the original DNA sequence of SEQ ID NO: 4 revealed no mutations in the protease dimer sequence.
Figure 6B:
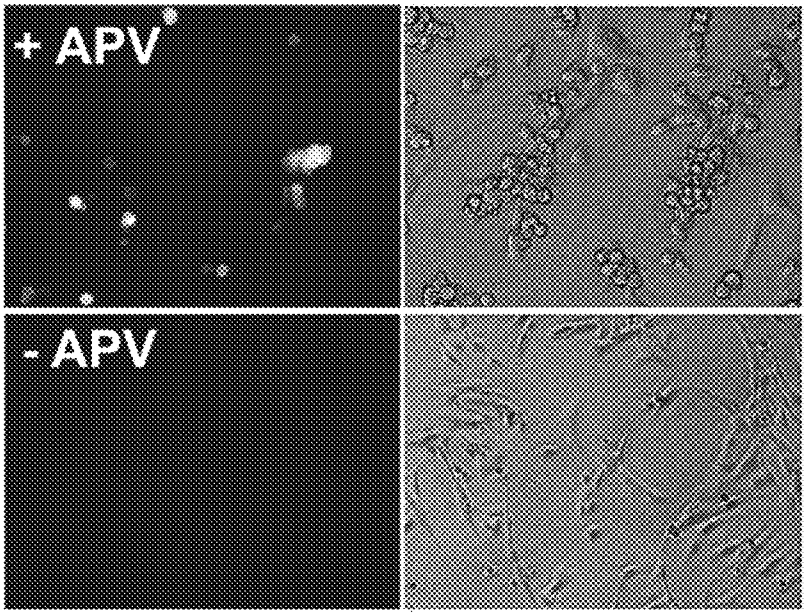
Figure 6C:
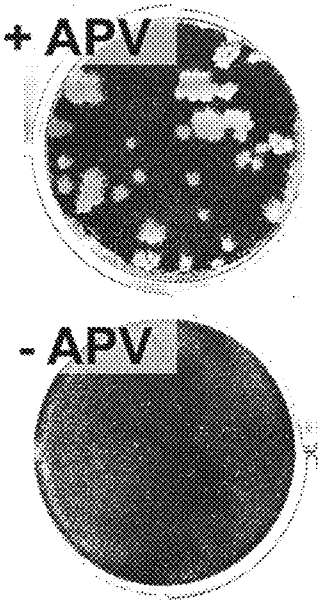

We next generated a recombinant VSV expressing P196PR2 in place of its native P-protein (VSV-P-prot), which also contained an eGFP reporter gene in 5th gene position (FIG. 4). Rescue and propagation of VSV-P-prot was done in medium condition containing 10 μM amprenavir. PCR amplification and sequencing confirmed the correct integration of the P196PR2 construct into the VSV genome (FIG. 6A). Infection of BHK cells with VSV-P-prot resulted in strong GFP signal within 24 hours in the presence but not in the absence of amprenavir (10 μM) indicating the supplied protease inhibition controlled gene expression of VSV-P-prot (FIG. 6B). Conversely, viral replication observed by virus plaque formation of VSV-P-prot was also found to be protease inhibitor-dependent (FIG. 6C). Viral RNA was reverse transcribed and subject to sequence confirmation. Sequence of the insert from viral genomic sequence fully aligned with the virus construction plasmid.

Figure 7A:
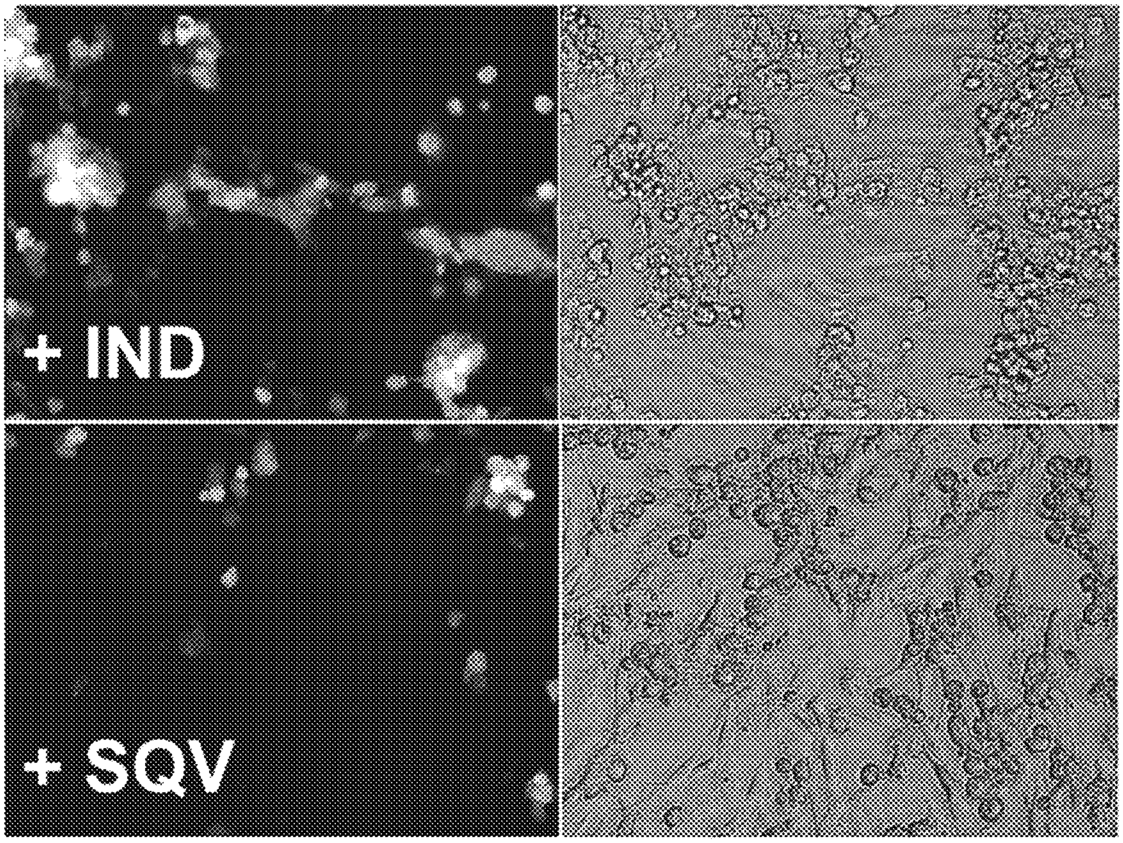
FIG. 7. VSV-P-prot activity can be regulated by various HIV protease inhibitors. We tested whether VSV-P-prot can replicate with second generation protease inhibitors such as saquinavir and indinavir. Fluorescence signal of the reporter gene eGFP (A: left hand pictures), cytopathic effect (A: right hand pictures) and plaque formation (B) confirmed the functionality of VSV-P-prot with saquinavir (SQV) and indinavir (IND).
Figure 7B:
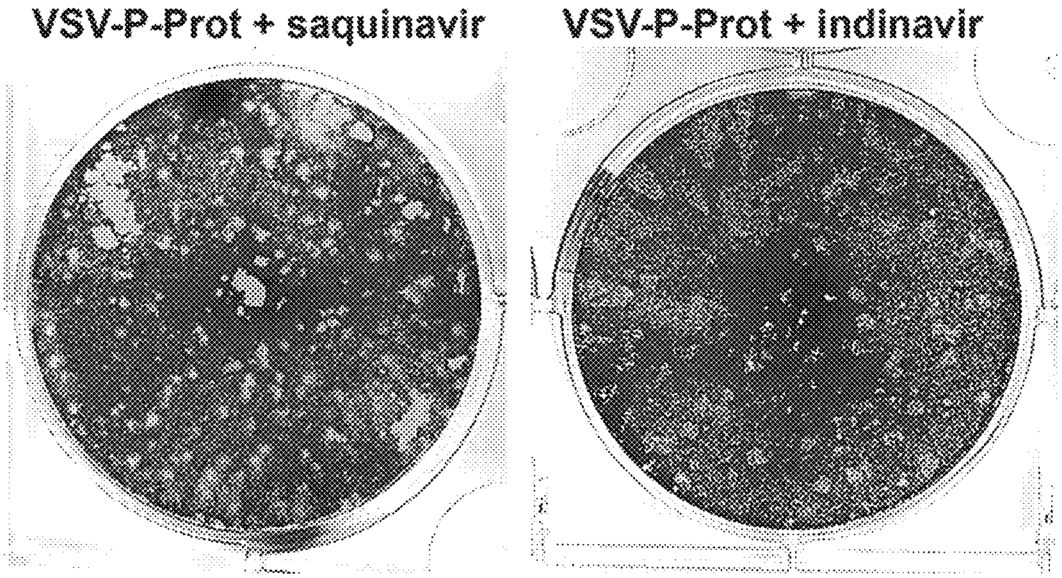

Example 2: VSV-P-Prot can be Regulated in a Dose-Dependent Fashion and by Various HIV Protease Inhibitors To test whether the amprenavir-dependent activity of VSV-P-prot would generalize to other members of the HIV protease inhibitor class, BHK cells were incubated with second generation compounds saquinavir (10 μM) and indinavir (10 μM) followed by infection with VSV-P-prot at an MOI of 0.01. In line with the amprenavir effect, both inhibitors facilitated viral gene expression (GFP signal) and viral replication (plaque formation) (FIG. 7) confirming the universal targetability of the HIV protease-based VSV on-switch system. Also lopinavir (10 μM) and other HIV protease inhibitors were shown to regulate VSV-P-prot (data not shown).

Figure 8A:
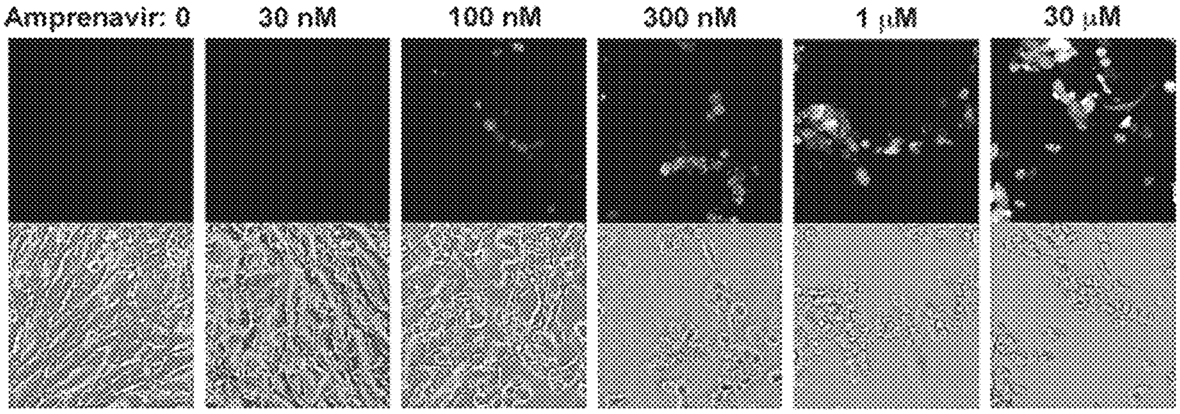
FIG. 8. Protease inhibitor amprenavir regulates VSV-P-Prot activity in a dose-dependent fashion. Dose response of HIV protease inhibitor amprenavir on virus activity of VSV-P-prot. BHK cells were infected with an MOI of 1 and viral spread assessed after 24 hours. A: Viral eGFP expression and cytopathic effect increases with increasing APV dose. B: VSV-P-prot replication started at amprenavir doses of 100 nM, reached a plateau of maximum activity at a dose range between 3 and 100 μM and deteriorated at higher doses. The replication curve revealed a slight attenuation of VSV-P-prot over VSV.
Figure 8B:
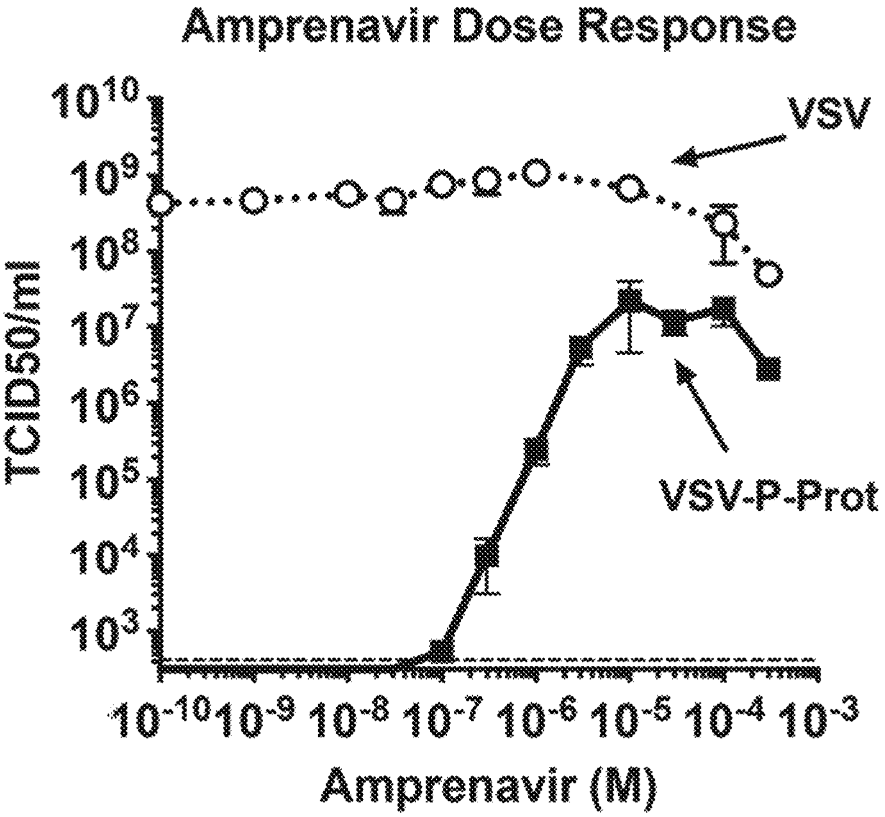

The amprenavir dose used for virus production and initial studies was chosen according to previously described APV plasma concentrations in patients treated orally with APV (Sadler et al., Antimicrob Agents Chemother, 1999, 43(7): 1686-1692). Additionally, a dose response study was performed to address whether the amprenavir-controlled activity of VSV-P-prot is dose dependent. As discussed before, the effect of amprenavir on both viral gene expression (GFP) and viral replication ($TCID_{50}$ replication assay) was assessed. BHK cells were infected with an MOI of 1 and viral infection assessed after 24 hours (FIG. 8A). A single step growth curved revealed that VSV-Pprot activity started at amprenavir doses of 100 nM, reached a plateau of maximum activity at a dose range between 3 and 100 M and deteriorated at higher doses (FIG. 8B). Viral replication of standard recombinant VSV without P-prot control mechanism resulted in 1.5 log higher titers and was not affected by amprenavir doses up to 30 μM, indicating that amprenavir does not control VSV replication in the absence of the P-prot switch. The replication curve revealed a slight attenuation of VSV-P-prot over VSV.

Example 3: Lack of Neurotoxicity and Intracranial Spread of VSV-Pprot

Figure 9A:
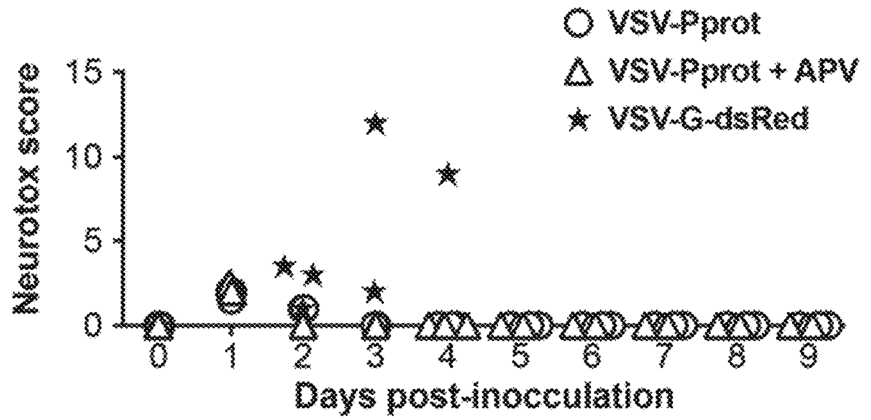
FIG. 9. Abrogation of neurotoxicity of VSV-P-prot. A: Intracranial instillation of wildtype-based VSV-dsRed ($2\times10^5$ $TCID_{50}$ in 2 μl) led to profound signs of neurotoxicity. No neurotoxicity was observed with VSV-P-prot with or without amprenavir. B: Survival graph showing VSV-dsRed-injected mice had to be sacrificed within 4 days for humane reasons. C: Body weight chart shows severe weight drop in VSV-dsRed-injected mice. D: Histological fluorescence analysis of coronal brain sections revealed extended spread of VSV-dsRed expressing red fluorescence. Virus infection was found throughout the striatum, subcortical areas and hypothalamus (bilateral). In contrast, GFP expression from VSV-P-Prot with or without amprenavir was highly restricted to the immediate lining of the injection needle track without any signs of intracranial spread.
Figure 9B:
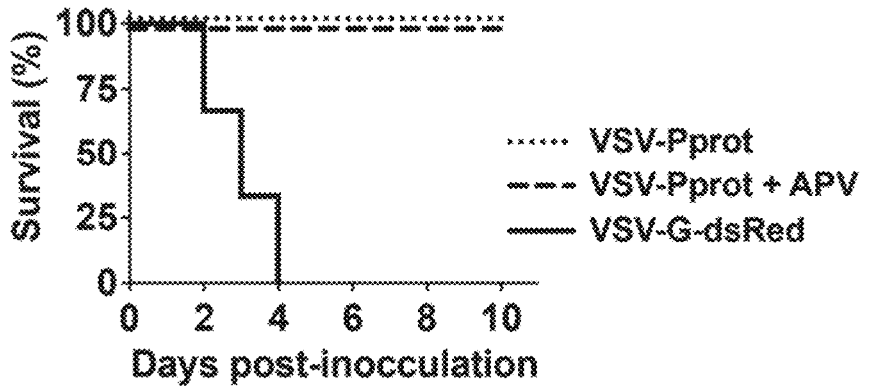
Figure 9C:
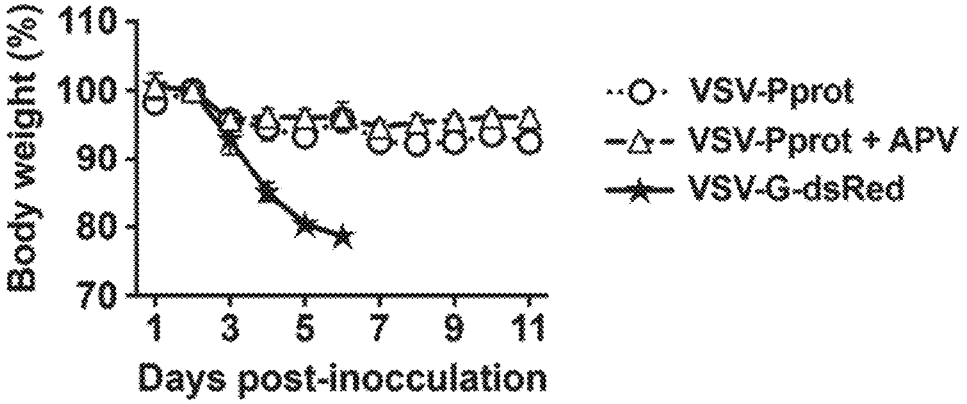
Figure 9D:
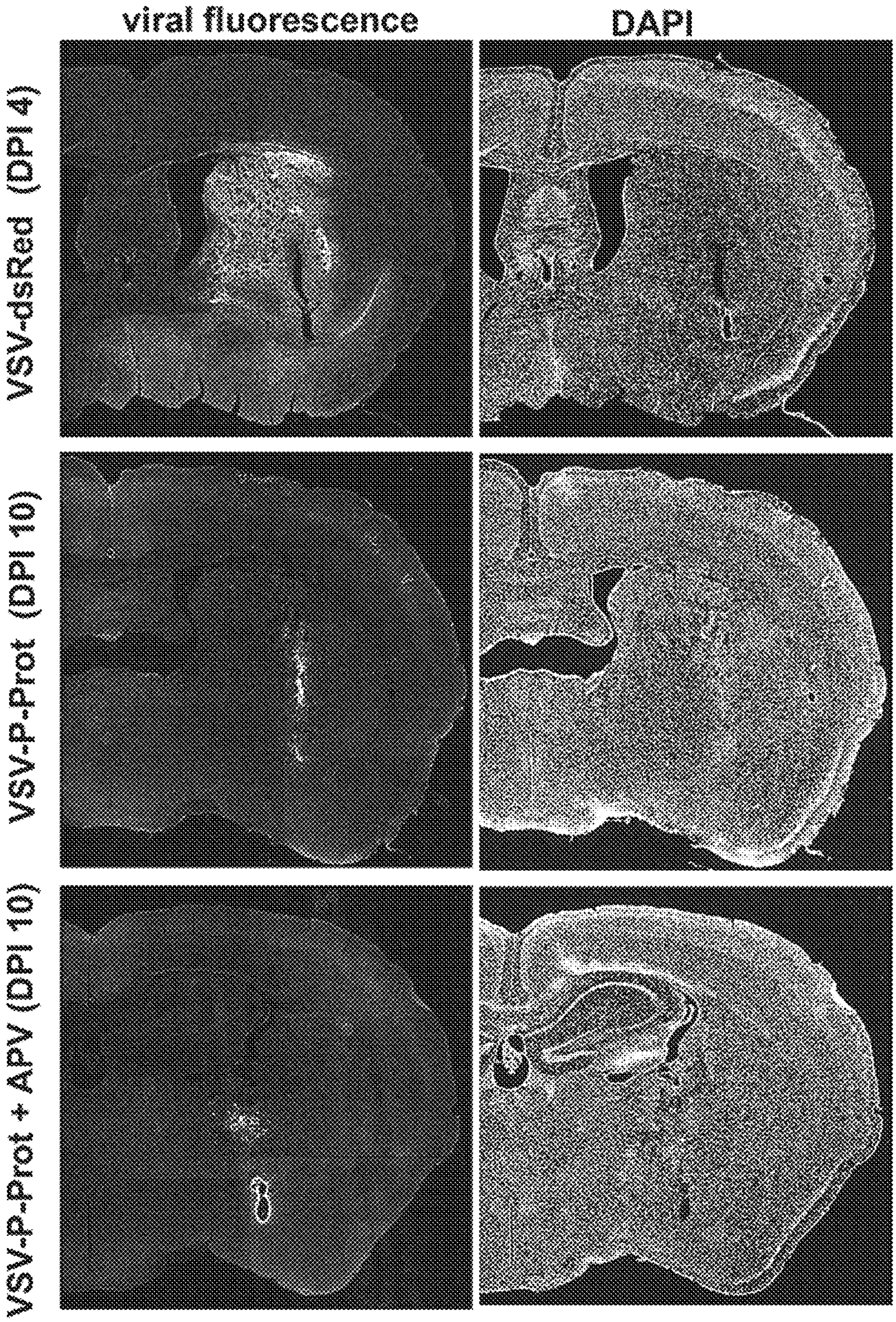

VSV is known for pronounced neurotoxicity in laboratory animals once entered into the CNS space. The VSV glycoprotein shows a strong affinity to neurons and both anterograde and retrograde axonal spread have been described. To address to what extend neurotoxicity of VSV-P-prot is abrogated compared to normal VSV, we employed direct stereotactic injection into the mouse striatum. Intracranial instillation of wildtype-based VSV-dsRed (2×105 TCID50 in 2 μl) led to profound signs of neurotoxicity (FIG. 9A) expressed as hind-limb paralysis, lack of coordination, hunched position, and severe weight drop (FIG. 9C) starting within 2 days post injection. All mice had to be euthanized within 4 days for humane reason (FIG. 9B). In stark contrast, injection of the brain with VSV-P-prot at the same dose resulted in no signs of neurotoxicity. Mice also showed no brain-related adverse signs after intracranial VSV-P-prot injection when treated simultaneously with amprenavir and ritonavir (100 μM amprenavir, 25 μM ritonavir (inhibits degradation of APV) in 100 μl PBS i.p., administered two times a day for 10 days) (FIG. 9A-C). To study potential intracranial spread after stereotactic injection, brains were harvested at day of toxicity-related euthanasia (VSV-dsRed) or at day 10 past VSV-P-prot inoculation. Histological fluorescence analysis of coronal brain sections revealed extended spread of VSV-dsRed expressing red fluorescence. Virus infection was found throughout the striatum, subcortical areas and hypothalamus (bilateral). In contrast, GFP expression from VSV-P-prot was highly restricted to the immediate lining of the injection needle track without any signs of intracranial spread of VSV-P-prot regardless of whether amprenavir was systemically applied or not (FIG. 9D). These data confirm that VSV-P-prot is not associated with the neurotoxicity and intracranial spread typical for VSV.

Thus, the ligand-dependent virus activity was also confirmed in vivo by complete abrogation of neurotoxicity and intracranial spread associated with the parental VSV. As amprenavir does not cross the blood brain barrier, systemic application of the compound did not confer virus activity and neurotoxicity was absent despite a systemically present ON system.

Example 4: Genetic Stability of Protease Inhibitor Dependency of VSV-P Prot

Figure 10A:
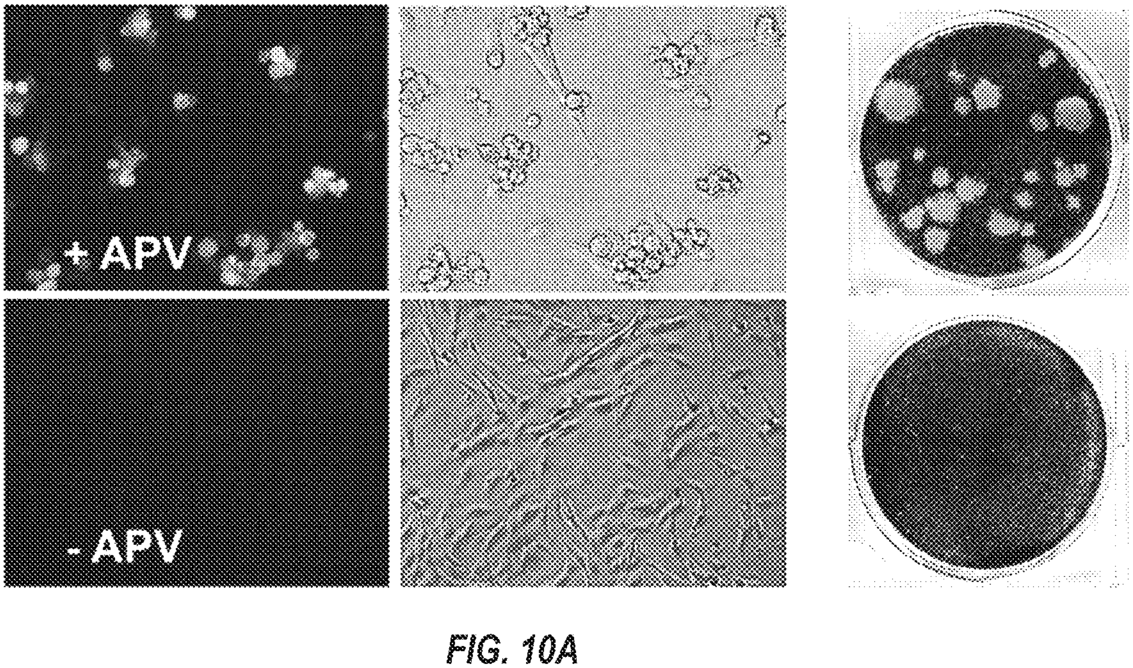
FIG. 10. Protease-regulated activity of VSV-P-Prot remains stable after multiple virus passage. Virus was passaged 20× with suboptimal APV concentration; every passage was transferred to cells without protease inhibitor to detect escape mutants. A: BHK cells inoculated with passaged VSV-P-Prot with and without APV. B: After passaging, viral genomic RNA was isolated and reverse transcribed. A PCR was performed on region of insert, subsequently PCR was sequenced. We found the P196PR2 and the protease negative P-protein PCR fragments to be at their expected sizes (expected size with P-Prot: 1490 bp; expected size without P-Prot: 773 bp).
Figure 10B:
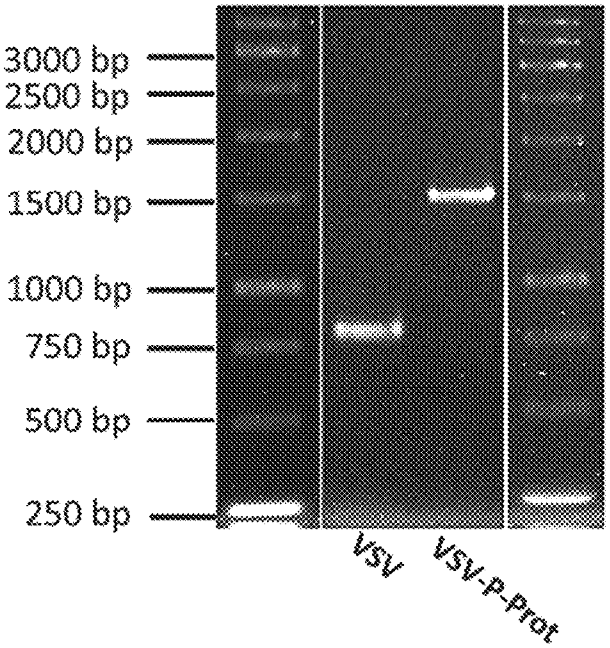

RNA viruses are prone to frequent mutations, in the case of VSV at a mutation rate of about 1 in 10,000 (Steinhauer and Holland 1986, Steinhauer, de la Torre et al. 1989). To test whether the regulatable viral control ON switch of VSV-P-prot remains functionally stable throughout a number of viral replication rounds, we employed in-vitro serial virus passage in optimal (10 μM) and suboptimal (1 μM) amprenavir conditions. After each passage protease inhibitor dependency was assessed by GFP expression after transferring a sample of the supernatant onto parallel dishes incubated without amprenavir. After 20 passages (P20), no amprenavir escape virus variants could be observed (FIG. 10A). To confirm the genomic integrity of VSV-P-prot, viral genomic RNA collected from passage P20 from the suboptimal amprenavir-treated virus propagation was purified, reverse transcribed and a PCR performed on the insert P-196PR2. A VSV variant without protease insertion was used as negative control. We found the P-196PR2 and the protease negative P-protein PCR fragments to be at their expected sizes (FIG. 10B). Subsequent sequencing of the P-prot site and alignment comparison with the respective sequence in the parental plasmid construct (SEQ ID NO: 4) revealed one mutation (protease 2: nucleotide G23A; amino acid R8K) in the construct, which did not render the construct non-functional. It remains to be seen if this mutation is functionally fully silent, reflects an adaptation to low APV concentration or an exchange of a rare codon (R: 7%) to a frequent codon (K: 74%).

Example 5: Identifying a Protease Insertion Site in VSV L-Protein

Figure 11A:
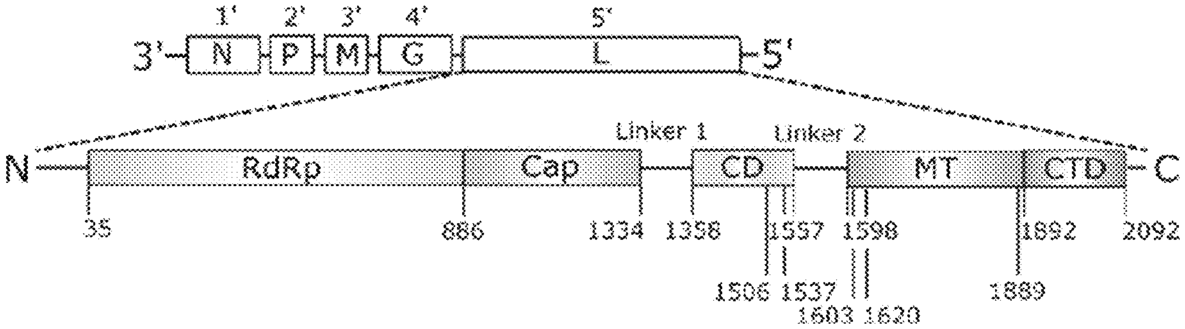
FIG. 11. Domain organization, structure and insertion sites in VSV. L-protein. A: Schematic VSV genome organization showing the genes in 3' to 5' direction and the VSV L-protein domain scheme with its corresponding domain borders labeled with numbers in the upper row (Liang et al., Cell, 2015, 162(2): 314-327). CD1506, CD1537, MT1603, MT1620 and MT1889 indicate candidate insertion sites tested herein. B: VSV L-protein structure as determined by structure information. Right panel visualizes the zoom to complementary domain (CD), methyltransferase domain (MT) and the C-terminal domain (CTD). C: Zoom on CD, MT and CTD with loops indicated that were chosen as insert site. D: Molecular model of VSV L-protein with mCherry insertion at position MT1620.
Figure 11B:
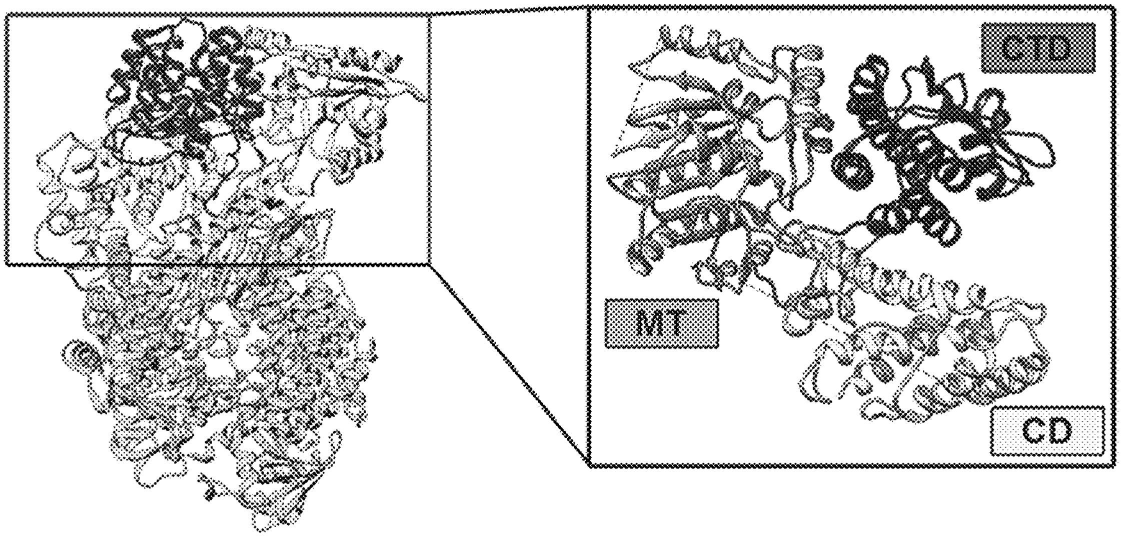
Figure 11C:
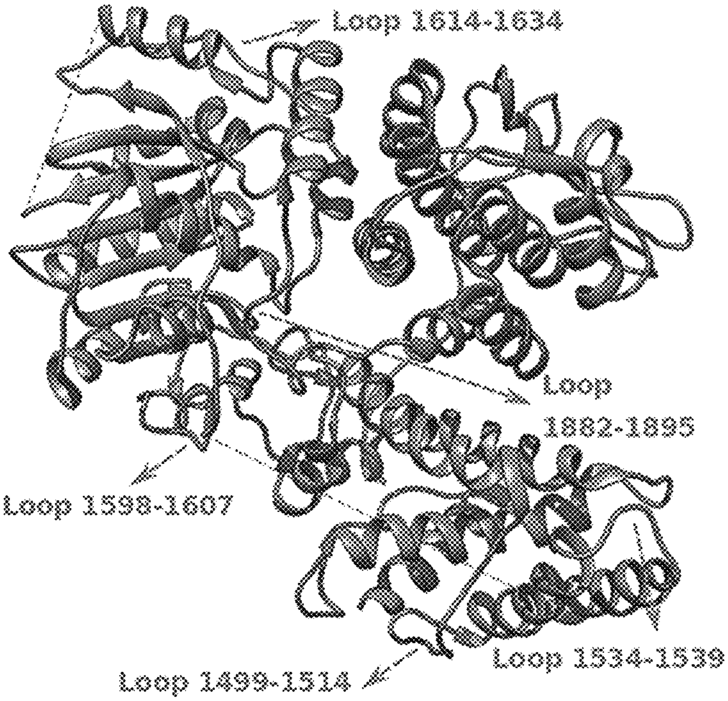
Figure 11D:
Figure 12A:
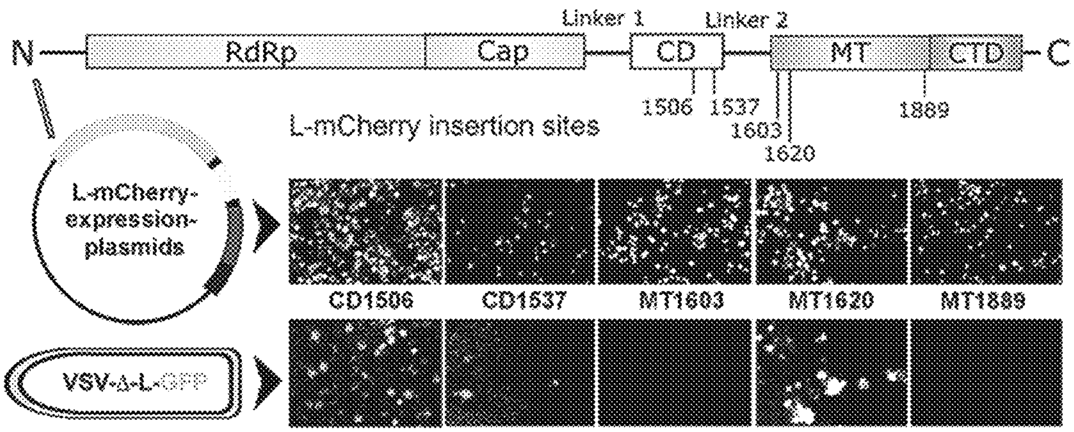
FIG. 12. Insertion of mCherry at position MT1620 leads to replication-competent virus. A: Top: VSV L-protein domain scheme with insertion sites. Photomicrographs depict 293T cells transfected with five different L-mCherry expression plasmids. The corresponding insertion sites are labeled with the domain abbreviation followed by amino acid number. Red (upper row) indicates L-mCherry expression. Bottom: The same transfected 293T cells are shown after infection with VSV-GFP-ΔL at an MOI of 10. Green fluorescence indicates functional L-mCherry fusion proteins and polymerase activity. B: Fluorescence and phase contrast images of VSV-L-mCherry, VSV-GFP-L-mCherry and VSV-L-mWasabi 24 h after infection of BHK-21 cells. Virus genome schemata are displayed above the fluorescence images. C: Immunoblot against mCherry under reducing conditions on 12% polyacrylamide gel. β-actin was used as loading control. VSV, VSV-GFP, VSV-L-mCherry and VSV-GFP-L-mCherry infected BHK-21 cells 8 h after infection were used to prepare lysates.
Figure 12B:
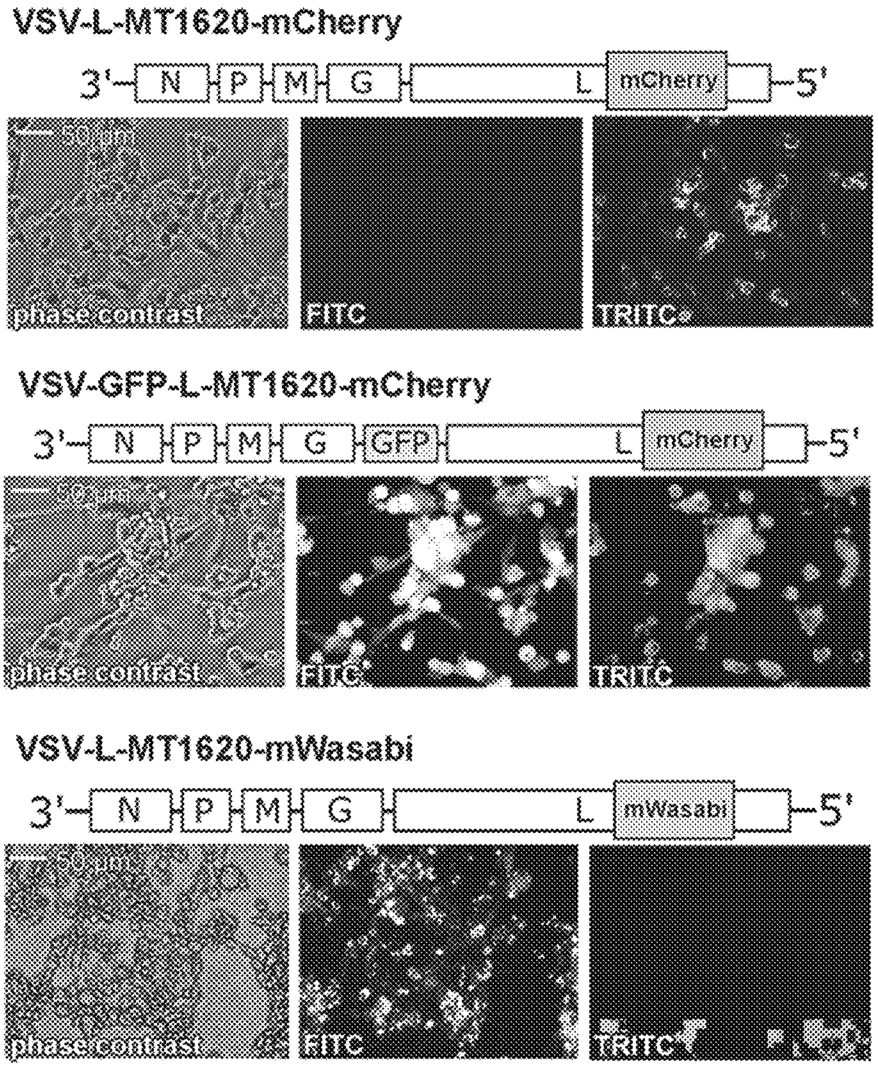
Figure 12C:
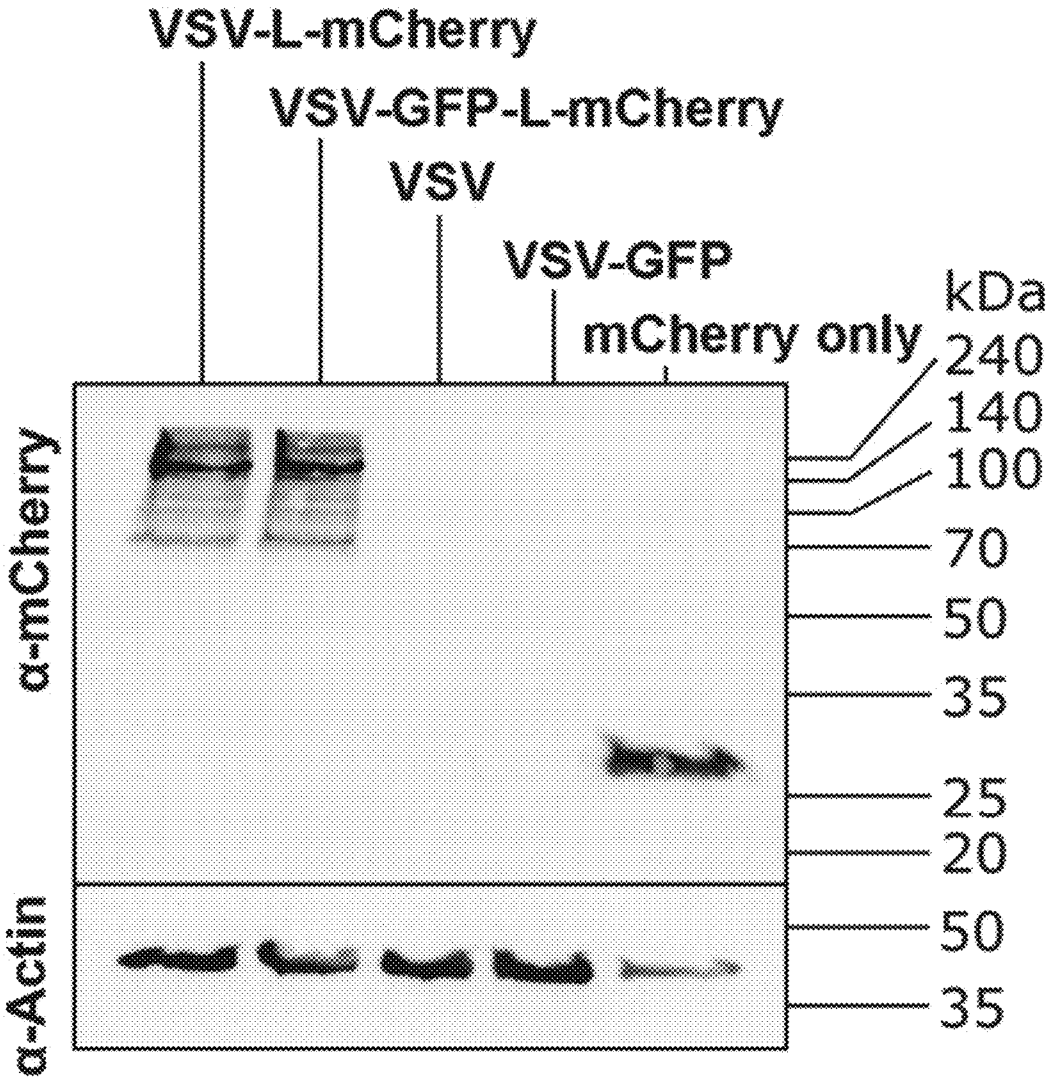

In order to test whether the virus-controlling autocatalytically active protease approach could also function when inserted in an alternative essential VSV protein, we sought to generate a VSV-L-prot. As stable and unattenuated intramolecular insertions have not been successfully reported to date (Ruedas and Perrault, J Virol, 2009, 83(23):12241-12252; Ruedas and Perrault, J Virol, 2014, 88(24): 14458-14466), we first set out to study the ability of VSV L-protein to tolerate an insertion of a reporter gene (mCherry) or not. We used a structure-guided approach to identify five different L-protein insertion sites (amino acid position CD1506, CD1537, MT1603, MT1620 and MT1889 of the L-protein having the amino acid sequence of SEQ ID NO: 28) for mCherry, which we deemed plausible because they were located at the surface and in flexible loops, which should minimize the possibility of steric clashes (FIG. 11A, C). We also avoided insertion sites within alpha-helices and beta-sheets to conserve structural integrity of the L-protein. FIG. 11D depicts a model of the insertion at MT1620, which resulted in a replication competent virus as explained below. To screen the proposed in silico designed structure predictions for candidate insertion sites, VSV L-protein expression vectors with insertions at CD1506, CD1537, MT1603, MT1620 and MT1889 were generated. After transfection of these five constructs in HEK cells, infection with a propagation-incompetent VSV-GFP-ΔL virus, coding for eGFP as reporter, was performed. In this screening all sites showed mCherry signal, but only two sites (CD1506, MT1620) showed eGFP signal, indicating transcriptional activity of L-mCherry fusion protein (FIG. 12A). Thus, every insertion site allows correct mCherry folding, although with varying efficiency, but only two insertions retain polymerase activity. To test the eGFP positive clones for viral replication competency, we chose to clone these sites (CD1506, MT1620) in a full VSV genome. Each site was cloned into two VSV backbones, one with eGFP as reporter at fifth position in the genome, the other without eGFP. Neither of the VSV variants with the CD1506 construct could be rescued, even after multiple attempts. In contrast, VSV-L-MT1620 and VSV-GFP-L-MT1620 virus rescue yielded replication competent viruses. This was confirmed by the cytopathic effect and fluorescent signal (FIG. 12B). As expected, VSV-eGFP-L-MT1620-mCherry showed fluorescent signals in both FITC (green) and TRITC (red) channels, and VSV-L-MT1620-mCherry only in TRITC channel. mCherry flanked by a linker on each side has the DNA sequence of SEQ ID NO: 11. VSV-L-MT1620-mWasabi showed green fluorescence in the FITC channel (FIG. 12B). The protein mWasabi is likewise flanked by a linker on each side and is encoded by the DNA sequence of SEQ ID NO: 12. To verify mCherry presence at protein level we performed immunoblots with an mCherry specific antibody. BHK-21 cells were infected with VSV, VSV-GFP, VSV-L-MT1620-mCherry and VSV-GFP-L-MT1620-mCherry. As a positive control, a vector containing only mCherry was transfected in BHK-21 cells. mCherry inside L-protein displayed a signal at high molecular weight (expected at 267 kDa), in accordance with the production of the L-mCherry fusion protein after viral infection (FIG. 12C).

Taken together these results show the successful insertion of mCherry at position MT1620 leading to a replication competent virus.

Figure 13A:
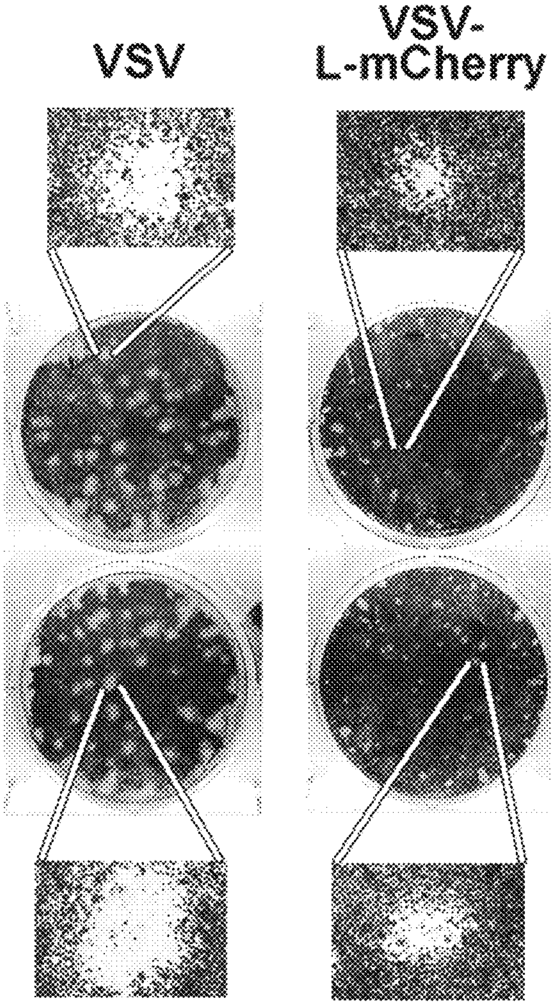
FIG. 13. Insertion of mCherry at position MT1620 leads to moderate attenuation. A: Viral replication fitness assessment with crystal violet plaque assays. Representative photographs from a 6-well dish are shown with corresponding microscopic insets for single plaque display. BHK-21 monolayers were inoculated with virus for 1 hour, washed and then incubated for 24 hours. B: Viral replication kinetics of different VSV strains. Single step growth kinetics of VSV (black dots), and VSV-L-mCherry (white triangles) in BHK-21 cells. Titers were quantified using $TCID_{50}$ assays. C: Comparison of virus induced cytotoxic activity in an IFN response MTT viability assays. IFN responsive BHK-21 cells were treated with increasing amounts (0, 10, 100, 500 and 1000 U/ml) of IFN and infected with MOIs 0.1, 1 and 10. The viability is shown normalized to untreated control. Bars represent means+/−SEM (n=4). In the absence of IFN treatment, both viruses lead to comparable reduction of viability in infected cells.
Figure 13B:
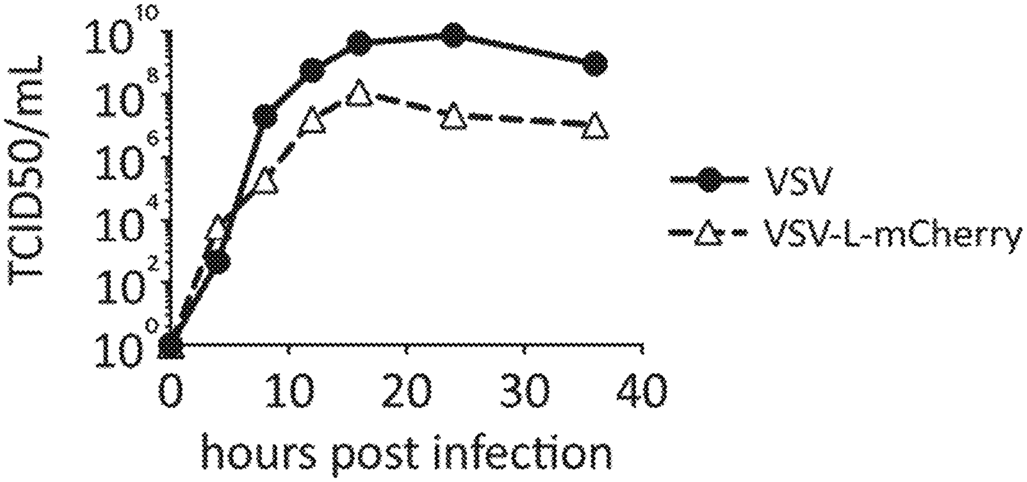
Figure 13C:
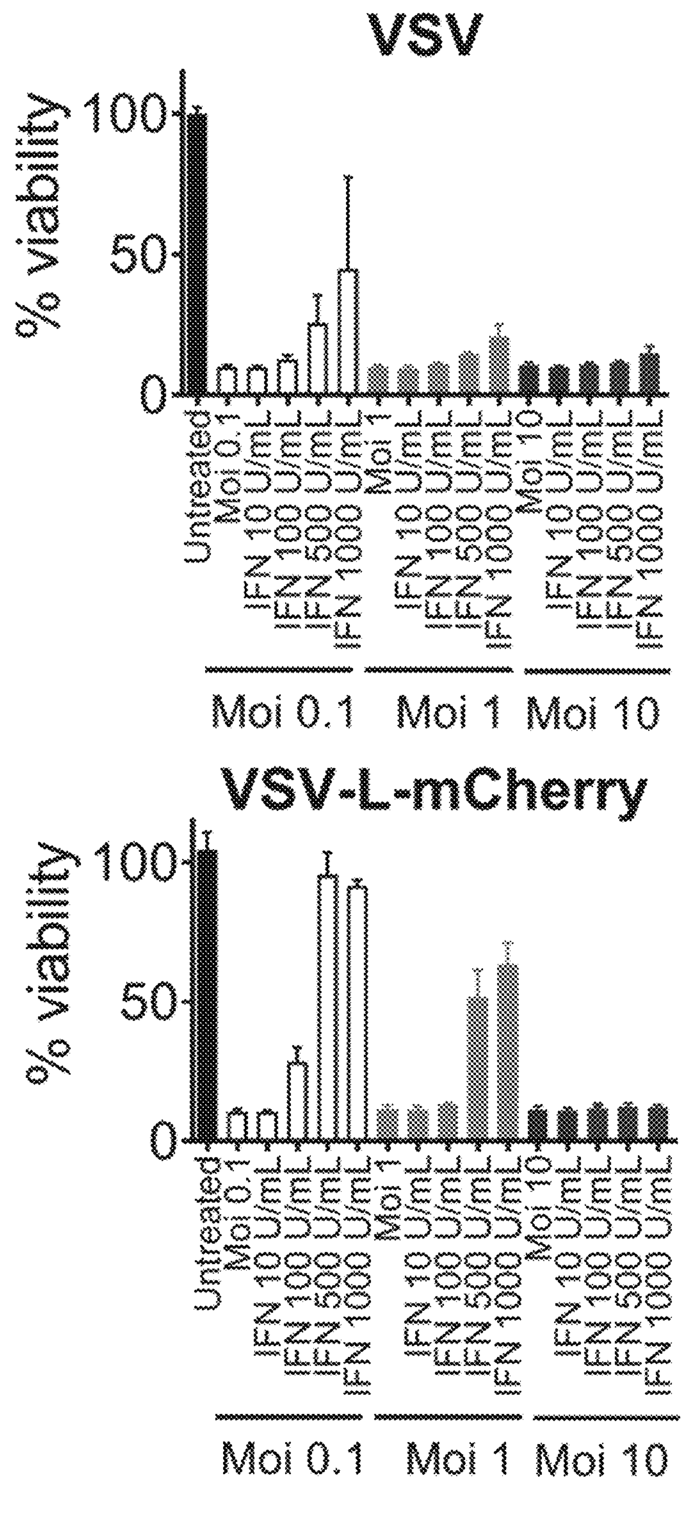

To assess the replication capability and potential attenuation of VSV-L-insert compared to wild-type based VSV, plaque assays were performed to illustrate plaque size (FIG. 13A) and TCID50 assay was performed to quantify virus replication (FIG. 13B). Both tests revealed an attenuation of VSV-L-insert compared to wildtype VSV, with a reduction in virus replication titers of about 1-2 logs. In addition, MTT viability assays were performed to assess the ability of VSV-L-insert to induce cell killing in BHK cells in the presence or absence of interferon compared to VSV. In the absence of IFN, virus cytotoxicity after VSV-L-insert infection was comparable to VSV infection (FIG. 13C). In the presence of IFN, the two L-MT1620-mCherry VSV variants showed a stronger IFN-dependency and consequently a slightly reduced killing compared to VSV and VSV-GFP (FIG. 13C; data for GFP variants not shown) corroborating the finding that insertions of mCherry at position MT1620 lead to mild attenuation compared to wild-type VSV, without significantly impairing its replicative or cytolytic potential.

The sequencing results of L-mCherry obtained in this example are provided as the sequence of SEQ ID NO: 13. Upon sequence confirmation of all rescued VSV-L-insertion variants we observed one to three secondary non-synonymous mutations in most viruses, which were located in proximity to the site of insertion. These mutations may be conditional and advantageous for proper polymerase function.

Example 6: Generating an Alternative Protease-Regulated ON-Switch, VSV-L-Prot

Figure 14A:
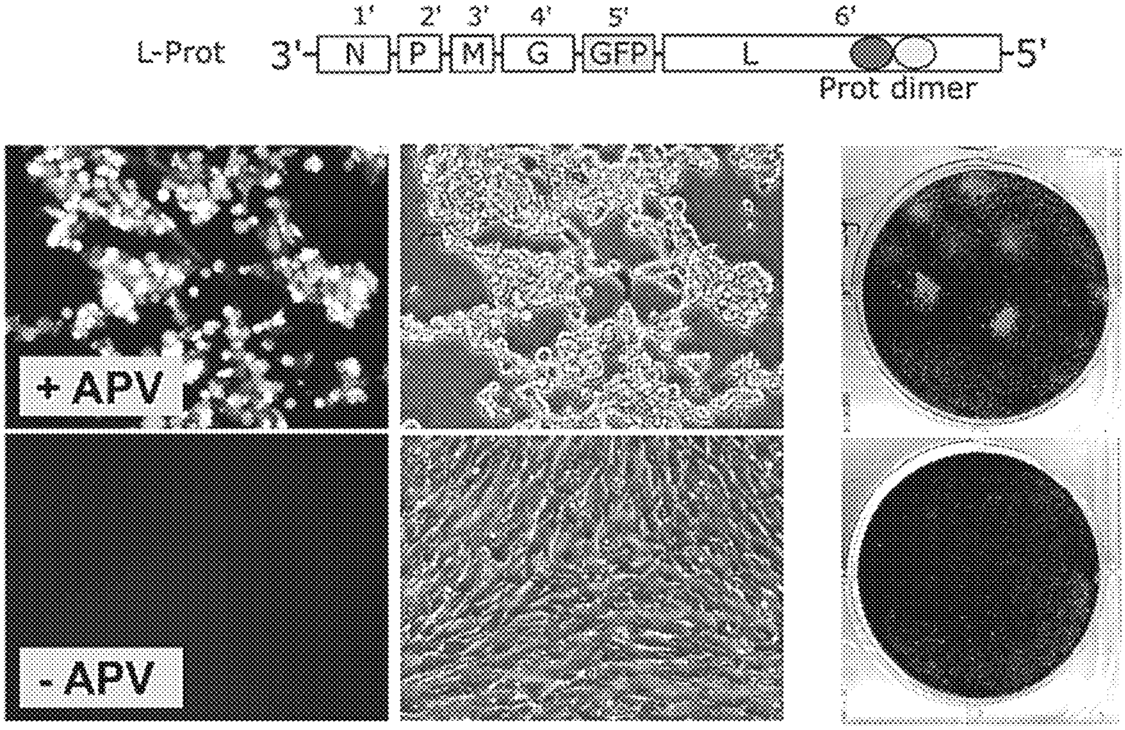
FIG. 14. Insertion of protease switch into the VSV L-protein, generating an alternative regulatable virus VSV-Lprot. A: BHK were cells inoculated with VSV-L-prot with and without APV. B: After plaque purification, viral genomic RNA was isolated and reverse transcribed. PCRs were performed on region of insert of VSV-L-prot and a control virus without insert (expected size of L-protein with insert: 1830 bp, expected size of L-protein without insert: 1114 bp), subsequently PCRs was sequenced with no mutations detected.

The finding of a functional insertion site within the VSV L-protein allowed us to generate an alternative regulatable VSV-prot variant, VSV-L-Prot. Like VSV-P-prot, the VSV-L-Prot comprises a protease insert in the L-protein (SEQ ID NO: 10) and is therefore responsive to APV and replicates to high titers in its presence (also with saquinavir and indinavir) and does not replicate without protease inhibitors (FIG. 14A).

Figure 14B:
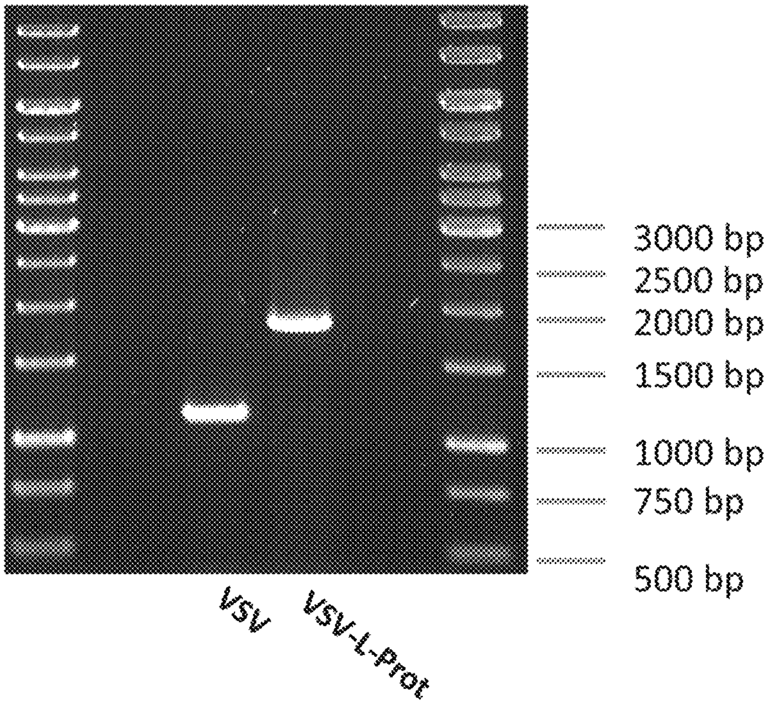

To test genomic integrity of VSV-L-Prot, viral genomic RNA was purified, reverse transcribed and a PCR performed on L-MT1620PR2. A VSV variant without protease insertion was used as negative control. We found the L-MT1620PR2 and the protease negative L-protein PCR fragments to be at their expected sizes (FIG. 14B).

We sequenced the site of insertion with two Sanger sequencing reactions to assess whether mutations have occurred within the protease dimer sequence. The sequencing results were aligned with the plasmid sequence. We observed no mutations in the protease dimer sequence).

Example 7: VSV-Lprot can be Regulated in a Dose-Dependent Fashion

Figure 15A:
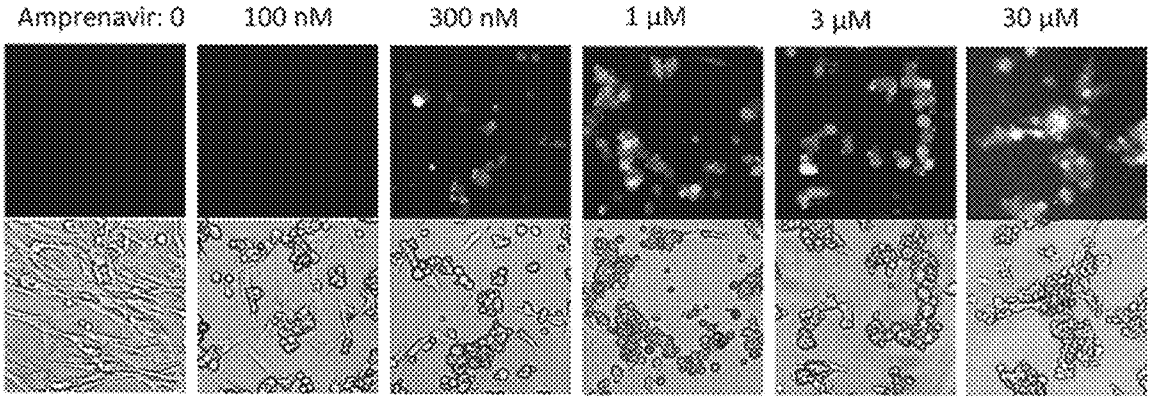
FIG. 15. Protease inhibitor amprenavir regulates VSV-L-prot activity in a dose-dependent fashion. We tested VSV-L-prot dose response to HIV protease inhibitor amprenavir. BHK cells were infected with an MOI of 1 and viral spread assessed after 24 hours. A: Viral GFP expression increases with increasing amprenavir dose. B: VSV-L-prot activity started at amprenavir doses of 100 nM, reached a maximum activity at 30 μM. Higher amprenavir concentrations were not tested for L-prot due to toxic effects on cells. The replication curve revealed a slight attenuation of VSV-Lprot over VSV.
Figure 15B:
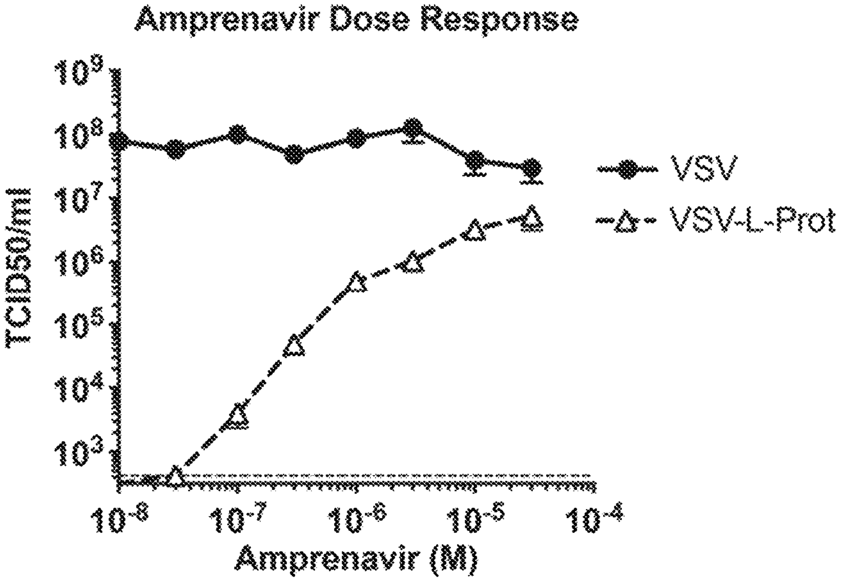

Like with VSV-P-prot, a dose response study was performed to address whether the amprenavir-controlled activity of VSV-L-prot is dose dependent. As discussed before, the effect of amprenavir on both viral gene expression (GFP) (FIG. 15A) and viral replication (TCID50 replication assay) was assessed (FIG. 15B). VSV-L-prot activity started at amprenavir doses of 100 nM and reached a maximum activity at a dose of 30 μM. Higher amprenavir concentrations were not tested for L-prot, since they had shown to decrease titers by being toxic for cells in our previous VSV-P-prot studies. The replication curve also revealed a mild attenuation of VSV-L-prot over VSV comparable to that seen by VSV-P-prot.

Example 8: Generating a Tandem Protease-Regulated ON-Switch, VSV-P-L-Prot

Figure 16A:
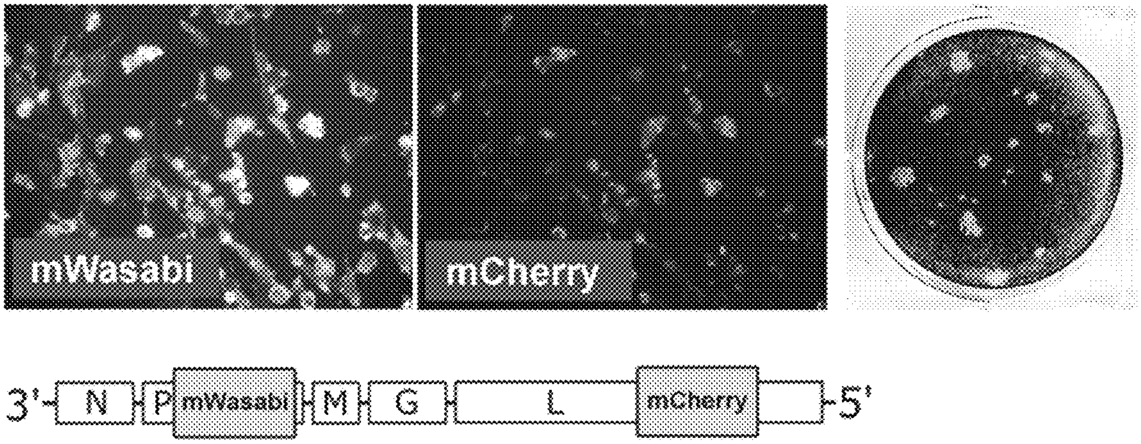
FIG. 16. Generation of VSV with functional double intramolecular insertion into P and L, generating VSV-P-mWasabi-L-mCherry. We generated VSV with functional double intramolecular insertion into P and L, VSV-P-mWasabi-L-mCherry, as a test for VSV-P-prot-L-prot. We confirmed the double insert function with the double fluorescence read-out and cytopathic effect in plaque assays (A, left: mWasabi, middle: mCherry, right: plaques, bottom: schematic drawing of construct) and the testing of genomic integrity by cDNA synthesis and PCR (B; 1. VSV P-site, 2. VSV-P-mWasabi-L-mCherry P-site, 3. VSV L-site, 4. VSV-P-mWasabi-L-mCherry L-site).

Addressing the possibility of revertant virus development that may lose the conditional ON switch control, we further investigated the possibility of an insert in the P-protein and in the L-protein. We next generated a VSV with functional double intramolecular insertion into P and L, VSV-P-mWasabi-L-mCherry, as an initial proof of concept for functional double insert VSV variants. We confirmed the double insert function with the double fluorescence read-out and cytopathic effect in plaque assays (FIG. 16A) and the testing of genomic integrity by cDNA synthesis/PCR and Sanger sequencing.

Figure 16B:
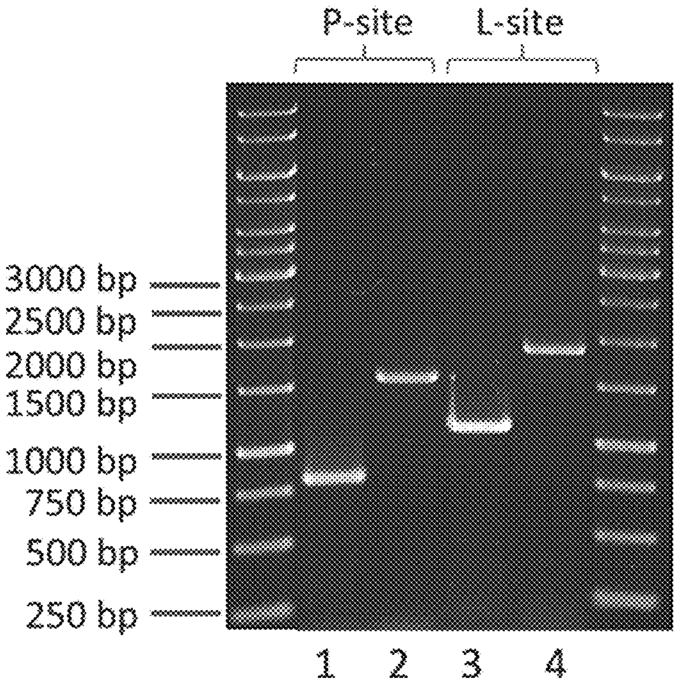

To test genomic integrity of VSV-P-mWasabi-L-mCherry, viral genomic RNA was purified, reverse transcribed and a PCR performed on P-196-mWasabi (SEQ ID NO: 15) and L-MT1620-mCherry (SEQ ID NO: 14). A VSV variant without fluorescent protein insertions was used as negative control. We found the P-196-mWasabi, L-MT1620-mCherry and the fluorescent protein negative P and L-proteins PCR fragments to be at their expected sizes (FIG. 16B).

We sequence-confirmed the sites of insertion with two Sanger sequencing reactions to assess whether mutations might have occurred within the fluorescence marker sequences. The sequencing results were aligned with the plasmid sequence. We observed no mutations in the insertion sequence. The sequencing results are provided in cDNA sequences of P-196-mWasabi and L-MT1620-mCherry of VSV-P-mWasabi-L-mCherry as SEQ ID NO: 14 and SEQ ID NO: 15, respectively.

After confirming the feasibility of tandem intramolecular insertions we next generated a double ON switch regulated VSV variant, VSV-P-L-prot. The virus has been successfully rescued and seems to behave similar to both single switch constructs, VSV-P-prot and VSV-L-prot. This virus also showed protease inhibitor dependency, generating plaques only in the presence of amprenavir (data not shown). However, the double-switch virus showed slightly stronger attenuation compared to the single-switch virus.

Thus, overall we generated constructs, where the HIV protease dimer was inserted INTRA molecularly into two proteins of the vesicular stomatitis virus (VSV) that make up the polymerase complex (P-protein and L-protein, separately and in combination). In the presence of protease inhibitor, the integrity of the viral proteins was preserved and the viruses could replicate. Without protease inhibitors, the HIV protease dimer was autocatalytically active, cleaving the essential viral proteins upon translation. Analogous to regulatory modules in DNA viruses (e.g. Tet-On), we termed this mechanism “prot-ON”.

We optimized the codon usage of the flexible linkers and protease dimer to avoid homology between the first and second protease. This precaution was taken, since so called “copy-choice” recombination events in VSV have been described previously (Simon-Loriere and Holmes 2011), in which the viral polymerase, the L-protein, can switch between templates and also skip sequence stretches. “Copy-choice” occurs preferentially when the polymerase is guided by sequence homology of the nascent RNA strand with the newly chosen template. Furthermore, point mutations arise frequently in RNA viruses, in the case of VSV at a mutation rate of about 1 nucleotide in 10,000. Theoretically, every genome carries one mutation, which leads virologists to refer to the VSV genome (and other RNA virus genomes) not as one sequence, but to a mixture of so called “quasi-species”. Therefore, occurrence of mutations within the HIV protease sequence rendering the proteolytic switch inactive are a real possibility. To avoid such escape mutants or revertant viruses that may lose the conditional ON switch control, we doubled the protease module (ON-switch) by introducing protease dimers in a second essential VSV protein the P-protein and the L-protein.

The only other previously published functional intramolecular insertion site in a VSV protein, which would support viral replication over continuous passaging had been described in the M-protein (Soh and Whelan, Virol, 2015, 89(23):117050-11760). However, it is preferred to control the replication machinery of VSV directly, since regulation of the M-protein would still allow the virus to undergo replication, possibly facilitating escape mutations. Insertion sites within the L-protein have been described, but the resulting viruses were temperature sensitive and instable after passage (Ruedas and Perrault 2009, Ruedas and Perrault 2014). In contrast, we were able to generate functional insertions with initially fluorescence proteins and subsequently the HIV protease dimer. Both P-prot and L-prot responded to the presence of every HIV protease inhibitor we tested and replicated in a compound dose-dependent fashion. In the absence of protease inhibitors, virus gene expression ceased and replication stopped.

Although not tested in this study, the ON switch system inherently harbors an additional environmental safety element. As virus progeny depend on presence of protease inhibitor, potentially shed virus is not active for productive infection. This is of particular importance when therapeutic RNA viruses can cause or mimic notifiable animal diseases.

Example 9: Generating a Protease-Regulated OFF-Switch, VSV-GFP-Prot-L

Figure 18A:
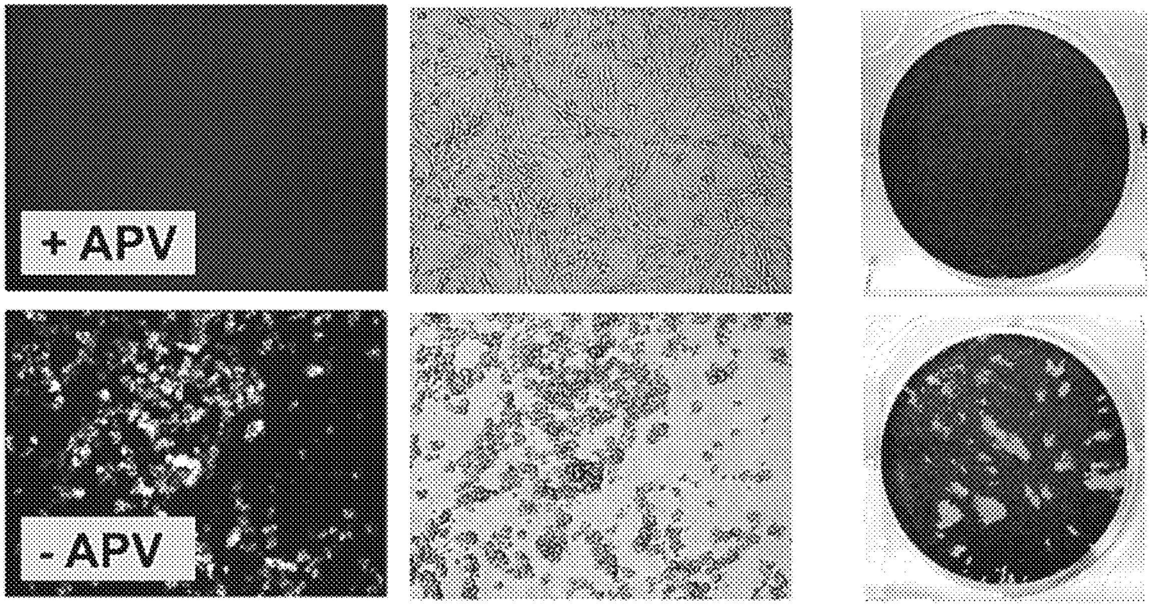
FIG. 18. Generation of VSV with functional replacement of an intergenic region with HIV protease dimer. A: BHK cells inoculated with VSV-GFP-Prot-L without $(GGSG)_3$ linker, (construct with linker not shown). Addition of 10 μM amprenavir leads to stop of virus activity. B: After plaque purification, viral genomic RNA of VSV-GFP-Prot-L with and without $(GGSG)_3$ linker was isolated and reverse transcribed. PCRs were performed on region of insert of both Prot-Off viruses and a control virus, subsequently PCRs were sequenced. Shown is 1. GFP-L fragment without protease (959 bp), 2. GFP-Prot-L fragment with $(GGSG)_3$ linker (1559 bp), 3. GFP-Prot-L fragment without $(GGSG)_3$ linker (1487 bp)). Sequence alignment of rescued VSV-Prot-Off virus (without $(GGSG)_3$ linker) with construct plasmid of the region of the HIV protease insert and the consensus sequence of the plasmid sequence did not reveal any mutations.

Following the generation of a protease-based ON-switch we also generated a VSV variant VSV-Prot-Off that can be switched off. Using the same HIV protease mediated autocatalytic switch system, a location change of the insertion from INTRA- to INTER-molecular site results in a reversal of direction from virus promoting to virus stopping control. For this OFF-switch, the protease dimer with a variant codon optimization was inserted into the VSV genome to create a fusion protein of GFP, the protease dimer and the viral polymerase L. This large fusion protein with the protease dimer fused to the N-terminus of the L protein is expected to be functionally inactive, but to be activated by proteolytic liberation of L protein in the absence of protease inhibitor. In this OFF construct we replaced an intergenic region of VSV with the HIV protease flanked by its cleavage sites. Intergenic regions play a crucial part in generating multiple proteins from one RNA strand. We chose the intergenic region between the non-essential reporter protein GFP and the L-protein (FIG. 17A) in VSV-GFP and generated two viruses. The first one carried flexible linker regions surrounding the HIV protease dimer construct (SEQ ID NO: 16) and a second one having no regions surrounding the HIV protease dimer construct (SEQ ID NO: 17). It would be advantageous to avoid flexible linker regions, because they would remain as C-terminal tag on GFP and N-terminal tag on the L-protein, after the HIV protease dimer has cleaved its recognition sequence. However, the two constructs differ only slightly in their replicative capacity. Adding of amprenavir (10 M) resulted in stop of virus activity both at the level of viral transgene expression (GFP) as well as virus replication (plaque assays) (FIG. 18A). An additional unique safety feature has been added to this system. In theory, a potential loss of the protease insert could result in viral progeny escaping the OFF switch control. We therefore put the protease OFF switch in place of the intergenic region, so that an insert loss would come with a penalty of forming a fusion protein of two neighboring VSV proteins or in this case a VSV protein with GFP resulting in a dysfunctional virus.

Figure 18B:
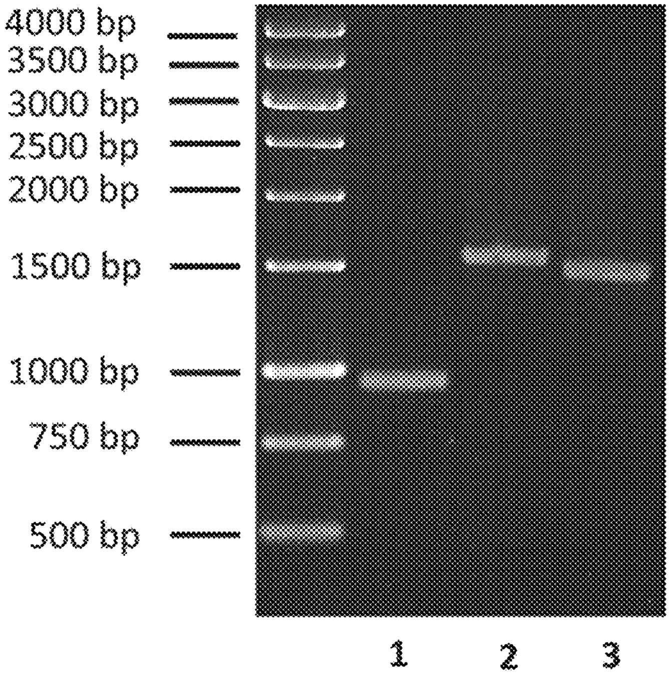

To test genomic integrity of VSV-GFP-Prot-L, viral genomic RNA was purified, reverse transcribed and a PCR performed on GFP-Prot-L. A VSV variant without protease insertion was used as negative control. We found the VSF-GFP-Prot-L and the protease negative L-protein PCR fragments to be at their expected sizes (FIG. 18B).

We sequenced the site of insertion with two Sanger sequencing reactions to assess whether mutations have occurred within the protease dimer sequence. The sequencing results were aligned with the plasmid sequence. We observed one mutation in the protease dimer sequence in each construct. The mutations are at amino acid positions 85 in the construct with linker corresponding to nt 623 of the cDNA sequence of the protease dimer with linker having the sequence of SEQ ID NO: 18 (or nt 254 of the second protease nucleotide sequence) and at amino acid position 86 in the construct without linker corresponding to nt 589 of the cDNA sequence of the protease dimer without linker having the sequence of SEQ ID NO: 19 (or nt 256 of the second protease nucleotide sequence), both in the second protease. The mutations are not described as typical protease inhibitor resistance mutations and do not interfere with regulation by protease inhibitors. Possibly these mutations made the protease more active when fused between GFP and L.

Figure 19A:
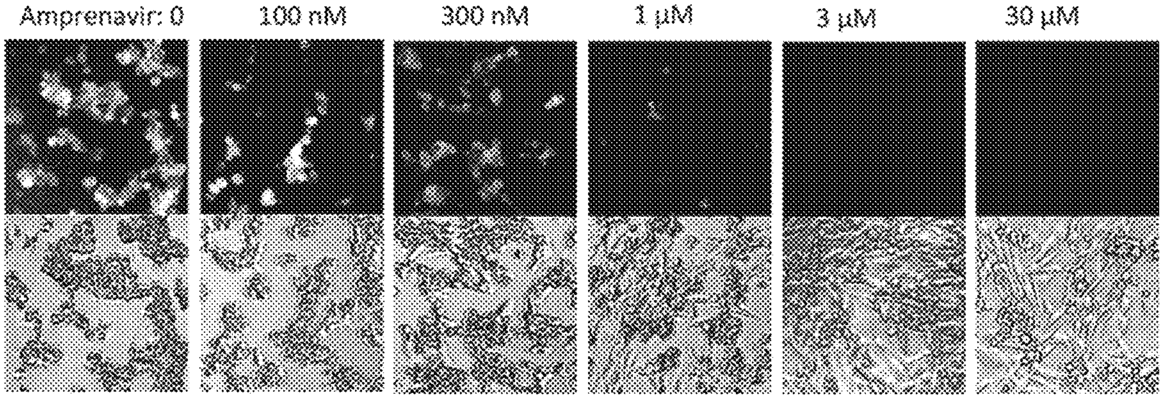
FIG. 19. Protease inhibitor amprenavir regulates VSV-Prot-off activity in a dose-dependent fashion. Dose response of HIV protease inhibitor on virus activity of VSV-Prot-OFF. A: BHK cells were infected with an MOI of 1 and viral infection assessed after 24 hours. Viral GFP expression decreases with increasing amprenavir (APV) dose. B: Virus replication measured at 24 hpi. VSV-Prot-OFF activity started to decrease at APV doses of 30 nM. The highest dose of APV we tested was 30 μM. Higher APV concentrations than 30 μM were not tested for VSV-Prot-OFF due to toxic effects on cells. 10 μM saquinavir (SQV, white symbols) showed strongest suppression of viral replication. C: Virus replication measured at 24 hpi using the indicated saquinavir concentrations. D: BHK cells were infected at an MOI of 3 of indicated VSV variants VSV-GFP or VSV-Prot-Off for a single-step replication kinetic. Virus titer in the harvested supernatant was determined and is shown as $Log_{10}$ $TCID_{50}$/ml.
Figure 19B:
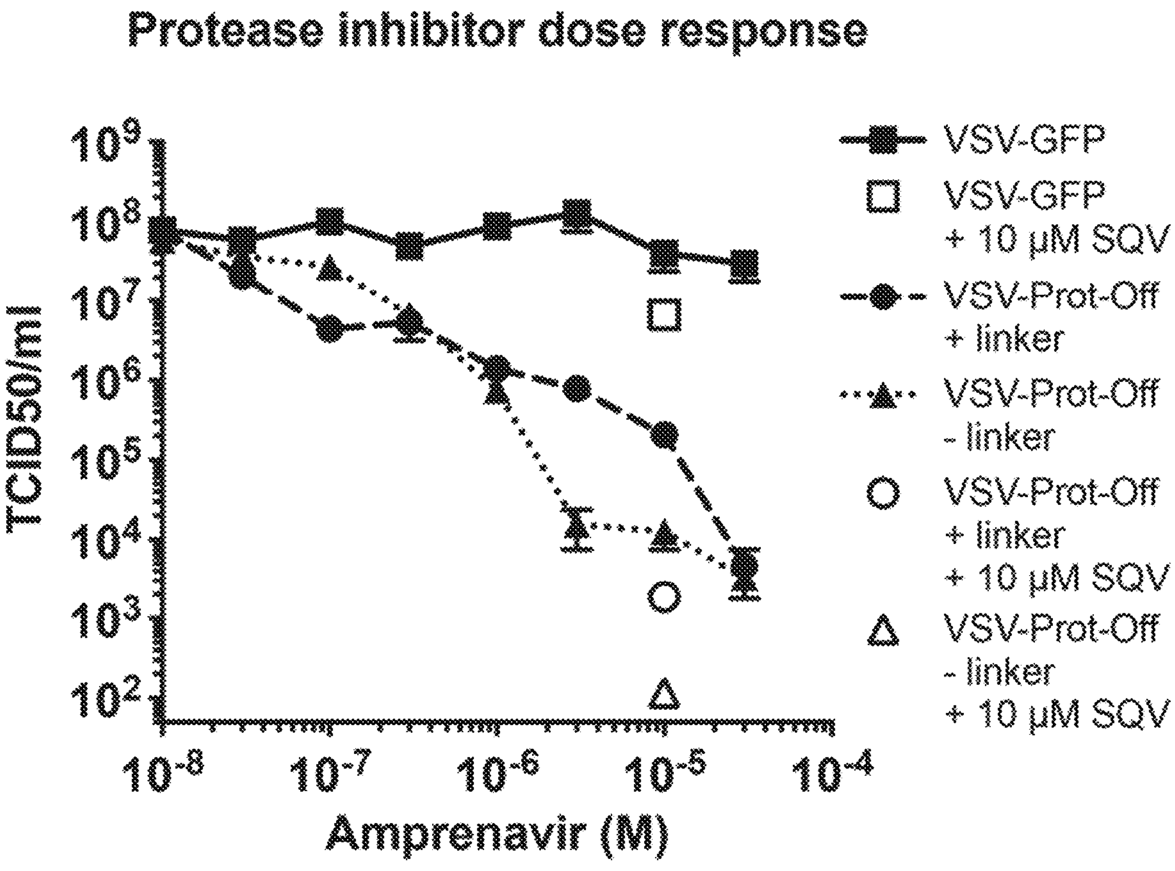
Figure 19C:
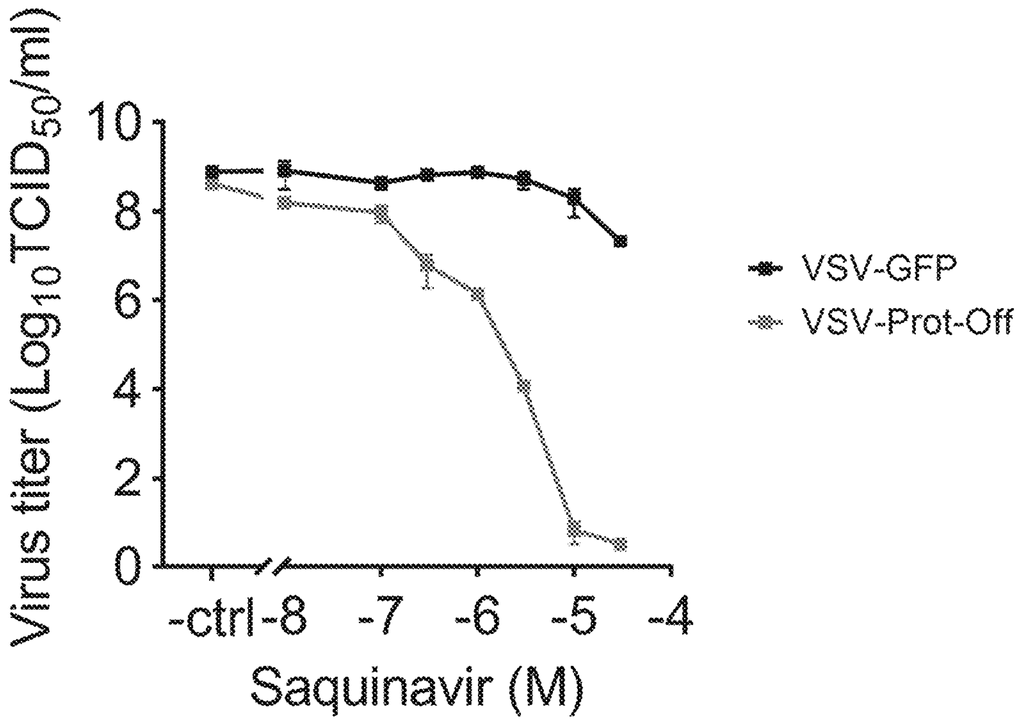
Figure 19D:
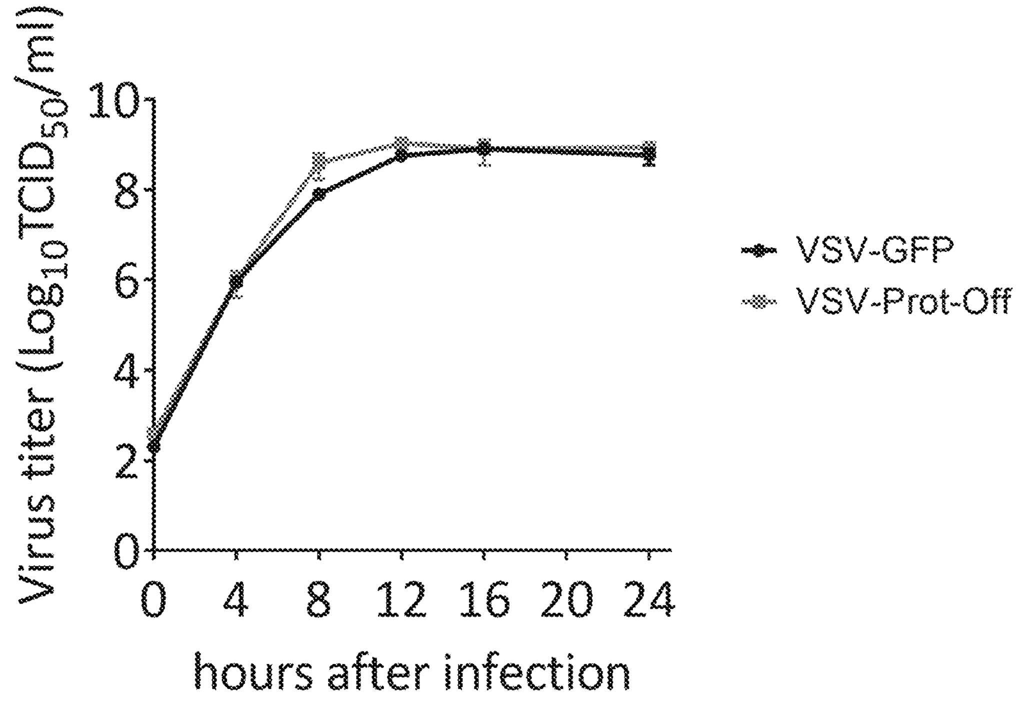

Example 10: VSV-GFP-Prot-L can be Regulated in a Dose-Dependent Fashion and by Different Protease Inhibitors Like with the two prot-ON constructs, a dose response study was performed to address whether the amprenavir-controlled activity of VSV-GFP-Prot-L (VSV-Prot-Off) is dose dependent. As discussed before, the effect of amprenavir on both viral gene expression (GFP) and viral replication (TCID50 replication assay) was assessed (FIGS. 19A and B). In the absence of protease inhibitors, VSV-GFP-Prot-L activity was unattenuated compared to normal VSV. VSV-GFP-Prot-L activity was high at low amprenavir concentrations (0-300 nM) and started to decline at 1 μM. We also tested whether VSV-GFP-Prot-L would respond to other protease inhibitors than amprenavir. 10 μM saquinavir treatment resulted in even stronger inhibition of virus replication than amprenavir (FIG. 19B). This was further confirmed in FIG. 19C using saquinavir concentrations of 0-30 μM). Further a single step replication kinetic was determined by seeding 105 BHK cells per well in 12-Well plates and infected at an MOI of 3 with VSV-Prot-Off or VSV-GFP (FIG. 19D). One hour after infection, cells were washed twice with PBS and incubated in 500 μl GMEM until indicated time points. For starting values, i.e. 0-hour time points, the 500 μl GMEM were collected immediately. VSV-Prot-Off showed no attenuation compared to VSV-GFP (FIG. 19D).

Thus, using the same autoproteolytic system as in the “prot-ON” constructs but in a functionally different genome location, we also developed the reversal mechanism of protease-dependent OFF regulation, which works by the replacement of an intergenic region with the HIV protease dimer. In this construct the protease must be active to separate two viral proteins, similar as it does in HIV. Adding protease inhibitor in this construct leads to non-functional fusion proteins (polyproteins), which inhibit viral activity. Continuing the Tet-On/Tet-Off analogy, we termed this construct “prot-Off”. For optimal virus activity control, both ON and OFF switches were designed to interfere with an early stage of virus propagation by modulating proteins of the viral replication/transcription machinery. Hence our approach expands and potentially bests the current methods of RNA virus regulation.

The replacement of the intergenic region in the Prot-Off viruses has been exemplified between a non-essential reporter protein, GFP, and the essential L-protein, however, the Prot-Off may equally replace an intergenic region that links an essential viral protein with a further viral protein, thereby making the virus safer, since deletion of the protease construct would result in a non-functional fusion protein. Classical resistance mutations, as they occur in HIV under continuous treatment with protease inhibitors could theoretically still occur in the Prot-OFF construct. However, the broad spectrum of available protease inhibitors could compensate for such point mutations.

Figure 20A:
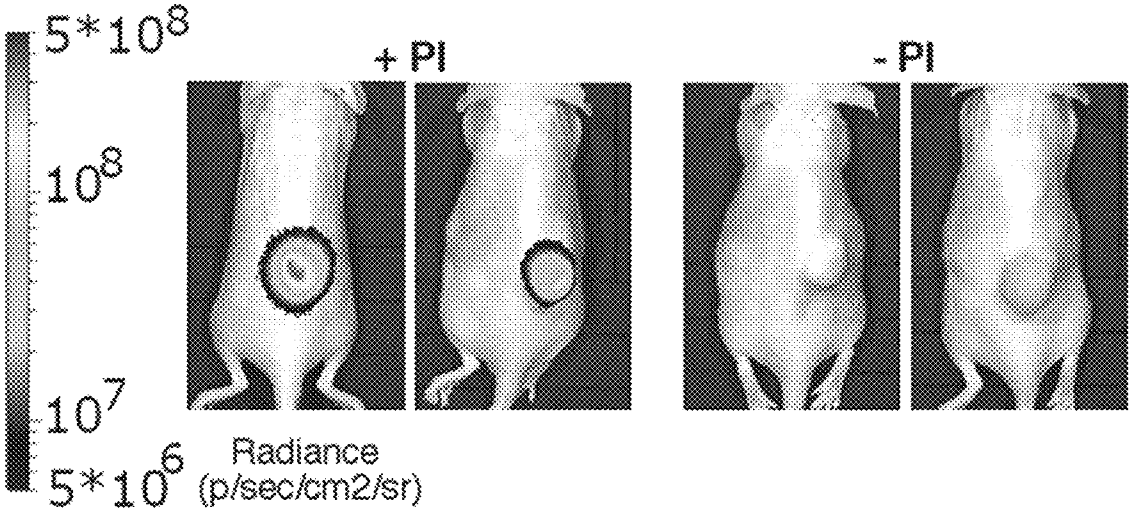
FIG. 20. VSV-P-prot can be regulated in vivo by administration of protease inhibitor. Nude mice were subcutaneously xenografted with U87 glioblastoma cells and at a median volume of 0.1 $cm^3$ intratumorally injected with a single dose of the indicated virus VSV-P-prot-Luc or control buffer. A protease inhibitor (PI) mix comprising 0.8 mM amprenavir (APV) and 0.2 mM ritonavir (RTV) and was administered intraperitoneally at 50 μl every 12 hours. A: Representative bioluminescence images are shown from 8 days post virus inoculation. B: Bioluminescence imaging (BLI) quantification of luciferase signals from VSV-P-prot-Luc treated tumors in mice receiving PI (black squares) or drug vehicle (grey circles) (n=5; mean SD; * $p<0.05$) are shown.
Figure 20B:
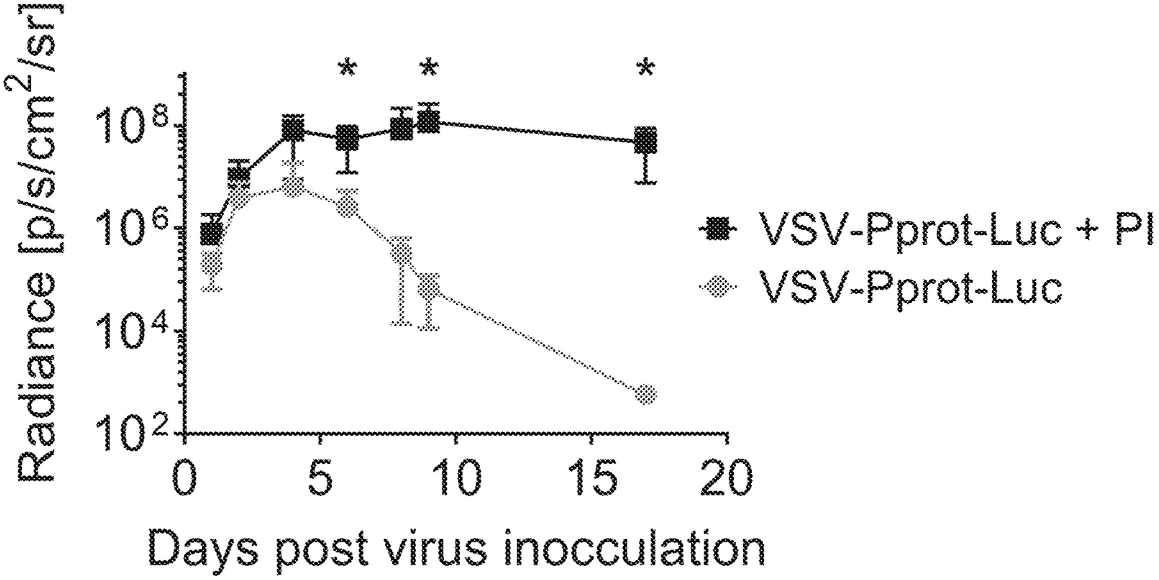

Example 11: VSV-Pprot can be Regulated In Vivo by Administration of Protease Inhibitor To validate the ON-switch viruses in vivo, a luciferase expressing variant VSV-P-prot-Luc was generated as described in Example 1 and shown in FIG. 4, comprising a luciferase reporter gene in place of the eGFP reporter gene for in vivo imaging. Six- to eight-week old female athymic nude mice (Janvier Labs, Le Genest-Saint-Isle, France) were housed in a BL2 facility with a 12-hour light/dark cycle with unrestricted access to food and water. For subcutaneous xenografts, 100 μl human U87 glioblastoma cell suspension containing $2\times10^6$ cells were injected into the right flanks of nude mice. After an engraftment period, U87 xenografts with a median volume of 0.1 $cm^3$ were intratumorally injected with a single dose of 30 μl containing 107 virus (titrated via TCID50) of VSV-Pprot-Luc or control buffer. Protease inhibitor treatment (50 μl intraperitoneal of 0.8 mM APV+0.2 mM RTV every 12 hours in drug vehicle containing 10% DMSO, 40% PEG300, 5% Tween80 and 45% PBS) was initiated one hour before virus application. Ritonavir serves as a blocker of degradation enzymes (Cyp family) in vivo. It augments the concentration of the other PI. RTV is also used as additive in the treatment of HIV for exactly that purpose. Additionally it blocks p-glycoproteins and therefore increases the concentration of the other PI in the brain. Bioluminescence in vivo imaging of luciferase expressing VSV variants was performed using an IVIS® Lumina II (Perkin Elmer, Waltham, MA) system as described by Urbiola C. et al., (int. J. Cancer, 2018, 148:1786-1796). FIG. 20A shows representative bioluminescence images from 8 days after virus injection. At day 8, luminescence is only detected in mice that have been treated with protease inhibitor. This is also confirmed by the bioluminescence imaging (BLI) quantified luciferase signal data shown in FIG. 20B. In the absence of protease inhibitor the luciferase signal is maximal between days 2 to 3 and then starts to decline. The initial bioluminescence signal independent of protease inhibitor application can be explained by the fact that the virus preparation contained amprenavir to block autoproteolysis during virus production and storage. Without further protease inhibitor injections, the bioluminescence signal decreased significantly after 3 days (FIG. 20B), followed by loss of tumor control (data not shown). By contrast, in the presence of protease inhibitor the luciferase signal plateaued for 17 days at an overall much higher level (FIG. 20B) and tumors were controlled in size (data not shown). These data demonstrates in vivo functionality of the ON switch construct, allowing virus replication and expression of a transgene, such as the reporter gene luciferase as used in this experiment or a therapeutic protein, in the presence of a protease inhibitor.

Figure 21A:
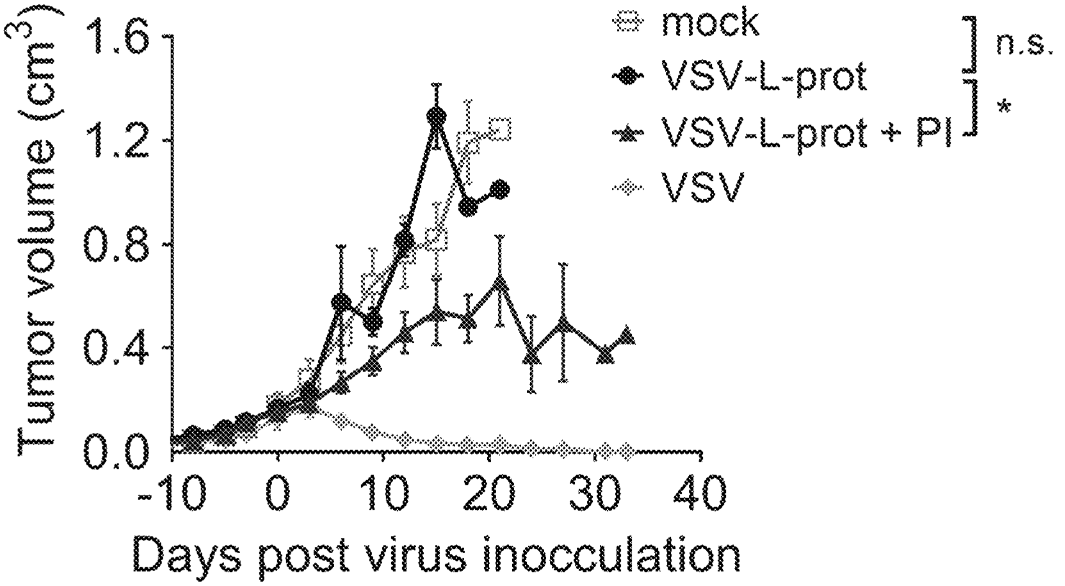
FIG. 21. VSV-L-prot can be regulated in vivo by administration of protease inhibitor. Nude mice were subcutaneously xenografted with U87 glioblastoma cells and at a median volume of 0.1 $cm^3$ intratumorally injected with a single dose of the indicated virus VSV-L-prot, VSV control or control buffer (mock). A protease inhibitor (PI) mix comprising 0.8 mM amprenavir (APV) and 0.2 mM ritonavir (RTV) was administered intraperitoneally at 50 μl every 12 hours. A: Tumors were measured with a caliper and volume was calculated using the formula: length×width$^2$×0.4. Intratumoral treatment of subcutaneous U87 tumors with VSV-L-prot resulted in reduced tumor growth. B: Survival plots are shown, demonstrating increased survival in animals treated with VSV-L-prot and PI (solid thin line) compared to tumors in mice treated with VSV-L-prot in the absence of PI (solid bold line) (Lprot virus treatment+/−PI n=5; VSV n=3; PBS n=6; mean SD, * p<0.0X, ** $p<0.01$).
Figure 21B:
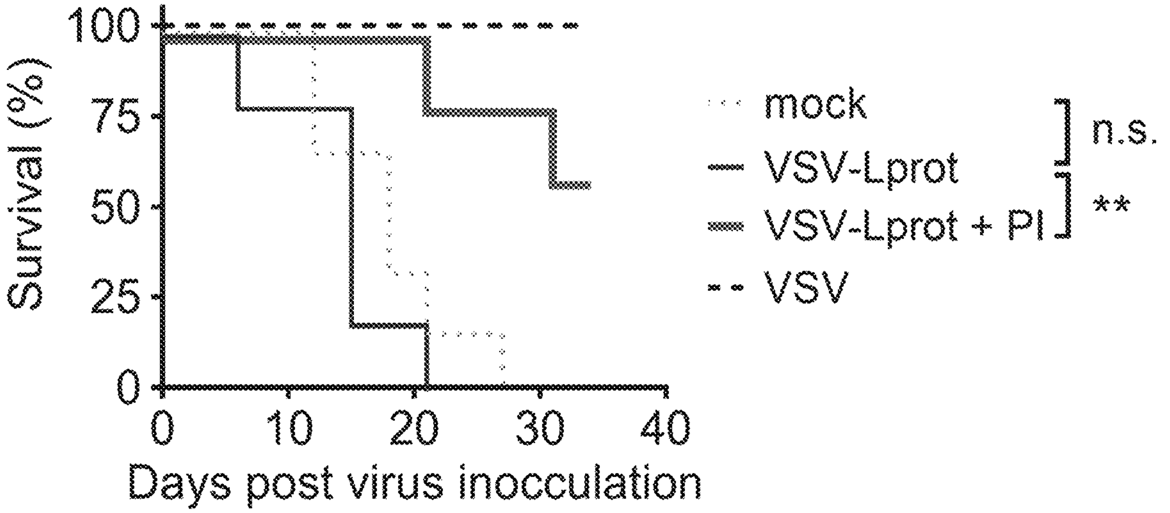

Example 12: VSV-L-Prot can be Regulated In Vivo by Administration of Protease Inhibitor The in vivo data could be further confirmed using VSV-L-prot, expressing GFP as a reporter. Nude mice were subcutaneously xenografted with U87 glioblastoma cells as described in Example 11. At a median volume of 0.1 $cm^3$ mice were intratumorally injected with a single dose of VSV-L-prot, VSV control or control buffer (mock). The generation of VSV-L-prot is described in Example 6 above. A protease inhibitor (PI) mix comprising 0.8 mM amprenavir (APV) and 0.2 mM ritonavir (RTV) and was administered intraperitoneally at 50 μl every 12 hours. Tumors were measured with a caliper and volume was calculated using the formula: length×width$^2$×0.4. Intratumoral treatment of subcutaneous U87 tumors with VSV-L-prot resulted in reduced tumor growth (FIG. 21A) and survival benefits increased survival (FIG. 21B) in the presence of protease inhibitor mix compared to treatment without the protease inhibitor. The concentration of protease inhibitor used in this proof-of-concept study is relatively low and could be further increased. Overall, these data further validate the in vivo applicability of the virus ON-switch.

Example 13: Protease Inhibitor Regulates VSV-Prot-Off Activity In Vivo

Figure 22A:
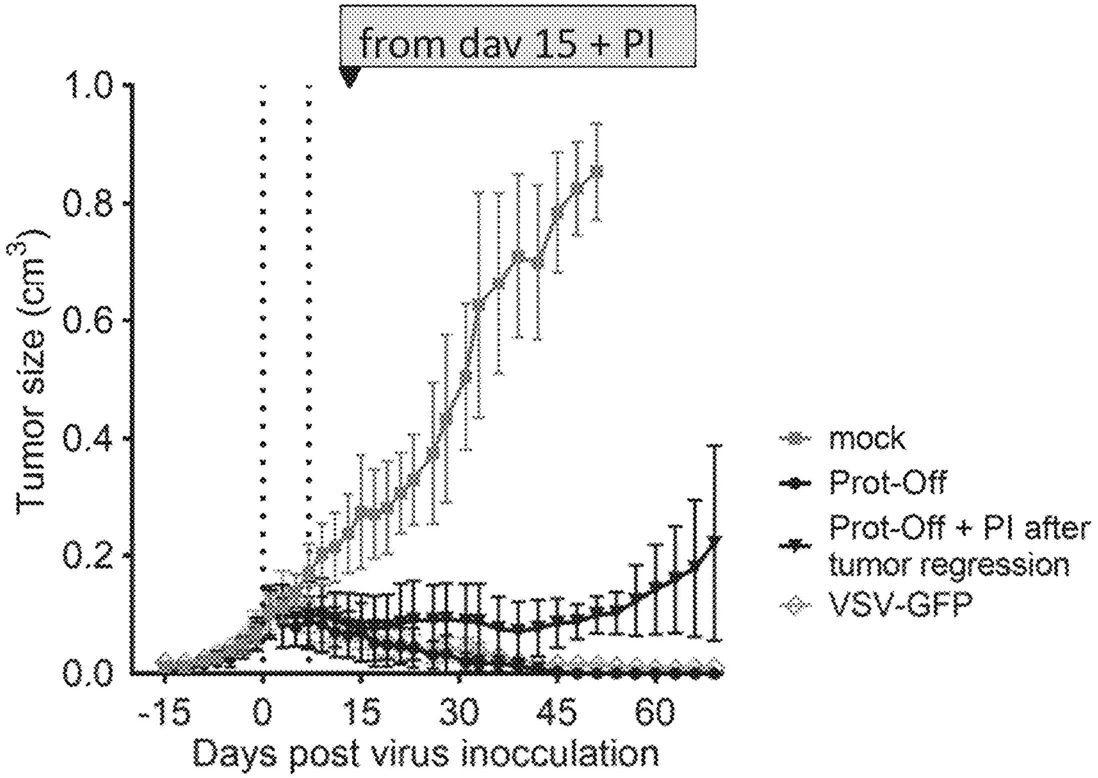
FIG. 22. Protease inhibitor regulates VSV-Prot-off activity in vivo as shown by tumor volume and survival. NOD-SCID mice were subcutaneously xenografted with 100 μl G62 glioma cell suspension and at a median volume of 0.07 $cm^3$ intratumorally injected with a single dose of the indicated virus VSV-Prot-Off, VSV-GFP or control buffer (mock) and again 7 days later as indicated by vertical black dotted lines in A and B. A protease inhibitor (PI) mix comprising 0.8 mM saquinavir (SQV) and 0.2 mM ritonavir (RTV) was administered intraperitoneally at 50 μl every 8 hours. PI treatment started 8 days post second virus injection when tumor regression was observed. A: Tumors were measured with a caliper and volume was calculated using the formula: length×width$^2$×0.4. B: Survival plots are shown, reflecting survival of viral neurotoxicity and/or tumor development over the observation period (VSV-Prot-Off virus treatment+/−PI n=8; VSV-GFP n=8; mean SD).
Figure 22B:
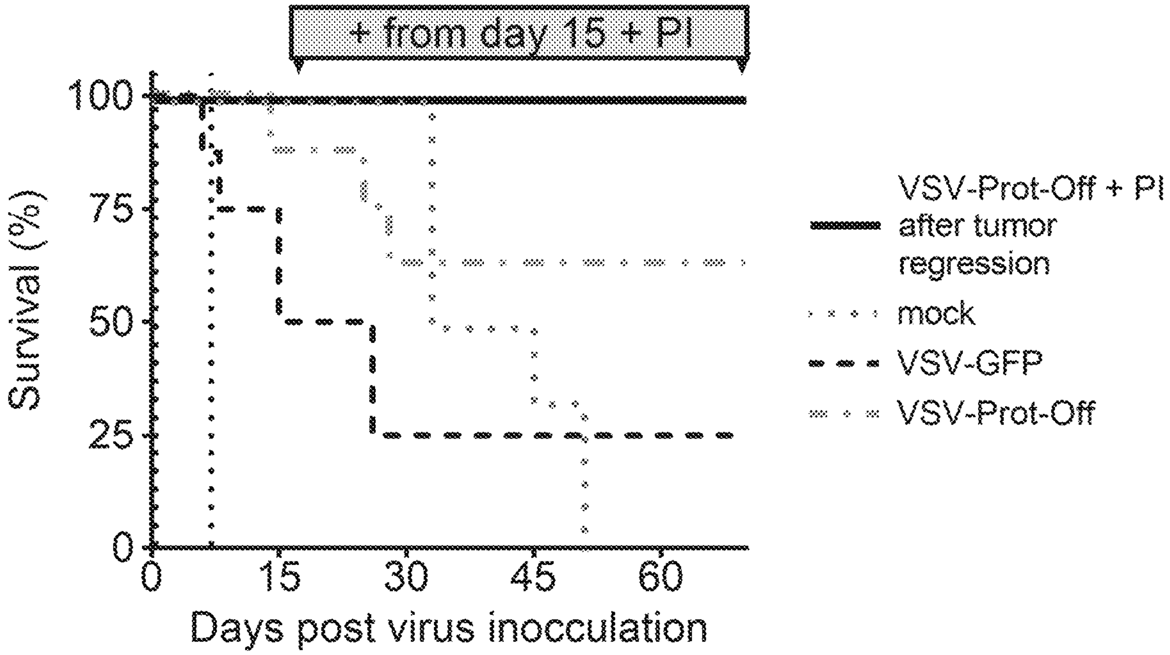

We further tested the OFF-switch in vivo. Six- to eight-week old female NOD.CB-17-Prkdcscid/Rj mice (Janvier Labs, Le Genest-Saint-Isle, France) were housed in a BL2 facility with a 12-hour light/dark cycle with unrestricted access to food and water. For subcutaneous xenografts, 100 μl glioblastoma cell suspension containing $2\times10^6$ human G62 glioma cells were injected into the right flanks of NOD-SCID mice. To test the OFF-switch system, G62 xenografts with a median volume of 0.07 $cm^3$ were intratumorally injected with 30 μl containing $2\times10^7$ virus ($TCID_{50}$) of VSV-Prot-Off (n=16), VSV-GFP (n=8) or control buffer (mock; n=7). Virus treatment was repeated seven days later. The generation of VSV-Prot-OFF (VSV-GFP-prot-L) is described in Example 6 above and depicted in FIG. 17A. Protease inhibitor mix treatment (50 μl intraperitoneal of 0.8 mM SQV+0.2 mM RTV every 8 hours in drug vehicle containing 10% DMSO, 40% PEG300, 5% Tween80 and 45% PBS) was initiated 8 days post second virus injection when tumor regression was observed. Tumors were measured with a caliper and volume was calculated using the formula: length×width$^2$×0.4. Starting on day 6, mice treated with VSV-GFP showed signs of neurotoxicity (FIG. 22B). 15 days post-treatment, the first among the mice treated with VSV-Prot-Off developed neurological symptoms, the remaining mice were randomly divided into 2 groups. One group (n=7) received no protease inhibitor allowing continuous virus replication, which maintained tumor control but also led to further neurotoxicity in some mice. However, neurotoxicity was reduced compared to parental VSV-GFP treated mice (3 vs 6 out of 8 mice). The second group (n=8) was subsequently treated with the protease inhibitor mix (SQV+RTV) 3 times a day to initiate the OFF switch. No signs of neurotoxicity were observed in this group. No signs of neurotoxicity were observed in this group (FIG. 22B). After OFF switch activation, tumor control was diminished and relapse occurred (FIG. 22A).

Figure 23:
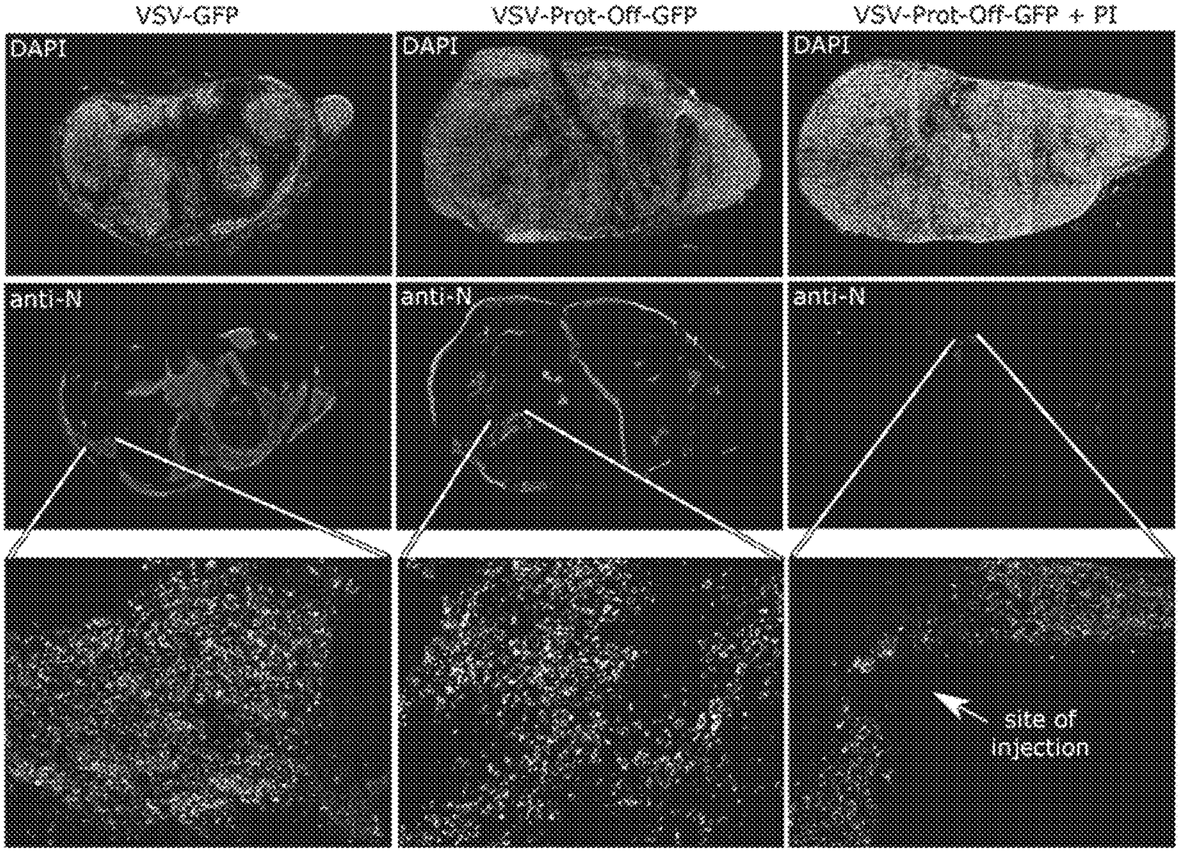
FIG. 23. Protease inhibitor regulates VSV-Prot-off activity in vivo as shown by immunofluorescence. G62 xenografts with a median volume of 0.07 $cm^3$ were intratumorally injected with the indicated VSV variants VSV-Prot-Off or VSV-GFP or control buffer (mock). PI treatment (SQV+RTV) was initiated 3 days post single virus treatment for histological studies. Representative images of immunofluorescence staining of 3 mice per group are shown; upper panel: DAPI stain; middle panel: Anti-VSV-N antibody staining; lower panel: enlarged areas of Anti-VSV-N antibody staining. PI treatment limited spread of VSV-Prot-Off-GFP mainly to the injection site.

Example 14: Protease Inhibitor Regulates VSV-Prot-Off Activity In Vivo as Shown by Immunofluorescence Xenografts were engrafted as described in Example 13. G62 xenografts with a median volume of 0.07 $cm^3$ were intratumorally injected with 30 μl containing $2\times10^6$ virus ($TCID_{50}$) of VSV-Prot-Off or VSV-GFP and protease inhibitor treatment (50 μl intraperitoneal of 0.8 mM SQV+0.2 mM RTV every 8 hours in drug vehicle containing 10% DMSO, 40% PEG300, 5% Tween80 and 45% PBS) was initiated 3 days post single virus treatment. One week later (day 10) tumors were harvested and analysed for virus spread using anti-VSV-N antibody staining. Representative images (FIG. 23) show wide intratumoral spread of VSV-GFP and slightly reduced intratumoral spread of VSV-Prot-OFF in the absence of protease inhibitor, suggesting that VSV-Prot OFF is attenuated to some extent in vivo. In contrast, protease inhibitor treatment starting 3 days after virus inoculation abrogated spread of the virus, which was limited to a minor isolated region.

Figure 24A:
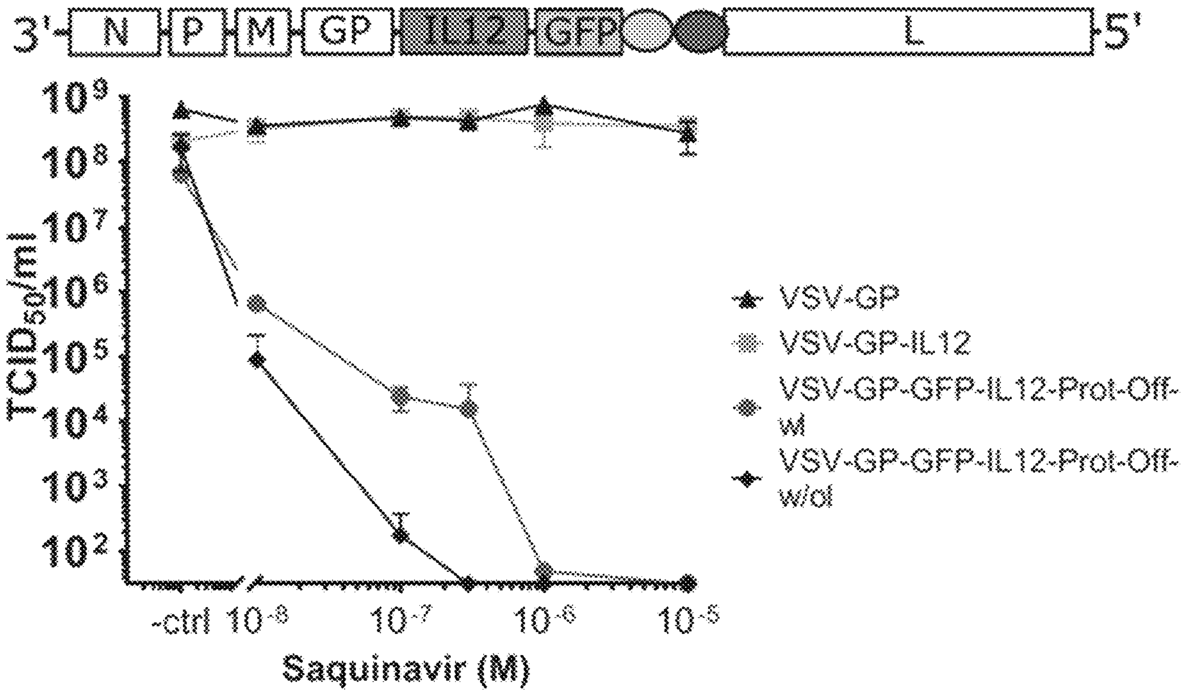
FIG. 24. Saquinavir dose response for VSV-Prot-off activity encoding soluble IL12 in vitro. BHK cells were infected at an MOI of 0.1 with the indicated VSV variants VSV-GP, VSV-GP-IL12, VSV-GP-GFP-IL12-Prot-Off-wl or VSV-GP-GFP-IL12-Prot-Off-w/ol and after washing cultured without (-ctrl) or in the presence of 10, 100, 300, 1.000, 10.000 nmol of protease inhibitor (PI) saquinavir. 30 hours post infection, supernatants were collected. A: Schematic representation of VSV-GP-GFP-IL12-Prot-Off genome organization showing the genes in 3' to 5' direction (top). Virus titers were determined in the supernatant via $TCID_{50}$. Virus titer of VSV-GP-IL12-Prot-Off with and without linker (wl, w/ol) inversely correlated with the saquinavir concentration. B: Enzyme-linked immunosorbant assay (ELISA) was performed to determine the expressed transgene IL12 in the supernatant. IL12 expression inversely correlated with the saquinavir concentration. As a control VSV-GP-IL12 samples without saquinavir (-ctrl) were diluted and measured.
Figure 24B:
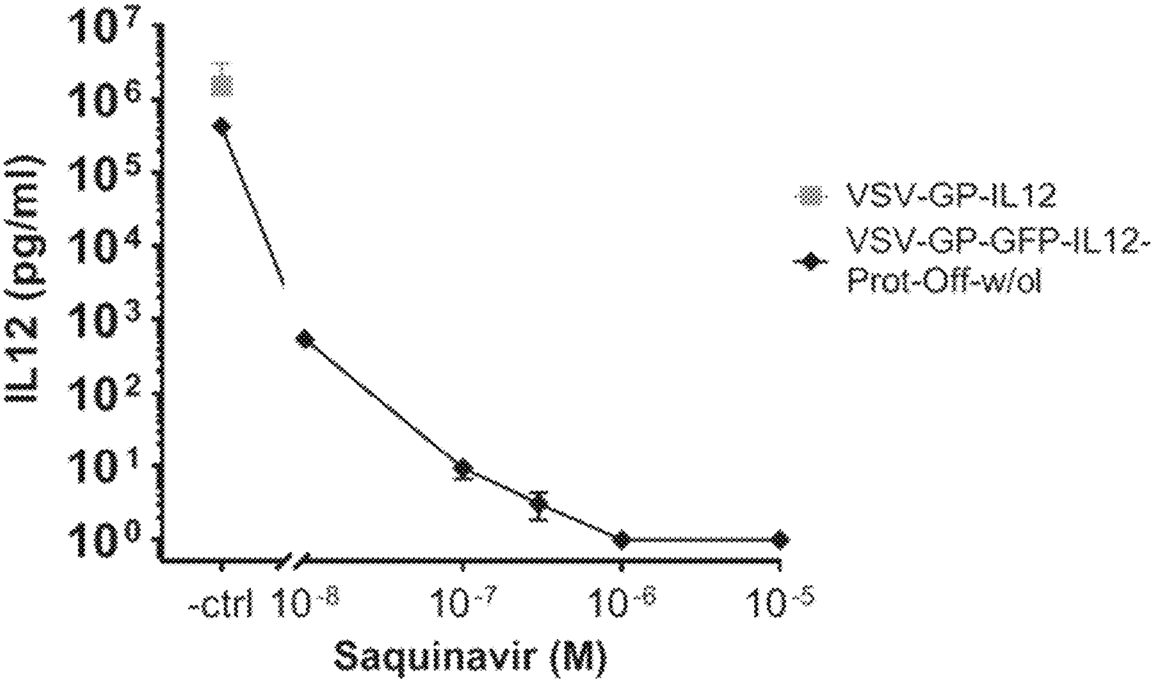

Example 15: Protease Inhibitor Saquinavir Regulates Soluble IL12 Expression Using VSV with a Protease-Regulated OFF-Switch To further investigate whether transgene expression of a therapeutic protein can be regulated using the OFF-switch VSV-GP-IL12-Prot-Off was tested in cell culture. VSV-GP-IL12-Prot-Off (schematically depicted in FIG. 24A, top) is based on VSV-GP pseudotyped with the glycoprotein (GP) of the lymphocytic choriomeningitis virus (LCMV) and has been developed to overcome the neurotoxicity of VSV as described in more detail in WO 2010/040526. $10^5$ BHK cells per well were seeded in 12-Well plates. Cells were infected at an MOI of 0.1 of VSV variants VSV-GP, VSV-GP-IL12, VSV-GP-GFP-IL12-Prot-Off-wl or VSV-GP-GFP-IL12-Prot-Off_w/ol. One hour after infection, cells were washed with PBS and incubated with standard GMEM without protease inhibitor (-ctrl) or 10, 100, 300, 1.000, 10.000 nmol of protease inhibitor saquinavir. 30 hours post infection, supernatants were collected. Virus titers were determined via $TCID_{50}$. Virus titer of VSV-GP-IL12-Prot-Off with and without linker (wl, w/ol) were dependent on the presence and concentration of PI saquinavir (FIG. 24A). Next, an enzyme-linked immunosorbant assay (ELISA) was performed to determine, whether the expressed transgene IL12 was also dependent on saquinavir concentration. VSV-GP-IL12-Prot-Off-w/ol had mildly preferable titer characteristics (higher titers without and stronger response to PI) and was therefore used for the subsequent ELISA. VSV-GP-IL12 and non-inhibited Prot-Off viruses resulted in IL12 concentrations above the assay detection limit. Only control samples without PI (-ctrl) were diluted and measured. IL12 concentration was proportional to virus titer in the Prot-Off virus treated with different doses of saquinavir (FIG. 24B).

Figure 25A:
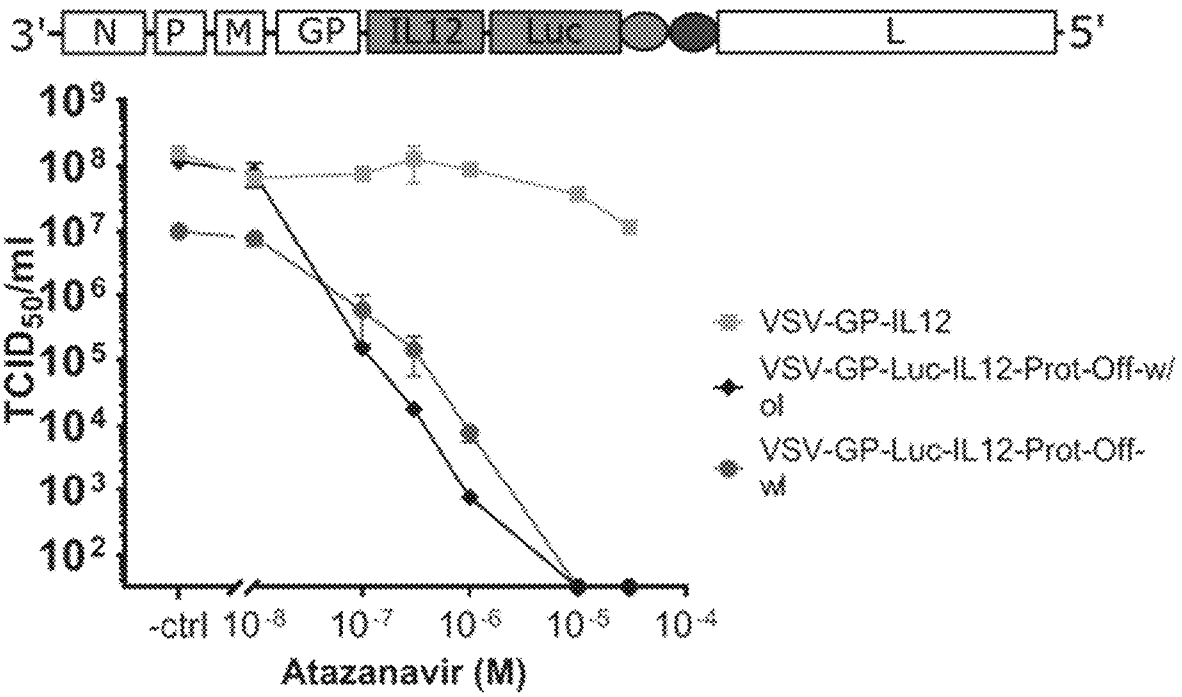
FIG. 25. Atazanavir dose response for VSV-Prot-off activity encoding soluble IL12 in vitro. BHK cells were infected at an MOI of 1 of indicated VSV variants VSV-GP-IL12, VSV-GP-Luc-IL 12-Prot-Off-w/ol or VSV-GP-Luc-IL12-Prot-Off-wl and after washing cultured without (-ctrl) or in the presence of 10, 100, 300, 1.000, 10.000 nmol of atazanavir. 30 hours post infection, supernatants were collected. A: Schematic representation of VSV-GP-Luc-IL12-Prot-Off genome organization showing the genes in 3' to 5' direction (top). Virus titers were determined in the supernatant via $TCID_{50}$. Virus titer of VSV-GP-Luc-IL12-Prot-Off with and without linker (wl, w/ol) inversely correlated with the atazanavir concentration. B: Enzyme-linked immunosorbant assay (ELISA) was performed to determine the expressed transgene IL12 in the supernatant. IL12 expression inversely correlated with the saquinavir concentration. As a control VSV-GP-IL12 samples without atazanavir (-ctrl) were diluted and measured.
Figure 25B:
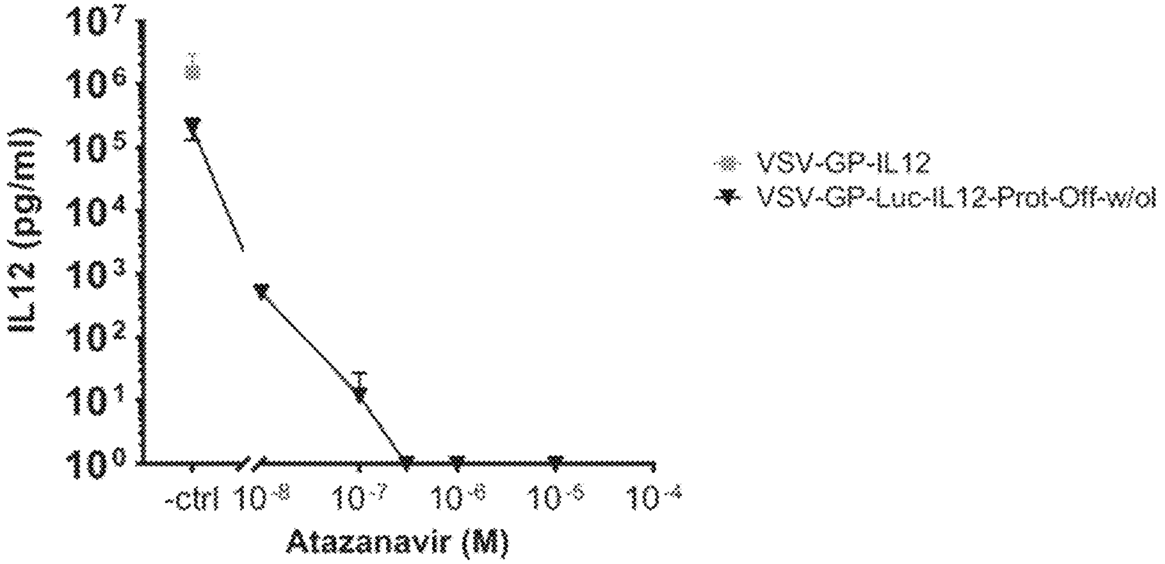

Example 16: Protease Inhibitor Atazanavir Regulates Soluble IL12 Expression Using VSV with a Protease-Regulated OFF-Switch $10^5$ BHK cells per well were seeded in 12-Well plates. Cells were infected at an MOI of 1 of VSV variants VSV-GP-IL12, VSV-GP-Luc-IL12-Prot-Off-wl (FIG. 25A), VSV-GP-Luc-IL12-Prot-Off-w/ol (comprising GFP instead of Luc as shown in 25A). One hour after infection, cells were washed with PBS and incubated with standard GMEM without PI (-ctrl) or 10, 100, 300, 1.000, 10.000 nmol of a more recently developed protease inhibitor called atazanavir. 30 hours post infection, supernatants were collected. Virus titers were determined via $TCID_{50}$. Again, the Prot-Off variant without linkers replicated to higher titers and reacted quicker to atazanavir (FIG. 25A). Therefore, this variant was used for the IL12 ELISA. VSV-GP-IL12 and non-inhibited Prot-Off viruses resulted in IL12 concentrations above the assay detection limit. Only control samples without PI (-ctrl) were diluted and measured (FIG. 25B).

Figure 26A:
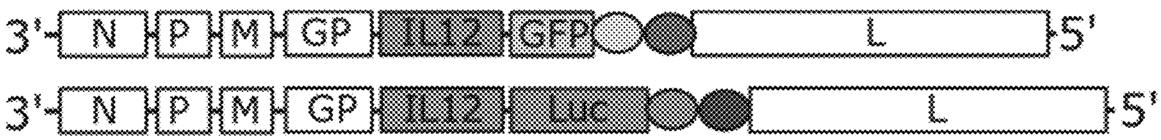
FIG. 26. Replication kinetics for two VSV-Prot-off constructs encoding both soluble IL12 but different reporter proteins. A: Schematic representation of VSV-Prot-Off genome organization of VSV variants encoding IL12 and either GFP (VSV-GP-Prot-Off-w/ol GFP IL12) or luciferase (VSV-GP-Prot-Off-w/ol Luc IL12) showing the genes in 3' to 5' direction encoding soluble IL12 and a fusion protein comprising either GFP or luciferase (Luc) fused (from N- to C-terminal) to the protease dimer and the L-protein. B: BHK cells were infected at an MOI of 3 of indicated VSV variant for a single-step replication kinetic. Following infection cells were washed and cultured in GMEM for the indicated time. Virus titer in the harvested supernatant was determined and is shown as $Log_{10}$ $TCID_{50}$/ml.
Figure 26B:
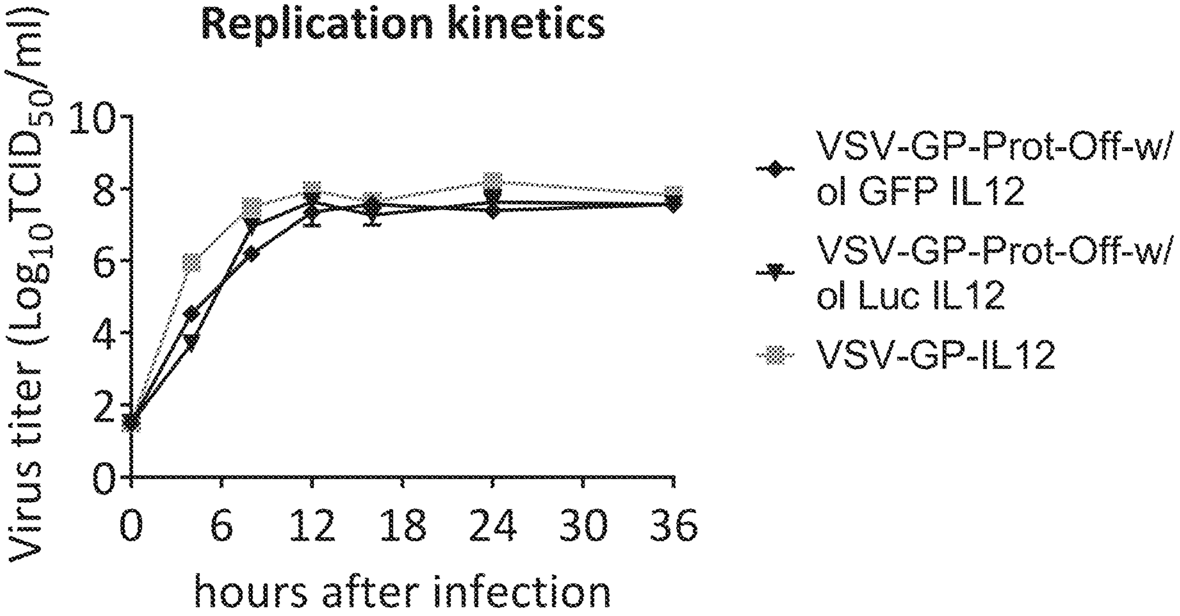

Example 17: Replication Kinetics of VSV with a Protease-Regulated OFF-Switch Encoding IL12 and a Reporter Protein $10^5$ BHK cells per well were seeded in 12-Well plates. Cells were infected at an MOI of 3 of VSV variants VSV-GP-IL12, VSV-GP-Prot-Off-w/ol GFP IL12 (FIG. 26A, top), VSV-GP-Prot-Off-w/ol Luc IL12 (FIG. 26A, bottom) for a single-step replication kinetic. One hour after infection, cells were washed twice with PBS and incubated in 500 μl GMEM until indicated time points. For starting values, i.e. 0-hour time points, the 500 μl GMEM were collected immediately. VSV-Prot-Off variants showed mild attenuation in early time points compared to origin virus VSV-GP-IL12 (FIG. 26B).

Figure 27A:
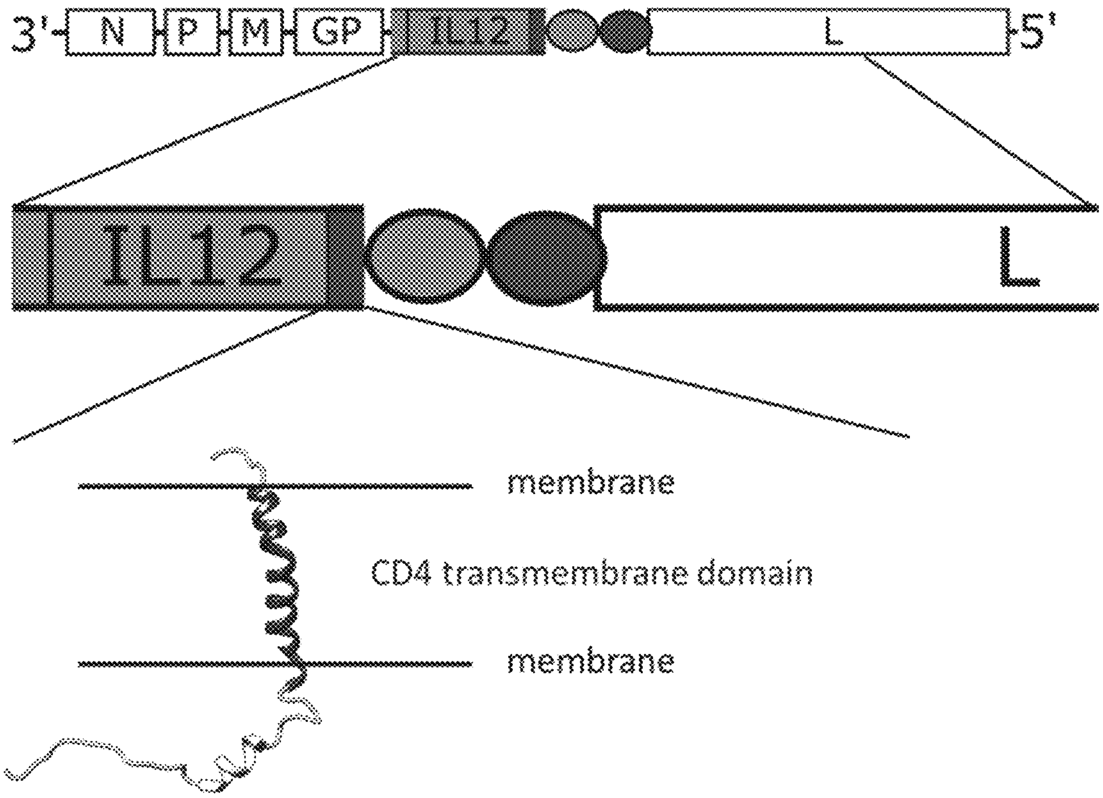
FIG. 27. Schematic representation of a VSV-Prot-off construct encoding membrane anchored IL12. A: Schematic representation of VSV-Prot-off genome organization showing the genes in 3' to 5' direction encoding a fusion protein comprising IL12 fused to a CD4 transmembrane domain, a protease and the L-protein. B. Schematic representation of the fusion protein comprising IL12, the CD4 transmembrane domain (TM), the protease (prot dimer) and the L-protein (L) located at the transmembrane domain.
Figure 27B:
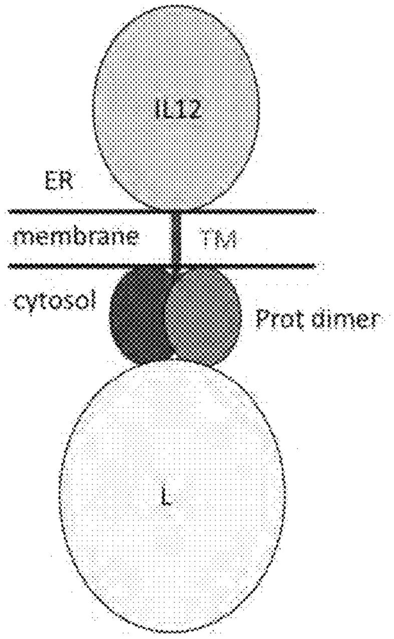

Example 18: Proof-of-Concept for the Expression of Membrane Bound Therapeutic Proteins Using a Protease-Regulated OFF-Switch (FIGS. 27 and 28)

Due to strong toxicity of systemically applied IL12, membrane anchored variants have been developed to retain IL12 at desired sites (Poutou, J. et al., Gene Therapy (2015) 22, 696-706). We applied this principle to gain several advantages over soluble IL12 constructs. First, as has been described by Poutou et al., locally produced IL12 decreases systemic toxicity. Nevertheless, toxicity is not abrogated completely; therefore, further regulation is still desirable. By fusing IL12 with a transmembrane domain of CD4 directly to the VSV polymerase (L protein) as shown in FIG. 27, both viral replication and transgene expression can be decreased through the presence of protease inhibitors. Furthermore, in the context of virus escape mutants, fusing the possibly toxic transgene to the protease dimer in the regulatory virus OFF-switch variant would force the virus to delete both transgene and regulatory switch at once. Deletion of only the switch would still result in a non-functional transgene-polymerase fusion protein. Additionally, by combining both transgene and OFF-switch, coding capacity the virus is economized. Typically, genes are added to the VSV genome by further intergenic regions. VSV genes are transcribed in a continuous gradient, whereby every intergenic region reduces the expression of the downstream transcript. Therefore, introduction of a transgene without the need for an extra intergenic region could reduce virus attenuation.

Previous Prot-Off constructs showed that a flexible linker between the HIV protease dimer and the polymerase result both in lower titers in the absence of protease inhibitors and a slightly less stringent regulation. Residual linker after protease cleavage attached to the N-terminus of the polymerase could be an explanation for the first phenomenon. A flexible linker between the HIV protease and the polymerase could furthermore allow some activity due to less stringent sterical hindrance, possibly resulting in less stringent regulation. Transmembrane anchored IL12 virus variants were therefore designed with either a flexible linker only between IL12-TM and the HIV protease dimer (forward linker—fl) or without any linker flanking the protease (without linker—w/ol). We designed the forward linker construct to provide some additional space between the CD4 membrane anchor and the protease-polymerase fusion protein. The transmembrane domain has the amino acid sequence of SEQ ID NO: 31 (encoded by nucleic acid sequence of SEQ ID NO: 32) and is separated from IL12 encoded by the nucleotide sequence of SEQ ID NO: 33 by a linker having the amino acid sequence of SEQ ID NO: 34 (encoded by nucleic acid sequence of SEQ ID NO: 35).

Figure 28A:
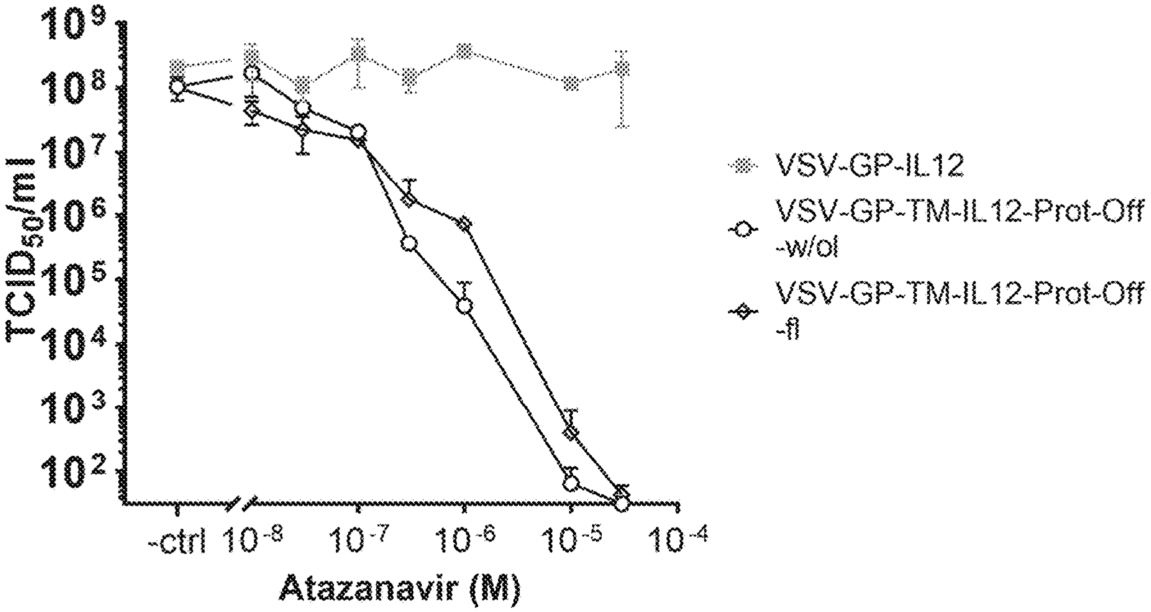
FIG. 28. Proof-of-principle for the expression of membrane bound therapeutic proteins using a VSV-Prot-off construct. By fusing IL12 with a transmembrane domain of CD4 directly to the polymerase, both viral replication and transgene expression can be decreased through the presence of protease inhibitors (Pls). BHK cells were infected at an MOI of 1 of indicated VSV variant and after washing cells were cultured without (-ctrl) or in the presence of 10, 100, 300, 1.000, 10.000 nmol of atazanavir (ATV). 30 hours post infection, supernatants were collected. A: Virus titers were determined in the supernatant via $TCID_{50}$. Virus titer of VSV-GP-TM-IL 12-Prot-Off without linker (-w/ol) or just with a forward linker between the transmembrane domain of IL12 and the HIV protease dimer (-fl) inversely correlated with the AZV concentration, while VSV-GP-IL12 was unefected. B: Unfiltered supernatants of cultures infected with VSV-GP-TM-IL12-Prot-Off without linker (-w/ol) or just with a forward linker (-fl) were tested for IL12 in an Enzyme-linked immunosorbant assay (ELISA). C: Cells infected with VSV-GP-TM-IL12-Prot-Off-fl were diluted in cell lysis buffer and IL12 concentration was measured by ELISA in the lysed sample (supernatant+lysed cells) in comparison to the supernatant with cells (not lysed) or the filtered supernatant alone (n=2). D: BHK cells were infected at an MOI of 3 of indicated VSV variant and cultured for the indicated time periods. VSV-Prot-Off transmembrane IL12 variants without (-w/ol) or with a forward linker (-fl) showed modest attenuation only in early time points compared to origin virus VSV-GP-IL12.
Figure 28B:
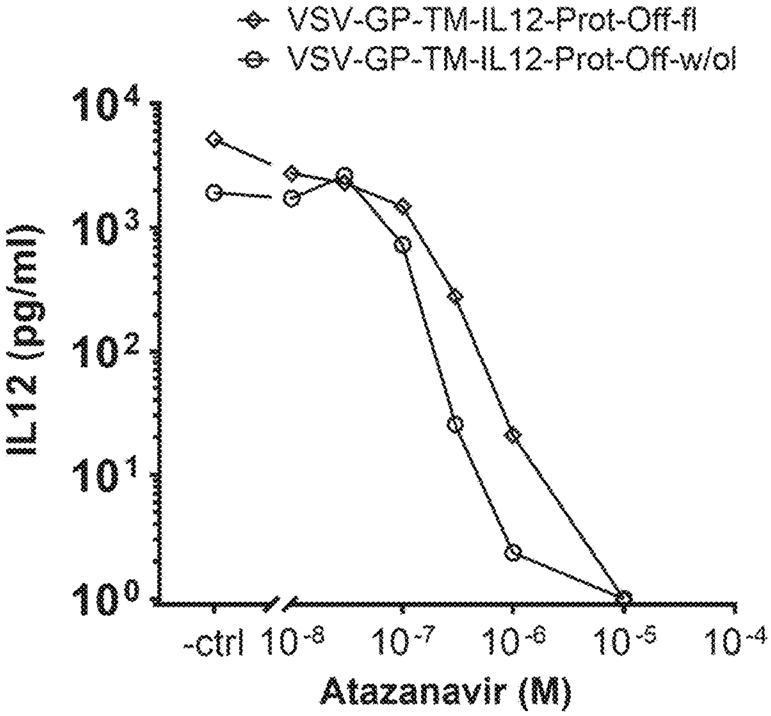
Figure 28C:
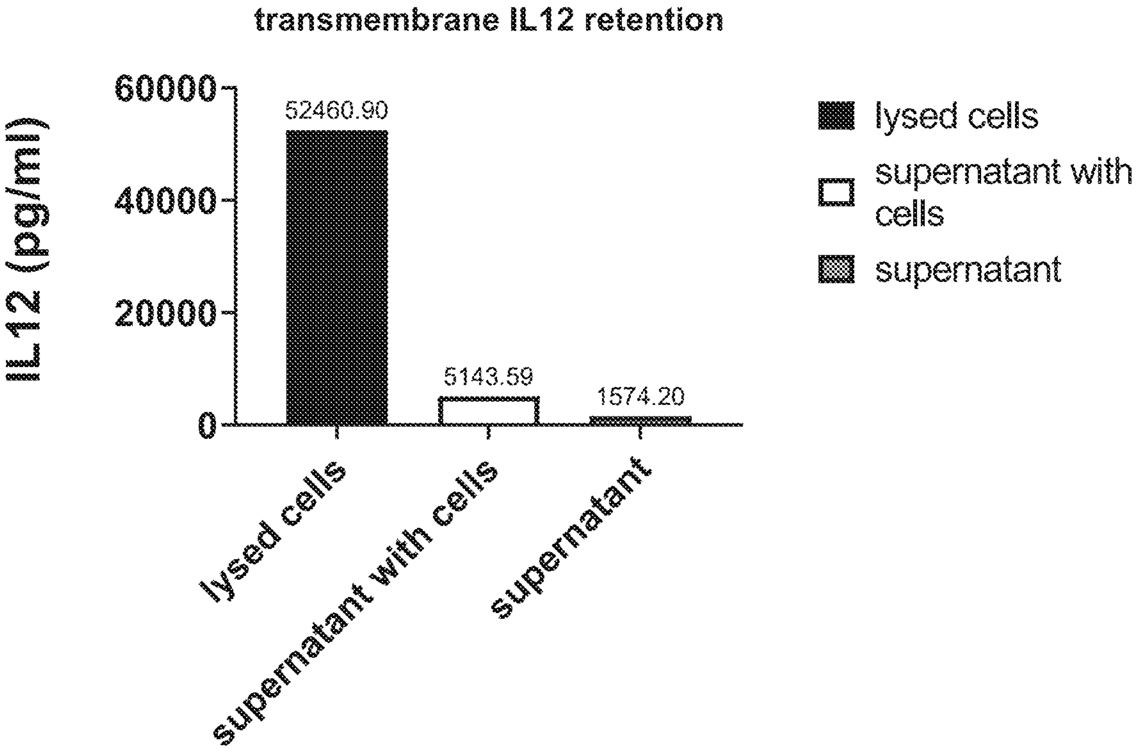

Viral titer and IL-12 expression was determined in cell culture. 105 BHK cells per well were seeded in 12-Well plates. Cells were infected at an MOI of 1 of VSV variants VSV-GP-TM-IL12-Prot-Off-w/ol, VSV-GP-TM-IL12-Prot-Off-fl or VSV-GP-IL12 (control). One hour after infection, cells were washed with PBS and incubated with standard GMEM without PI (-ctrl) or 10, 100, 300, 1.000, 10.000 nmol of atazanavir. 30 hours post infection, supernatants were collected. Virus titers were determined via TCID50 (FIG. 28A). Furthermore, unfiltered supernatants were tested for IL12 in an ELISA. Since IL12 was membrane-bound, in principle only virus-lysed cells would shed the protein. Indeed, maximal IL12 concentrations were lower in PI-negative control samples compared to secreted IL12 (compare FIG. 28B with FIGS. 24B and 25B). Other than with secreted variants, the ELISA assay limit was not exceeded by 2-3 log scales in undiluted samples.

We therefore compared samples comprising lysed cells, supernatant with cells and supernatant only. Lysed cells comprise the cells, non-filtered supernatant with dead cells and lysis buffer added at 1:1. Supernatant with cells refers to non-filtered supernatant with dead cells and supernatant has been centrifuged to remove dead cells. Thus, in supernatant only comprises IL12 liberated by virus cell killing. When samples were diluted in cell lysis buffer, IL12 concentration increased 10-fold due to protein liberated from cellular membranes. Vice-versa, centrifugation and therefore clearance of supernatants from remaining IL12-bearing cells further decreased the concentration of IL12 in the sample.

Figure 28D:
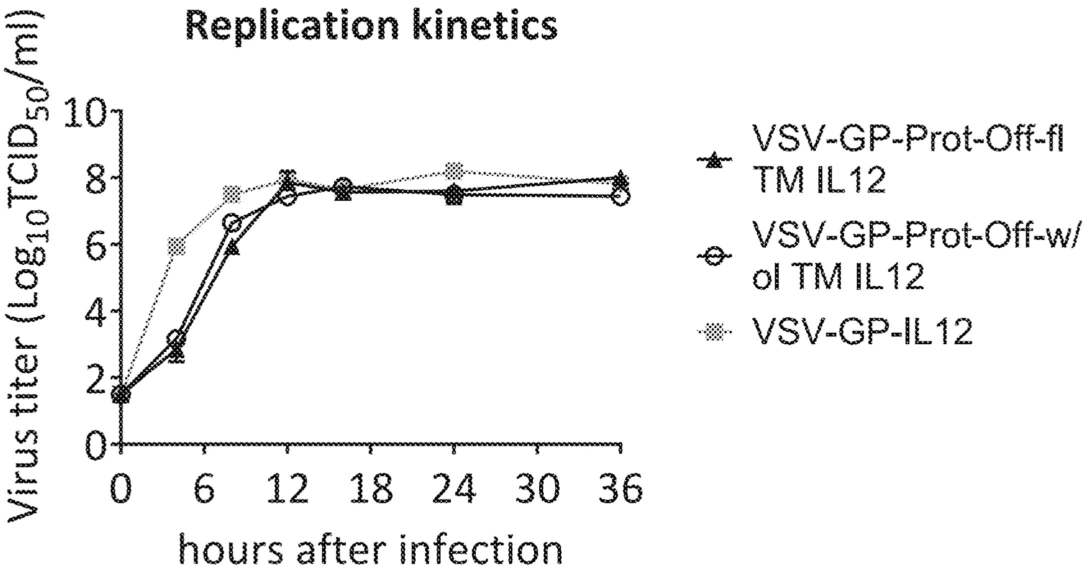

We further analysed replication kinetics of transmembrane IL12 encoding VSV in cell culture. $10^5$ BHK cells per well were seeded in 12-Well plates. Cells were infected at an MOI of 3 of VSV variants VSV-GP-TM-IL12-Prot-Off-fl, VSV-GP-TM-IL12-Prot-Off-w/ol or VSV-GP-IL12 for a single-step replication kinetic. One hour after infection, cells were washed twice with PBS and incubated in 500 μl GMEM until indicated time points. For starting values, i.e. 0-hour time points, 500 μl GMEM were collected immediately. VSV-Prot-Off transmembrane IL12 variants showed modest attenuation in early time points compared to origin virus VSV-GP-IL12 (FIG. 28D). Possibly this early attenuation is caused by expression of the IL12-protease-polymerase fusion protein at the endoplasmic reticulum. VSVs replication complexes however form within the cytoplasm. Thus, liberated polymerase has to diffuse from the ER to virus replication sites. At later time points, however, no attenuation was apparent and further no difference between the constructs with forward linker or without linker has been observed.

SEQUENCE TABLE

| | |
|---|---|
| SEQ ID NO: 1 | P-protein VSV Indiana |
| SEQ ID NO: 2 | L-protein VSV Indiana |
| SEQ ID NO: 3 | P-protein with protease insert |
| SEQ ID NO: 4 | protease dimer with cut and linker (codon optimized DNA sequence) |
| SEQ ID NO: 5 | single chain HIV protease dimer |
| SEQ ID NO: 6 | HIV protease cleavage site 1 (cut1) |
| SEQ ID NO: 7 | HIV protease cleavage site 2 (cut2) |
| SEQ ID NO: 8 | GGSG linker 1 |
| SEQ ID NO: 9 | GGSG linker 2 |
| SEQ ID NO: 10 | L-protein with protease insert |
| SEQ ID NO: 11 | mCherry with linker |
| SEQ ID NO: 12 | mWasabi with linker |
| SEQ ID NO: 13 | L-protein with mCherry insert |
| SEQ ID NO: 14 | L-protein with mCherry insert (P-mWasabi-L-mCherry) |
| SEQ ID NO: 15 | P-protein with mWasabi (P-mWasabi-L-mCherry) |
| SEQ ID NO: 16 | GFP-protease (with linker)-L-protein |
| SEQ ID NO: 17 | GFP-protease (without linker)-L-protein |
| SEQ ID NO: 18 | Prot-off protease dimer with mutation with linker |
| SEQ ID NO: 19 | Prot-off protease dimer with mutation without linker |
| SEQ ID NO: 20 | VSV Indiana vector |
| SEQ ID NO: 21 | VSV Indiana GFP vector |
| SEQ ID NO: 22 | Vesicular stomatitis Indiana virus, complete genome |
| SEQ ID NO: 23 | primer 49 bp-before-FseI based on VSV Indiana GFP |
| SEQ ID NO: 24 | primer 50 bp-after-SfoI based on VSV Indiana GFP |
| SEQ ID NO: 25 | MT1620insertGGSG for |
| SEQ ID NO: 26 | MT1620insertGGSG rev |
| SEQ ID NO: 27 | P-protein amino acid sequence |
| SEQ ID NO: 28 | L-protein amino acid sequence |
| SEQ ID NO: 29 | protease dimer with cut and linker, amino acid sequence |
| SEQ ID NO: 30 | degron sequence |
| SEQ ID NO: 31 | CD4 transmembrane domain (TM) (amino acid sequence) |
| SEQ ID NO: 32 | CD4 transmembrane domain (nucleic acid sequence) |
| SEQ ID NO: 33 | IL12 (nucleic acid sequence) |
| SEQ ID NO: 34 | Linker between TM and IL12 (amino acid sequence) |
| SEQ ID NO: 35 | Linker between TM and IL12 (nucleic acid sequence) |

The invention claimed is:

1. A single-stranded RNA virus comprising a modified genome of the virus comprising a polynucleotide sequence encoding protein essential for viral transcription and/or replication, an autocatalytic protease, and a cleavage site for said protease, wherein the single-stranded RNA virus is Vesicular Stomatitis Virus (VSV), the protease is the hepatitis C virus (HCV) NS3 protease or a single chain dimer of the human immunodeficiency virus 1 (HIV-1) protease and the protein essential for viral transcription and/or replication is VSV P-protein or VSV L-protein, wherein (a) the protein essential for viral transcription and/or replication comprises an insert at an intramolecular insertion site comprising at least the cleavage site for said protease and further the protease, and wherein the intramolecular insertion site is (i) in the flexible hinge region of the VSV P-protein, or (ii) in the loop of the methyltransferase domain of the L-protein corresponding to amino acids 1614 to 1634 of the amino acid sequence of SEQ ID NO: 28; or (b) the protein essential for viral transcription and/or replication is encoded as a fusion protein comprising the protease fused to the N-terminal end, separated by the cleavage site for said protease, wherein the fusion protein does not comprise the amino acid sequence of SEQ ID NO: 30.

2. The single-stranded RNA virus of claim 1, wherein the protease is a single chain dimer of the HIV-1 protease, and wherein the protease can be inhibited by a protease inhibitor selected from the group consisting of indinavir, saquinavir, ritonavir, nelfinavir, lopinavir, amprenavir, fosamprenavir, atazanavir, tipranavir and darunavir.

3. The single-stranded RNA virus of claim 1, wherein at least the cleavage site for said protease and the protease are located within the intramolecular insertion site of the least one protein essential for viral transcription and/or replication, and wherein (a) proteolytic cleavage of the protein cleaves the protein essential for viral transcription and/or replication at the cleavage site for said protease within the intramolecular insertion site;

(b) cleavage within the intramolecular insertion site inactivates the protein essential for viral transcription and/or replication;

(c) cleavage within the intramolecular insertion site of the protein essential for viral transcription and/or replication inhibits viral transcription and/or replication;

(d) the virus is active in the presence of a specific inhibitor of the protease and inactive in the absence of a specific inhibitor of the protease; or (e) the virus further encodes at least one heterologous protein, wherein the heterologous protein is expressed if the virus is active in the presence of a specific inhibitor of the protease and is not expressed if the virus is inactive in the absence of a specific inhibitor of the protease.

4. The single-stranded RNA virus of claim 1, wherein the protein essential for viral transcription and/or replication is encoded as a fusion protein comprising the protease fused to the N-terminal end of the protein essential for viral transcription and/or replication separated by the cleavage site for said protease and wherein (a) proteolytic cleavage of the fusion protein releases the protein essential for viral transcription and/or replication in its active form;

(b) the protein essential for viral transcription and/or replication in the fusion protein comprising the protease fused to the N-terminal end of the protein essential for viral transcription and/or replication separated by the cleavage site for said protease is inactive without proteolytic cleavage;

(c) the proteolytic cleavage of the fusion protein is inhibited using a specific inhibitor of the protease;

(d) the virus is inactive in the presence of a specific protease inhibitor of the protease and active in the absence of a specific inhibitor of the protease;

(e) the virus further encodes at least one heterologous protein, wherein the heterologous protein is not expressed if the virus is inactive in the presence of a specific inhibitor of the protease and is expressed if the virus is active in the absence of a specific inhibitor of the protease;

(f) the fusion protein further comprises a further viral protein or a heterologous protein fused to the opposite end of the protease fused to the N-terminal end of the protein essential for viral transcription and/or replication, and wherein said further viral protein or heterologous protein and said protease are also separated by a cleavage site for said protease;

(g) the protease flanked by the cleavage site for said protease on either side replaces an intergenic region that links the protein essential for viral transcription and/or replication with a further viral protein or a heterologous protein; or (h) the protease flanked by the cleavage site for said protease on either side replaces an intergenic region that links the protein essential for viral transcription and/or replication with a further viral protein or a heterologous protein, wherein loss of the protease leads to a further inactive fusion protein comprising the protein essential for viral transcription and/or replication and the further viral protein or heterologous protein.

5. The single-stranded RNA virus of claim 1, wherein the protein essential for viral transcription and/or replication is encoded as a fusion protein comprising the protease fused to the N-terminal end of the protein essential for viral transcription and/or replication separated by the cleavage site for said protease, wherein the protein essential for viral transcription and/or replication is an L protein.

6. The single-stranded RNA virus of claim 1, wherein the protein essential for viral transcription and/or replication is encoded as a fusion protein (a) consisting of the protease fused to the N-terminal end of the protein essential for viral transcription and/or replication, separated by the cleavage site for said protease;

(b) consisting of the protease fused to the N-terminal end of the protein essential for viral transcription and/or replication, separated by the cleavage site for said protease, wherein the fusion protein further comprises a linker between the protease and the protein essential for viral transcription and/or replication; or (c) comprising the protease fused to the N-terminal end of the protein essential for viral transcription and/or replication, separated by the cleavage site for said protease, and a further viral protein or a heterologous protein fused to the opposite end of the protease fused to the N-terminal end of the protein essential for viral transcription and/or replication, and wherein said further viral protein or heterologous protein and said protease are also separated by a cleavage site for said protease.

7. The single-stranded RNA virus of claim 1, wherein the protease is the single chain dimer of HIV-1 protease flanked by the cleavage site for said protease on either side according to the amino acid sequence of SEQ ID NO: 29.

* * * * *